US012247227B2

(12) United States Patent
Ingber et al.

(10) Patent No.: US 12,247,227 B2
(45) Date of Patent: *Mar. 11, 2025

(54) METHODS RELATING TO INTESTINAL ORGAN-ON-A-CHIP

(71) Applicant: PRESIDENT AND FELLOWS OF HARVARD COLLEGE, Cambridge, MA (US)

(72) Inventors: Donald E. Ingber, Cambridge, MA (US); Magdalena Kasendra, Cambridge, MA (US); Alexandra Sontheimer-Phelps, Cambridge, MA (US); Alessio Tovaglieri, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/242,731

(22) Filed: Sep. 6, 2023

(65) Prior Publication Data
US 2023/0416691 A1 Dec. 28, 2023

Related U.S. Application Data

(63) Continuation of application No. 17/539,452, filed on Dec. 1, 2021, now Pat. No. 11,976,304, which is a (Continued)

(51) Int. Cl.
C12N 5/071 (2010.01)
C12N 5/00 (2006.01)
G01N 33/50 (2006.01)

(52) U.S. Cl.
CPC ......... *C12N 5/0697* (2013.01); *C12N 5/0062* (2013.01); *C12N 5/0068* (2013.01);
(Continued)

(58) Field of Classification Search
CPC .. C12N 5/0697; C12N 5/0062; C12N 5/0068; C12N 5/0679; C12N 2501/11;
(Continued)

(56) References Cited

U.S. PATENT DOCUMENTS 3,300,386 A 1/1967 Aron-Brunetiere
3,313,290 A 4/1967 Chance
(Continued)

FOREIGN PATENT DOCUMENTS

WO 2002048318 6/2002
WO 2004059299 A1 7/2004
(Continued)

OTHER PUBLICATIONS

US 6,465,252 B1, 10/2002, Toner (withdrawn)
(Continued)

Primary Examiner — Blaine Lankford
Assistant Examiner — Lauren K Van Buren
(74) Attorney, Agent, or Firm — Nixon Peabody LLP; David S. Resnick; Nicole D. Kling

(57) ABSTRACT

Described herein are methods for providing an in vitro intestinal model system, e.g., using primary cells instead of cell lines and/or cancerous cells.

4 Claims, 28 Drawing Sheets

Related U.S. Application Data continuation of application No. 16/331,718, filed as application No. PCT/US2017/051296 on Sep. 13, 2017, now Pat. No. 12,104,174.

(60) Provisional application No. 62/393,711, filed on Sep. 13, 2016.

(52) U.S. Cl.
CPC ....... *C12N 5/0679* (2013.01); *G01N 33/5088* (2013.01); *C12N 2501/11* (2013.01); *C12N 2501/345* (2013.01); *C12N 2501/415* (2013.01); *C12N 2502/1323* (2013.01)

(58) Field of Classification Search
CPC ........ C12N 2501/345; C12N 2501/415; C12N 2502/1323; G01N 33/5088
See application file for complete search history.

(56) References Cited

U.S. PATENT DOCUMENTS

| | | | |
|---|---|---|---|
| 3,722,504 A | 3/1973 | Sawyer |
| 3,941,662 A | 3/1976 | Munder |
| 3,948,732 A | 4/1976 | Haddad |
| 4,225,671 A | 9/1980 | Puchinger |
| 4,436,824 A | 3/1984 | Bishop |
| 4,446,229 A | 5/1984 | Indech |
| 4,537,860 A | 8/1985 | Tolbert |
| 4,610,878 A | 9/1986 | Wilson |
| 4,629,686 A | 12/1986 | Gruenberg |
| 4,650,766 A | 3/1987 | Harm |
| 4,673,650 A | 6/1987 | William |
| 4,720,462 A | 1/1988 | Rosenson |
| 4,734,372 A | 3/1988 | Rotman |
| 4,737,455 A | 4/1988 | De Baetselier |
| 4,749,654 A | 6/1988 | Karrer |
| 4,835,102 A | 5/1989 | Bell |
| 4,839,280 A | 6/1989 | Banes |
| 4,851,354 A | 7/1989 | Winston |
| 4,929,542 A | 5/1990 | Risley |
| 4,940,853 A | 7/1990 | Vandenburgh |
| 5,002,890 A | 3/1991 | Morrison |
| 5,043,260 A | 8/1991 | Jauregui |
| 5,108,926 A | 4/1992 | Klebe |
| 5,160,490 A | 11/1992 | Naughton |
| 5,217,899 A | 6/1993 | Shapiro |
| 5,290,684 A | 3/1994 | Kelly |
| 5,316,905 A | 5/1994 | Mori |
| 5,348,879 A | 9/1994 | Shapiro |
| 5,486,335 A | 1/1996 | Wilding |
| 5,496,697 A | 3/1996 | Parce |
| 5,498,392 A | 3/1996 | Wilding |
| 5,587,128 A | 12/1996 | Wilding |
| 5,612,188 A | 3/1997 | Shuler |
| 5,637,469 A | 6/1997 | Wilding |
| 5,726,026 A | 3/1998 | Wilding |
| 5,744,366 A | 4/1998 | Kricka |
| 5,750,329 A | 5/1998 | Quinn |
| 5,811,281 A | 9/1998 | Quaroni |
| 5,820,769 A | 10/1998 | Chou |
| 5,900,160 A | 5/1999 | Whitesides |
| 5,906,828 A | 5/1999 | Cima |
| 6,048,723 A | 4/2000 | Banes |
| 6,054,277 A | 4/2000 | Furcht |
| 6,133,030 A | 10/2000 | Bhatia |
| 6,197,575 B1 | 3/2001 | Griffith |
| 6,255,106 B1 | 7/2001 | Marx |
| 6,306,644 B1 | 10/2001 | Marx |
| 6,329,195 B1 | 12/2001 | Pfaller |
| 6,454,924 B2 | 9/2002 | Jedrzejewski |
| 6,472,202 B1 | 10/2002 | Banes |
| 6,530,370 B1 | 3/2003 | Heinonen |
| 6,562,616 B1 | 5/2003 | Toner |
| 6,586,235 B1 | 7/2003 | Banes |
| 6,593,136 B1 | 7/2003 | Geiss |
| 6,630,801 B2 | 10/2003 | Schuurmans |
| 6,645,432 B1 | 11/2003 | Anderson |
| 6,645,759 B2 | 11/2003 | Banes |
| 6,653,124 B1 | 11/2003 | Freeman |
| 6,730,516 B2 | 5/2004 | Jedrzejewski |
| 6,921,253 B2 | 7/2005 | Shuler |
| 6,998,265 B2 | 2/2006 | Banes |
| 7,049,057 B2 | 5/2006 | Atala |
| 7,288,405 B2 | 10/2007 | Shuler |
| 7,314,718 B1 | 1/2008 | Dasgupta |
| 7,438,856 B2 | 10/2008 | Jedrzejewski |
| 7,727,550 B2 | 6/2010 | Siegal |
| 7,745,209 B2 | 6/2010 | Martin |
| 7,763,456 B2 | 7/2010 | Li |
| 7,790,028 B1 | 9/2010 | Weinberg |
| 7,960,166 B2 | 6/2011 | Vacanti |
| 7,964,078 B2 | 6/2011 | Lee |
| 7,976,795 B2 | 7/2011 | Zhou |
| 7,977,089 B2 | 7/2011 | Wikswo |
| 7,985,336 B2 | 7/2011 | Weinberg |
| 8,030,061 B2 | 10/2011 | Shuler |
| 8,147,562 B2 | 4/2012 | Vacanti |
| 8,187,863 B2 | 5/2012 | Sim |
| 8,268,152 B2 | 9/2012 | Stelzle |
| 8,273,572 B2 | 9/2012 | Martin |
| 8,318,479 B2 | 11/2012 | Domansky |
| 8,343,740 B2 | 1/2013 | Gonda |
| 8,357,528 B2 | 1/2013 | Vacanti |
| 8,460,546 B2 | 6/2013 | Weinberg |
| 8,470,589 B2 | 6/2013 | Martin |
| 8,647,861 B2 | 2/2014 | Ingber |
| 8,968,543 B2 | 3/2015 | Stelzle |
| 9,079,189 B2 | 7/2015 | Garcia |
| 9,182,387 B2 | 11/2015 | Goldkorn |
| 9,322,752 B2 | 4/2016 | Wanders |
| 11,976,304 B2 * | 5/2024 | Ingber ............... G01N 33/5088 |
| 2002/0129813 A1 | 9/2002 | Litherland |
| 2002/0173033 A1 | 11/2002 | Hammerick |
| 2003/0021792 A1 | 1/2003 | Roben |
| 2003/0040033 A1 | 2/2003 | Kim |
| 2003/0082795 A1 | 5/2003 | Shuler |
| 2003/0096405 A1 | 5/2003 | Takayama |
| 2003/0175824 A1 | 9/2003 | Pishko |
| 2003/0180807 A1 | 9/2003 | Hess |
| 2003/0215941 A1 | 11/2003 | Campbell |
| 2004/0034435 A1 | 2/2004 | Atala |
| 2004/0063205 A1 | 4/2004 | Xu |
| 2004/0132166 A1 | 7/2004 | Miller |
| 2005/0032205 A1 | 2/2005 | Smith |
| 2005/0169962 A1 | 8/2005 | Bhatia |
| 2005/0266393 A1 | 12/2005 | Baxter |
| 2005/0273995 A1 | 12/2005 | Kanagasabapathi |
| 2006/0019326 A1 | 1/2006 | Vacanti |
| 2006/0099116 A1 | 5/2006 | Manger |
| 2006/0154361 A1 | 7/2006 | Wikswo |
| 2006/0263336 A1 | 11/2006 | Caplan |
| 2006/0270023 A1 | 11/2006 | Leduc |
| 2007/0015273 A1 | 1/2007 | Shuler |
| 2007/0015274 A1 | 1/2007 | Shuler |
| 2007/0015275 A1 | 1/2007 | Shuler |
| 2007/0020693 A1 | 1/2007 | Shuler |
| 2007/0026519 A1 | 2/2007 | Shuler |
| 2007/0037273 A1 | 2/2007 | Shuler |
| 2007/0037275 A1 | 2/2007 | Shuler |
| 2007/0037277 A1 | 2/2007 | Shuler |
| 2007/0048727 A1 | 3/2007 | Shuler |
| 2007/0122794 A1 | 5/2007 | Shuler |
| 2007/0122896 A1 | 5/2007 | Shuler |
| 2007/0144514 A1 | 6/2007 | Yeates |
| 2007/0166816 A1 | 7/2007 | Campbell |
| 2007/0172943 A1 | 7/2007 | Freedman |
| 2007/0207194 A1 | 9/2007 | Grayburn |
| 2007/0207537 A1 | 9/2007 | Cui et al. |
| 2007/0224677 A1 | 9/2007 | Neumann |
| 2007/0243627 A1 | 10/2007 | Takayama |
| 2007/0272000 A1 | 11/2007 | Kahl |
| 2007/0275435 A1 | 11/2007 | Kim |
| 2007/0275455 A1 | 11/2007 | Hung |

(56) References Cited

U.S. PATENT DOCUMENTS

| | | |
|---|---|---|
| 2007/0275882 A1 | 11/2007 | Meijer |
| 2007/0281353 A1 | 12/2007 | Vacanti |
| 2008/0032380 A1 | 2/2008 | Kleis |
| 2008/0064088 A1 | 3/2008 | Shuler |
| 2008/0166794 A1 | 7/2008 | Shuler |
| 2008/0166795 A1 | 7/2008 | Shuler |
| 2008/0220516 A1 | 9/2008 | Eddington |
| 2008/0233607 A1 | 9/2008 | Yu |
| 2008/0318334 A1 | 12/2008 | Robotti |
| 2009/0028755 A1 | 1/2009 | Jedrzejewski |
| 2009/0074623 A1 | 3/2009 | Park |
| 2009/0078614 A1 | 3/2009 | Varghese |
| 2009/0131858 A1 | 5/2009 | Fissell |
| 2009/0134235 A1 | 5/2009 | Ivri |
| 2009/0220932 A1 | 9/2009 | Ingber |
| 2010/0041128 A1 | 2/2010 | Banes |
| 2010/0043494 A1 | 2/2010 | Gascon |
| 2010/0048411 A1 | 2/2010 | Przyborski |
| 2010/0267136 A1 | 10/2010 | Vacanti |
| 2010/0294986 A1 | 11/2010 | Sultana |
| 2010/0304355 A1 | 12/2010 | Shuler |
| 2010/0323439 A1 | 12/2010 | Takayama |
| 2010/0325747 A1 | 12/2010 | Grompe |
| 2011/0000482 A1 | 1/2011 | Gumaste |
| 2011/0027804 A1 | 2/2011 | Yarmush |
| 2011/0053207 A1 | 3/2011 | Hoganson |
| 2011/0086382 A1 | 4/2011 | Marx |
| 2011/0183312 A1 | 7/2011 | Huang |
| 2011/0250585 A1 | 10/2011 | Ingber |
| 2011/0269226 A1 | 11/2011 | Van Noort |
| 2011/0287469 A1 | 11/2011 | Guenther |
| 2012/0003732 A1 | 1/2012 | Hung |
| 2012/0028355 A1 | 2/2012 | Sato |
| 2012/0088693 A1 | 4/2012 | Lee |
| 2012/0129207 A1 | 5/2012 | Yarmush |
| 2012/0135446 A1 | 5/2012 | Collins |
| 2012/0135452 A1 | 5/2012 | Shuler |
| 2012/0199487 A1 | 8/2012 | Stelzle |
| 2012/0214189 A1 | 8/2012 | Shuler |
| 2012/0318726 A1 | 12/2012 | Charest |
| 2012/0322097 A1 | 12/2012 | Charest |
| 2013/0059322 A1 | 3/2013 | Hung |
| 2013/0109594 A1 | 5/2013 | Gonda |
| 2013/0157360 A1 | 6/2013 | March |
| 2013/0236972 A1 | 9/2013 | Noh |
| 2013/0309677 A1 | 11/2013 | Blackman |
| 2014/0038279 A1* | 2/2014 | Ingber .................... C12N 5/068 |
| | | 435/297.2 |
| 2014/0158233 A1 | 6/2014 | Leslie |
| 2014/0186414 A1 | 7/2014 | Ingber |
| 2014/0199764 A1 | 7/2014 | Domansky |
| 2014/0342445 A1 | 11/2014 | Ingber |
| 2015/0004077 A1 | 1/2015 | Wikswo |
| 2015/0079670 A1 | 3/2015 | Domansky |
| 2015/0209783 A1 | 7/2015 | Ingber |
| 2015/0306596 A1 | 10/2015 | Thompson |
| 2016/0243738 A1 | 8/2016 | Katrycz |
| 2018/0002672 A1* | 1/2018 | Allbritton ............ C12N 5/0679 |

FOREIGN PATENT DOCUMENTS

| | | |
|---|---|---|
| WO | 2010009307 A2 | 1/2010 |
| WO | 2010118857 A2 | 10/2010 |
| WO | 2012032646 A1 | 3/2012 |
| WO | 2013086486 A1 | 6/2013 |
| WO | 2013086502 A1 | 6/2013 |
| WO | 2013158939 A1 | 10/2013 |
| WO | 2014151921 A1 | 9/2014 |
| WO | 2014210364 A2 | 12/2014 |
| WO | 2015006751 A1 | 1/2015 |
| WO | 2015013332 A1 | 1/2015 |
| WO | 2015138032 A2 | 9/2015 |
| WO | 2015138034 A2 | 9/2015 |
| WO | 2017136462 A2 | 8/2017 |

OTHER PUBLICATIONS

Attayek et al., "In vitro polarization of colonoids to create an intestinal stem cell compartment." PloS one 11(4)1-23 (2016).
Bale et al. "A novel low-volume two-chamber microfabricated platform for evaluating drug metabolism and toxicity." Technology 3(04):155-162 (2015).
Barry, R. A. et al. (2009) "Direct-Write Assem bl y of 3D Hydrogel Scaffolds for Guided Cell Growth," Advanced Materials 21(23), 2407-2410.
Basson, "Paradigms for mechanical signal transduction in the intestinal epithelium", Digestion 68(4):217-225 (2004).
Bischel, L. L. et al. (2012) "A Practical Method for Patterning Lumens through ECM Hydro gels via Viscous Finger Patterning," Journal of Laboratory Automation 17(2), 96-103.
Carvalho et al., "A three-dimensional tissue culture model for the study of attach and efface lesion formation by enteropathogenic and enterohaemorrhagic *Escherichia coli*", Cell. Microbiol. 7(12):1771-1781 (2005).
Chaturvedi et al., "Repetitive deformation activates focal adhesion kinase and ERK mitogenic signals in human Caco-2 intestinal epithelial cells through src and rac1", J. Biol. Chem. 282(1):14-28 (2006).
Chuah et al., "The Effects of Poly(dimethylsiloxane) Surface Silanization on Mesenchymal Stem Cell Fate", Biomaterials Science 3(2):383-390 (2015).
Cross et al. "Dense type I collagen matrices that support cellular remodeling and microfabrication for studies of tumor angiogenesis and vasculogenesis in vitro." Biomaterials 31(33): 8596-8607 (2010).
Dockray et al. "Gastrin: old hormone, new functions." Pflügers Archiv 449(4): 344-355 (2005).
Eveillard et al., "Identification and characterization of adhesive factors of Clostridium difficile involved in adhesion to human colonic enterocyte-like Caco-2 and mucus-secreting HT29 cells in culture", Molecular Microbiology 7(3):371-381 (1993).
Foulke-Abel et al. "Human enteroids as an ex-vivo model of host-pathogen interactions in the gastrointestinal tract." Experimental Biology and Medicine 239(9): 1124-1134 (2014).
Grajek and Olejnik, Polish Journal of Food and Nutrition Sciences, 13/54(1s):5-24 (2004). "Epithelial cell cultures in vitro as a model to study functional properties of food."
Hanson-Shepherd, J. N. et al. (2011) "3D Microperiodic Hydrogel Scaffolds for Robust Neuronal Cultures," Advanced Functional Materials 21(1), 47-54.
Huh et al. "Microengineered physiological biomimicry: Organs-on-Chips." Lab on a Chip 12(12): 2156-2164 (2012).
Huh et al., "Microfabrication of human organs-on-chips", Nature Protocols 8(11):2135-2157 (2013).
Huh et al., "Reconstituting Organ-Level Lung Functions on a Chip", Science 328:1662-1668 (2010).
Imura et al., "Micro Total Bioassay System for Ingested Substances: Assessment of Intestinal Absorption, Hepatic Metabolism, and Bioactivity", Anal. Chem. 82(24):9983-9988 (2010).
Miyoshi et al., "In vitro expansion and genetic modification of gastrointestinal stem cells in spheroid culture", Nature Protocols 8(12):2471-2482 (2013).
Murnin et al., "Effects of glutamine isomers on human (Caco-2) intestinal epithelial proliferation, strain-responsiveness, and differentiation", J. Gastrointest. Surg. 4(4):435-442 (2000).
Sato et al. "Long-term expansion of epithelial organoids from human colon, adenoma, adenocarcinoma, and Barrett's epithelium." Gastroenterology 141(5):1762-1772 (2011).
Sato et al., "Single Lgr5 stem cells build crypt-villus structures in vitro without a mesenchymal niche" Nature 459(7244):262-265 (2009).
Sun, L. et al. (2012) "Direct-Write Assembly of 3D Silk/Hydroxyapatite Scaffolds for Bone Co-Cultures," Advanced Healthcare Materials 1(6), 729-735.
Sung et al. "Microscale 3-D hydrogel scaffold for biomimetic gastrointestinal (GI) tract model." Lab on a Chip, Royal Society of Chemistry 11(3): 389-392 (2011).

(56) References Cited

OTHER PUBLICATIONS

Thangawng, A. L. et al. (2007) "An ultra-thin PDMS membrane as a bio/micro-nano interface: fabrication and characterization," Biomedical Microdevices 9(4), 587-595.
Vandussen et al. "Development of an enhanced human gastrointestinal epithelial culture system to facilitate patient-based assays." Gut 64(6):911-920 (2014).
Vu et al. "Cell migration on planar and three-dimensional matrices: a hydrogel-based perspective." Tissue Engineering Part B: Reviews 21.1 (2015): 67-74.
Whitesides, G. M. et al. (2001) "Soft Lithography in Biology and Biochemistry," Annual Review of Biomedical En?ineerin? 3(1), 335-373.
Womack et al., "Quantitative assessment of villous motility." Am. J. Physiol. 252(2 Pt 1):G250-256 (1987).
Wu, W. et al. (2011) "Omnidirectional Printing of 3D Microvascular Networks," Advanced Materials 23(24), HI78-HI 83.
Wu, W. et al. (2010) "Direct-write assembly of biomimetic microvascular networks for efficient fluid transport," Soft Matter 6(4), 739-742.
Yin et al., "Niche-independent high-purity cultures of Lgr5+ intestinal stem cells and their progeny", Nature Methods 11:106-112 (2014).
Zhang et al., "Regulation of the Intestinal epithelial response to cyclic strain by extracellular matrix proteins", FASEB J. 17(8):926-928 (2003).
Zietek et al., "Intestinal organoids for assessing nutrient transport, sensing and incretin secretion." Scientific Reports 5:16831 (2015).
Kamiguchi, N. et al. (2010) "A 96-Well Plate Assay for CYP4503A Induction Using Cryopreserved Human Hepatocytes," Dru? Metabolism and Disposition 38(11), 1912.

Kim et al., "Co-culture of epithelial cells and bacteria for investigating host-pathogen interactions", Lab Chip 10(1):43-50 (2010).
Kim et al., "Contributions of microbiome and mechanical deformation to intestinal bacterial overgrowth and inflammation in a human gut-on-a-chip." PNAS 113(1):E7-E15 (2016).
Kim et al., "Gut-on-a-Chip microenvironment induces human intestinal cells to undergo villus differentiation." Integrative Biology 5(9):1130-1140 (2013).
Kim et al., "Human gut-on-a-chip inhabited by microbial flora that experiences intestinal perstalsis-like motions and flow", Lab Chip 12(12):2165-2174 (2012).
Kim et al., "Microfluidic biomechanical device for compressive cell stimulation and lysis", Sensors and Actuators B: Chemical, 128:108-116 (2007).
Kimura et al., "An integrated microfluidic system for long-term perfusion culture and on-line monitoring of intestinal tissue models", Lab on a Chip 8(5):741-746 (2008).
Konkel et al., "Translocation of Campylobacter jejuni across Human Polarized Epithelial Cell Monolayer Cultures", The Oxford Journal of Infectious Diseases 166(2):308-315 (1992).
Lee et al., "The ability of *Salmonella* to enter mammalian cells is affected by bacterial growth state", Proc. Natl. Acad. Sci. USA 87(11):4304-4308 (1990).
Mahe et al. "Establishment of human epithelial enteroids and colonoids from whole tissue and biopsy." JoVE (Journal of Visualized Experiments) 97: e52483 pp. 1-13 (2015).
Mahler et al., "Characterization of a Gastrointestinal Tract Microscale Cell Culture Analog Used to Predict Drug Toxicity", Biotechnology and Bioengineering 104(1):193-205 (2009).

\* cited by examiner

Epithelium: E-cadherin        Endothelium: Actin / DAPI

METHODS RELATING TO INTESTINAL ORGAN-ON-A-CHIP

CROSS-REFERENCE TO RELATED APPLICATIONS

This application is a continuation under 35 U.S.C. § 120 of U.S. application Ser. No. 17/539,452 filed Dec. 1, 2021 now issued as U.S. Pat. No. 11,976,304 on May 7, 2024, which is a continuation under 35 U.S.C. § 120 of U.S. application Ser. No. 16/331,718 filed Mar. 8, 2019, which is a 35 U.S.C. § 371 National Phase Entry Application of International Application No. PCT/US2017/051296 filed Sep. 13, 2017, which designates the U.S. and claims benefit under 35 U.S.C. § 119(e) of U.S. Provisional Application No. 62/393,711 filed Sep. 13, 2016, the contents of which are incorporated herein by reference in their entireties.

GOVERNMENT SUPPORT

This invention was made with government support under Grant Nos. W911NF-12-2-0036 and W911 NF-16-C-0050 awarded by the Department of Defense and Grant No. HHSF223201310079C awarded by the Food and Drug Administration. The government has certain rights in the invention.

TECHNICAL FIELD

The technology described herein relates to relate to the culturing and maintaining of in vitro intestinal organoids and/or model systems.

BACKGROUND

Drug development continues to suffer from the use of animal models, which are costly, labor-intensive, time-consuming and ethically questionable. Of even greater concern is that animal models often do not predict results obtained in humans, and this is a particular problem when addressing challenges relating to metabolism, transport, and oral absorption of drugs and nutrients. For these reasons, there has been increasing interest in development of in vitro models of human intestinal function. However, to date, the systems and methods which can replicate actual intestinal tissue (e.g., supporting the formation of villi and/or multiple layers of the intestinal wall) and peristaltic activity have been limited by requiring the use of tumor cell line-derived intestinal epithelial cells, e.g., Caco-2 cells.

SUMMARY

Provided herein are methods and compositions that permit the use of primary intestinal epithelial cells, e.g., in organ-on-a-chip devices, to form co-cultures of intestinal epithelium and endothelium which support native intestinal structures and/or activities.

In one aspect of any of the embodiments, described herein is a method of providing an in vitro intestinal model system, the method comprising:
a. providing i) an intestinal enteroid or colonoid comprising primary intestinal epithelial cells, ii) a microfluidic culture device, the device comprising a porous membrane having first and second surfaces, said membrane in fluidic communication with a microchannel, said microchannel in fluidic communication with a source of fluid;
b. disrupting said intestinal enteroid or colonoid comprising primary intestinal epithelial cells into enteroid or colonoid fragments;
c. seeding said second surface of said porous membrane with said enteroid or colonoid fragments so as to create seeded primary intestinal epithelial cells;
d. expanding said seeded primary intestinal epithelial cells so as to create a monolayer of cells; and
e. differentiating said monolayer of cells so as to create two or more different differentiated intestinal cell types.

In some embodiments of any of the aspects, the method further comprises providing intestinal endothelial cells and/or fibroblasts; and establishing a culture of said intestinal endothelial cells and/or fibroblasts on said first surface of said porous membrane.

In one aspect of any of the embodiments, described herein is a method of providing an in vitro intestinal model system, the method comprising:
a. providing i) primary intestinal epithelial cells and ii) a microfluidic culture device, the device comprising a porous membrane having first and second surfaces, said membrane in fluidic communication with a microchannel, said microchannel in fluidic communication with a source of fluid;
b. seeding said second surface of said porous membrane with said primary intestinal epithelial cells so as to create seeded primary intestinal epithelial cells;
c. expanding said seeded primary intestinal epithelial cells so as to create a monolayer of cells, and
d. differentiating said monolayer of cells so as to create two or more different differentiated intestinal cell types.

In some embodiments of any of the aspects, the method further comprises providing intestinal endothelial cells and/or fibroblasts; and establishing a culture of said intestinal endothelial cells and/or fibroblasts on said first surface of said porous membrane.

In some embodiments of any of the aspects, said one or more monolayers is exposed to a cyclic stretching regimen of said membrane. In some embodiments of any of the aspects, said one or more monolayers is exposed to said fluid from said source of fluid. In some embodiments of any of the aspects, said epithelial monolayer is exposed to said fluid at a flow rate whereupon intestinal villi; folds; and/or an intact intestinal barrier form. In some embodiments of any of the aspects, said epithelial monolayer is exposed to both a cyclic stretching regimen of said membrane and fluid at a flow rate. In some embodiments of any of the aspects, said monolayer is exposed to said stretching and said flow rate for a period of days. In some embodiments of any of the aspects, said period of days comprises 11 days. In some embodiments of any of the aspects, said period of days comprises more than 10 days.

In one aspect of any of the embodiments, described herein is a method of providing an in vitro intestinal model system, the method comprising:
a. providing an intestinal microfluidic organ-on-a-chip culture device, the device comprising a porous membrane having a molecular coating that mediates cell adhesion;
b. disrupting an intestinal enteroid, colonoid, or organoid comprising intestinal epithelial cells into enteroid, colonoid, or organoid fragments comprising intestinal epithelial cells in the presence of a ROCK inhibitor;
c. establishing a culture of intestinal epithelial cells on a second surface of the porous membrane of the intestinal microfluidic organ-on-a-chip culture device by contacting the second surface with the enteroid, colonoid, or organoid fragments comprising intestinal epithelial cells resulting from step b; and
d. maintaining the culture of the intestinal epithelial cells in the intestinal microfluidic organ-on-a-chip culture device.

In some embodiments of any of the aspects, the method further comprises establishing a culture of intestinal endothelial cells and/or fibroblasts on a first surface of a porous membrane of an intestinal microfluidic organ-on-a-chip culture device; and maintaining the culture of the intestinal endothelial cells and/or fibroblasts and intestinal epithelial cells in the intestinal microfluidic organ-on-a-chip culture device. In one aspect of any of the embodiments, described herein is a method of providing an in vitro intestinal model system, the method comprising:
 a. providing an intestinal microfluidic organ-on-a-chip culture device, the device comprising a porous membrane;
 b. establishing a culture of intestinal epithelial cells on a second surface of the porous membrane of the intestinal microfluidic organ-on-a-chip culture device by contacting the surface with intestinal epithelial cells; and
 c. maintaining the culture of intestinal epithelial cells in the intestinal microfluidic organ-on-a-chip culture device.

In some embodiments of any of the aspects, the method further comprises establishing a culture of intestinal endothelial cells and/or fibroblasts on a first surface of the porous membrane of the intestinal microfluidic organ-on-a-chip culture device by contacting the surface with intestinal epithelial cells; and maintaining the culture of intestinal epithelial cells and intestinal endothelial cells and/or fibroblasts in the intestinal microfluidic organ-on-a-chip culture device.

In one aspect of any of the embodiments, described herein is a method of providing an in vitro intestinal model system, the method comprising:
 a. providing an intestinal microfluidic organ-on-a-chip culture device, the device comprising a porous membrane wherein said membrane comprises a first and a second surface;
 b. providing i) a sample of intestinal epithelial tissue, wherein said tissue comprises intestinal epithelial cells associated with intestinal crypts ii) one or more extra-cellular-matrix degrading enzymes and iii) a hydrogel;
 c. washing said sample of intestinal epithelial tissue;
 d. removing any associated muscle or mucosa layers from said tissue and then placing said tissue in solution;
 e. contacting said tissue with said one or more extracellular-matrix degrading enzymes, thereby releasing said intestinal crypts from said tissue into said solution;
 f. removing said intestinal crypt from said enzyme treated tissue solution then culturing said crypt in said hydrogel in the presence of Wnt3A, R-spondin, Noggin, and EGF to form an intestinal enteroid and/or colonoid;
 g. disrupting the intestinal enteroid and/or colonoid comprising intestinal epithelial cells into enteroid and/or colonoid fragments comprising intestinal epithelial cells in the presence of a ROCK inhibitor;
 h. establishing a culture of intestinal epithelial cells on a second surface of the porous membrane of the intestinal microfluidic organ-on-a-chip culture device by contacting the second surface with the enteroid and/or colonoid fragments comprising intestinal epithelial cells resulting from step g; and
 i. maintaining the culture of the intestinal epithelial cells in the intestinal microfluidic organ-on-a-chip culture device by providing culture medium under continuous flow.

In one aspect of any of the embodiments, described herein is a method of providing an in vitro intestinal model system, the method comprising:
 a. providing an intestinal microfluidic organ-on-a-chip culture device, the device comprising a porous membrane wherein said membrane comprises a first and a second surface;
 b. providing i) a sample of intestinal epithelial tissue, wherein said tissue comprises intestinal epithelial cells associated with intestinal crypts ii) one or more extra-cellular-matrix degrading enzymes and iii) a hydrogel;
 c. washing said sample of intestinal epithelial tissue;
 d. removing any associated muscle or mucosa layers from said tissue and then placing said tissue in solution;
 e. contacting said tissue with said one or more extracellular-matrix degrading enzymes, thereby releasing said intestinal crypts from said tissue into said solution;
 f. removing said intestinal crypt from said enzyme treated tissue solution then culturing said crypt in said hydrogel in the presence of Wnt3A, R-spondin, Noggin, and EGF to form an intestinal enteroid and/or colonoid;
 g. disrupting the intestinal enteroid and/or colonoid comprising intestinal epithelial cells into enteroid and/or colonoid fragments comprising intestinal epithelial cells in the presence of a ROCK inhibitor;
 h. establishing a culture of intestinal epithelial cells on a second surface of the porous membrane of the intestinal microfluidic organ-on-a-chip culture device by contacting the second surface with the enteroid and/or colonoid fragments comprising intestinal epithelial cells resulting from step g; and
 i. maintaining the culture of the intestinal epithelial cells in the intestinal microfluidic organ-on-a-chip culture device by providing culture medium under continuous flow for at least 12 days of culture.

In some embodiments of any of the aspects, the sample is obtained from a subject.

In one aspect of any of the embodiments, described herein is a method comprising:
 a. providing an intestinal microfluidic organ-on-a-chip culture device, the device comprising a porous membrane:
  i. having a molecular coating that mediates cell adhesion; and
  ii. wherein said membrane comprises a first and a second surface;
 b. providing an intestinal enteroid, colonoid, or organoid comprising intestinal epithelial cells;
 c. disrupting said intestinal enteroid, colonoid, or organoid comprising intestinal epithelial cells into enteroid, colonoid, or organoid fragments comprising intestinal epithelial cells in the presence of a ROCK inhibitor;
 d. establishing a culture of intestinal epithelial cells on a second surface of the porous membrane of the intestinal microfluidic organ-on-a-chip culture device by contacting the second surface with the enteroid, colonoid, or organoid fragments comprising intestinal epithelial cells resulting from step c; and
 e. maintaining the culture of the intestinal epithelial cells in the intestinal microfluidic organ-on-a-chip culture device, thereby forming an intact intestinal barrier;
 f. contacting the intestinal epithelial cells with bacterial cells of one or more species; and g. measuring the permeability of the intestinal barrier and/or translocation of the bacterial cells across the intestinal barrier.

In some embodiments of any of the aspects, the method further comprises establishing a culture of intestinal endothelial cells and/or fibroblasts on a first surface of a porous membrane of an intestinal microfluidic organ-on-a-chip culture device; and maintaining the culture of the intestinal endothelial cells and/or fibroblasts and intestinal epithelial cells in the intestinal microfluidic organ-on-a-chip culture device. In one aspect of any of the embodiments, described herein is a method comprising:
- a. providing an intestinal microfluidic organ-on-a-chip culture device, the device comprising a porous membrane:
  - i. having a molecular coating that mediates cell adhesion; and
  - ii. wherein said membrane comprises a first and a second surface;
- b. providing intestinal epithelial cells;
- c. establishing a culture of intestinal epithelial cells on a second surface of the porous membrane of the intestinal microfluidic organ-on-a-chip culture device by contacting the surface with said intestinal epithelial cells; and
- d. maintaining the culture of intestinal epithelial cells in the intestinal microfluidic organ-on-a-chip culture device, thereby forming an intact intestinal barrier;
- e. contacting the intestinal epithelial cells with bacterial cells of one or more species; and
- f. measuring the permeability of the intestinal barrier and/or translocation of the bacterial cells across the intestinal barrier.

In some embodiments, the method further comprises establishing a culture of intestinal endothelial cells and/or fibroblasts on a first surface of the porous membrane of the intestinal microfluidic organ-on-a-chip culture device by contacting the surface with intestinal epithelial cells; and maintaining the culture of intestinal epithelial cells and intestinal endothelial cells and/or fibroblasts in the intestinal microfluidic organ-on-a-chip culture device.

In some embodiments of any of the aspects, said different differentiated intestinal cell types comprise absorptive enterocytes, Paneth cells, goblet cells and enteroendocrine cells. In some embodiments of any of the aspects, at least one of said differentiated intestinal cell types exhibits digestive capacity. In some embodiments of any of the aspects, at least one of said differentiated intestinal cell types exhibits mucus secretion. In some embodiments of any of the aspects, the differentiated intestinal cells form a differentially permeable intestinal barrier. In some embodiments of any of the aspects, said different differentiated intestinal cell types are human cells.

In some embodiments of any of the aspects, the porous membrane has a molecular coating that mediates cell adhesion.

In some embodiments of any of the aspects, prior to establishing the culture of intestinal epithelial cells on a second surface of the porous membrane, the culture of intestinal endothelial cells and/or fibroblasts has been established on a first surface of the porous membrane. In some embodiments of any of the aspects, prior to establishing the culture of intestinal endothelial cells and/or fibroblasts on a first surface of the porous membrane, the culture of intestinal epithelial cells has been established on a second surface of the porous membrane. In some embodiments of any of the aspects, the culture of intestinal endothelial cells and/or fibroblasts is established on a first surface of the porous membrane concurrently with establishing the culture of intestinal epithelial cells on a second surface of the porous membrane.

In some embodiments of any of the aspects, contacting the surface with intestinal epithelial cells comprises contacting the surface with an intestinal enteroid, colonoid, or organoid comprising intestinal epithelial cells. In some embodiments of any of the aspects, the intestinal enteroid, colonoid, or organoid comprising intestinal epithelial cells is disrupted into enteroid, colonoid, or organoid fragments prior to establishing the culture of intestinal epithelial cells on the first surface of the porous membrane. In some embodiments of any of the aspects, disruption of the intestinal enteroid, colonoid, or organoid is performed in the presence of a ROCK inhibitor.

In some embodiments of any of the aspects, the method further comprises exposing the cells to an agent. In some embodiments of any of the aspects, said agent is a candidate intestinal effector agent. In some embodiments of any of the aspects, the method further comprises measuring the response of the cells to determine the effect of said candidate intestinal effector agent.

In some embodiments of any of the aspects, the molecular coating that mediates cell adhesion comprises a hydrogel. In some embodiments of any of the aspects, the molecular coating that mediates cell adhesion comprises an extracellular matrix hydrogel. In some embodiments of any of the aspects, the molecular coating that mediates cell adhesion comprises a basement membrane preparation. In some embodiments of any of the aspects, the molecular coating that mediates cell adhesion comprises at least one extracellular matrix molecule. In some embodiments of any of the aspects, the extracellular matrix molecule is selected from the group consisting of: laminin, heparan sulfate proteoglycan; fibronectin; collagen; type I collagen; and type IV collagen.

In some embodiments of any of the aspects, the porous membrane is activated for chemical cross-linking before being exposed to the molecular coating that mediates cell adhesion. In some embodiments of any of the aspects, the porous membrane comprises PDMS; polyester (PET); and/or polycarbonate. In some embodiments of any of the aspects, the method further comprises coating the porous membrane with the molecular coating that mediates cell adhesion by oxidizing the porous membrane; and contacting the porous membrane with the molecular coating that mediates cell adhesion. In some embodiments of any of the aspects, the method further comprises coating the porous membrane with the molecular coating that mediates cell adhesion by: oxidizing the porous membrane; functionalizing the porous membrane by silanization; and contacting the porous membrane with the molecular coating that mediates cell adhesion. In some embodiments of any of the aspects, oxidation of the porous membrane comprises exposing the porous membrane to oxygen plasma; plasma discharge; polyethylene glycol (PEG); polyvinyl alcohol (PVA); or a liquid oxidizer. In some embodiments of any of the aspects, silanization is performed using a silane selected from the group consisting of: aminosilane; (3-aminopropyl)triethoxy silane; sulfhydrylsilane; and epoxysilane. In some embodiments of any of the aspects, the functionalizing step further comprises treating the porous membrane with a cross-linker after silanization. In some embodiments of any of the aspects, the cross-linker is selected from the group consisting of: N-γ-maleimidobutyryloxy succinimide ester; DMA; DMS; glutaraldehyde (GA); carbodiimide (1-ethyl-3-(3-dimethyl aminopropyl)-carbodiimide (EDC)); epoxy compounds; six methylene diisocyanate, glycerin; alginate; genipin (GP); nordihydroguaiaretic acid (NDGA); tannic acid; and procyanidins (PC). In some embodiments of any of the aspects, the method further comprises coating the porous membrane with the molecular coating that mediates cell adhesion by: oxidizing the porous membrane; functionalizing the porous membrane by silanization; and contacting the porous membrane with the molecular coating that mediates cell adhesion.

In some embodiments of any of the aspects, establishing a culture of intestinal endothelial cells and/or fibroblasts on a first surface of a porous membrane of an intestinal culture fluidics device comprises culturing the cells under conditions suitable for them to form a monolayer on the porous membrane.

In some embodiments of any of the aspects, the intestinal endothelial cells and/or fibroblasts are mammalian intestinal endothelial cells and/or fibroblasts. In some embodiments of any of the aspects, the intestinal endothelial cells and/or fibroblasts are human intestinal endothelial cells and/or fibroblasts. In some embodiments of any of the aspects, the intestinal endothelial cells and/or fibroblasts are mouse intestinal endothelial cells and/or fibroblasts. In some embodiments of any of the aspects, the intestinal endothelial cells and/or fibroblasts are primary intestinal endothelial cells and/or fibroblasts. In some embodiments of any of the aspects, the intestinal endothelial cells and/or fibroblasts are obtained from a subject. In some embodiments of any of the aspects, the intestinal endothelial cells are small intestine endothelial cells or colon endothelial cells.

In some embodiments of any of the aspects, the intestinal enteroid, colonoid, or organoid is disrupted into enteroid fragments to provide groups of from about 2 to about 100 intestinal epithelial cells. In some embodiments of any of the aspects, the intestinal enteroid, colonoid, or organoid is disrupted into enteroid fragments to provide groups of from about 10 to about 30 intestinal epithelial cells. In some embodiments of any of the aspects, the intestinal enteroid, colonoid, or organoid is disrupted into enteroid fragments to provide fragments of from about 10 μm to about 500 μm in diameter. In some embodiments of any of the aspects, the intestinal enteroid, colonoid, or organoid is disrupted into enteroid fragments to provide fragments of from about 40 μm to about 100 μm in diameter.

In some embodiments of any of the aspects, the intestinal enteroid or colonoid is obtained from a subject. In some embodiments of any of the aspects, the intestinal enteroid or colonoid is obtained from a resected intestinal tissue or an endoscopic biopsy tissue. In some embodiments of any of the aspects, the enteroids or colonoids are derived from histologically normal duodenal, jejunal, and ileal endoscopic biopsies. In some embodiments of any of the aspects, the intestinal epithelial cells are obtained from induced pluripotent stem cells. In some embodiments of any of the aspects, the intestinal epithelial cells are mammalian intestinal epithelial cells. In some embodiments of any of the aspects, the intestinal epithelial cells are human intestinal epithelial cells. In some embodiments of any of the aspects, the intestinal epithelial cells are mouse intestinal epithelial cells. In some embodiments of any of the aspects, the intestinal epithelial cells are not tumor cell line-derived cells. In some embodiments of any of the aspects, the intestinal epithelial cells are small intestine epithelial cells or colon epithelial cells.

In some embodiments of any of the aspects, the intestinal enteroid or colonoid is obtained by: washing a resected intestinal tissue or an endoscopic biopsy tissue and removing any associated muscle or mucosa layers; contacting the tissue with one or more extracellular-matrix degrading enzymes; removing an intestinal crypt from the supernatant resulting from the contacting step; embedding the intestinal crypt in a hydrogel; and maintaining the intestinal crypt in the hydrogel to form an intestinal enteroids and/or colonoids.

In some embodiments of any of the aspects, the ROCK inhibitor is selected from the group consisting of: fasudil; Y27632; Y39983; Wf-536; SLx-2119; an azabenzimidazole-aminofurazan; DE-104; an olefin; an isoquinoline; an indazole; a pyridinealkene derivative; H-1152P; an ROKα inhibitor (BF); XD-4000; HMN-1152; a 4-(1-aminoalkyl)-N-(4-pyridyl)cyclohexane-carboxamide; rhostatin; BA-210; BA-207; BA-215; BA-285; BA-1037; Ki-23095; VAS-012; and a quinazoline.

In some embodiments of any of the aspects, a glycogen synthase kinase 3 (GSK-3) inhibitor is present during the disruption step.

In some embodiments of any of the aspects, the maintaining step comprises providing a flow of culture medium through each channel of the intestinal microfluidic organ-on-a-chip culture device (and/or past each surface of the membrane) at a volumetric flow rate of about 10 to about 5000 μl h$^{-1}$. In some embodiments of any of the aspects, the maintaining step comprises providing a flow of culture medium through each channel of the intestinal microfluidic organ-on-a-chip culture device (and/or past each surface of the membrane) at a volumetric flow rate of about 10 to about 500 μl h$^{-1}$. In some embodiments of any of the aspects, the maintaining step comprises providing a flow of culture medium through each channel of the intestinal microfluidic organ-on-a-chip culture device (and/or past each surface of the membrane) at a volumetric flow rate of about 60 μl h$^{-1}$.

In some embodiments of any of the aspects, the maintaining step comprises stretching the porous membrane at about 0-1 Hz with an about 0-20% mean cell strain. In some embodiments of any of the aspects, the maintaining step comprises stretching the porous membrane at about 0-1 Hz with an about 0-10% mean cell strain. In some embodiments of any of the aspects, the maintaining step comprises stretching the porous membrane at about 0.15 Hz with an about 10% mean cell strain.

In some embodiments of any of the aspects, the maintaining step comprises culturing the cells under continuous flow and stretching that mimics physical forces experienced by the cells present in the native intestine.

In some embodiments of any of the aspects, the maintaining step comprises providing the endothelial cells and/or fibroblasts with EGM2-MV medium. In some embodiments of any of the aspects, the maintaining step comprises providing the epithelial cells with expansion medium comprising one or more of the following: Wnt-3A; EGF; Rspo1; Noggin; gastrin; TGF-β receptor inhibitor; p38 MAPK inhibitor. In some embodiments of any of the aspects, the maintaining step comprises providing the epithelial cells with expansion medium comprising Wnt-3A; EGF; Rspo1; Noggin; gastrin; TGF-β receptor inhibitor; and p38 MAPK inhibitor. In some embodiments of any of the aspects, the maintaining step comprises providing i) the epithelial cells and/or ii) the intestinal endothelial cells and/or fibroblasts with expansion medium comprising one or more of the following: Wnt-3A; EGF; Rspo1; Noggin; gastrin; TGF-β receptor inhibitor; p38 MAPK inhibitor; Jagged (JAG) polypeptide and an inhibitor of GSK. In some embodiments of any of the aspects, the maintaining step comprises providing i) the epithelial cells and/or ii) the intestinal endothelial cells and/or fibroblasts with expansion medium comprising: Wnt-3A; EGF; Rspo1; Noggin; gastrin; TGF-β receptor inhibitor; p38 MAPK inhibitor; Jagged (JAG) polypeptide and an inhibitor of GSK.

In some embodiments of any of the aspects, the expansion medium further comprises nicotamide. In some embodiments of any of the aspects, the expansion medium further comprises a ROCK inhibitor for about 1 to about 7 days after introducing the epithelial cells to the intestinal microfluidic organ-on-a-chip culture device (and/or to a surface of the membrane). In some embodiments of any of the aspects, expansion medium further comprises a ROCK inhibitor for about 1 to about 4 days after introducing the epithelial cells to the intestinal microfluidic organ-on-a-chip culture device (and/or to a surface of the membrane). In some embodiments of any of the aspects, the expansion medium further comprises a ROCK inhibitor for about 2 days after introducing the epithelial cells to the intestinal microfluidic organ-on-a-chip culture device (and/or to a surface of the membrane).

In some embodiments of any of the aspects, the maintaining step comprises contacting at least the endothelial cells with a glycogen synthase kinase 3 (GSK-3) inhibitor for at least the first two days of the maintaining step. In some embodiments of any of the aspects, the expansion medium further comprises a GSK inhibitor for about 2 days after introducing the epithelial cells to the intestinal microfluidic organ-on-a-chip culture device (and/or to a surface of the membrane).

In some embodiments of any of the aspects, the maintaining step comprises morphological and functional differentiation of the intestinal epithelial cells in co-culture with the intestinal endothelial cells and/or fibroblasts. In some embodiments of any of the aspects, said differentiation of the intestinal epithelial cells comprises differentiation of the cells to at least two or more of: absorptive enterocytes, Paneth cells, goblet cells and enteroendocrine cells. In some embodiments of any of the aspects, at least one of said differentiated cells exhibits digestive capacity. In some embodiments of any of the aspects, at least one of said differentiated cells exhibits mucus secreting capacity. In some embodiments of any of the aspects, the epithelial cells exhibit polarized distribution of one or more ion transporters following the expansion and/or maintaining step. In some embodiments of any of the aspects, the one or more ion transporters are NHE3 and/or Na+/K+-ATPase. In some embodiments of any of the aspects, polarized distribution of NHE3 comprises higher concentrations of NHE3 at the brush border membrane of an epithelial cell as compared to other membranes of the epithelial cell; and/or polarized distribution of Na+/K+-ATPase comprises higher concentrations of Na+/K+-ATPase at the basolateral membrane of an epithelial cell as compared to other membranes of the epithelial cell. In some embodiments of any of the aspects, polarized distribution of NHE3 comprises NHE3 being detectable exclusively at the brush border membrane of an epithelial cell as compared to other membranes of the epithelial cell; and/or polarized distribution of Na+/K+-ATPase comprises Na+/K+-ATPase being detectable exclusively at the basolateral membrane of an epithelial cell as compared to other membranes of the epithelial cell.

In some embodiments of any of the aspects, the step of differentiating comprises providing a medium to the intestinal epithelial cells which: comprises an inhibitor of Notch signaling; and does not comprise Wnt-3A; nicotamide; and SB2001190. In some embodiments of any of the aspects, the inhibitor of Notch signaling is DAPT.

In some embodiments of any of the aspects, the method further comprises contacting the intestinal epithelial cells with bacterial cells of one or more species. In some embodiments of any of the aspects, the method further comprises co-culturing the epithelial cells and bacterial cells for at least 24 hours. In some embodiments of any of the aspects, the method further comprises co-culturing the epithelial cells and bacterial cells for at least 48 hours. In some embodiments of any of the aspects, the co-culture step further comprises: providing medium to the intestinal epithelial cells and bacterial cells at at least 60 µL/hr; or providing medium to the intestinal epithelial cells and bacterial cells at about 120 µL/hr. In some embodiments of any of the aspects, the co-culture step further comprises: providing medium to the intestinal epithelial cells and bacterial cells at at least 60 µL/hr; providing medium to the intestinal epithelial cells and bacterial cells at about 120 µL/hr; causing the membrane to strain along at least one axis at about 10% strain; and/or causing the membrane to strain along at least one axis at a frequency of about 0.2 Hz.

In some embodiments of any of the aspects, the method further comprises contacting the intestinal epithelial cells with at least one endotoxin. In some embodiments of any of the aspects, the endotoxin is lipopolysaccharide (LPS).

In one aspect of any of the embodiments, described herein is a method of providing an in vitro intestinal model system, the method comprising: providing i) an intestinal enteroid or colonoid comprising primary intestinal epithelial cells, ii) intestinal endothelial cells and/or fibroblasts, and iii) a microfluidic culture device, the device comprising a porous membrane having first and second surfaces, said membrane in fluidic communication with a microchannel, said microchannel in fluidic communication with a source of fluid; establishing a culture of said intestinal endothelial cells and/or fibroblasts on said first surface of said porous membrane; disrupting said intestinal enteroid or colonoid comprising primary intestinal epithelial cells into enteroid or colonoid fragments; seeding said second surface of said porous membrane with said enteroid or colonoid fragments so as to create seeded primary intestinal epithelial cells; expanding said seeded primary intestinal epithelial cells so as to create a monolayer of cells; and differentiating said monolayer of cells so as to create two or more different differentiated intestinal cell types. In one aspect of any of the embodiments, described herein is a method of providing an in vitro intestinal model system, the method comprising: providing i) primary intestinal epithelial cells, ii) intestinal endothelial cells and/or fibroblasts, and iii) a microfluidic culture device, the device comprising a porous membrane having first and second surfaces, said membrane in fluidic communication with a microchannel, said microchannel in fluidic communication with a source of fluid; establishing a culture of said intestinal endothelial cells and/or fibroblasts on said first surface of said porous membrane; seeding said second surface of said porous membrane with said primary intestinal epithelial cells so as to create seeded primary intestinal epithelial cells; expanding said seeded primary intestinal epithelial cells so as to create a monolayer of cells; and differentiating said monolayer of cells so as to create two or more different differentiated intestinal cell types. In some embodiments of any of the aspects, said monolayer is exposed to a cyclic stretching regimen of said membrane. In some embodiments of any of the aspects, said monolayer is exposed to said fluid from said source of fluid. In some embodiments of any of the aspects, said monolayer is exposed to said fluid at a flow rate whereupon intestinal villi form. In some embodiments of any of the aspects, said monolayer is exposed to both a cyclic stretching regimen of said membrane and fluid at a flow rate. In some embodiments of any of the aspects, said monolayer is exposed to said stretching and said flow rate for a period of days. In some embodiments of any of the aspects, said period of days comprises 11 days. In some embodiments of any of the aspects, said different differentiated intestinal cell types comprise absorptive enterocytes, Paneth cells, goblet cells and enteroendocrine cells. In some embodiments of any of the aspects, at least one of said differentiated intestinal cell types exhibits digestive capacity. In some embodiments of any of the aspects, said different differentiated intestinal cell types are human cells.

In one aspect of any of the embodiments, described herein is a method of providing an in vitro intestinal model system, the method comprising: a) providing an intestinal microfluidic organ-on-a-chip culture device, the device comprising a porous membrane having a molecular coating that mediates cell adhesion; b) establishing a culture of intestinal endothelial cells and/or fibroblasts on a first surface of a porous membrane of an intestinal microfluidic organ-on-a-chip culture device; c) disrupting an intestinal enteroid, colonoid, or organoid comprising intestinal epithelial cells into enteroid, colonoid, or organoid fragments comprising intestinal epithelial cells in the presence of a ROCK inhibitor; d) establishing a culture of intestinal epithelial cells on a second surface of the porous membrane of the intestinal microfluidic organ-on-a-chip culture device by contacting the second surface with the enteroid, colonoid, or organoid fragments comprising intestinal epithelial cells resulting from step c, and e) maintaining the culture of the intestinal endothelial cells and/or fibroblasts and intestinal epithelial cells in the intestinal microfluidic organ-on-a-chip culture device.

In one aspect of any of the embodiments, described herein is a method of providing an in vitro intestinal model system, the method comprising: providing an intestinal microfluidic organ-on-a-chip culture device, the device comprising a porous membrane; establishing a culture of intestinal epithelial cells on a first surface of the porous membrane of the intestinal microfluidic organ-on-a-chip culture device by contacting the surface with intestinal epithelial cells; and maintaining the culture of the intestinal endothelial cells and/or fibroblasts and intestinal epithelial cells in the intestinal microfluidic organ-on-a-chip culture device. In some embodiments of any of the aspects, the porous membrane has a molecular coating that mediates cell adhesion. In some embodiments of any of the aspects, prior to establishing the culture of intestinal epithelial cells on a first surface of the porous membrane, a culture of intestinal endothelial cells and/or fibroblasts has been established on a second surface of the porous membrane. In some embodiments of any of the aspects, contacting the surface with intestinal epithelial cells comprises contacting the surface with an intestinal enteroid, colonoid, or organoid comprising intestinal epithelial cells. In some embodiments of any of the aspects, the intestinal enteroid, colonoid, or organoid comprising intestinal epithelial cells is disrupted into enteroid, colonoid, or organoid fragments prior to establishing the culture of intestinal epithelial cells on the first surface of the porous membrane. In some embodiments of any of the aspects, the disruption of the intestinal enteroid, colonoid, or organoid is performed in the presence of a ROCK inhibitor.

In some embodiments of any of the aspects, the molecular coating that mediates cell adhesion comprises a hydrogel. In some embodiments of any of the aspects, the molecular coating that mediates cell adhesion comprises an extracellular matrix hydrogel. In some embodiments of any of the aspects, the molecular coating that mediates cell adhesion comprises a basement membrane preparation. In some embodiments of any of the aspects, the molecular coating that mediates cell adhesion comprises at least one extracellular matrix molecule. In some embodiments of any of the aspects, the extracellular matrix molecule is selected from the group consisting of: laminin, heparan sulfate proteoglycan; fibronectin; collagen; type I collagen; and type IV collagen. In some embodiments of any of the aspects, the porous membrane is activated for chemical cross-linking before being exposed to the molecular coating that mediates cell adhesion. In some embodiments of any of the aspects, the porous membrane comprises PDMS; polyester (PET); and/or polycarbonate. In some embodiments of any of the aspects, the method further comprises coating the porous membrane with the molecular coating that mediates cell adhesion by: oxidizing the porous membrane; and contacting the porous membrane with the molecular coating that mediates cell adhesion. In some embodiments of any of the aspects, the method further comprises coating the porous membrane with the molecular coating that mediates cell adhesion by: oxidizing the porous membrane; functionalizing the porous membrane by silanization; and contacting the porous membrane with the molecular coating that mediates cell adhesion. In some embodiments of any of the aspects, oxidation of the porous membrane comprises exposing the porous membrane to oxygen plasma; plasma discharge; polyethylene glycol (PEG); polyvinyl alcohol (PVA); or a liquid oxidizer. In some embodiments of any of the aspects, the silanization is performed using a silane selected from the group consisting of: aminosilane; (3-aminopropyl)triethoxy silane; sulfhydrylsilane; and epoxysilane. In some embodiments of any of the aspects, the functionalizing step further comprises treating the porous membrane with a cross-linker after silanization. In some embodiments of any of the aspects, the cross-linker is selected from the group consisting of: N-γ-maleimidobutyryloxy succinimide ester; DMA; DMS; glutaraldehyde (GA); carbodiimide (1-ethyl-3-(3-dimethyl aminopropyl)-carbodiimide (EDC)); epoxy compounds; six methylene diisocyanate, glycerin; alginate; genipin (GP); nordihydroguaiaretic acid (NDGA); tannic acid; and procyanidins (PC). In some embodiments of any of the aspects, the method further comprises coating the porous membrane with the molecular coating that mediates cell adhesion by: oxidizing the porous membrane; functionalizing the porous membrane by silanization; and contacting the porous membrane with the molecular coating that mediates cell adhesion.

In some embodiments of any of the aspects, establishing a culture of intestinal endothelial cells and/or fibroblasts on a first surface of a porous membrane of an intestinal culture fluidics device comprises culturing the cells under conditions suitable for them to form a monolayer on the porous membrane. In some embodiments of any of the aspects, the intestinal endothelial cells and/or fibroblasts are mammalian intestinal endothelial cells and/or fibroblasts. In some embodiments of any of the aspects, the intestinal endothelial cells and/or fibroblasts are human intestinal endothelial cells and/or fibroblasts. In some embodiments of any of the aspects, the intestinal endothelial cells and/or fibroblasts are primary intestinal endothelial cells and/or fibroblasts. In some embodiments of any of the aspects, the intestinal endothelial cells and/or fibroblasts are obtained from a subject.

In some embodiments of any of the aspects, the intestinal enteroid, colonoid, or organoid is disrupted into enteroid, colonoid, or organoid fragments to provide groups of from about 1 to about 100 intestinal epithelial cells. In some embodiments of any of the aspects, the intestinal enteroid, colonoid, or organoid is disrupted into enteroid, colonoid, or organoid fragments to provide groups of from about 2 to about 100 intestinal epithelial cells. In some embodiments of any of the aspects, the intestinal enteroid, colonoid, or organoid is disrupted into enteroid, colonoid, or organoid fragments to provide groups of from about 10 to about 30 intestinal epithelial cells. In some embodiments of any of the aspects, the intestinal enteroid, colonoid, or organoid is disrupted into enteroid, colonoid, or organoid fragments to provide fragments of from about 10 µm to about 500 µm in diameter. In some embodiments of any of the aspects, the intestinal enteroid, colonoid, or organoid is disrupted into enteroid or colonoid fragments to provide fragments of from about 40 µm to about 100 µm in diameter. In some embodiments of any of the aspects, the intestinal enteroid or colonoid is obtained from a subject. In some embodiments of any of the aspects, the intestinal enteroid or colonoid is obtained from a resected intestinal tissue or an endoscopic biopsy tissue. In some embodiments of any of the aspects, the intestinal epithelial cells are mammalian intestinal epithelial cells. In some embodiments of any of the aspects, the intestinal epithelial cells are human intestinal epithelial cells. In some embodiments of any of the aspects, the intestinal epithelial cells are not tumor cell line-derived cells. In some embodiments of any of the aspects, the intestinal enteroid or colonoid is obtained by: washing a resected intestinal tissue or an endoscopic biopsy tissue and removing any associated muscle or mucosa layers; contacting the tissue with one or more extracellular-matrix degrading enzymes; removing an intestinal crypt from the supernatant resulting from the contacting step; embedding the intestinal crypt in a hydrogel; and maintaining the intestinal crypt in the hydrogel to form an intestinal enteroid or colonoids.

In some embodiments of any of the aspects, the ROCK inhibitor is selected from the group consisting of: fasudil; Y27632; Y39983; Wf-536; SLx-2119; an azabenzimidazole-aminofurazan; DE-104; an olefin; an isoquinoline; an indazole; a pyridinealkene derivative; H-1152P; an ROKα inhibitor (BF); XD-4000; HMN-1152; a 4-(1-aminoalkyl)-N-(4-pyridyl)cyclohexane-carboxamide; rhostatin; BA-210; BA-207; BA-215; BA-285; BA-1037; Ki-23095; VAS-012; and a quinazoline.

In some embodiments of any of the aspects, a glycogen synthase kinase 3 (GSK-3) inhibitor is present during the disruption step.

In some embodiments of any of the aspects, the maintaining step comprises providing a flow of culture medium through each channel of the intestinal microfluidic organ-on-a-chip culture device at a volumetric flow rate of about 10 to about 5000 µl h$^{-1}$. In some embodiments of any of the aspects, the maintaining step comprises providing a flow of culture medium through each channel of the intestinal microfluidic organ-on-a-chip culture device at a volumetric flow rate of about 10 to about 500 µl h$^{-1}$. In some embodiments of any of the aspects, the maintaining step comprises providing a flow of culture medium through each channel of the intestinal microfluidic organ-on-a-chip culture device at a volumetric flow rate of about 60 µl h$^{-1}$. In some embodiments of any of the aspects, the maintaining step comprises stretching the porous membrane at about 0-1 Hz with an about 0-20% mean cell strain. In some embodiments of any of the aspects, the maintaining step comprises stretching the porous membrane at about 0.15 Hz with an about 10% mean cell strain.

In some embodiments of any of the aspects, the maintaining step comprises providing the endothelial cells and/or fibroblasts with EGM2-MV medium. In some embodiments of any of the aspects, the maintaining step comprises providing the epithelial cells with expansion medium comprising one or more of the following: Wnt-3A; EGF; Rspo1; Noggin; gastrin; TGF-β receptor inhibitor; p38 MAPK inhibitor. In some embodiments of any of the aspects, the maintaining step comprises providing the epithelial cells with expansion medium comprising Wnt-3A; EGF; Rspo1; Noggin; gastrin; TGF-β receptor inhibitor; and p38 MAPK inhibitor. In some embodiments of any of the aspects, the expansion medium further comprises nicotamide. In some embodiments of any of the aspects, the expansion medium further comprises a ROCK inhibitor for about 1 to about 4 days after introducing the epithelial cells to the intestinal microfluidic organ-on-a-chip culture device. In some embodiments of any of the aspects, the expansion medium further comprises a ROCK inhibitor for about 2 days after introducing the epithelial cells to the intestinal microfluidic organ-on-a-chip culture device.

In some embodiments of any of the aspects, the maintaining step comprises morphological and functional differentiation of the intestinal epithelial cells in co-culture with the intestinal endothelial cells and/or fibroblasts. In some embodiments of any of the aspects, differentiation of the intestinal epithelial cells comprises differentiation of the cells to at least two or more of: absorptive enterocytes, Paneth cells, goblet cells and enteroendocrine cells. In some embodiments of any of the aspects, at least one of said differentiated cells exhibits digestive capacity.

The methods and compositions described herein relate to, e.g., small intestine-chips established from duodenal biopsies which exhibited the characteristics more typical of gastric epithelium, where a more prominent Muc5AC staining can be observed the apical surface of differentiated epithelium. Moreover the presence of gel-forming mucin 2 secreted into the apical effluents of chips (obtained from enteroids fragments derived from 3 different patients) was detected. The total Muc 2 concentration was 10-fold higher than that measured in a previously described gut-on-a-chip that is lined by the established Caco-2 intestinal cell line. Additionally, methods and compositions described herein relating to small intestine epithelial cells relate to the formation of villi in such embodiments. Immunofluorescence staining of the engineered intestinal villi for Ki67 and mucin 5AC (MUC5AC) confirmed that the proliferative Ki67-positive cells were limited to regions at the base of the villi (FIG. 18C) whereas mucin producing cells were present primarily along their apical regions (FIG. 18D), much as is observed in living intestinal villi. Computerized image analysis of these cross-sectional immunofluorescence views revealed that the maximum villus height was approximately 250 µm in these studies.

The methods and compositions described herein, e.g., in embodiments relating to both intestinal epithelium and endothelium exhibit a much greater barrier to the transfer of both sized dyes than chips lined by endothelium alone, and the growth and maturation of these microfluidic cultures is associated with parallel increases in barrier function from 2 to 12 days of culture (FIG. 5A). Interestingly, the optimal level of apparent permeability in the compositions described herein is reached by 4 days when using a 40 KDa fluorescent dextran as a probe, and by 6 days when the much smaller (450 Da) Lucifer yellow dye is utilized. This barrier is at least 10 times more restrictive than the barrier generated by the endothelium alone (FIG. 5A), highlighting the importance of a tissue-tissue interface for the functional separation of the gut lumen and the vascular compartment.

BRIEF DESCRIPTION OF THE DRAWINGS

FIG. 1C depicts a phase contrast micrograph showing villi formed by primary duodenal epithelial cells grown on-chip for 12 days (bar, 100 µm). FIG. 1D depicts a confocal immunofluorescence image of similar intestinal villi stained for F-actin and nuclei (bar, 50 µm). Vertical (FIG. 1E) and horizontal (FIG. 1F-1G) cross-sections of confocal immunofluorescence images depict epithelial junction proteins (E-cadherin) and endothelium (VE-cadherin)(bar, 100 µm). FIG. 1H depicts confocal immunofluorescence images representing the presence of 4 different small intestinal cell types: goblet cells (Muc5AC), paneth cells (Lysozyme), enteroendocrine cells (Chromogranin A) and enterocytes (Villin) (bar, 50 µm).

FIG. 2A depicts a photograph of the optically clear, human small intestine-on-chip microdevice with two microchannel systems and two hollow vacuum microchambers alongside (the channels were better visualized by filling them with colored dye). FIG. 2B depicts a schematic cross-sectional view (top) and a phase contrast micrograph of the chip viewed from above (bottom) showing the upper (epithelial) and lower (microvascular) cell culture microchannels separated by a porous, ECM-coated, PDMS membrane sandwiched in-between. The membrane is elastic and can be extended and retracted by the application of cyclic vacuum to the hollow side chambers. This actuation causes outward deflection of the vertical side walls and lateral extension of the attached horizontal, porous elastic membrane, which induces mechanical deformation of the adherent tissue layers cultured in the central channels. FIG. 2C depicts a schematic representation of the step-by-step procedure involved in the establishment of microfluidic co-cultures of primary human intestinal epithelium and intestinal microvascular endothelium in the small intestine-on-chip (see PROCEDURES in Example 2 for details).

FIG. 3A depicts a comparison of the efficiency of intestinal epithelial cell monolayer formation and development of villi-like structures between organ-on-a-chip devices initially seeded with isolated primary epithelial cells or enteroid or colonoid fragments in the presence or absence of human intestinal microvascular endothelial cells (HIMECs), and then were maintained for 1 or 12 days under continuous fluid flow. White areas delineate empty spaces where initially plated cells detached from the membrane when flow was initiated; dark areas represent patches of attached cells. Note that within 12 days of culture intestinal villi-like structures form only in the presence of HIMECs (bar, 100 µm). FIG. 3B depicts a graph showing maturation of the intestinal barrier function on chips cultured under the same conditions: 8 days of growth in expansion medium (2-8 days) followed by 4 days of differentiation (8-12 d), measured by quantifying permeability of fluorescent Lucifer yellow. Note that the epithelium develops a much higher barrier resistance much more quickly when HIMECs are present. FIG. 3C depicts representative differential interference contrast images of the primary intestinal epithelium cultured on chip with HIMECs for 4, 6 or 12 days under continuous flow compared to 12 days in the absence of flow (note that intestinal villi formation only occurred in the presence of flow (bar, 100 µm).

FIG. 4A depicts phase contrast (left) and confocal fluorescence (right) micrographs of human primary intestinal epithelium cultured in a microfluidic device under peristalsis-like motions and flow for 12 days. The dark edges of the villi-like structures visible at the left correspond precisely to regions where the continuous brush border of the apical membranes of adjacent epithelial villus protrusion juxtapose in close proximity, as visualized by labeling of the brush border by staining for F-actin and for nuclei with DAPI; of the bar, 50 µm. FIG. 4B depicts high magnification SEMs of the apical surface of the villus epithelium cultured on-chip showing a Goblet cell (left) and absorptive enterocytes (right) with apical microvilli (magnified in the inset), bar, 10 µm. FIG. 4C depicts immunofluorescence microscopic views of the intestinal epithelium cultured on-chip viewed from above (left) and in cross-section (right) showing polarized orientation of Na+/H+ exchanger 3 (NHE3), which localizes to the apical membrane and Na+/K+ ATPase at the basolateral membrane (bar, 50 µm). FIG. 4D depicts confocal immunofluorescence micrographs showing the presence of apical intact tight junctions in the intestinal epithelium and underlying endothelium labeled with ZO-1 as well as adherens junctions labeled for E-cadherin and VE-cadherin. (bar, 50 µm).

FIG. 5A depicts a comparison of barrier function measured in the intact small intestine-on-chip with epithelium and endothelium versus chips lined by endothelium alone by measuring paracellular passage of 450 Da Lucifer Yellow and 40 kDa Texas Red Dextran over 2 to 12 days of culture (12 days in EGM-2-MV for endothelium-on-a-chip and 8 days in EM, followed by 4 days in DM for small intestine-on-chip). Data are presented as mean±standard deviation (SD; n=6). FIG. 5B depicts a comparison of intestinal epithelial cell sucrase activity in the small intestine-on-chip showing that specific enzyme activity increases from 4 to 12 days of culture as the cells increase their level of villus differentiation. Data are presented as means f SD (n=6; *P<0.005). FIG. 5C depicts a graph showing the fold change in the levels of transcripts from epithelial cells cultured in the small intestine-on-chip and assessed at the day 4 of differentiation (grown for 8 days in EM and additional 4 days in DM) relative to the transcript levels in the undifferentiated state assessed at the day 8 of growth in EM medium Genes analyzed include sucrase isomaltose (SI) and alkaline phosphatase (ALPI) that are specific for absorptive enterocytes; mucin 2 (MUC2) and mucin 5AC (MUC5AC) for goblet cells; chromogranin A (CHGA) and synaptophysin (SYP) for enteroendocrine cells; lysozyme (LYZ) for Paneth cells; and leucine-rich-repeat-containing G-protein-coupled receptor 5 (LGR5) and polycomb complex protein BMI-1 (BMI1) for stem cells (Error bars indicate standard error of the mean; n=6). FIG. 5D depicts a schematic representation of the crypt-villus unit in the mature human small intestine (left) and confocal immunofluorescence cross-sectional views of the human intestinal epithelium cultured on-chip. Proliferative and Paneth cells reside in the crypts, while differentiated cells occupy the villus-like structures in vivo, and vertical cross-sections of the differentiated epithelium stained for lysozyme (Lyz), mucin 5AC (Muc5AC), chromogranin A (ChgA) and villin revealed a similar distribution pattern (bar, 50 µm). FIG. 5E depicts a comparison of Muc2 levels in the apical secretions collected in the effluent from the epithelial channel of the small intestine-on-chip generated from enteroids derived from 3 different donors versus that measured in effluents of a gut-on-a-chip lined with the established Caco-2 human intestinal epithelial cell line.

FIG. 17A depicts a schematic cross-sectional view (top) and a phase contrast micrograph of the chip viewed from above (bottom) showing the upper (epithelial) and lower (microvascular) cell culture microchannels separated by a porous, ECM-coated, PDMS membrane sandwiched in-between. The membrane is elastic and can be extended and retracted by the application of cyclic vacuum to the hollow side chambers. This actuation causes outward deflection of the vertical side walls and lateral extension of the attached horizontal, porous elastic membrane, which induces mechanical deformation of the adherent tissue layers cultured in the central channels. FIG. 17B depicts a schematic representation of the step-by-step procedure involved in the establishment of microfluidic co-cultures of primary human intestinal epithelium and intestinal microvascular endothelium in the Small Intestine-Chip.

FIG. 18A depicts microscopic views showing the villus morphology of the primary intestinal epithelium cultured for 12 days in the Small Intestine Chip with under continuous flow (60 ml hr$^{-1}$), when viewed from above by DIC imaging (bar, 100 µm). FIG. 18B depicts representative 3D confocal immunofluorescence micrographic reconstruction of the human villus intestinal epithelium formed inside the Small Intestine Chip. (F-actin; DAPI-stained nuclei; bar, 200 µm). FIG. 18C depicts representative vertical cross sectional, confocal, micrographic views through the intestinal epithelium-membrane interface of the Small Intestine Chip, when immunostained for F-actin and Ki67. FIG. 18D depicts representative vertical cross sectional, confocal, micrographic views through the intestinal epithelium-membrane interface of the Small Intestine Chip when immunostained for F-actin and MUC5AC, and nuclei with DAPI (in FIGS. 18C and 18D, white dashed lines indicate upper surfaces of the porous matrix-coated membrane; bars, 50 µm).

FIG. 19A depicts a schematic cross-sectional representation of the 3D intestinal epithelial tissue architecture developed on chip (top) and confocal immunofluorescence micrographs (bottom) showing vertical cross-sections of the differentiated epithelium in Intestine-Chip stained for lysozyme (Lyz), mucin 2 (Muc2), chromogranin A (ChgA) and villin. Cell nuclei were counterstained with DAPI (bar, 50 µm). FIG. 19B depicts a graph showing the fold change in the levels of transcripts from epithelial cells cultured in the Small Intestine Chip and assessed at day 12 relative to the transcript levels in the undifferentiated state assessed at the day 8 (culture medium was switched from EM to DM on day 8). Genes analyzed include sucrase isomaltose (SI) and alkaline phosphatase (ALPI) that are specific for absorptive enterocytes: mucin 2 (MUC2) and mucin 5AC (MUC5AC) for goblet cells; chromogranin A (CHGA) and synaptophysin (SYP) for enteroendocrine cells; lysozyme (LYZ) for Paneth cells; and leucine-rich-repeat-containing G-protein-coupled receptor 5 (LGR5) and polycomb complex protein BMI-1 (BMI1) for stem cells (Error bars indicate S.E.M.; n=9).

FIG. 21A depicts a comparison of barrier function measured in the intact Small Intestine Chips lined with epithelium derived from 3 different patients and HIMECs versus chips lined by endothelium only by measuring paracellular passage of 450 Da Lucifer Yellow over 2 to 12 days of culture. Data are presented as mean±standard deviation (SD; n=9). FIG. 21B depicts a comparison of intestinal epithelial cell sucrase isomaltose activity in the Small Intestine Chip and Caco-2 Gut Chip showing that specific enzyme activity increases in both from 4 to 12 days of culture as the cells differentiate into mature absorptive enterocytes. The increased concentration of glucose in the chip effluents results from the hydrolysis of 30 mM sucrose (added into the apical channel) to glucose and fructose, that does not occur when 30 mM control mannitol is used instead of sucrose. Data are presented as means t SEM (n=9; ***P<0.001). FIG. 21C depicts a comparison of MUC2 levels in the apical secretions collected in the effluent from the epithelial channel of the Small Intestine Chip generated from enteroids derived from 3 different donors versus that measured in effluents of a human Caco-2 cell line-based Gut Chip at day 12. FIG. 21D depicts maximum projection confocal images showing greater colonization of the primary Small Intestine Chip by pathogenic GFP-labeled *E. coli* 41949 (bottom) than non-pathogenic GFP-labeled *E. coli* K12 (top) after 24 hours of co-culture on-chip with the primary intestinal epithelium (nuclear DAPI staining, bar, 50 μm). FIG. 21E depicts kinetics of intestinal barrier disruption in Intestine Chips infected with sepsis-associated *E. coli* 41949 versus the non-pathogenic *E. coli* K12 strain or control uninfected Chips (No Bacteria). *E. coli* strains were added to the apical channel (intestinal lumen) of Intestine Chip and paracellular passage of fluorescent tracer (Cascade Blue hydrazide) from the apical to basolateral channel was measured at 3, 6, 12 and 24 hours post infection (n=3). FIG. 21F depicts increased bacterial translocation in Intestine Chips infected with *E. coli* 41949 in respect to *E. coli* K12 strain or No Bacteria control. Basal media effluents were sampled at 3, 6, 12 and 24 hours post infection and plated for CFU counts. FIG. 21G depicts increased release of immunomodulatory sepsis biomarkers, IL-6, IL-8, IL-10 and Fractalkine (FKN) into the vascular compartment of Intestine Chip in response to 6 hours infection with *E. coli* 41949 versus the non-pathogenic *E. coli* K12 or baseline release in uninfected control (No Bacteria). All data are expressed as means±SEM, *P<0.05, P<0.01, *P<0.001 by ANOVA.

FIG. 22A depicts H&E staining of human colon sections (6 μm). Colon tissue with intact epithelium, lamina propria, muscularis mucosa and submucosa (left). Dissociated epithelium including lamina propria (middle). Smear of a 2 day colonoid in matrigel culture (right). The arrows are marking mitotically active epithelial cells. The arrow head is indicating an intraepithelial lymphocyte. FIG. 22 B depicts primary human colonic epithelium in matrigel cultures. Colonic crypts embedded in matrigel after isolation from human colon resection (left). Shortening of crypt structure embedded in matrigel one day after isolation (middle). Closed colonic crypts (colonoids) in matrigel cultures 7 days after isolation (right).

FIG. 23A depicts immunofluorescence microscopic top views of the human primary colon epithelium and endothelium cultured on-chip under flow in undifferentiated condition for 14 days viewed from above. E-cadherin positive cells in the apical channel indicate the presence a monolayer of epithelial cells (left) (bar, 30 μm). Human intestinal microvasculature endothelial cells (HIMEC) in the basal channel stained for F-actin (gray) and nuclei staining with DAPI (right) (bar, 50 μm). FIG. 23B demonstrates barrier function measured in the colon-on-a-chip with epithelium specific for colon and primary intestinal endothelium by measuring paracellular passage of 450 Da Lucifer Yellow and 40 kDa Texas Red Dextran up to 14 days of undifferentiated culture and 4 days of differentiated culture. Data are presented as mean±standard deviation (SD; n=4 for undifferentiated and n=2 for differentiated). FIG. 23C depicts comparison of barrier function measured in the colon-on-a-chip with epithelium specific for colon and endothelium versus small intestine-on-a-chip with epithelium specific for small intestine and endothelium versus chips lined by endothelium alone by measuring paracellular passage of 450 Da Lucifer Yellow and 40 kDa Texas Red Dextran over 4 to 8 days of undifferentiated culture. Data are presented as mean t standard deviation (SD; n=4, n=3 for endothelium-on-a-chip). FIG. 23D depicts immunofluorescence microscopic top views of the human primary colon-on-a-chip epithelium showing goblet cell marker mucin2 in magenta and ZO1 immunostaining in green. (bar, 10 μm). FIG. 23E depicts 3D confocal immunofluorescence micrographic reconstruction of the human colon-on-a-chip (bar, 100 μum). FIG. 23F depicts immunofluorescence microscopic top views of the human primary colon epithelium brush border stained for F-actin (bar, 50 μm).

FIG. 24A depicts representative phase contrast images of the primary intestinal epithelium cultured on chip for 1, 8 or 28 days under continuous flow in expansion media on basal side and HBSS apically. FIG. 24B depicts representative differential interference contrast images of the primary intestinal epithelium cultured on chip 27 days under continuous flow in expansion media on basal side and HBSS apically (bar, 50 μm). FIG. 24C depicts a graph of barrier function measured in the colon-on-a-chip with epithelium specific for colon by measuring paracellular passage of 550 Da Cascade Blue up to 14 days of undifferentiated culture. Data are presented as mean f standard deviation (SD; n=3-11). FIG. 24D depicts immunofluorescence microscopic cross section view (top) and 3D reconstruction (bottom) of the human primary colon-on-a-chip epithelium showing goblet cell marker mucin2 and nuclei stained with Hoechst. (bar, 50 μm). FIG. 24E depicts visualization of mucus layer on colon-on-a-chip. 3D reconstruction of a confocal z-stack image with cells stained with calcein AM in yellow and 1 um diameter fluorescent beads in magenta at 28 days of culture. Fluorescent beads were perfused into the apical channel and left in static for 40 min up to 72 h before performing live confocal microscopy. Non penetrable mucus layer ranged from 50-200 μm between different chips (bar, 100 μm).

DETAILED DESCRIPTION

Figures 1A, 1B, 1C, 1D, 1E, 1F, 1G, 1H:
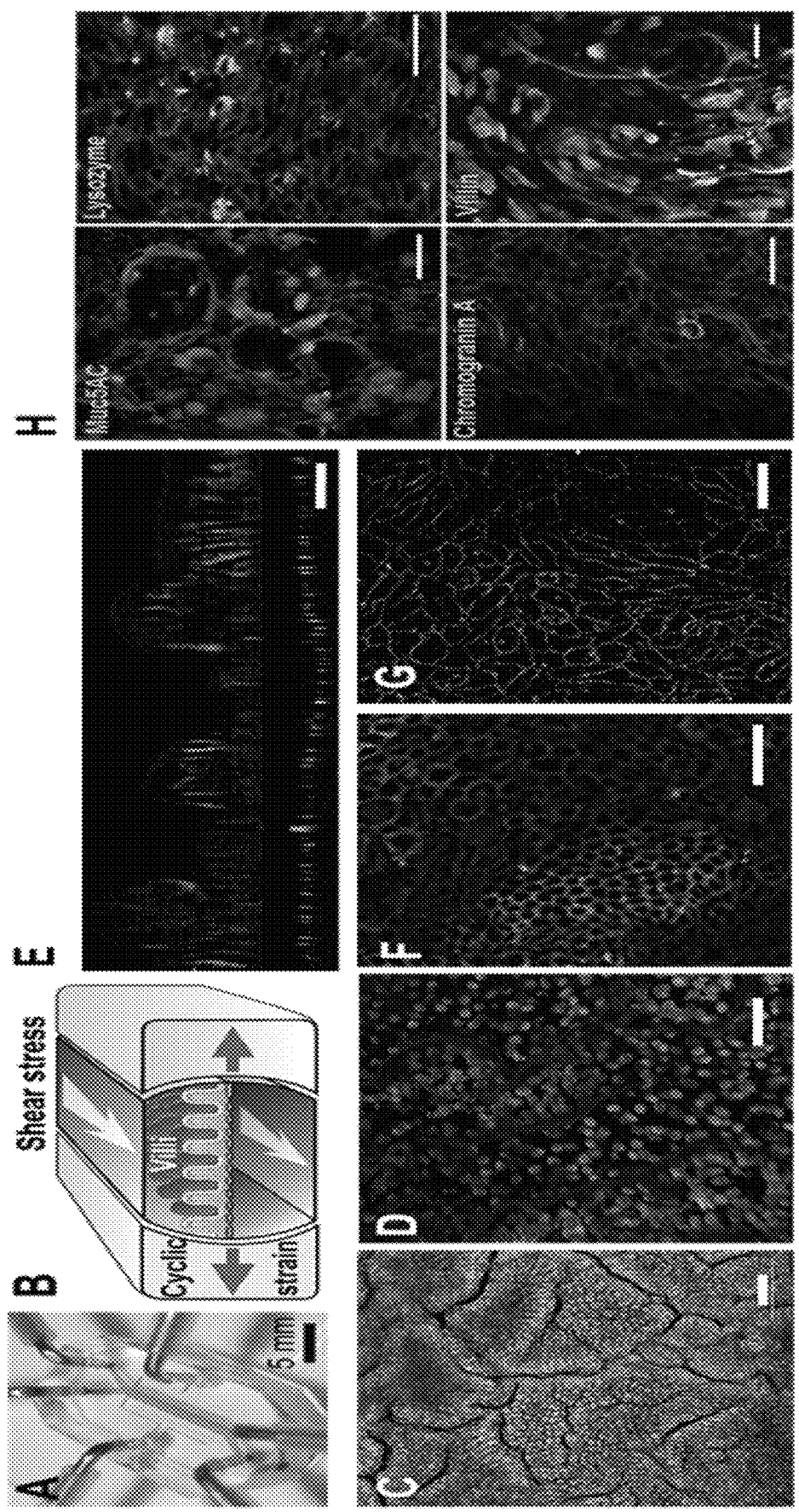
FIGS. 1A-1H depict exemplary embodiments of the human Primary Gut-on-a-Chip. Photograph (FIG. 1A) and schematic (FIG. 1B) of a 3D cross-section of an exemplary embodiment of the Gut-on-chip microfluidic device.

The methods and compositions described herein permit the in vitro culture of primary intestinal epithelial cells, particularly in the context of an organ-on-a-chip device that supports the development of native intestinal structures such as villi different cell type layers, and/or peristalic motion. Previously described methods were limited to the use of tumor-derived epithelial cells. The advance in cell culture technology described herein relies upon 4 different innovations, namely, 1) establishing a culture of intestinal endothelial cells and/or fibroblasts within the culture device before seeding the epithelial cells, 2) coating/activating the culture device as described herein, 3) use of appropriately-sized intestinal enteroid fragments as a source of intestinal epithelial cells, and 4) the presence of ROCK inhibitor during the fragmentation of the intestinal enteroid or colonoids. Each of these factors can individually promote the successful culture of primary intestinal epithelial cells.

Accordingly, in one aspect of any of the embodiments, described herein is a method of providing an in vitro intestinal model system, the method comprising: 1) providing an intestinal fluidic organ-on-a-chip culture device, the device comprising a porous membrane having a molecular coating that mediates cell adhesion; 2) establishing a culture of intestinal endothelial and/or fibroblast cells on a first surface of the porous membrane of an intestinal fluidic organ-on-a-chip culture device; 3) disrupting an intestinal enteroid, colonoid, or organoid comprising intestinal epithelial cells into enteroid, colonoid, or organoid fragments comprising intestinal epithelial cells in the presence of a ROCK inhibitor; 4) establishing a culture of intestinal epithelial cells on a second surface of the porous membrane of the intestinal fluidic organ-on-a-chip culture device by contacting the second surface with the enteroid, colonoid, or organoid fragments comprising intestinal epithelial cells resulting from the disruption step; and 5) maintaining the culture of the intestinal endothelial cells and/or fibroblasts and intestinal epithelial cells in the intestinal fluidic organ-on-a-chip culture device. In some embodiments of any of the aspects, the intestinal fluidic organ-on-a-chip culture device can be an intestinal microfluidic organ-on-a-chip culture device.

Each of the four innovative factors identified above herein can be used individually or in combination with 1, 2 or 3 of the other factors in any possible combination to provide an in vitro intestinal model system. In one aspect of any of the embodiments, described herein is a method of providing an in vitro intestinal model system, the method comprising: 1) providing an intestinal fluidic organ-on-a-chip culture device, the device comprising a porous membrane having a molecular coating that mediates cell adhesion; 2) establishing a culture of intestinal endothelial cells and/or fibroblasts on a first surface of the porous membrane of an intestinal fluidic organ-on-a-chip culture device; 3) disrupting an intestinal enteroid, colonoid, or organoid comprising intestinal epithelial cells into enteroid, colonoid, or organoid fragments comprising intestinal epithelial cells in the presence of a ROCK inhibitor; 4) establishing a culture of intestinal epithelial cells on a second surface of the porous membrane of the intestinal fluidic organ-on-a-chip culture device by contacting the second surface with the enteroid, colonoid, or organoid fragments comprising intestinal epithelial cells resulting from the disruption step; and 5) maintaining the culture of the intestinal endothelial cells and/or fibroblasts and intestinal epithelial cells in the intestinal fluidic organ-on-a-chip culture device. In one aspect of any of the embodiments, described herein a method of providing an in vitro intestinal model system, the method comprising: 1) providing an intestinal fluidic organ-on-a-chip culture device, the device comprising a porous membrane; 2) establishing a culture of intestinal epithelial cells on a first surface of the porous membrane of the intestinal fluidic organ-on-a-chip culture device by contacting the surface with an intestinal enteroid, colonoid, or organoid comprising intestinal epithelial cells; and 3) maintaining the culture of intestinal epithelial cells in the intestinal fluidic organ-on-a-chip culture device. In some embodiments of any of the aspects, the porous membrane has a molecular coating that mediates cell adhesion. In some embodiments of any of the aspects, prior to establishing the culture of intestinal epithelial cells on a first surface of the porous membrane, a culture of intestinal endothelial cells and/or fibroblasts has been established on a second surface of the porous membrane. In some embodiments of any of the aspects, the intestinal enteroid, colonoid, or organoid comprising intestinal epithelial cells is disrupted into enteroid, colonoid, or organoid fragments prior to establishing the culture of intestinal epithelial cells on the first surface of the porous membrane. In some embodiments of any of the aspects, the disruption of the intestinal enteroid, colonoid, or organoid is performed in the presence of a ROCK inhibitor. In some embodiments of any of the aspects, the intestinal fluidic organ-on-a-chip culture device can be an intestinal microfluidic organ-on-a-chip culture device.

In one aspect of any of the embodiments, described herein is a method of providing an in vitro intestinal model system, the method comprising: providing an intestinal microfluidic organ-on-a-chip culture device, the device comprising a porous membrane; establishing a culture of intestinal epithelial cells on a first surface of the porous membrane of the intestinal microfluidic organ-on-a-chip culture device by contacting the surface with intestinal epithelial cells; and maintaining the culture of intestinal epithelial cells in the intestinal microfluidic organ-on-a-chip culture device. In some embodiments of any of the aspects, contacting the surface with intestinal epithelial cells comprises contacting the surface with an intestinal enteroid, colonoid, or organoid comprising intestinal epithelial cells. In some embodiments of any of the aspects, the intestinal enteroid, colonoid, or organoid comprising intestinal epithelial cells is disrupted into enteroid, colonoid, or organoid fragments prior to establishing the culture of intestinal epithelial cells on the first surface of the porous membrane. In some embodiments of any of the aspects, the disruption of the intestinal enteroid, colonoid, or organoid is performed in the presence of a ROCK inhibitor.

As used herein, an "in vitro intestinal model system" refers to an in vitro system comprising at least intestinal epithelial cells and intestinal endothelial cells and/or fibroblasts. In some embodiments of any of the aspects, the culture displays morphological characteristics of intestinal tissue, e.g., villi: four different intestinal cell types (absorptive enterocytes, mucus-secreting goblet cells, enteroendocrine and Paneth cells); and/or the formation of relevant barrier functions.

As used herein, an "intestinal fluidic organ-on-a-chip culture device" refers to a fluidic device having at least two fluid channels, with a porous membrane positioned such that a first plane of the membrane faces a first fluid channel and the second plane of the membrane faces a second fluid channel.

As used herein "fluidic device" refers to a device of any size or orientation which comprises one or more fluid channels and is suitable for the culture of living cells. A fluidic device can be capable of moving any amount of fluid within the fluid flow ranges described herein below, e.g. a fluidic device can be a microfluidic device or a device capable of moving larger volumes of fluid. In some embodiments of any of the aspects, the intestinal fluidic organ-on-a-chip culture device can be an intestinal microfluidic organ-on-a-chip culture device. The term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

Throughout the specification and figures, the intestinal fluidic organ-on-a-chip culture devices described herein are referred to interchangeably as "gut on a chip" or "organ on a chip." Exemplary, but non-limiting, intestinal microfluidic organ-on-a-chip culture devices are described in US Patent Publication US 2014/0038279; which is incorporated by reference herein its entirety.

"Channels" are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron. Channels can include capillaries, tubes, pathways, and/or grooves deposed within or upon a medium or substrate.

In some embodiments of any of the aspects, the intestinal fluidic organ-on-a-chip culture device can comprise at least two fluid channels, with a porous membrane positioned such that a first plane of the membrane faces a first fluid channel and the second plane of the membrane faces a second fluid channel. In some embodiments of any of the aspects, the intestinal fluidic organ-on-a-chip culture device can comprise a fluid channel with a porous membrane positioned within the fluid channel to divide the fluid channel into a first fluid channel and a second fluid channel. In some embodiments of any of the aspects, the membrane can be attached to one or more membrane support elements, e.g., membrane support elements coupled to membrane strain mechanisms capable of moving the membrane support elements and causing the membrane to stretch along at least one dimension of the membrane.

As used herein, "a membrane support element" is a portion of the device to which the membrane is attached. A membrane support element can be a wall of the fluid channel(s) or a separate structure such as a post, a series of posts, a clamp, or a port comprised by the fluid channel(s). In some embodiments of any of the aspects, a membrane support element can change position, change orientation, and/or flex; thereby imparting a strain or movement to the membrane. As used herein, a "membrane strain mechanism" refers to a means of causing a membrane support element to change position, change orientation, and/or flex; thereby causing a membrane to stretch in at least one direction. A membrane strain mechanism can cause the membrane to stretch by moving or flexing the membrane support element. Non-limiting examples of membrane strain mechanisms include vacuum chambers, fluid chambers connected to pumps, plungers, and the like. Exemplary, but non-limiting, membrane support elements and membrane strain mechanisms are described in US Patent Publication US 2014/0038279; which is incorporated by reference herein its entirety.

As used herein, "porous membrane" refers to a membrane being at least partially porous. In some embodiments of any of the aspects, the porous membrane can be made of and/or comprise one or more of PDMS, polyester (PET), and/or polycarbonate. Further examples of biocompatible materials suitable for membrane construction are described elsewhere herein.

In some embodiments of any of the aspects, the pores of the membrane can be from 0.5 µm to 10 µm in diameter. In some embodiments of any of the aspects, the pores of the membrane can be approximately 10 µm in diameter. In some embodiments of any of the aspects, the pores of the membrane can be approximately 5 µm in diameter. In some embodiments of any of the aspects, the pores can be irregularly spaced. In some embodiments of any of the aspects, the pores can be regularly spaced. In some embodiments of any of the aspects, the pores can be 5 µm or further apart, e.g. 5 µm apart, 10 µm, apart, 25 µm apart, 50 um apart, 100 µm apart, 1000 µm apart, 5 mm apart, or further apart.

In some embodiments of any of the aspects, the membrane is at least partially flexible. In some embodiments the membrane is flexible in at least one dimension, e.g., the membrane can stretch in one dimension, or in two dimensions, or in three dimensions.

In some embodiments of any of the aspects, the membrane can be planar. In some embodiments of any of the aspects, the membrane can be cylindrical. In some embodiments of any of the aspects, the membrane is from 15 µm or greater in thickness, e.g. 15 µm or greater in thickness, 20 µm or greater in thickness, 25 µm or greater in thickness, 30 µm or greater in thickness, 35 µm or greater in thickness, or 40 µm or greater in thickness. In some embodiments of any of the aspects, the membrane can be from 15 µm to 40 µm in thickness. In some embodiments of any of the aspects, the membrane can be from 25 µm to 30 µm in thickness. In some embodiments of any of the aspects, the membrane can be approximately 30 µm in thickness.

As used herein, "a molecular coating that mediates cell adhesion" refers to a material added to the membrane itself which promotes the adhesion of intestinal epithelial and/or endothelial cells and/or fibroblasts to the membrane. The coating can be applied to the membrane with or without chemical cross-linking or conjugation.

In some embodiments of any of the aspects, the molecular coating can be and/or comprise a hydrogel. As used herein, the term "hydrogel" refers to a three-dimensional polymeric structure that is insoluble in water or some other liquid but which is capable of absorbing and retaining large quantities of water or some other liquid to form a stable, often soft and pliable, structure. In some embodiments of any of the aspects, water or some other liquid can penetrate in between the polymer chains of the polymer network, subsequently causing swelling and the formation of a hydrogel. Hydrogels can comprise natural or synthetic polymers and can be a colloidal gel in which water is the dispersion medium. In some embodiments, the hydrogel can comprise at least about 50% or more, including, e.g., at least about 60%, at least about 70%, at least about 80%, at least about 90%, at least about 95% or up to 99%, of its weight as water. Examples of a hydrogel include, but are not limited to polyethylene glycol (PEG), polyvinylpyrrolidone (PVP), agarose, alginate, and a combination of two or more thereof.

In some embodiments of any of the aspects, the hydrogel can be an extracellular matrix hydrogel, e.g., a hydrogel comprising one or more compounds and/or molecules found in the extracellular matrix (e.g., the intestinal extracellular matrix). Extracellular matrix hydrogels are known in the art and include commercially-available products such as MATRIGEL (e.g., Cat Nos. 356234, 354234, 356235, 356237, 354248, 354262, 354263, 356230, 354230, 354263, 356231, 356237, 354262, 356231, and 354277; Corning; Corning, NY). In some embodiments of any of the aspects, the molecular coating can comprise one or more compounds and/or molecules found in the extracellular matrix (e.g., the intestinal extracellular matrix). Non-limiting examples of extracellular matrix compounds and/or molecules can include laminin, heparan sulfate proteoglycan; fibronectin; collagen; type I collagen; and/or type IV collagen. Non-limiting examples of extracellular matrix compounds and/or molecules can include collagen Type II; collagen Type III; collagen Type V; collagen Type VI; collagen Type VII; collagen Type VIII; collagen Type IX, collagen Type X; collagen Type XI; collagen Type XII; collagen Type XIII; collagen Type XIV; proteoglycan; vitronectin; poly-D-lysine; elastin; hyaluronic acid; glycoasaminoglycans; integrin; polypeptides, oligonucleotides, DNA, and/or polysaccharide. In some embodiments of any of the aspects, the molecular coating can comprise a basement membrane preparation, e.g., a material made from a basement membrane and/or comprising compounds found in a basement membrane.

In some embodiments of any of the aspects, the extracellular matrix compounds and/or molecules can include a compound and/or molecule bound by a molecule on the surface of an intestinal epithelial cell. In some embodiments of any of the aspects, the extracellular matrix compounds and/or molecules can include a compound and/or molecule which binds a molecule on the surface of an intestinal epithelial cell.

In some embodiments of any of the aspects, an extracellular matrix compound and/or molecule is obtained from a mammal. In some embodiments of any of the aspects, an extracellular matrix compound and/or molecule is synthesized or obtained from a transgenic organism. In some embodiments of any of the aspects, an extracellular matrix compound and/or molecule is human in origin. In some embodiments of any of the aspects, an extracellular matrix compound and/or molecule is mammalian in origin e.g. murine or primate in origin. One of ordinary skill in the art is well aware of methods of synthesizing or producing the carbohydrates and peptide sequences described herein. Such molecules are also available commercially, e.g. laminin (Cat No. 354232; BD Biosciences Franklin Lakes, NJ). In some embodiments of any of the aspects, the concentration of a extracellular matrix compound and/or molecule can be from 10 µg/mL to 1,000 µg/mL, e.g., 10 µg/mL, 50 µg/mL, 100 µg/mL, 200 µg/mL, 300 µg/mL, 500 µg/mL, 1,000 µg/mL or any value in between.

In some embodiments of any of the aspects, the porous membrane can be oxidized, activated, and/or functionalized before contacting it with the molecular coating. In some embodiments of any of the aspects, the method further comprises 1) oxidizing the porous membrane; and 2) contacting the porous membrane with the molecular coating that mediates cell adhesion. In some embodiments of any of the aspects, the method further comprises 1) oxidizing the porous membrane; 2) functionalizing the porous membrane by silanization; and 3) contacting the porous membrane with the molecular coating that mediates cell adhesion.

One of skill in the art is familiar with methods for oxidizing membranes, e.g. PDMS, PET and/or polycarbonate membranes. Exemplary methods for oxidation can include, but are not limited to, exposing the porous membrane to oxygen plasma; plasma discharge; polyethylene glycol (PEG); polyvinyl alcohol (PVA); or a liquid oxidizer.

Silanization of the membrane can cause hydroxyl groups to react with alkoxysilanes to form covalent Si—O—Si bonds to the membrane. Silanization of the membrane can be performed using, by way of non-limiting example, aminosilane; (3-aminopropyl)triethoxy silane; sulfhydrylsilane; and epoxysilane.

Following silanization, the porous membrane can be further treated with a cross-linker reagent. Exemplary, non-limiting cross-linking reagents can include N-γ-maleimidobutyryloxy succinimide ester; DMA; DMS; glutaraldehyde (GA); carbodiimide (1-ethyl-3-(3-dimethyl aminopropyl)-carbodiimide (EDC)); epoxy compounds; six methylene diisocyanate, glycerin; alginate; genipin (GP); nordihydroguaiaretic acid (NDGA); tannic acid; and procyanidins (PC). One of skill in the art can readily determine suitable cross-linker reagents to generate desired crosslinked products given a particular substrate. For example, ThermoFisher Scientific provides a Crosslinker Selection Tool (available on the world wide web at thermofisher.com/us/en/home/life-science/protein-biology/protein-labeling-crosslinking/protein-crosslinking/crosslinker-selection-tool.html). For further discussion of suitable reagents, substrates, and cross-link products, see, e.g., Crosslinking Technical Handbook; Thermo Scientific; 2012; which is incorporated by reference herein in its entirety.

As used herein, "intestinal endothelial cell" refers to a cell lining the vasculature (e.g., a vein, artery, or capillary) in the intestine. In some embodiments of any of the aspects, the intestinal endothelial cells are mammalian intestinal endothelial cells. In some embodiments of any of the aspects, the intestinal endothelial cells are human intestinal endothelial cells. In some embodiments of any of the aspects, the intestinal endothelial cells are primary intestinal endothelial cells. In some embodiments of any of the aspects, the intestinal endothelial cells are obtained from a subject. In some embodiments of any of the aspects, the intestinal endothelial cells are HUVEC (Human Umbilical Vein Endothelial Cells) or HIMEC (Human Intestinal Microvascular Endothelial Cells). In some embodiments of any of the aspects, the intestinal endothelial cells are umbilical vein endothelial cells or intestinal microvascular endothelial cells.

The term "primary cells" as used in the present description is well known to a person skilled in the art. Primary cells are cells that have been freshly isolated from an animal or human tissue, organ, or organism, or the untransformed and mortal descendants thereof. The cells may be isolated directly from samples of tissue obtained by biopsy, autopsy, surgical or medical procedure, donation, or harvesting. Primary cells are not able to continuously and indefinitely replicate and divide. Primary cultures are typically neither transformed nor immortal. Primary cells as used herein are not cells of cell lines, which typically have undergone many generations or passages of culture in vitro. For example, primary cells divide in cell culture less than 100 times, often less than 50 times, often less than 25 times.

In some embodiments of any of the aspects, establishing a culture of intestinal endothelial cells and/or fibroblasts on a first surface of a porous membrane of an intestinal fluidic organ-on-a-chip culture device comprises culturing the intestinal endothelial cells and/or fibroblasts under conditions suitable for them to form a monolayer on the porous membrane. In some embodiments of any of the aspects, a monolayer comprises a culture in which the cells cover at least 50%, at least 60%, at least 70%, at least 80%, at least 90% or more of the surface on which they are grown. In some embodiments of any of the aspects, a monolayer displays a single cell thickness over at least 50%, at least 60%, at least 70%, at least 80%, at least 90% or more of its area. As demonstrated in the Examples herein, in the presence of intestinal endothelial cells (e.g. HUVECs or HIMECs) or fibroblasts, devices seeded with single epithelial cells instead of multi-cell enteroid or colonoid fragments can support development of a fully confluent and mature intestinal epithelium in the same device.

In some embodiments of any of the aspects, one surface of the membrane can be contacted with fibroblasts. In some embodiments of any of the aspects, one surface of the membrane can be contacted with intestinal endothelial cells. In some embodiments of any of the aspects, one surface of the membrane can be contacted with a combination of fibroblasts and intestinal endothelial cells.

As used herein, "intestinal epithelial cells" refers to cells which are found in a single-cell layer in the intestinal wall and which are in direct contact with the lumen of the intestine. Intestinal epithelial cells can include enterocytes, Goblet cells, enteroendocrine cells, Paneth cells, microfold cells, cup cells, tuft cells, progenitors thereof, and stem cells.

In some embodiments of any of the aspects, the intestinal epithelial cells are mammalian intestinal epithelial cells. In some embodiments of any of the aspects, the intestinal epithelial cells are human intestinal epithelial cells. In some embodiments of any of the aspects, the intestinal epithelial cells are primary cells. In some embodiments of any of the aspects, the intestinal epithelial cells are not tumor cell line-derived cells. In some embodiments of any of the aspects, the intestinal epithelial cells are primary cells, primary small intestine cells, primary large intestine cells, small intestine cells, large intestine cells, cultured cells, passaged cells, immortalized cells, transgenic cells, genetically modified cells, cancerous cells or cells from a subject or animal with an intestinal cancer, cells from a subject or animal with an intestinal disease or disorder, stem cells, embryonic stem cells (ESCs), induced pluripotent stem cells (IPSCs), paneth cells, crypt cells, or mucus-secreting cells.

In some embodiments of any of the aspects, the intestinal epithelial cells can be seeded in a device as described herein at a concentration of from about $1\times10^2/cm^2$ to about $1\times10^{10}/cm^2$. In some embodiments of any of the aspects, the intestinal epithelial cells can be seeded in a device as described herein at a concentration of from about $1\times10^4/cm^2$ to about $1\times10^7/cm^2$. In some embodiments of any of the aspects, the intestinal epithelial cells can be seeded in a device as described herein at a concentration of from about $7\times10^4/cm^2$ to about $7\times10^6/cm^2$. In some embodiments of any of the aspects, the intestinal epithelial cells can be seeded in a device as described herein at a concentration of about $7\times10^5/cm^2$.

In some embodiments of any of the aspects, the intestinal epithelial cells can be seeded in a device as described herein at a concentration of from $1\times10^2/cm^2$ to $1\times10^{10}/cm^2$. In some embodiments of any of the aspects, the intestinal epithelial cells can be seeded in a device as described herein at a concentration of from $1\times10^4/cm^2$ to $1\times10^7/cm$. In some embodiments of any of the aspects, the intestinal epithelial cells can be seeded in a device as described herein at a concentration of from $7\times10^4/cm^2$ to $7\times10^6/cm^2$. In some embodiments of any of the aspects, the intestinal epithelial cells can be seeded in a device as described herein at a concentration of $7\times10^5/cm^2$.

As used herein, "intestinal enteroid" refers to a group of cells comprising intestinal epithelial cells displaying crypt-like morphology and cellular polarity. An intestinal enteroid can be derived from cells obtained from the small intestine, large intestine, or colon. Intestinal enteroids do not comprise mesenchyme tissue or endothelial cells. Intestinal enteroids can be spherical, e.g., with the apical ends of the epithelial cells oriented to the lumen of the spherical structure. A colonoid is an intestinal enteroid obtained from the colon.

In some embodiments of any of the aspects, enteroids and/or colonoids are isolated from endoscopic biopsies and/or resections of intestinal tissue. In some embodiments of any of the aspects, the methods described herein can relate to the use of intestinal organoids, which are groups of epithelial cells derived from iPSCs. Enteroids, colonoids, and intestinal organoids are grown in the form of 3D spheroids embedded in a gel prior to use in the methods described herein. Methods of isolating and maintaining enteroids, colonoids, and intestinal organoids are known in the art.

An intestinal enteroid, colonoid, or organoid can be disrupted and/or fragmented into fragments. It was found that epithelial cell seeding and monolayer formation were most optimal when using enteroid fragments, as single intestinal cell suspensions (produced using longer exposure to the Enteroid Dissociation medium) do not expand adequately to develop a functional mucosal barrier, and whole enteroids remain in their cystic spherical form loosely adhering to the ECM-coated porous membrane under flow and fail to form a continuous monolayer. As used herein, "fragment", when used in the context of intestinal enteroid, colonoid, and/or organoid fragments refers to a group of at least two physically contiguous cells which does not form a complete spheroid. Fragments in solution do not include single cell suspensions. Each fragment can contain one or more intestinal epithelial cells. In some embodiments of any of the aspects, an intestinal enteroid, colonoid, or organoid is disrupted into enteroid, colonoid, or organoid fragments to provide groups of from about 1 to about 100 intestinal epithelial cells. In some embodiments of any of the aspects, an intestinal enteroid, colonoid, or organoid is disrupted into enteroid, colonoid, or organoid fragments to provide groups of from about 2 to about 100 intestinal epithelial cells. In some embodiments of any of the aspects, an intestinal enteroid, colonoid, or organoid is disrupted into enteroid, colonoid, or organoid fragments to provide groups of from about 5 to about 100 intestinal epithelial cells. In some embodiments of any of the aspects, an intestinal enteroid, colonoid, or organoid is disrupted into enteroid, colonoid, or organoid fragments to provide groups of from 1 to 100 intestinal epithelial cells. In some embodiments of any of the aspects, an intestinal enteroid, colonoid, or organoid is disrupted into enteroid, colonoid, or organoid fragments to provide groups of from 2 to 100 intestinal epithelial cells. In some embodiments of any of the aspects, an intestinal enteroid, colonoid, or organoid is disrupted into enteroid, colonoid, or organoid fragments to provide groups of from 5 to 100 intestinal epithelial cells. In some embodiments of any of the aspects, an intestinal enteroid, colonoid, or organoid is disrupted into enteroid, colonoid, or organoid fragments to provide groups of from about 10 to about 30 intestinal epithelial cells. In some embodiments of any of the aspects, an intestinal enteroid, colonoid, or organoid is disrupted into enteroid, colonoid, or organoid fragments to provide groups of from 10 to 30 intestinal epithelial cells. In some embodiments of any of the aspects, an intestinal enteroid, colonoid, or organoid is disrupted into enteroid, colonoid, or organoid fragments to provide groups of from about 5 to about 30 intestinal epithelial cells. In some embodiments of any of the aspects, an intestinal enteroid, colonoid, or organoid is disrupted into enteroid, colonoid, or organoid fragments to provide groups of from 5 to 30 intestinal epithelial cells. In some embodiments of any of the aspects, an intestinal enteroid, colonoid, or organoid is disrupted into enteroid, colonoid, or organoid fragments to provide fragments of from about 10 μm to about 500 μm in diameter. In some embodiments of any of the aspects, an intestinal enteroid, colonoid, or organoid is disrupted into enteroid, colonoid, or organoid fragments to provide fragments of from 10 μm to 500 μm in diameter. In some embodiments of any of the aspects, an intestinal enteroid, colonoid, or organoid is disrupted into enteroid, colonoid, or organoid fragments to provide fragments of from about 40 μm to about 100 μm in diameter. In some embodiments of any of the aspects, an intestinal enteroid, colonoid, or organoid is disrupted into enteroid, colonoid, or organoid fragments to provide fragments of from 40 μm to 100 μm in diameter. The disruption step can be conducted under conditions suitable to provide fragments of the desired size and/or the fragments can be sorted (e.g., by centrifugation, SEC, filtration, or FACS) after fragmentation to provide a population of fragments of the desired size.

Disruption can be accomplished by any means known in the art, e.g., by mechanical and/or enzymatic means for disrupting or dissociating groups of cells. In some embodiments of any of the aspects, disruption can be performed by contacting the enteroid, colonoid, or organoid with trypsin or TrypLE (Cat No. 12605036; ThermoFisher Scientific; Waltham, MA).

In some embodiments of any of the aspects, the intestinal enteroid or colonoid is obtained from a subject. In some embodiments of any of the aspects, the intestinal enteroid or colonoid is obtained from a resected intestinal tissue or an endoscopic biopsy tissue. In some embodiments of any of the aspects, washing a resected intestinal tissue or an endoscopic biopsy tissue and removing any associated muscle or mucosa layers; contacting the tissue with one or more extracellular-matrix degrading enzymes; removing an intestinal crypt from the supernatant resulting from the contacting step; embedding the intestinal crypt in a hydrogel; and maintaining the intestinal crypt in the hydrogel to form an intestinal enteroid or colonoids. For further details of isolating, culturing, and/or maintaining intestinal enteroid or colonoids, see, e.g., Sato and Vries. (2009). Nature 459: 262-265, Sato T, et al. (2011) Gastroenterology 141:1762-72; and Miyoshi and Stappenbeck. (2013) Nat Protoc 8:2471-82; each of which is incorporated by reference herein in its entirety.

In some embodiments of any of the aspects, the disruption and/or fragmentation of an intestinal enteroid, colonoid, or organoid is performed in the presence of a ROCK inhibitor. The presence of the ROCK inhibitor can rescue dissociated epithelial cells from anioksis. As used herein, "ROCK inhibitor" refers to an inhibitor of one or more Rho-associated Kinases (ROCKs). ROCKs are serine-threonine kinases that act on the cytoskeleton. ROCKs include ROCK 1 and ROCK2 and sequences for both are known for a variety of species, e.g., human ROCK1 (NCBI Gene ID No: 6093) and human ROCK2 (NCBI Gene ID No: 9475). ROCK inhibitors can be specific for either ROCK1 or ROCK2 or inhibit both ROCK1 and ROCK2. Non-limiting examples of ROCK inhibitors can include fasudil; Y27632; Y39983; Wf-536; SLx-2119; an azabenzimidazole-aminofurazan; DE-104; an olefin; an isoquinoline; an indazole; a pyridinealkene derivative; H-1152P; an ROKα inhibitor (BF); XD-4000; HMN-1152; a 4-(1-aminoalkyl)-N-(4-pyridyl)cyclohexane-carboxamide; rhostatin; BA-210; BA-207; BA-215; BA-285; BA-1037; Ki-23095; VAS-012; and a quinazoline.

In some embodiments of any of the aspects, of any of the aspects, a glycogen synthase kinase 3 (GSK-3) inhibitor is present during the disruption and/or fragmentation of the intestinal enteroid, colonoid, or organoid. As used herein, "GSK-3 inhibitor" refers to an inhibitor of Glycogen Synthase Kinase 3 (GSK-3). GSK-3 is a serine-threonine protein kinase that phosphorylates a number of targets including glycogen synthase. Sequences for GSK-3 are known for a variety of species, including humans, e.g., GSK-3A (NCBI Gene ID No: 2931) and GSK-3B (NCBI Gene ID No: 2932). Non-limiting examples of GSK-3 inhibitors can include 6-BIO; dibromocantharelline; hymenialdesine; indirubins; meridianis; CT98014; CT98023; CT99021; TWS119; SB-216763; SB-41528; AR-A014418; AZD-1080; alsterpaullone; cazpaullone; kenpaullone; manzamine A; palinurine; tricantine; TDZD-8; NP00111; NP031115; tideglusib; HMK-32; L803-mts; and ketamine.

As used herein, "maintaining" or "culturing" refers to continuing the viability of a tissue or population of cells. A maintained tissue will have a population of metabolically active cells. The number of these cells can be roughly stable over a period of at least 3 days or can grow.

As used herein, "establishing" a culture or population of cells refers to introducing one or more cells to a culture location, device, system, container, or vessel such that the cells can be maintained and preferably such that the cells expand.

As used herein, "conditions suitable" for a particular activity refers to conditions under which a detectable level of the activity occurs. Examples of suitable conditions are provided, e.g., in the Examples herein.

Media and culture conditions suitable for establishing and/or maintaining a culture of, e.g., intestinal epithelial cells and/or intestinal endothelial cells and/or fibroblasts are known in the art. Exemplary media are provided herein. Media can comprise cell culture medium, solutions, buffers, nutrients, tracer compounds, dyes, antimicrobials, or other compounds not toxic to the cells being cultured in the cell culture system described herein. One of ordinary skill in the art is well aware of suitable media for culturing or maintaining intestinal cells, intestinal epithelial cells, endothelial cells and/or fibroblasts, immune cells, connective tissue cells, and/or microbial cells.

By way of non-limiting example, media suitable for maintaining or culturing intestinal epithelial cells can include; Dulbecco's Modified Eagle Medium containing 4.5 g/L glucose (DMEM; Gibco, Grand Island, NY) supplemented with 20% fetal bovine serum (FBS; Gibco), 100 units/mL penicillin, 100 μg/mL streptomycin (Gibco), 100 μg/mL Normocin (Invivogen, San Diego, CA), and 25 mM HEPES or Dulbecco's Modified Eagle Medium containing 4.5 g/L glucose (DMEM; Gibco, Grand Island, NY) supplemented with 20% fetal bovine serum (FBS; Gibco), and 25 mM HEPES. In some embodiments of any of the aspects, the maintaining step can comprise providing the intestinal endothelial cells and/or fibroblasts, e.g., providing the channel on the side of the porous membrane contacted with intestinal endothelial cells and/or fibroblasts with EGM2-MV medium.

In some embodiments of any of the aspects, the maintaining step can comprise providing the intestinal epithelial cells, e.g., providing the channel on the side of the porous membrane contacted with intestinal epithelial cells with expansion medium comprising one or more of the following: Wnt-3A; EGF; Rspo1: Noggin: gastrin; a TGF-β receptor inhibitor; and/or a p38 MAPK inhibitor. In some embodiments of any of the aspects, the maintaining step can comprise providing the intestinal epithelial cells, e.g., providing the channel on the side of the porous membrane contacted with intestinal epithelial cells with expansion medium comprising Wnt-3A; EGF; Rspo1; Noggin; gastrin; a TGF-β receptor inhibitor; and/or a p38 MAPK inhibitor. In some embodiments of any of the aspects, the expansion medium further comprises nicotamide. In some embodiments of any of the aspects, the expansion medium further comprises a ROCK inhibitor for about 1 to about 4 days after introducing the epithelial cells to the intestinal culture fluidics device. In some embodiments of any of the aspects, the expansion medium further comprises a ROCK inhibitor for 1 to 4 days after introducing the epithelial cells to the intestinal culture fluidics device. In some embodiments of any of the aspects, the expansion medium further comprises a ROCK inhibitor for about 2 days after introducing the epithelial cells to the intestinal culture fluidics device. In some embodiments of any of the aspects, the expansion medium further comprises a ROCK inhibitor for 2 days after introducing the epithelial cells to the intestinal culture fluidics device.

In some embodiments of any of the aspects, the medium provided to either channel of the intestinal culture fluidics devices can further comprise Jagged (JAG) polypeptide and/or an inhibitor of GSK. In some embodiments of any of the aspects, the medium provided to either channel of the intestinal culture fluidics devices, e.g., an expansion or differentiation medium, can further comprise Jagged (JAG) polypeptide and/or an inhibitor of GSK. Such reagents are known in the art.

In some embodiments of any of the aspects, each channel of the intestinal fluidic organ-on-a-chip culture device can be provided with a different medium. In some embodiments of any of the aspects, both channels of the intestinal fluidic organ-on-a-chip culture device can be provided with the same medium.

In some embodiments of any of the aspects, the surface of the membrane not contacted with intestinal epithelial cells can be provided with expansion medium. In some embodiments of any of the aspects, both surfaces of the intestinal fluidic organ-on-a-chip culture can be provided with expansion medium. In some embodiments of any of the aspects, the expansion medium can comprise fetal bovine serum and VEGF. In some embodiments of any of the aspects, the expansion medium can be an endothelial-optimized expansion medium, e.g., EGM2-MV (Cat. No. CC-3202 Lonza, Basel; Switzerland). In some embodiments of any of the aspects, the surface of the membrane not contacted with intestinal epithelial cells can be contacted with endothelial-optimized expansion medium, e.g., EGM2-MV (Cat. No. CC-3202 Lonza, Basel; Switzerland).

In some embodiments of any of the aspects, the method can comprise providing fluid to one or more fluid channels by connecting the fluid channel(s) to a fluid source, e.g, a fluid source comprised by a fluidics system. In some embodiments of any of the aspects, a device described herein can comprise a connection of a fluid channel(s) to a fluid source, e.g., a fluid source comprised by a fluidics system. In some embodiments of any of the aspects, the connection can be via a port in the intestinal fluidic organ-on-a-chip culture device.

In some embodiments of any of the aspects, control of the fluid flow from the fluid source through a fluid channel or the membrane strain mechanism can be automated. In an embodiment in which control of the flow of solution from the fluid source or the membrane strain mechanism is automated, a syringe pump or solenoid can be used. In other embodiments, one or more computing devices or systems may be used to control fluid flow or a membrane strain mechanism. Alternatively or additionally, a computing device may be coupled to fluid source or port in order to control the flow of fluid from the fluid source. Alternatively or additionally, a computing device may be coupled to a membrane strain mechanism to automate movement of a membrane support element and stretching of the membrane. Exemplary, but non-limiting, embodiments of automated devices are described in US Patent Publication US 2014/0038279; which is incorporated by reference herein its entirety.

In some embodiments of any of the aspects, the maintaining step comprises providing a flow of culture medium through each channel of the intestinal fluidic organ-on-a-chip culture device at a volumetric flow rate of about 10 to about 5000 $\mu l\ h^{-1}$. In some embodiments of any of the aspects, the maintaining step comprises providing a flow of culture medium through each channel of the intestinal fluidic organ-on-a-chip culture device at a volumetric flow rate of 10 to 5000 $\mu l\ h^{-1}$. In some embodiments of any of the aspects, the maintaining step comprises providing a flow of culture medium through each channel of the intestinal fluidic organ-on-a-chip culture device at a volumetric flow rate of about 10 to about 500 $\mu l\ h^{-1}$. In some embodiments of any of the aspects, the maintaining step comprises providing a flow of culture medium through each channel of the intestinal fluidic organ-on-a-chip culture device at a volumetric flow rate of 10 to 500 $\mu l\ h^{-1}$. In some embodiments of any of the aspects, the maintaining step comprises providing a flow of culture medium through each channel of the intestinal fluidic organ-on-a-chip culture device at a volumetric flow rate of about 60 $\mu l\ h^{-1}$. In some embodiments of any of the aspects, the maintaining step comprises providing a flow of culture medium through each channel of the intestinal fluidic organ-on-a-chip culture device at a volumetric flow rate of 60 $\mu l\ h^{-1}$.

In some embodiments of any of the aspects, the fluid flow rate through the one or more channels of the intestinal fluidic organ-on-a-chip culture device can be a fluid flow rate equivalent to that encountered in the intestine of a mammal. In some embodiments of any of the aspects, the fluid flow rate in the one or more channels of the intestinal fluidic organ-on-a-chip culture device can be a fluid flow rate equivalent to that encountered in the intestine of a mammal suffering from an intestinal disorder. By way of non-limiting example, an intestinal disorder could be a disease or a blockage. In some embodiments of any of the aspects, the fluid flow rate can be less than or equal to 500 μL/hr, e.g. it can be 500 μL/hr, 400 μL/hr, 300 μL/hr, 200 μL/hr, 100 μL/hr, 50 μL/hr, 10 μL/hr or less. In some embodiments of any of the aspects, the fluid flow rate can be approximately the same for the duration of the time during which intestinal epithelial cells are cultured in the intestinal fluidic organ-on-a-chip culture device. In some embodiments of any of the aspects, the fluid flow rate can be increased and/or decreased during the time in which intestinal cells are cultured in the intestinal fluidic organ-on-a-chip culture device, e.g. the fluid flow rate can be decreased for a time to allow newly added cells to attach to the membrane and/or pre-existing cells. In some embodiments of any of the aspects, the fluid flow rate can be varied in a regular, cyclic pattern. In some embodiments the fluid flow rate can be varied in an irregular pattern.

In some embodiments of any of the aspects, the maintaining step comprises stretching the porous membrane at about 0 to about 1 Hz with an about 0 to about 20% mean cell strain. In some embodiments of any of the aspects, the maintaining step comprises stretching the porous membrane at 0 to 1 Hz with an 0 to 20% mean cell strain. In some embodiments of any of the aspects, the maintaining step comprises stretching the porous membrane at about 0.15 Hz with an about 10% mean cell strain. In some embodiments of any of the aspects, the maintaining step comprises stretching the porous membrane at 0.15 Hz with a 10% mean cell strain.

In some embodiments of any of the aspects, the maintaining step comprises morphological and functional differentiation of the intestinal epithelial cells in co-culture with the intestinal endothelial cells and/or fibroblasts, e.g., the formation of villi; differentiation into four different intestinal cell types: absorptive enterocytes, mucus-secreting goblet cells, enteroendocrine and Paneth cells; and/or the formation of relevant barrier functions. Co-culture can comprise simultaneous maintenance of two cultures for at least, e.g., 1 day, 2 days, 3 days, 4 days, 5 days, 6 days, 1 week, 2 weeks, 3 weeks, or longer.

In some embodiments either side of the membrane can further be contacted with immune cells, connective tissue cells, pathogens, and/or microbial cells. As used herein, an "immune cell" is any cell of the immune system involved in adaptive or humoral immunity. Non-limiting examples of immune cells include peripheral blood mononuclear cells (PBMC), plasmacytoid dendritic cells (PDC), myeloid dendritic cells (MDC), B cells, macrophages, monocytes, natural killer cells, NKT cells, CD4+ T cells, CD8+ T cells, granulocytes or precursors thereof. As used herein, a "connective cell" refers to cells of those animal tissues that support organs, fill spaces between them, or perform mechanical functions such as connecting muscles to bone (tendons and ligaments) or providing low friction weighing surface as in articular cartilage. Connective tissues are characterized by their relatively avascular matrices and low cell densities. The most abundant connective tissues are the reticular stroma, muscle, adipose tissue, cartilage and bone. Further examples of connective tissue include, but are not limited to, mesenchyme, mucous connective, areolar (loose), elastic, or blood. Included within the definition of "connective tissue" are terminally differentiated cells as well as precursor cells that have the potential to differentiate into connective tissue cells and tissues. In some embodiments of any of the aspects, the microbial cells and/or pathogens can be present in the same fluid channel as the intestinal epithelial cells. In some embodiments of any of the aspects, the microbial cells can be microbial cells found in the intestine or gut of a healthy animal (e.g., commensal microbial cells). In some embodiments of any of the aspects, the microbial cells and/or pathogens can be organisms found in the intestine or gut of an unhealthy animal, e.g. one with an intestinal disease or disorder. In some embodiments of any of the aspects, the microbial cells and/or pathogens can be organisms that cause or contribute to a disease or disorder of the intestine.

In some embodiments of any of the aspects, bacterial cells can be co-cultured with the eukaryotic cells found on one or both sides of the membrane. In some embodiments of any of the aspects, bacterial cells can be co-cultured with the intestinal epithelial cells. In some embodiments of any of the aspects, the methods described herein can further comprise contacting or seeding the channel comprising intestinal epithelial cells with one or more bacterial cells or bacterial species. In some embodiments of any of the aspects, during bacterial cell co-culture, the culture medium is caused to move through either or both channels at about 120 µL/hr. In some embodiments of any of the aspects, during bacterial cell co-culture, the membrane separating the two channels is caused to stretch at about 10% strain at a rate of about 0.2 Hz. In some embodiments of any of the aspects, during bacterial cell co-culture, the culture medium is caused to move through either or both channels at 120 µL/hr. In some embodiments of any of the aspects, during bacterial cell co-culture, the membrane separating the two channels is caused to stretch at about 10% strain at a rate of 0.2 Hz.

As used herein, "co-culture" refers to maintaining the growth of a population of eukaryotic cells and a population of bacterial cells in the same cell culture medium and/or physical space, wherein at least a portion of the eukaryotic cells are in direct physical contact with at least a portion of the bacterial cells, and at least half of the eukaryotic cells maintain viability over a 24 hour period. In some embodiments of any of the aspects, at least 90% of the eukaryotic cells maintain viability over a 24 hour period. In some embodiments of any of the aspects, at least 95% of the eukaryotic cells maintain viability over a 24 hour period. In some embodiments of any of the aspects, at least 98% of the eukaryotic cells maintain viability over a 24 hour period.

In some embodiments of any of the aspects, at least 90% of the eukaryotic cells maintain viability over a 48 hour period. In some embodiments of any of the aspects, at least 95% of the eukaryotic cells maintain viability over a 48 hour period. In some embodiments of any of the aspects, at least 98% of the eukaryotic cells maintain viability over a 48 hour period.

The structures of the intestinal fluidic organ-on-a-chip culture devices described herein (e.g. the membrane and/or the membrane support structures) can be formed, such as by etching, 3-D printing, machining, or micro-machining. In some embodiments of any of the aspects, the cell culture system described herein is etching-free. Exemplary, but non-limiting, methods for fabrication of intestinal fluidic organ-on-a-chip culture devices are described in US Patent Publication US 2014/0038279; which is incorporated by reference herein its entirety.

The intestinal fluidic organ-on-a-chip culture devices described herein can be made of a biocompatible flexible material or a biocompatible non-flexible material according to the design and application requirements. The intestinal fluidic organ-on-a-chip culture devices and/or portions thereof can be made of a flexible material, including but not limited to, a biocompatible material such as polydimethyl siloxane (PDMS), polyurethane or polyimide. The intestinal fluidic organ-on-a-chip culture devices and/or portions thereof can also be made of non-flexible materials like glass, silicon, polysulfone, hard plastic, and the like, as well as combinations of these materials.

A biocompatible polymer refers to materials which do not have toxic or injurious effects on biological functions. Biocompatible polymers include natural or synthetic polymers. Examples of biocompatible polymers include, but are not limited to, collagen, poly(alpha esters) such as poly (lactate acid), poly(glycolic acid), polyorthoesters and polyanhydrides and their copolymers, polyglycolic acid and polyglactin, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, polyglactin, or copolymers or physical blends of these materials.

A biocompatible material can also be, for example, ceramic coatings on a metallic substrate. But any type of coating material and the coating can be made of different types of materials: metals, ceramics, polymers, hydrogels or a combination of any of these materials. Biocompatible materials include, but are not limited to an oxide, a phosphate, a carbonate, a nitride or a carbonitride. Among the oxide the following ones are preferred: tantalum oxide, aluminum oxide, iridium oxide, zirconium oxide or titanium oxide. Substrates are made of materials such as metals, ceramics, polymers or a combination of any of these. Metals such as stainless steel, Nitinol, titanium, titanium alloys, or aluminum and ceramics such as zirconia, alumina, or calcium phosphate are of particular interest.

The methods and intestinal fluidic organ-on-a-chip culture devices described herein can be used to study the effect of non-intestinal cells, tissues, and/or factors on the cells comprised by the intestinal fluidic organ-on-a-chip culture device as described herein. In some embodiments of any of the aspects, the intestinal fluidic organ-on-a-chip culture device is connected to or coupled to a second cell culture system of any design, comprising cells or tissues which are not intestinal epithelial cells. In some embodiments of any of the aspects, the cells or tissues comprised by the second cell culture system are liver cells and/or tissue. In some embodiments of any of the aspects, some fraction of an effluent of the second cell culture system and/or factors derived from cells which are not intestinal epithelial cells (e.g. signaling molecules, growth factors, or hormones) is introduced into the fluid flowing through one or more fluid channels of the intestinal fluidic organ-on-a-chip culture device. The response of the intestinal epithelial cells, endothelial cells and/or fibroblasts, immune cells, and/or connective tissue cells, and/or microbial cells in the intestinal fluidic organ-on-a-chip culture device can then be determined.

In some embodiments of any of the aspects, the methods and/or devices described herein can further comprise a system (or use of such a system) for evaluating intestinal treatments, function, and/or pathologies. In some embodiments of any of the aspects, the cells in the intestinal fluidic organ-on-a-chip culture devices can be obtained from a subject suffering from an intestinal disorder, e.g. celiac, Crohn's disease, ulcerative colitis, or irritable bowel syndrome. In some embodiments of any of the aspects, the conditions in the intestinal fluidic organ-on-a-chip culture devices can be modified to simulate an intestinal disorder. By way of non-limiting example, intestinal disorders can be simulated and/or modeled by introducing pathogenic microbial cells to the intestinal fluidic organ-on-a-chip culture devices; introducing high levels of microbial cells to the intestinal fluidic organ-on-a-chip culture devices; or increasing fluid flow rates to simulate diarrhea.

In some embodiments of any of the aspects, the methods and devices described herein can further comprise a system (or use of such a system) for evaluating intestinal effector agents. In some embodiments of any of the aspects, described herein is a method of evaluating intestinal effector agents comprising contacting the intestinal epithelial cells maintained in an intestinal fluidic organ-on-a-chip culture device as described herein with at least one candidate intestinal effector agent and measuring the response of the cells to determine the effect of the at least one candidate intestinal effector agent.

In some embodiments of any of the aspects, an intestinal effector agent can be a compound, mixture, or organism. A candidate effector agent can be an agent known to modulate the behavior of intestinal epithelial cells and/or microbes that can be found in the intestine or it can be an agent that is to be tested to see if it can modulate the behavior of intestinal epithelial cells and/or microbes that can be found in the intestine. In some embodiments of any of the aspects, an intestinal effector agent is a treatment or drug. In some embodiments of any of the aspects, an intestinal effector agent is a pathogen and/or toxin. Non-limiting examples of intestinal effector agents are therapeutics, small molecules, nutriceuticals, antidiarrheals, probiotics, natural intestinal microflora and/or microbes, foods, vitamins, pathogens, and toxins. In some embodiments of any of the aspects, the intestinal effector agent is an agent which can be administered to a subject or a patient orally.

In some embodiments of any of the aspects, the cells maintained in an intestinal fluidic organ-on-a-chip culture device as described herein can be contacted with one or more intestinal effector agents, e.g. one effector agent, two effector agents, three effector agents, or more effector agents. In some embodiments of any of the aspects, the intestinal epithelial cells maintained in an intestinal fluidic organ-on-a-chip culture device as described herein are contacted with one or more intestinal effector agents. In some embodiments of any of the aspects, the microbial or pathogen cells maintained in an intestinal fluidic organ-on-a-chip culture device as described herein are contacted with one or more intestinal effector agents. In some embodiments of any of the aspects, the endothelial, immune, or connective cells maintained in an intestinal fluidic organ-on-a-chip culture device as described herein are contacted with one or more intestinal effector agents. By way of non-limiting example, the intestinal epithelial cells maintained in an intestinal fluidic organ-on-a-chip culture device as described herein can be contacted with two or more intestinal effector agents to determine if, e.g., two drugs interact or if a drug modulates the natural gut microflora.

In some embodiments of any of the aspects, the response of the cells can be measured to determine the effect of at least one candidate intestinal effector agent. In some embodiments of any of the aspects, the response of the intestinal epithelial cells is measured. In some embodiments of any of the aspects, the response of the microbial cells is measured. In some embodiments of any of the aspects, the response of the endothelial cells and/or fibroblasts, immune cells, and/or connective tissue cells are measured. Measuring the response of the cells can include, but is not limited to, determining changes in morphology, viability, cell number, metabolic rate, transcription, translation, marker gene expression, levels of a reporter gene, transport, barrier function, morphology of tight junctions, and/or permeability of the cell layer. Measuring the response of the cells can include, but is not limited to, determining the rate at which an intestinal effector agent is taken up by cells, metabolized by cells, secreted by cells, or crosses one or more layers of cells. Measuring the response of the cells can include, but is not limited to, determining how cells metabolize an intestinal effector agent. The drug metabolizing functions of cells also can be assayed before or after villi formation by measuring CYP3A4 enzyme activities using a chemical or luminogenic substrate which is converted to a luminescent form by active CYP3A4 enzyme. Assays for CYP3A4 activity are well known in the art and substrates for detecting CYP3A4 activity are commercially available, e.g. Luciferin-IPA (Cat No V9001; Promega Madison, WI). Non-limiting examples of measuring the response of the cells can include determining cellular morphology using confocal microscopy; determining levels of proteins using immunofluorescence microscopy; and/or determining the integrity of the intestinal epithelial cell monolayer resulting from establishment of apical tight junctions by measuring trans-epithelial electrical resistance (TEER) using a voltage-ohm meter (87V Industrial Multimeter, Fluke Corporation, Everett, WA) coupled to Ag/AgCl electrode wires (0.008" in diameter; A-M systems, Inc., Sequim, WA).

The methods and devices described herein can be used to examine or test intestinal effector agents for the purposes of pharmacology, toxicology, drug development, drug delivery, protein or peptide delivery, drug metabolism, antibiotic effect, suitability and degradability of drug coatings, IgA transport, screening of genetically modified organisms for allergenicity and toxicity, drug-drug interaction drug bioavailability, drug clearance, multi-organ interactions, nanotoxicology, diagnostics, therapeutics, nutritional applications, physiology of intestinal barrier, gastrointestinal (GI) disease models and their mechanism, etiology of disease in the GI tract, wound healing, tissue regeneration, tissue engineering, intestinal homeostasis, intestinal stem cell researches, host-microbes interactions, microbial communities in the GI tract, microbial biofilm in the mucus layer, and probiotics therapies.

In some embodiments of any of the aspects, the methods and devices described herein can be used with cells comprising drug transporter polymorphisms for the purposes of drug development, drug delivery, drug metabolism, and drug clearance studies.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, the terms "fluidic device" and "fluidic chip are used interchangeably and refer to a structure or substrate having fluidic structures contained therein or thereon. In some embodiments of any of the aspects, the chip can be detachably connected to a fluidic system. In some embodiments of any of the aspects, the fluidics device, structure, and/or system can be microfluidic.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease and/or physiology. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors. A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

As used herein, the term "inhibitor" refers to an agent which can decrease the expression and/or activity of a target, e.g. by at least 10% or more, e.g. by 10% or more, 50% or more, 70% or more, 80% or more, 90% or more, 95% or more, or 98% or more. The efficacy of an inhibitor of one or more targets, e.g. its ability to decrease the level and/or activity of the target can be determined, e.g. by measuring the level of an expression product of the target and/or the activity of the target. Methods for measuring the level of a given mRNA and/or polypeptide are known to one of skill in the art, e.g. RT-PCR with primers can be used to determine the level of RNA and Western blotting with an antibody can be used to determine the level of a polypeptide. The activity of, e.g. a ROCK enzyme can be determined using methods known in the art, e.g. using commercially available kits for ROCK activity (e.g. Cat No. CSA001; EMD Millipore; Darmstadt, Germany). In some embodiments, the inhibitor can be an inhibitory nucleic acid; an aptamer; an antibody reagent; an antibody; or a small molecule.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid source such as a fluid reservoir. Two components may be coupled to each other even though they are not in direct contact with each other. For example, two components may be coupled to each other through an intermediate component (e.g. tubing or other conduit).

As used herein, the term "expanding" refers to increasing the number of like cells through cell division (mitosis). The term "proliferating" and "expanding" are used interchangeably.

As used herein, "differentiate", or "differentiating" is a relative term meaning a "differentiated cell" is a cell that has progressed further down the developmental pathway than its precursor cell. Thus in some embodiments, an intestinal epithelial cell as this term is defined herein, can differentiate to an end-stage differentiated cell, which plays a characteristic role in a certain tissue type, and may or may not retain the capacity to proliferate further. In some embodiments of any of the aspects, differentiated intestinal epithelial cells have or exhibit sucrase isomaltose activity, e.g., as compared to undifferentiated intestinal epithelial cells. As used herein, "intact intestinal barrier" refers to a layer (monolayer or greater) of intestinal epithelial cells which is capable of controlling the translocation of intestinal luminal material from the apical side to the basal side while permitting absorption of nutrients. Accordingly, an intact intestinal barrier lacks gaps and has tight junctions between the epithelial cells. An intact intestinal barrier usually comprises differentiated epithelial cells types. The intestinal luminal material which is prevented from translocation can include commensal bacterial cells, undigested food material, and the like. The presence of an intact intestinal barrier can be determined, e.g., by determining if the barrier is differentially permeable and/or by testing translocation of commensal bacteria.

As used herein, "differentially permeable", e.g., in reference to an intestinal barrier, refers to the intestinal barrier displaying a resistance to the passage of certain molecules as compared to monolayers of, e.g., endothelial cells or undifferentiated intestinal epithelial cells. The permeability of an intestinal barrier is typically measured by measuring the permeability of the barrier to tracer molecules such as Lucifer yellow and/or dextran. Such assays are described in the Examples herein in detail. Briefly, the apical side of the intestinal barrier is contacted with one or more tracer molecules and the concentration of the tracer later found on the basal side of the intestinal barrier. In some embodiments, the permeability can be calculated using the following formula:

$$P\_app = J/(A \cdot \Delta C)$$

With Papp=Apparent permeability, J=Molecular flux, A=Total area of diffusion, and ΔC=Average gradient (~1 because of the low flow rate)[22].

Optimal Papp for small intestine-on-chip is ~1×10$^6$ for 450 Da Lucifer Yellow and ~1-2×10$^7$ for 40 kDa Dextran (~10% and ~0.1-0.2% of tracer leakage into the basal channel).

Bacterial translocation can be measured by providing bacterial cells to the apical side of an intestinal epithelial cell culture and measuring the number of bacteria which are able to translocate to the basal side. Such measurements can be done by microscopy, CFU's, FACS, or any other suitable method known in the art.

As used herein, "exhibits digestive capacity" refers to the ability of a cell or cells to successfully enzymatically catalyze one or more digestive reactions, e.g., proteolysis (e.g., by carboxypeptidase) and/or hydrolysis of carbohydrates (e.g., by amylase, dextrinase, glucoamylase, and lactase, and sucrase isomaltose). In some embodiments of any of the aspects, digestive capacity can be exhibited by detectable levels of sucrase isomaltose (a brush border enzyme which breaks down sucrose to release glucose and fructose) and/or sucrase isomaltose activity. In some embodiments of any of the aspects, digestive capacity can be exhibited by production of one or more active brush border enzymes.

As used herein, "oxidizing the porous membrane" refers to a process that involves deliberately contacting the porous membrane with an oxidizing reagent. In some embodiments, oxidizing excludes naturally occurring oxidizing processes, such as those that occur when biological samples are exposed to oxygen, such as may be present in ambient air. Rather, the term encompasses oxidizing processes resulting from deliberate contact with an oxidizing agent.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.)

John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of providing an in vitro intestinal model system, the method comprising:
    a. providing i) an intestinal enteroid comprising primary intestinal epithelial cells, ii) intestinal endothelial cells, and iii) a microfluidic culture device, the device comprising a porous membrane having first and second surfaces, said membrane in fluidic communication with a microchannel, said microchannel in fluidic communication with a source of fluid;
    b. establishing a culture of said intestinal endothelial cells on said first surface of said porous membrane;
    c. disrupting said intestinal enteroid comprising primary intestinal epithelial cells into enteroid fragments;
    d. seeding said second surface of said porous membrane with said enteroid fragments so as to create seeded primary intestinal epithelial cells;
    e. expanding said seeded primary intestinal epithelial cells so as to create a monolayer of cells; and
    f. differentiating said monolayer of cells so as to create two or more different differentiated intestinal cell types.
2. A method of providing an in vitro intestinal model system, the method comprising:
    a. providing i) primary intestinal epithelial cells, ii) intestinal endothelial cells, and iii) a microfluidic culture device, the device comprising a porous membrane having first and second surfaces, said membrane in fluidic communication with a microchannel, said microchannel in fluidic communication with a source of fluid;
    b. establishing a culture of said intestinal endothelial cells on said first surface of said porous membrane;
    c. seeding said second surface of said porous membrane with said primary intestinal epithelial cells so as to create seeded primary intestinal epithelial cells;
    d. expanding said seeded primary intestinal epithelial cells so as to create a monolayer of cells; and
    e. differentiating said monolayer of cells so as to create two or more different differentiated intestinal cell types.
3. The method of any of paragraphs 1-2, wherein said monolayer is exposed to a cyclic stretching regimen of said membrane.
4. The method of any of paragraphs 1-3, wherein said monolayer is exposed to said fluid from said source of fluid.
5. The method of paragraph 4, wherein said monolayer is exposed to said fluid at a flow rate whereupon intestinal villi form.
6. The method of paragraph 5, wherein said monolayer is exposed to both a cyclic stretching regimen of said membrane and fluid at a flow rate.
7. The method of paragraph 6, wherein said monolayer is exposed to said stretching and said flow rate for a period of days.
8. The method of paragraph 7, wherein said period of days comprises 11 days.
9. The method of any of paragraphs 1-8, wherein said different differentiated intestinal cell types comprise absorptive enterocytes, Paneth cells, goblet cells and enteroendocrine cells.
10. The method of paragraph 9, wherein at least one of said differentiated intestinal cell types exhibits digestive capacity.
11. The method of paragraph 9, wherein said different differentiated intestinal cell types are human cells.
12. A method of providing an in vitro intestinal model system, the method comprising:
    a. providing an intestinal microfluidic organ-on-a-chip culture device, the device comprising a porous membrane having a molecular coating that mediates cell adhesion;

b. establishing a culture of intestinal endothelial cells on a first surface of a porous membrane of an intestinal microfluidic organ-on-a-chip culture device;
c. disrupting an intestinal enteroid comprising intestinal epithelial cells into enteroid fragments comprising intestinal epithelial cells in the presence of a ROCK inhibitor;
d. establishing a culture of intestinal epithelial cells on a second surface of the porous membrane of the intestinal microfluidic organ-on-a-chip culture device by contacting the second surface with the enteroid fragments comprising intestinal epithelial cells resulting from step c; and
e. maintaining the culture of the intestinal endothelial cells and intestinal epithelial cells in the intestinal microfluidic organ-on-a-chip culture device.

13. A method of providing an in vitro intestinal model system, the method comprising:
a. providing an intestinal microfluidic organ-on-a-chip culture device, the device comprising a porous membrane;
b. establishing a culture of intestinal epithelial cells on a first surface of the porous membrane of the intestinal microfluidic organ-on-a-chip culture device by contacting the surface with intestinal epithelial cells; and
c. maintaining the culture of the intestinal endothelial cells and intestinal epithelial cells in the intestinal microfluidic organ-on-a-chip culture device.

14. The method of paragraph 13, wherein the porous membrane has a molecular coating that mediates cell adhesion.

15. The method of any of paragraphs 13-14, wherein prior to establishing the culture of intestinal epithelial cells on a first surface of the porous membrane, a culture of intestinal endothelial cells has been established on a second surface of the porous membrane.

16. The method of any of paragraphs 13-15, wherein contacting the surface with intestinal epithelial cells comprises contacting the surface with an intestinal enteroid comprising intestinal epithelial cells.

17. The method of paragraph 16, wherein the intestinal enteroid comprising intestinal epithelial cells is disrupted into enteroid fragments prior to establishing the culture of intestinal epithelial cells on the first surface of the porous membrane.

18. The method of paragraph 17, wherein the disruption of the intestinal enteroid is performed in the presence of a ROCK inhibitor.

19. The method of any of paragraphs 1-18, wherein the molecular coating that mediates cell adhesion comprises a hydrogel.

20. The method of any of paragraphs 1-19, wherein the molecular coating that mediates cell adhesion comprises an extracellular matrix hydrogel.

21. The method of any of paragraphs 1-20, wherein the molecular coating that mediates cell adhesion comprises a basement membrane preparation.

22. The method of any of paragraphs 1-21, wherein the molecular coating that mediates cell adhesion comprises at least one extracellular matrix molecule.

23. The method of paragraph 22, wherein the extracellular matrix molecule is selected from the group consisting of:
laminin, heparan sulfate proteoglycan; fibronectin; collagen; type I collagen; and type IV collagen.

24. The method of any of paragraphs 1-23, wherein the porous membrane is activated for chemical cross-linking before being exposed to the molecular coating that mediates cell adhesion.

25. The method of any of paragraphs 1-24, wherein the porous membrane comprises PDMS; polyester (PET); and/or polycarbonate.

26. The method of any of any paragraphs 1-25, wherein the method further comprises coating the porous membrane with the molecular coating that mediates cell adhesion by: oxidizing the porous membrane; and
contacting the porous membrane with the molecular coating that mediates cell adhesion.

27. The method of any of any paragraphs 1-26, wherein the method further comprises coating the porous membrane with the molecular coating that mediates cell adhesion by:
oxidizing the porous membrane;
functionalizing the porous membrane by silanization; and
contacting the porous membrane with the molecular coating that mediates cell adhesion.

28. The method of any of paragraphs 26-27, wherein oxidation of the porous membrane comprises exposing the porous membrane to oxygen plasma; plasma discharge; polyethylene glycol (PEG); polyvinyl alcohol (PVA); or a liquid oxidizer.

29. The method of any of paragraphs 27-28, wherein the silanization is performed using a silane selected from the group consisting of: aminosilane; (3-aminopropyl) triethoxy silane; sulfhydrylsilane; and epoxysilane.

30. The method of any of paragraphs 27-29, wherein the functionalizing step further comprises treating the porous membrane with a cross-linker after silanization.

31. The method of paragraph 30, wherein the cross-linker is selected from the group consisting of:
N-γ-maleimidobutyryloxy succinimide ester; DMA; DMS; glutaraldehyde (GA); carbodiimide (1-ethyl-3-(3-dimethyl aminopropyl)-carbodiimide (EDC)); epoxy compounds; six methylene diisocyanate, glycerin; alginate; genipin (GP); nordihydroguaiaretic acid (NDGA); tannic acid; and procyanidins (PC).

32. The method of any of any paragraphs 1-31, wherein the method further comprises coating the porous membrane with the molecular coating that mediates cell adhesion by:
oxidizing the porous membrane;
functionalizing the porous membrane by silanization; and
contacting the porous membrane with the molecular coating that mediates cell adhesion.

33. The method of any of paragraphs 1-32, wherein establishing a culture of intestinal endothelial cells on a first surface of a porous membrane of an intestinal culture fluidics device comprises culturing the cells under conditions suitable for them to form a monolayer on the porous membrane.

34. The method of any of paragraphs 1-33, wherein the intestinal endothelial cells are mammalian intestinal endothelial cells.

35. The method of any of paragraphs 1-34, wherein the intestinal endothelial cells are human intestinal endothelial cells.

36. The method of any of paragraphs 1-35, wherein the intestinal endothelial cells are primary intestinal endothelial cells.

37. The method of any of paragraphs 1-36, wherein the intestinal endothelial cells are obtained from a subject.
38. The method of any of paragraphs 1-37, wherein the intestinal enteroid is disrupted into enteroid fragments to provide groups of from about 1 to about 100 intestinal epithelial cells.
39. The method of any of paragraphs 1-38, wherein the intestinal enteroid is disrupted into enteroid fragments to provide groups of from about 10 to about 30 intestinal epithelial cells.
40. The method of any of paragraphs 1-39, wherein the intestinal enteroid is disrupted into enteroid fragments to provide fragments of from about 10 μm to about 500 μm in diameter.
41. The method of any of paragraphs 1-40, wherein the intestinal enteroid is disrupted into enteroid fragments to provide fragments of from about 40 μm to about 100 μm in diameter.
42. The method of any of paragraphs 1-41, wherein the intestinal enteroid is obtained from a subject.
43. The method of any of paragraphs 1-42, wherein the intestinal enteroid is obtained from a resected intestinal tissue or an endoscopic biopsy tissue.
44. The method of any of paragraphs 1-43, wherein the intestinal epithelial cells are mammalian intestinal epithelial cells.
45. The method of any of paragraphs 1-44, wherein the intestinal epithelial cells are human intestinal epithelial cells.
46. The method of any of paragraphs 1-45, wherein the intestinal epithelial cells are not tumor cell line-derived cells.
47. The method of any of paragraphs 1-46, wherein the intestinal enteroid is obtained by: washing a resected intestinal tissue or an endoscopic biopsy tissue and removing any associated muscle or mucosa layers;
contacting the tissue with one or more extracellular-matrix degrading enzymes;
removing an intestinal crypt from the supernatant resulting from the contacting step;
embedding the intestinal crypt in a hydrogel; and
maintaining the intestinal crypt in the hydrogel to form an intestinal enteroids.
48. The method of any of paragraphs 1-47, wherein the ROCK inhibitor is selected from the group consisting of:
fasudil; Y27632; Y39983; Wf-536; SLx-2119; an azabenzimidazole-aminofurazan; DE-104; an olefin; an isoquinoline; an indazole; a pyridinealkene derivative; H-1152P; an ROKα inhibitor (BF) XD-4000; HMN-1152; a 4-(1-aminoalkyl)-N-(4-pyridyl)cyclohexane-carboxamide; rhostatin; BA-210; BA-207; BA-215; BA-285; BA-1037; Ki-23095; VAS-012; and a quinazoline.
49. The method of any of paragraphs 1-48, wherein a glycogen synthase kinase 3 (GSK-3) inhibitor is present during the disruption step.
50. The method of any of paragraphs 1-49, wherein the maintaining step comprises providing a flow of culture medium through each channel of the intestinal microfluidic organ-on-a-chip culture device at a volumetric flow rate of about 10 to about 5000 μl h$^{-1}$.
51. The method of any of paragraphs 1-50, wherein the maintaining step comprises providing a flow of culture medium through each channel of the intestinal microfluidic organ-on-a-chip culture device at a volumetric flow rate of about 10 to about 500 μl h$^{-1}$.
52. The method of any of paragraphs 1-51, wherein the maintaining step comprises providing a flow of culture medium through each channel of the intestinal microfluidic organ-on-a-chip culture device at a volumetric flow rate of about 60 μl h$^{-1}$.
53. The method of any of paragraphs 1-52, wherein the maintaining step comprises stretching the porous membrane at about 0-1 Hz with an about 0-20% mean cell strain.
54. The method of any of paragraphs 1-53, wherein the maintaining step comprises stretching the porous membrane at about 0.15 Hz with an about 10% mean cell strain.
55. The method of any of paragraphs 1-54, wherein the maintaining step comprises providing the endothelial cells with EGM2-MV medium.
56. The method of any of paragraphs 1-55, wherein the maintaining step comprises providing the epithelial cells with expansion medium comprising one or more of the following:
Wnt-3A; EGF; Rspo1; Noggin; gastrin; TGF-β receptor inhibitor; p38 MAPK inhibitor.
57. The method of any of paragraphs 1-56, wherein the maintaining step comprises providing the epithelial cells with expansion medium comprising Wnt-3A; EGF; Rspo1; Noggin; gastrin; TGF-β receptor inhibitor; and p38 MAPK inhibitor.
58. The method of any of paragraphs 56-57, wherein the expansion medium further comprises nicotamide.
59. The method of paragraph 1-58, wherein the expansion medium further comprises a ROCK inhibitor for about 1 to about 4 days after introducing the epithelial cells to the intestinal microfluidic organ-on-a-chip culture device.
60. The method of paragraph 1-59, wherein the expansion medium further comprises a ROCK inhibitor for about 2 days after introducing the epithelial cells to the intestinal microfluidic organ-on-a-chip culture device.
61. The method of any of paragraphs 1-60, wherein the maintaining step comprises morphological and functional differentiation of the intestinal epithelial cells in co-culture with the intestinal endothelial cells.
62. The method of paragraph 61, wherein said differentiation of the intestinal epithelial cells comprises differentiation of the cells to at least two or more of: absorptive enterocytes, Paneth cells, goblet cells and enteroendocrine cells.
63. The method of paragraph 62, wherein at least one of said differentiated cells exhibits digestive capacity.

Some embodiments of the technology described herein can be defined according to any of the following numbered paragraphs:
1. A method of providing an in vitro intestinal model system, the method comprising:
   a. providing i) an intestinal enteroid or colonoid comprising primary intestinal epithelial cells, ii) a microfluidic culture device, the device comprising a porous membrane having first and second surfaces, said membrane in fluidic communication with a microchannel, said microchannel in fluidic communication with a source of fluid;
   b. disrupting said intestinal enteroid or colonoid comprising primary intestinal epithelial cells into enteroid or colonoid fragments;
   c. seeding said second surface of said porous membrane with said enteroid or colonoid fragments so as to create seeded primary intestinal epithelial cells;

d. expanding said seeded primary intestinal epithelial cells so as to create a monolayer of cells; and
e. differentiating said monolayer of cells so as to create two or more different differentiated intestinal cell types.

2. The method of paragraph 1, the method further comprising:
providing intestinal endothelial cells and/or fibroblasts; and
establishing a culture of said intestinal endothelial cells and/or fibroblasts on said first surface of said porous membrane.

3. A method of providing an in vitro intestinal model system, the method comprising:
a. providing i) primary intestinal epithelial cells and ii) a microfluidic culture device, the device comprising a porous membrane having first and second surfaces, said membrane in fluidic communication with a microchannel, said microchannel in fluidic communication with a source of fluid;
b. seeding said second surface of said porous membrane with said primary intestinal epithelial cells so as to create seeded primary intestinal epithelial cells;
c. expanding said seeded primary intestinal epithelial cells so as to create a monolayer of cells; and
d. differentiating said monolayer of cells so as to create two or more different differentiated intestinal cell types.

4. The method of paragraph 3, further comprising providing intestinal endothelial cells and/or fibroblasts; and
establishing a culture of said intestinal endothelial cells and/or fibroblasts on said first surface of said porous membrane.

5. The method of any of paragraphs 1-4, wherein said one or more monolayers is exposed to a cyclic stretching regimen of said membrane.

6. The method of any of paragraphs 1-5, wherein said one or more monolayers is exposed to said fluid from said source of fluid.

7. The method of paragraph 7, wherein said epithelial monolayer is exposed to said fluid at a flow rate whereupon intestinal villi; folds; and/or an intact intestinal barrier form.

8. The method of any of paragraphs 7-8, wherein said epithelial monolayer is exposed to both a cyclic stretching regimen of said membrane and fluid at a flow rate.

9. The method of paragraph 8, wherein said monolayer is exposed to said stretching and said flow rate for a period of days.

10. The method of paragraph 9, wherein said period of days comprises 11 days.

11. The method of paragraph 9, wherein said period of days comprises more than 10 days.

12. The method of any of paragraphs 1-11, wherein said different differentiated intestinal cell types comprise absorptive enterocytes, Paneth cells, goblet cells and enteroendocrine cells.

13. The method of paragraph 12, wherein at least one of said differentiated intestinal cell types exhibits digestive capacity.

14. The method of paragraph 12, wherein at least one of said differentiated intestinal cell types exhibits mucus secretion.

15. The method of paragraph 12, wherein the differentiated intestinal cells form a differentially permeable intestinal barrier.

16. The method of paragraph 12, wherein said different differentiated intestinal cell types are human cells.

17. A method of providing an in vitro intestinal model system, the method comprising:
a. providing an intestinal microfluidic organ-on-a-chip culture device, the device comprising a porous membrane having a molecular coating that mediates cell adhesion;
b. disrupting an intestinal enteroid, colonoid, or organoid comprising intestinal epithelial cells into enteroid, colonoid, or organoid fragments comprising intestinal epithelial cells in the presence of a ROCK inhibitor;
c. establishing a culture of intestinal epithelial cells on a second surface of the porous membrane of the intestinal microfluidic organ-on-a-chip culture device by contacting the second surface with the enteroid, colonoid, or organoid fragments comprising intestinal epithelial cells resulting from step b; and
d. maintaining the culture of the intestinal epithelial cells in the intestinal microfluidic organ-on-a-chip culture device.

18. The method of paragraph 17, further comprising:
establishing a culture of intestinal endothelial cells and/or fibroblasts on a first surface of a porous membrane of an intestinal microfluidic organ-on-a-chip culture device; and
maintaining the culture of the intestinal endothelial cells and/or fibroblasts and intestinal epithelial cells in the intestinal microfluidic organ-on-a-chip culture device.

19. A method of providing an in vitro intestinal model system, the method comprising:
a. providing an intestinal microfluidic organ-on-a-chip culture device, the device comprising a porous membrane;
b. establishing a culture of intestinal epithelial cells on a second surface of the porous membrane of the intestinal microfluidic organ-on-a-chip culture device by contacting the surface with intestinal epithelial cells; and
c. maintaining the culture of intestinal epithelial cells in the intestinal microfluidic organ-on-a-chip culture device.

20. The method of paragraph 19, the method further comprising:
establishing a culture of intestinal endothelial cells and/or fibroblasts on a first surface of the porous membrane of the intestinal microfluidic organ-on-a-chip culture device by contacting the surface with intestinal epithelial cells, and
maintaining the culture of intestinal epithelial cells and intestinal endothelial cells and/or fibroblasts in the intestinal microfluidic organ-on-a-chip culture device.

21. The method of any of paragraphs 1-20, wherein the porous membrane has a molecular coating that mediates cell adhesion.

22. The method of any of paragraphs 1-21, wherein prior to establishing the culture of intestinal epithelial cells on a second surface of the porous membrane, the culture of intestinal endothelial cells and/or fibroblasts has been established on a first surface of the porous membrane.

23. The method of any of paragraphs 1-22, wherein prior to establishing the culture of intestinal endothelial cells and/or fibroblasts on a first surface of the porous membrane, the culture of intestinal epithelial cells has been established on a second surface of the porous membrane.

24. The method of any of paragraphs 1-23, wherein the culture of intestinal endothelial cells and/or fibroblasts is established on a first surface of the porous membrane concurrently with establishing the culture of intestinal epithelial cells on a second surface of the porous membrane.

25. The method of any of paragraphs 1-24, wherein contacting the surface with intestinal epithelial cells comprises contacting the surface with an intestinal enteroid, colonoid, or organoid comprising intestinal epithelial cells.

26. The method of paragraph 25, wherein the intestinal enteroid, colonoid, or organoid comprising intestinal epithelial cells is disrupted into enteroid, colonoid, or organoid fragments prior to establishing the culture of intestinal epithelial cells on the first surface of the porous membrane.

27. The method of paragraph 26, wherein the disruption of the intestinal enteroid, colonoid, or organoid is performed in the presence of a ROCK inhibitor.

28. The method of any of paragraphs 1-27, wherein the method further comprises exposing the cells to an agent.

29. The method of paragraph 28, wherein said agent is a candidate intestinal effector agent.

30. The method of paragraph 29, wherein the method further comprises measuring the response of the cells to determine the effect of said candidate intestinal effector agent.

31. The method of any of paragraphs 1-30, wherein the molecular coating that mediates cell adhesion comprises a hydrogel.

32. The method of any of paragraphs 1-31, wherein the molecular coating that mediates cell adhesion comprises an extracellular matrix hydrogel.

33. The method of any of paragraphs 1-32, wherein the molecular coating that mediates cell adhesion comprises a basement membrane preparation.

34. The method of any of paragraphs 1-33, wherein the molecular coating that mediates cell adhesion comprises at least one extracellular matrix molecule.

35. The method of paragraph 34, wherein the extracellular matrix molecule is selected from the group consisting of:
laminin, heparan sulfate proteoglycan; fibronectin; collagen; type I collagen; and type IV collagen.

36. The method of any of paragraphs 1-35, wherein the porous membrane is activated for chemical cross-linking before being exposed to the molecular coating that mediates cell adhesion.

37. The method of any of paragraphs 1-36, wherein the porous membrane comprises PDMS; polyester (PET); and/or polycarbonate.

38. The method of any of paragraphs 1-37, wherein the method further comprises coating the porous membrane with the molecular coating that mediates cell adhesion by:
oxidizing the porous membrane; and
contacting the porous membrane with the molecular coating that mediates cell adhesion.

39. The method of any of any paragraphs 1-38, wherein the method further comprises coating the porous membrane with the molecular coating that mediates cell adhesion by.
oxidizing the porous membrane;
functionalizing the porous membrane by silanization; and
contacting the porous membrane with the molecular coating that mediates cell adhesion.

40. The method of any of paragraphs 38-39, wherein oxidation of the porous membrane comprises exposing the porous membrane to oxygen plasma; plasma discharge; polyethylene glycol (PEG); polyvinyl alcohol (PVA); or a liquid oxidizer.

41. The method of any of paragraphs 39-40, wherein the silanization is performed using a silane selected from the group consisting of: aminosilane; (3-aminopropyl) triethoxy silane; sulfhydrylsilane; and epoxysilane.

42. The method of any of paragraphs 39-41, wherein the functionalizing step further comprises treating the porous membrane with a cross-linker after silanization.

43. The method of paragraph 42, wherein the cross-linker is selected from the group consisting of:
N-γ-maleimidobutyryloxy succinimide ester, DMA; DMS; glutaraldehyde (GA); carbodiimide (1-ethyl-3-(3-dimethyl aminopropyl)-carbodiimide (EDC)); epoxy compounds; six methylene diisocyanate, glycerin; alginate; genipin (GP); nordihydroguaiaretic acid (NDGA); tannic acid, and procyanidins (PC).

44. The method of any of any paragraphs 1-43, wherein the method further comprises coating the porous membrane with the molecular coating that mediates cell adhesion by:
oxidizing the porous membrane;
functionalizing the porous membrane by silanization; and
contacting the porous membrane with the molecular coating that mediates cell adhesion.

45. The method of any of paragraphs 1-44, wherein establishing a culture of intestinal endothelial cells and/or fibroblasts on a first surface of a porous membrane of an intestinal culture fluidics device comprises culturing the cells under conditions suitable for them to form a monolayer on the porous membrane.

46. The method of any of paragraphs 1-45, wherein the intestinal endothelial cells and/or fibroblasts are mammalian intestinal endothelial cells and/or fibroblasts.

47. The method of any of paragraphs 1-46, wherein the intestinal endothelial cells and/or fibroblasts are human intestinal endothelial cells and/or fibroblasts.

48. The method of any of paragraphs 1-47, wherein the intestinal endothelial cells and/or fibroblasts are mouse intestinal endothelial cells and/or fibroblasts.

49. The method of any of paragraphs 1-48, wherein the intestinal endothelial cells and/or fibroblasts are primary intestinal endothelial cells and/or fibroblasts.

50. The method of any of paragraphs 1-49, wherein the intestinal endothelial cells and/or fibroblasts are obtained from a subject.

51. The method of any of paragraphs 1-50, wherein the intestinal endothelial cells are small intestine endothelial cells or colon endothelial cells.

52. The method of any of paragraphs 1-51, wherein the intestinal enteroid, colonoid, or organoid is disrupted into enteroid fragments to provide groups of from about 2 to about 100 intestinal epithelial cells.

53. The method of any of paragraphs 1-52, wherein the intestinal enteroid, colonoid, or organoid is disrupted into enteroid fragments to provide groups of from about 10 to about 30 intestinal epithelial cells.

54. The method of any of paragraphs 1-53, wherein the intestinal enteroid, colonoid, or organoid is disrupted into enteroid fragments to provide fragments of from about 10 μm to about 500 μm in diameter.

55. The method of any of paragraphs 1-54, wherein the intestinal enteroid, colonoid, or organoid is disrupted into enteroid fragments to provide fragments of from about 40 μm to about 100 μm in diameter.

56. The method of any of paragraphs 1-55, wherein the intestinal enteroid or colonoid is obtained from a subject.

57. The method of any of paragraphs 1-56, wherein the intestinal enteroid or colonoid is obtained from a resected intestinal tissue or an endoscopic biopsy tissue.

58. The method of any of paragraphs 1-57, wherein the enteroids or colonoids are derived from histologically normal duodenal, jejunal, and ileal endoscopic biopsies.

59. The method of any of paragraphs 1-58, wherein the intestinal epithelial cells are obtained from induced pluripotent stem cells.

60. The method of any of paragraphs 1-59, wherein the intestinal epithelial cells are mammalian intestinal epithelial cells.

61. The method of any of paragraphs 1-60, wherein the intestinal epithelial cells are human intestinal epithelial cells.

62. The method of any of paragraphs 1-60, wherein the intestinal epithelial cells are mouse intestinal epithelial cells.

63. The method of any of paragraphs 1-62, wherein the intestinal epithelial cells are not tumor cell line-derived cells.

64. The method of any of paragraphs 1-63, wherein the intestinal epithelial cells are small intestine epithelial cells or colon epithelial cells.

65. The method of any of paragraphs 1-64, wherein the intestinal enteroid or colonoid is obtained by:
    washing a resected intestinal tissue or an endoscopic biopsy tissue and removing any associated muscle or mucosa layers;
    contacting the tissue with one or more extracellular-matrix degrading enzymes; removing an intestinal crypt from the supernatant resulting from the contacting step;
    embedding the intestinal crypt in a hydrogel; and
    maintaining the intestinal crypt in the hydrogel to form an intestinal enteroids and/or colonoids.

66. The method of any of paragraphs 1-65, wherein the ROCK inhibitor is selected from the group consisting of:
    fasudil; Y27632; Y39983; Wf-536; SLx-2119; an azabenzimidazole-aminofurazan; DE-104; an olefin; an isoquinoline; an indazole; a pyridinealkene derivative; H-1152P; an ROKα inhibitor (BF); XD-4000; HMN-1152; a 4-(1-aminoalkyl)-N-(4-pyridyl)cyclohexane-carboxamide; rhostatin; BA-210; BA-207; BA-215; BA-285; BA-1037; Ki-23095, VAS-012; and a quinazoline.

67. The method of any of paragraphs 1-66, wherein a glycogen synthase kinase 3 (GSK-3) inhibitor is present during the disruption step.

68. The method of any of paragraphs 1-67, wherein the maintaining step comprises providing a flow of culture medium through each channel of the intestinal microfluidic organ-on-a-chip culture device at a volumetric flow rate of about 10 to about 5000 μl h$^{-1}$.

69. The method of any of paragraphs 1-68, wherein the maintaining step comprises providing a flow of culture medium through each channel of the intestinal microfluidic organ-on-a-chip culture device at a volumetric flow rate of about 10 to about 500 μl h$^{-1}$.

70. The method of any of paragraphs 1-69, wherein the maintaining step comprises providing a flow of culture medium through each channel of the intestinal microfluidic organ-on-a-chip culture device at a volumetric flow rate of about 60 μl h$^{-1}$.

71. The method of any of paragraphs 1-70, wherein the maintaining step comprises stretching the porous membrane at about 0-1 Hz with an about 0-20% mean cell strain.

72. The method of any of paragraphs 1-71, wherein the maintaining step comprises stretching the porous membrane at about 0-1 Hz with an about 0-10% mean cell strain.

73. The method of any of paragraphs 1-72, wherein the maintaining step comprises stretching the porous membrane at about 0.15 Hz with an about 10% mean cell strain.

74. The method of any of paragraphs 1-73, wherein the maintaining step comprises providing the endothelial cells and/or fibroblasts with EGM2-MV medium.

75. The method of any of paragraphs 1-74, wherein the maintaining step comprises culturing the cells under continuous flow and stretching that mimics physical forces experienced by the cells present in the native intestine.

76. The method of any of paragraphs 1-75, wherein the maintaining step comprises providing the epithelial cells with expansion medium comprising one or more of the following:
    Wnt-3A; EGF; Rspo1; Noggin; gastrin; TGF-β receptor inhibitor; p38 MAPK inhibitor.

77. The method of any of paragraphs 1-76, wherein the maintaining step comprises providing the epithelial cells with expansion medium comprising Wnt-3A; EGF; Rspo1; Noggin; gastrin; TGF-β receptor inhibitor; and p38 MAPK inhibitor.

78. The method of any of paragraphs 1-77, wherein the maintaining step comprises providing i) the epithelial cells and/or ii) the intestinal endothelial cells and/or fibroblasts with expansion medium comprising one or more of the following:
    Wnt-3A; EGF; Rspo1; Noggin; gastrin; TGF-β receptor inhibitor; p38 MAPK inhibitor; Jagged (JAG) polypeptide and an inhibitor of GSK.

79. The method of any of paragraphs 1-78, wherein the maintaining step comprises providing i) the epithelial cells and/or ii) the intestinal endothelial cells and/or fibroblasts with expansion medium comprising:
    Wnt-3A; EGF; Rspo1; Noggin; gastrin; TGF-β receptor inhibitor; p38 MAPK inhibitor: Jagged (JAG) polypeptide and an inhibitor of GSK.

80. The method of any of paragraphs 1-79, wherein the maintaining step comprises contacting at least the endothelial cells with a glycogen synthase kinase 3 (GSK-3) inhibitor for at least the first two days of the maintaining step.
81. The method of any of paragraphs 74-80, wherein the expansion medium further comprises nicotamide.
82. The method of paragraph 1-81, wherein the expansion medium further comprises a ROCK inhibitor for about 1 to about 7 days after introducing the epithelial cells to the intestinal microfluidic organ-on-a-chip culture device.
83. The method of paragraph 1-82, wherein the expansion medium further comprises a ROCK inhibitor for about 1 to about 4 days after introducing the epithelial cells to the intestinal microfluidic organ-on-a-chip culture device.
84. The method of paragraph 1-83, wherein the expansion medium further comprises a ROCK inhibitor for about 2 days after introducing the epithelial cells to the intestinal microfluidic organ-on-a-chip culture device.
85. The method of paragraph 1-84, wherein the expansion medium further comprises a GSK inhibitor for about 2 days after introducing the epithelial cells to the intestinal microfluidic organ-on-a-chip culture device.
86. The method of any of paragraphs 1-85, wherein the maintaining step comprises morphological and functional differentiation of the intestinal epithelial cells in co-culture with the intestinal endothelial cells and/or fibroblasts.
87. The method of paragraph 86, wherein said differentiation of the intestinal epithelial cells comprises differentiation of the cells to at least two or more of: absorptive enterocytes, Paneth cells, goblet cells and enteroendocrine cells.
88. The method of paragraph 87, wherein at least one of said differentiated cells exhibits digestive capacity.
89. The method of paragraph 87, wherein at least one of said differentiated cells exhibits mucus secreting capacity.
90. The method of any of paragraphs 1-89, wherein the epithelial cells exhibit polarized distribution of one or more ion transporters following the expansion and/or maintaining step.
91. The method of paragraph 90, wherein the one or more ion transporters are NHE3 and Na+/K+-ATPase.
92. The method of paragraph 91, wherein polarized distribution of NHE3 comprises higher concentrations of NHE3 at the brush border membrane of an epithelial cell as compared to other membranes of the epithelial cell; and/or polarized distribution of Na+/K+-ATPase comprises higher concentrations of Na+/K+-ATPase at the basolateral membrane of an epithelial cell as compared to other membranes of the epithelial cell.
93. The method of paragraph 91, wherein polarized distribution of NHE3 comprises NHE3 being detectable exclusively at the brush border membrane of an epithelial cell as compared to other membranes of the epithelial cell; and/or polarized distribution of Na+/K+-ATPase comprises Na+/K+-ATPase being detectable exclusively at the basolateral membrane of an epithelial cell as compared to other membranes of the epithelial cell.
94. The method of any of paragraphs 1-93, wherein the step of differentiating comprises providing a medium to the intestinal epithelial cells which:
  a. comprises an inhibitor of Notch signaling; and
  b. does not comprise Wnt-3A; nicotamide; and SB2001190.
95. The method of paragraph 94, wherein the inhibitor of Notch signaling is DAPT.
96. The method of any of paragraphs 1-95, wherein the method further comprises contacting the intestinal epithelial cells with bacterial cells of one or more species.
97. The method of paragraph 96, wherein the method further comprises co-culturing the epithelial cells and bacterial cells for at least 24 hours.
98. The method of paragraph 96, wherein the method further comprises co-culturing the epithelial cells and bacterial cells for at least 48 hours.
99. The method of any of paragraphs 96-98, wherein the co-culture step further comprises:
  a. providing medium to the intestinal epithelial cells and bacterial cells at at least 60 µL/hr;
  b. providing medium to the intestinal epithelial cells and bacterial cells at about 120 µL/hr.
100. The method of any of paragraphs 97-99, wherein the co-culture step further comprises:
  a. providing medium to the intestinal epithelial cells and bacterial cells at at least 60 µL/hr;
  b. providing medium to the intestinal epithelial cells and bacterial cells at about 120 µL/hr;
  c. causing the membrane to strain along at least one axis at about 10% strain; and/or
  d. causing the membrane to strain along at least one axis at a frequency of about 0.2 Hz.
101. The method of any of paragraphs 1-100, wherein the method further comprises contacting the intestinal epithelial cells with at least one endotoxin.
102. The method of paragraph 101, wherein the endotoxin is lipopolysaccharide (LPS).
103. A method of providing an in vitro intestinal model system, the method comprising:
  a. providing an intestinal microfluidic organ-on-a-chip culture device, the device comprising a porous membrane wherein said membrane comprises a first and a second surface;
  b. providing i) a sample of intestinal epithelial tissue, wherein said tissue comprises intestinal epithelial cells associated with intestinal crypts ii) one or more extracellular-matrix degrading enzymes and iii) a hydrogel;
  c. washing said sample of intestinal epithelial tissue;
  d. removing any associated muscle or mucosa layers from said tissue and then placing said tissue in solution;
  e. contacting said tissue with said one or more extracellular-matrix degrading enzymes, thereby releasing said intestinal crypts from said tissue into said solution;
  f. removing said intestinal crypt from said enzyme treated tissue solution then culturing said crypt in said hydrogel in the presence of Wnt3A, R-spondin, Noggin, and EGF to form an intestinal enteroid and/or colonoid;
  g. disrupting the intestinal enteroid and/or colonoid comprising intestinal epithelial cells into enteroid and/or colonoid fragments comprising intestinal epithelial cells in the presence of a ROCK inhibitor;
  h. establishing a culture of intestinal epithelial cells on a second surface of the porous membrane of the intestinal microfluidic organ-on-a-chip culture device by contacting the second surface with the enteroid and/or colonoid fragments comprising intestinal epithelial cells resulting from step g; and i. maintaining the culture of the intestinal epithelial cells in the intestinal microfluidic organ-on-a-chip culture device by providing culture medium under continuous flow.

104. A method of providing an in vitro intestinal model system, the method comprising:
   a. providing an intestinal microfluidic organ-on-a-chip culture device, the device comprising a porous membrane wherein said membrane comprises a first and a second surface;
   b. providing i) a sample of intestinal epithelial tissue, wherein said tissue comprises intestinal epithelial cells associated with intestinal crypts ii) one or more extracellular-matrix degrading enzymes and iii) a hydrogel;
   c. washing said sample of intestinal epithelial tissue;
   d. removing any associated muscle or mucosa layers from said tissue and then placing said tissue in solution;
   e. contacting said tissue with said one or more extracellular-matrix degrading enzymes, thereby releasing said intestinal crypts from said tissue into said solution;
   f. removing said intestinal crypt from said enzyme treated tissue solution then culturing said crypt in said hydrogel in the presence of Wnt3A, R-spondin, Noggin, and EGF to form an intestinal enteroid and/or colonoid;
   g. disrupting the intestinal enteroid and/or colonoid comprising intestinal epithelial cells into enteroid and/or colonoid fragments comprising intestinal epithelial cells in the presence of a ROCK inhibitor;
   h. establishing a culture of intestinal epithelial cells on a second surface of the porous membrane of the intestinal microfluidic organ-on-a-chip culture device by contacting the second surface with the enteroid and/or colonoid fragments comprising intestinal epithelial cells resulting from step g; and
   i. maintaining the culture of the intestinal epithelial cells in the intestinal microfluidic organ-on-a-chip culture device by providing culture medium under continuous flow for at least 12 days of culture.

105. The method of any of paragraphs 103-104, wherein the sample is obtained from a subject.

106. The method of any of paragraphs 103-105, further comprising:
   establishing a culture of intestinal endothelial cells and/or fibroblasts on a first surface of a porous membrane of an intestinal microfluidic organ-on-a-chip culture device; and
   maintaining the culture of the intestinal endothelial cells and/or fibroblasts and intestinal epithelial cells in the intestinal microfluidic organ-on-a-chip culture device.

107. The method of any of paragraphs 103-105, wherein prior to establishing the culture of intestinal epithelial cells on a second surface of the porous membrane, the culture of intestinal endothelial cells and/or fibroblasts has been established on a first surface of the porous membrane.

108. The method of any of paragraphs 103-105, wherein prior to establishing the culture of intestinal endothelial cells and/or fibroblasts on a first surface of the porous membrane, the culture of intestinal epithelial cells has been established on a second surface of the porous membrane.

109. The method of any of paragraphs 103-105, wherein the culture of intestinal endothelial cells and/or fibroblasts is established on a first surface of the porous membrane concurrently with establishing the culture of intestinal epithelial cells on a second surface of the porous membrane.

110. The method of any of paragraphs 103-109, wherein the method further comprises exposing the cells to an agent.

111. The method of paragraph 110, wherein said agent is a candidate intestinal effector agent.

112. The method of paragraph 111, wherein the method further comprises measuring the response of the cells to determine the effect of said candidate intestinal effector agent.

113. The method of any of paragraphs 103-112, wherein the porous membrane has a molecular coating that mediates cell adhesion.

114. The method of any of paragraphs 103-113, wherein the molecular coating that mediates cell adhesion comprises a hydrogel.

115. The method of any of paragraphs 103-114, wherein the molecular coating that mediates cell adhesion comprises an extracellular matrix hydrogel.

116. The method of any of paragraphs 103-115, wherein the molecular coating that mediates cell adhesion comprises a basement membrane preparation.

117. The method of any of paragraphs 103-116, wherein the molecular coating that mediates cell adhesion comprises at least one extracellular matrix molecule.

118. The method of paragraph 117, wherein the extracellular matrix molecule is selected from the group consisting of.
   laminin, heparan sulfate proteoglycan; fibronectin; collagen; type I collagen; and type IV collagen.

119. The method of any of paragraphs 103-118, wherein the porous membrane is activated for chemical cross-linking before being exposed to the molecular coating that mediates cell adhesion.

120. The method of any of paragraphs 103-119, wherein the porous membrane comprises PDMS; polyester (PET); and/or polycarbonate.

121. The method of any of any paragraphs 103-120, wherein the method further comprises coating the porous membrane with the molecular coating that mediates cell adhesion by:
   oxidizing the porous membrane; and
   contacting the porous membrane with the molecular coating that mediates cell adhesion.

122. The method of any of any paragraphs 103-121, wherein the method further comprises coating the porous membrane with the molecular coating that mediates cell adhesion by:
   oxidizing the porous membrane;
   functionalizing the porous membrane by silanization; and
   contacting the porous membrane with the molecular coating that mediates cell adhesion.

123. The method of any of paragraphs 121-122, wherein oxidation of the porous membrane comprises exposing the porous membrane to oxygen plasma; plasma discharge; polyethylene glycol (PEG); polyvinyl alcohol (PVA); or a liquid oxidizer.

124. The method of any of paragraphs 122-123, wherein the silanization is performed using a silane selected from the group consisting of: aminosilane; (3-aminopropyl)triethoxy silane, sulfhydrylsilane; and epoxysilane.

125. The method of any of paragraphs 122-124, wherein the functionalizing step further comprises treating the porous membrane with a cross-linker after silanization.

126. The method of paragraph 125, wherein the cross-linker is selected from the group consisting of:
N-γ-maleimidobutyryloxy succinimide ester; DMA; DMS; glutaraldehyde (GA); carbodiimide (1-ethyl-3-(3-dimethyl aminopropyl)-carbodiimide (EDC)); epoxy compounds; six methylene diisocyanate, glycerin; alginate; genipin (GP); nordihydroguaiaretic acid (NDGA); tannic acid; and procyanidins (PC).

127. The method of any of any paragraphs 103-126, wherein the method further comprises coating the porous membrane with the molecular coating that mediates cell adhesion by:
oxidizing the porous membrane;
functionalizing the porous membrane by silanization; and
contacting the porous membrane with the molecular coating that mediates cell adhesion.

128. The method of any of paragraphs 103-127, wherein establishing a culture of intestinal endothelial cells and/or fibroblasts on a first surface of a porous membrane of an intestinal culture fluidics device comprises culturing the cells under conditions suitable for them to form a monolayer on the porous membrane.

129. The method of any of paragraphs 103-128, wherein the intestinal endothelial cells and/or fibroblasts are mammalian intestinal endothelial cells and/or fibroblasts.

130. The method of any of paragraphs 103-129, wherein the intestinal endothelial cells and/or fibroblasts are human intestinal endothelial cells and/or fibroblasts.

131. The method of any of paragraphs 103-130, wherein the intestinal endothelial cells and/or fibroblasts are mouse intestinal endothelial cells and/or fibroblasts.

132. The method of any of paragraphs 103-131, wherein the intestinal endothelial cells and/or fibroblasts are primary intestinal endothelial cells and/or fibroblasts.

133. The method of any of paragraphs 103-132, wherein the intestinal endothelial cells are small intestine endothelial cells or colon endothelial cells.

134. The method of any of paragraphs 103-133, wherein the intestinal enteroid or colonoid, is disrupted into fragments to provide groups of from about 2 to about 100 intestinal epithelial cells.

135. The method of any of paragraphs 103-134, wherein the intestinal enteroid or colonoid, is disrupted into fragments to provide groups of from about 10 to about 30 intestinal epithelial cells.

136. The method of any of paragraphs 103-135, wherein the intestinal enteroid or colonoid, is disrupted into fragments to provide fragments of from about 10 μm to about 500 μm in diameter.

137. The method of any of paragraphs 103-136, wherein the intestinal enteroid or colonoid, is disrupted into fragments to provide fragments of from about 40 μm to about 100 μm in diameter.

138. The method of any of paragraphs 103-137, wherein the intestinal epithelial tissue is resected intestinal tissue or an endoscopic biopsy tissue.

139. The method of any of paragraphs 103-138, wherein the enteroids or colonoids are derived from histologically normal duodenal, jejunal, and ileal endoscopic biopsies.

140. The method of any of paragraphs 103-139, wherein the intestinal epithelial cells are mammalian intestinal epithelial cells.

141. The method of any of paragraphs 103-139, wherein the intestinal epithelial cells are human intestinal epithelial cells.

142. The method of any of paragraphs 103-139, wherein the intestinal epithelial cells are mouse intestinal epithelial cells.

143. The method of any of paragraphs 103-142, wherein the intestinal epithelial cells are not tumor cell line-derived cells.

144. The method of any of paragraphs 103-143, wherein the intestinal epithelial cells are small intestine epithelial cells or colon epithelial cells.

145. The method of any of paragraphs 103-144, wherein the ROCK inhibitor is selected from the group consisting of:
fasudil; Y27632; Y310383; Wf-536; SLx-2119; an azabenzimidazole-aminofurazan; DE-104; an olefin; an isoquinoline; an indazole; a pyridinealkene derivative; H-1152P; an ROKα inhibitor (BF); XD-4000; HMN-1152; a 4-(1-aminoalkyl)-N-(4-pyridyl)cyclohexane-carboxamide; rhostatin; BA-210; BA-207; BA-215; BA-285; BA-1037; Ki-23095, VAS-012; and a quinazoline.

146. The method of any of paragraphs 103-145, wherein a glycogen synthase kinase 3 (GSK-3) inhibitor is present during the disruption step.

147. The method of any of paragraphs 103-146, wherein the maintaining step comprises providing a flow of culture medium through each channel of the intestinal microfluidic organ-on-a-chip culture device at a volumetric flow rate of about 10 to about 5000 μl h$^{-1}$.

148. The method of any of paragraphs 103-147, wherein the maintaining step comprises providing a flow of culture medium through each channel of the intestinal microfluidic organ-on-a-chip culture device at a volumetric flow rate of about 10 to about 500 μl h$^{-1}$.

149. The method of any of paragraphs 103-148, wherein the maintaining step comprises providing a flow of culture medium through each channel of the intestinal microfluidic organ-on-a-chip culture device at a volumetric flow rate of about 60 μl h$^{-1}$.

150. The method of any of paragraphs 103-149, wherein the maintaining step comprises stretching the porous membrane at about 0-1 Hz with an about 0-20% mean cell strain.

151. The method of any of paragraphs 103-150, wherein the maintaining step comprises stretching the porous membrane at about 0-1 Hz with an about 0-10% mean cell strain.

152. The method of any of paragraphs 103-151, wherein the maintaining step comprises stretching the porous membrane at about 0.15 Hz with an about 10% mean cell strain.

153. The method of any of paragraphs 103-152, wherein the maintaining step comprises providing the endothelial cells and/or fibroblasts with EGM2-MV medium.

154. The method of any of paragraphs 103-153, wherein the maintaining step comprises culturing the cells under continuous flow and stretching that mimics physical forces experienced by the cells present in the native intestine.
155. The method of any of paragraphs 103-154, wherein the maintaining step comprises providing the epithelial cells with expansion medium comprising one or more of the following:
Wnt-3A; EGF; Rspo1; Noggin; gastrin; TGF-β receptor inhibitor; p38 MAPK inhibitor.
156. The method of any of paragraphs 103-155, wherein the maintaining step comprises providing the epithelial cells with expansion medium comprising Wnt-3A; EGF; Rspo1; Noggin; gastrin; TGF-β receptor inhibitor; and p38 MAPK inhibitor.
157. The method of any of paragraphs 103-1456, wherein the maintaining step comprises providing i) the epithelial cells and/or ii) the intestinal endothelial cells and/or fibroblasts with expansion medium comprising one or more of the following:
Wnt-3A; EGF; Rspo1; Noggin: gastrin; TGF-β receptor inhibitor; p38 MAPK inhibitor; Jagged (JAG) polypeptide and an inhibitor of GSK.
158. The method of any of paragraphs 103-157, wherein the maintaining step comprises providing i) the epithelial cells and/or ii) the intestinal endothelial cells and/or fibroblasts with expansion medium comprising:
Wnt-3A; EGF; Rspo1; Noggin; gastrin; TGF-β receptor inhibitor; p38 MAPK inhibitor; Jagged (JAG) polypeptide and an inhibitor of GSK.
159. The method of any of paragraphs 103-158, wherein the maintaining step comprises contacting at least the endothelial cells with a glycogen synthase kinase 3 (GSK-3) inhibitor for at least the first two days of the maintaining step.
160. The method of any of paragraphs 103-159, wherein the expansion medium further comprises nicotamide.
161. The method of paragraph 103-160, wherein the expansion medium further comprises a ROCK inhibitor for about 1 to about 7 days after introducing the epithelial cells to the intestinal microfluidic organ-on-a-chip culture device.
162. The method of paragraph 103-161, wherein the expansion medium further comprises a ROCK inhibitor for about 1 to about 4 days after introducing the epithelial cells to the intestinal microfluidic organ-on-a-chip culture device.
163. The method of paragraph 103-162, wherein the expansion medium further comprises a ROCK inhibitor for about 2 days after introducing the epithelial cells to the intestinal microfluidic organ-on-a-chip culture device.
164. The method of paragraph 103-163, wherein the expansion medium further comprises a GSK inhibitor for about 2 days after introducing the epithelial cells to the intestinal microfluidic organ-on-a-chip culture device.
165. The method of any of paragraphs 103-164, wherein the maintaining step comprises morphological and functional differentiation of the intestinal epithelial cells in co-culture with the intestinal endothelial cells and/or fibroblasts.
166. The method of paragraph 165, wherein said differentiation of the intestinal epithelial cells comprises differentiation of the cells to at least two or more of: absorptive enterocytes, Paneth cells, goblet cells and enteroendocrine cells.
167. The method of paragraph 166 wherein at least one of said differentiated cells exhibits digestive capacity.
168. The method of paragraph 166, wherein at least one of said differentiated cells exhibits mucus secreting capacity.
169. The method of any of paragraphs 103-168, wherein the epithelial cells exhibit polarized distribution of one or more ion transporters following the expansion and/or maintaining step.
170. The method of paragraph 169, wherein the one or more ion transporters are NHE3 and Na+/K+-ATPase.
171. The method of paragraph 170, wherein polarized distribution of NHE3 comprises higher concentrations of NHE3 at the brush border membrane of an epithelial cell as compared to other membranes of the epithelial cell; and/or polarized distribution of Na+/K+-ATPase comprises higher concentrations of Na+/K+-ATPase at the basolateral membrane of an epithelial cell as compared to other membranes of the epithelial cell.
172. The method of paragraph 170, wherein polarized distribution of NHE3 comprises NHE3 being detectable exclusively at the brush border membrane of an epithelial cell as compared to other membranes of the epithelial cell; and/or polarized distribution of Na+/K+-ATPase comprises Na+/K+-ATPase being detectable exclusively at the basolateral membrane of an epithelial cell as compared to other membranes of the epithelial cell.
173. The method of any of paragraphs 103-172, wherein the step of differentiating comprises providing a medium to the intestinal epithelial cells which:
a. comprises an inhibitor of Notch signaling; and
b. does not comprise Wnt-3A; nicotamide; and SB2001190.
174. The method of paragraph 173, wherein the inhibitor of Notch signaling is DAPT.
175. The method of any of paragraphs 103-174, wherein the method further comprises contacting the intestinal epithelial cells with bacterial cells of one or more species.
176. The method of paragraph 175, wherein the method further comprises co-culturing the epithelial cells and bacterial cells for at least 24 hours.
177. The method of paragraph 175, wherein the method further comprises co-culturing the epithelial cells and bacterial cells for at least 48 hours.
178. The method of any of paragraphs 175-177, wherein the co-culture step further comprises:
a. providing medium to the intestinal epithelial cells and bacterial cells at at least 60 μL/hr;
b. providing medium to the intestinal epithelial cells and bacterial cells at about 120 μL/hr.
179. The method of any of paragraphs 175-178, wherein the co-culture step further comprises:
a. providing medium to the intestinal epithelial cells and bacterial cells at at least 60 μL/hr;
b. providing medium to the intestinal epithelial cells and bacterial cells at about 120 L/hr;
c. causing the membrane to strain along at least one axis at about 10% strain; and/or
d. causing the membrane to strain along at least one axis at a frequency of about 0.2 Hz.
180. The method of any of paragraphs 103-179, wherein the method further comprises contacting the intestinal epithelial cells with at least one endotoxin.
181. The method of paragraph 180, wherein the endotoxin is lipopolysaccharide (LPS).

182. A method comprising:
   a. providing an intestinal microfluidic organ-on-a-chip culture device, the device comprising a porous membrane:
      i. having a molecular coating that mediates cell adhesion; and
      ii. wherein said membrane comprises a first and a second surface;
   b. providing an intestinal enteroid, colonoid, or organoid comprising intestinal epithelial cells;
   c. disrupting said intestinal enteroid, colonoid, or organoid comprising intestinal epithelial cells into enteroid, colonoid, or organoid fragments comprising intestinal epithelial cells in the presence of a ROCK inhibitor;
   d. establishing a culture of intestinal epithelial cells on a second surface of the porous membrane of the intestinal microfluidic organ-on-a-chip culture device by contacting the second surface with the enteroid, colonoid, or organoid fragments comprising intestinal epithelial cells resulting from step c; and
   e. maintaining the culture of the intestinal epithelial cells in the intestinal microfluidic organ-on-a-chip culture device, thereby forming an intact intestinal barrier;
   f. contacting the intestinal epithelial cells with bacterial cells of one or more species; and
   g. measuring the permeability of the intestinal barrier and/or translocation of the bacterial cells across the intestinal barrier.
183. The method of paragraph 182, further comprising:
   establishing a culture of intestinal endothelial cells and/or fibroblasts on a first surface of a porous membrane of an intestinal microfluidic organ-on-a-chip culture device; and
   maintaining the culture of the intestinal endothelial cells and/or fibroblasts and intestinal epithelial cells in the intestinal microfluidic organ-on-a-chip culture device.
184. A method comprising:
   a. providing an intestinal microfluidic organ-on-a-chip culture device, the device comprising a porous membrane:
      i. having a molecular coating that mediates cell adhesion; and
      ii. wherein said membrane comprises a first and a second surface;
   b. providing intestinal epithelial cells;
   c. establishing a culture of intestinal epithelial cells on a second surface of the porous membrane of the intestinal microfluidic organ-on-a-chip culture device by contacting the surface with said intestinal epithelial cells; and
   d. maintaining the culture of intestinal epithelial cells in the intestinal microfluidic organ-on-a-chip culture device, thereby forming an intact intestinal barrier;
   e. contacting the intestinal epithelial cells with bacterial cells of one or more species; and
   f. measuring the permeability of the intestinal barrier and/or translocation of the bacterial cells across the intestinal barrier.
185. The method of paragraph 184, the method further comprising:
   establishing a culture of intestinal endothelial cells and/or fibroblasts on a first surface of the porous membrane of the intestinal microfluidic organ-on-a-chip culture device by contacting the surface with intestinal epithelial cells, and
   maintaining the culture of intestinal epithelial cells and intestinal endothelial cells and/or fibroblasts in the intestinal microfluidic organ-on-a-chip culture device.
186. The method of any of paragraphs 182-185, wherein the porous membrane has a molecular coating that mediates cell adhesion.
187. The method of any of paragraphs 182-186, wherein prior to establishing the culture of intestinal epithelial cells on a second surface of the porous membrane, the culture of intestinal endothelial cells and/or fibroblasts has been established on a first surface of the porous membrane.
188. The method of any of paragraphs 182-186, wherein prior to establishing the culture of intestinal endothelial cells and/or fibroblasts on a first surface of the porous membrane, the culture of intestinal epithelial cells has been established on a second surface of the porous membrane.
189. The method of any of paragraphs 182-186, wherein the culture of intestinal endothelial cells and/or fibroblasts is established on a first surface of the porous membrane concurrently with establishing the culture of intestinal epithelial cells on a second surface of the porous membrane.
190. The method of any of paragraphs 182-189, wherein contacting the surface with intestinal epithelial cells comprises contacting the surface with an intestinal enteroid, colonoid, or organoid comprising intestinal epithelial cells.
191. The method of paragraph 190, wherein the intestinal enteroid, colonoid, or organoid comprising intestinal epithelial cells is disrupted into enteroid, colonoid, or organoid fragments prior to establishing the culture of intestinal epithelial cells on the first surface of the porous membrane.
192. The method of paragraph 191, wherein the disruption of the intestinal enteroid, colonoid, or organoid is performed in the presence of a ROCK inhibitor.
193. The method of any of paragraphs 182-192, wherein the method further comprises exposing the cells to an agent.
194. The method of paragraph 193, wherein said agent is a candidate intestinal effector agent.
195. The method of paragraph 194, wherein the method further comprises measuring the response of the cells to determine the effect of said candidate intestinal effector agent.
196. The method of any of paragraphs 182-195, wherein the molecular coating that mediates cell adhesion comprises a hydrogel.
197. The method of any of paragraphs 182-196, wherein the molecular coating that mediates cell adhesion comprises an extracellular matrix hydrogel.
198. The method of any of paragraphs 182-197, wherein the molecular coating that mediates cell adhesion comprises a basement membrane preparation.
199. The method of any of paragraphs 182-198, wherein the molecular coating that mediates cell adhesion comprises at least one extracellular matrix molecule.
200. The method of paragraph 199, wherein the extracellular matrix molecule is selected from the group consisting of:
   laminin, heparan sulfate proteoglycan; fibronectin; collagen; type I collagen; and type IV collagen.

201. The method of any of paragraphs 182-200, wherein the porous membrane is activated for chemical cross-linking before being exposed to the molecular coating that mediates cell adhesion.

202. The method of any of paragraphs 182-201, wherein the porous membrane comprises PDMS; polyester (PET); and/or polycarbonate.

203. The method of any of any paragraphs 182-202, wherein the method further comprises coating the porous membrane with the molecular coating that mediates cell adhesion by:
oxidizing the porous membrane; and
contacting the porous membrane with the molecular coating that mediates cell adhesion.

204. The method of any of any paragraphs 182-203, wherein the method further comprises coating the porous membrane with the molecular coating that mediates cell adhesion by:
oxidizing the porous membrane;
functionalizing the porous membrane by silanization; and
contacting the porous membrane with the molecular coating that mediates cell adhesion.

205. The method of any of paragraphs 203-204, wherein oxidation of the porous membrane comprises exposing the porous membrane to oxygen plasma; plasma discharge; polyethylene glycol (PEG); polyvinyl alcohol (PVA); or a liquid oxidizer.

206. The method of any of paragraphs 204-205, wherein the silanization is performed using a silane selected from the group consisting of: aminosilane; (3-aminopropyl)triethoxy silane, sulfhydrylsilane; and epoxysilane.

207. The method of any of paragraphs 204-206, wherein the functionalizing step further comprises treating the porous membrane with a cross-linker after silanization.

208. The method of paragraph 207, wherein the cross-linker is selected from the group consisting of:
N-γ-maleimidobutyryloxy succinimide ester; DMA; DMS; glutaraldehyde (GA); carbodiimide (1-ethyl-3-(3-dimethyl aminopropyl)-carbodiimide (EDC)); epoxy compounds; six methylene diisocyanate, glycerin; alginate; genipin (GP); nordihydroguaiaretic acid (NDGA); tannic acid; and procyanidins (PC).

209. The method of any of any paragraphs 182-208, wherein the method further comprises coating the porous membrane with the molecular coating that mediates cell adhesion by:
oxidizing the porous membrane;
functionalizing the porous membrane by silanization; and
contacting the porous membrane with the molecular coating that mediates cell adhesion.

210. The method of any of paragraphs 182-209, wherein establishing a culture of intestinal endothelial cells and/or fibroblasts on a first surface of a porous membrane of an intestinal culture fluidics device comprises culturing the cells under conditions suitable for them to form a monolayer on the porous membrane.

211. The method of any of paragraphs 182-210, wherein the intestinal endothelial cells and/or fibroblasts are mammalian intestinal endothelial cells and/or fibroblasts.

212. The method of any of paragraphs 182-211, wherein the intestinal endothelial cells and/or fibroblasts are human intestinal endothelial cells and/or fibroblasts.

213. The method of any of paragraphs 182-211, wherein the intestinal endothelial cells and/or fibroblasts are mouse intestinal endothelial cells and/or fibroblasts.

214. The method of any of paragraphs 182-213, wherein the intestinal endothelial cells and/or fibroblasts are primary intestinal endothelial cells and/or fibroblasts.

215. The method of any of paragraphs 182-214, wherein the intestinal endothelial cells and/or fibroblasts are obtained from a subject.

216. The method of any of paragraphs 182-215, wherein the intestinal endothelial cells are small intestine endothelial cells or colon endothelial cells.

217. The method of any of paragraphs 182-216, wherein the intestinal enteroid, colonoid, or organoid is disrupted into enteroid fragments to provide groups of from about 2 to about 100 intestinal epithelial cells.

218. The method of any of paragraphs 182-217, wherein the intestinal enteroid, colonoid, or organoid is disrupted into enteroid fragments to provide groups of from about 10 to about 30 intestinal epithelial cells.

219. The method of any of paragraphs 182-218, wherein the intestinal enteroid, colonoid, or organoid is disrupted into enteroid fragments to provide fragments of from about 10 μm to about 500 μm in diameter.

220. The method of any of paragraphs 182-219, wherein the intestinal enteroid, colonoid, or organoid is disrupted into enteroid fragments to provide fragments of from about 40 μm to about 100 μm in diameter.

221. The method of any of paragraphs 182-220, wherein the intestinal enteroid or colonoid is obtained from a subject.

222. The method of any of paragraphs 182-221, wherein the intestinal enteroid or colonoid is obtained from a resected intestinal tissue or an endoscopic biopsy tissue.

223. The method of any of paragraphs 99-222, wherein the enteroids or colonoids are derived from histologically normal duodenal, jejunal, and ileal endoscopic biopsies.

224. The method of any of paragraphs 182-223, wherein the intestinal epithelial cells are obtained from induced pluripotent stem cells.

225. The method of any of paragraphs 182-224, wherein the intestinal epithelial cells are mammalian intestinal epithelial cells.

226. The method of any of paragraphs 182-225, wherein the intestinal epithelial cells are human intestinal epithelial cells.

227. The method of any of paragraphs 182-225, wherein the intestinal epithelial cells are mouse intestinal epithelial cells.

228. The method of any of paragraphs 182-227, wherein the intestinal epithelial cells are not tumor cell line-derived cells.

229. The method of any of paragraphs 182-228, wherein the intestinal epithelial cells are small intestine epithelial cells or colon epithelial cells.

230. The method of any of paragraphs 182-229, wherein the intestinal enteroid or colonoid is obtained by:
washing a resected intestinal tissue or an endoscopic biopsy tissue and removing any associated muscle or mucosa layers;
contacting the tissue with one or more extracellular-matrix degrading enzymes; removing an intestinal crypt from the supernatant resulting from the contacting step;
embedding the intestinal crypt in a hydrogel; and maintaining the intestinal crypt in the hydrogel to form an intestinal enteroids and/or colonoids.

231. The method of any of paragraphs 182-230, wherein the ROCK inhibitor is selected from the group consisting of:
fasudil; Y27632; Y39983; Wf-536; SLx-2119; an azabenzimidazole-aminofurazan; DE-104; an olefin; an isoquinoline; an indazole; a pyridinealkene derivative; H-1152P; an ROKα inhibitor (BF); XD-4000; HMN-1152; a 4-(1-aminoalkyl)-N-(4-pyridyl)cyclohexane-carboxamide; rhostatin; BA-210; BA-207; BA-215; BA-285; BA-1037; Ki-23095; VAS-012; and a quinazoline.

232. The method of any of paragraphs 182-231, wherein a glycogen synthase kinase 3 (GSK-3) inhibitor is present during the disruption step.

233. The method of any of paragraphs 182-232, wherein the maintaining step comprises providing a flow of culture medium through each channel of the intestinal microfluidic organ-on-a-chip culture device at a volumetric flow rate of about 10 to about 5000 µl h$^{-1}$.

234. The method of any of paragraphs 182-233, wherein the maintaining step comprises providing a flow of culture medium through each channel of the intestinal microfluidic organ-on-a-chip culture device at a volumetric flow rate of about 10 to about 500 µl h$^{-1}$.

235. The method of any of paragraphs 182-234, wherein the maintaining step comprises providing a flow of culture medium through each channel of the intestinal microfluidic organ-on-a-chip culture device at a volumetric flow rate of about 60 µl h$^{-1}$.

236. The method of any of paragraphs 182-235, wherein the maintaining step comprises stretching the porous membrane at about 0-1 Hz with an about 0-20% mean cell strain.

237. The method of any of paragraphs 182-236, wherein the maintaining step comprises stretching the porous membrane at about 0-1 Hz with an about 0-10% mean cell strain.

238. The method of any of paragraphs 182-237, wherein the maintaining step comprises stretching the porous membrane at about 0.15 Hz with an about 10% mean cell strain.

239. The method of any of paragraphs 182-238, wherein the maintaining step comprises providing the endothelial cells and/or fibroblasts with EGM2-MV medium.

240. The method of any of paragraphs 182-239, wherein the maintaining step comprises culturing the cells under continuous flow and stretching that mimics physical forces experienced by the cells present in the native intestine.

241. The method of any of paragraphs 182-240, wherein the maintaining step comprises providing the epithelial cells with expansion medium comprising one or more of the following:
Wnt-3A; EGF; Rspo1; Noggin; gastrin; TGF-β receptor inhibitor; p38 MAPK inhibitor.

242. The method of any of paragraphs 182-241, wherein the maintaining step comprises providing the epithelial cells with expansion medium comprising Wnt-3A; EGF; Rspo1; Noggin; gastrin; TGF-β receptor inhibitor; and p38 MAPK inhibitor.

243. The method of any of paragraphs 182-242, wherein the maintaining step comprises providing i) the epithelial cells and/or ii) the intestinal endothelial cells and/or fibroblasts with expansion medium comprising one or more of the following:
Wnt-3A; EGF; Rspo1; Noggin; gastrin; TGF-β receptor inhibitor; p38 MAPK inhibitor; Jagged (JAG) polypeptide and an inhibitor of GSK.

244. The method of any of paragraphs 182-243, wherein the maintaining step comprises providing i) the epithelial cells and/or ii) the intestinal endothelial cells and/or fibroblasts with expansion medium comprising:
Wnt-3A; EGF; Rspo1; Noggin; gastrin; TGF-β receptor inhibitor; p38 MAPK inhibitor; Jagged (JAG) polypeptide and an inhibitor of GSK.

245. The method of any of paragraphs 182-244, wherein the maintaining step comprises contacting at least the endothelial cells with a glycogen synthase kinase 3 (GSK-3) inhibitor for at least the first two days of the maintaining step.

246. The method of any of paragraphs 182-245, wherein the expansion medium further comprises nicotamide.

247. The method of paragraph 182-246, wherein the expansion medium further comprises a ROCK inhibitor for about 1 to about 7 days after introducing the epithelial cells to the intestinal microfluidic organ-on-a-chip culture device.

248. The method of paragraph 182-247, wherein the expansion medium further comprises a ROCK inhibitor for about 1 to about 4 days after introducing the epithelial cells to the intestinal microfluidic organ-on-a-chip culture device.

249. The method of paragraph 182-248, wherein the expansion medium further comprises a ROCK inhibitor for about 2 days after introducing the epithelial cells to the intestinal microfluidic organ-on-a-chip culture device.

250. The method of paragraph 182-249, wherein the expansion medium further comprises a GSK inhibitor for about 2 days after introducing the epithelial cells to the intestinal microfluidic organ-on-a-chip culture device.

251. The method of any of paragraphs 182-250, wherein the maintaining step comprises morphological and functional differentiation of the intestinal epithelial cells in co-culture with the intestinal endothelial cells and/or fibroblasts.

252. The method of paragraph 251, wherein said differentiation of the intestinal epithelial cells comprises differentiation of the cells to at least two or more of: absorptive enterocytes, Paneth cells, goblet cells and enteroendocrine cells.

253. The method of paragraph 252, wherein at least one of said differentiated cells exhibits digestive capacity.

254. The method of paragraph 252, wherein at least one of said differentiated cells exhibits mucus secreting capacity.

255. The method of any of paragraphs 182-254, wherein the epithelial cells exhibit polarized distribution of one or more ion transporters following the expansion and/or maintaining step.

256. The method of paragraph 255, wherein the one or more ion transporters are NHE3 and Na+/K+-ATPase.

257. The method of paragraph 256, wherein polarized distribution of NHE3 comprises higher concentrations of NHE3 at the brush border membrane of an epithelial cell as compared to other membranes of the epithelial cell; and/or polarized distribution of Na+/K+-ATPase comprises higher concentrations of Na+/K+-ATPase at the basolateral membrane of an epithelial cell as compared to other membranes of the epithelial cell.

258. The method of paragraph 256, wherein polarized distribution of NHE3 comprises NHE3 being detectable exclusively at the brush border membrane of an epithelial cell as compared to other membranes of the epithelial cell; and/or polarized distribution of Na+/K+-ATPase comprises Na+/K+-ATPase being detectable exclusively at the basolateral membrane of an epithelial cell as compared to other membranes of the epithelial cell.

259. The method of any of paragraphs 182-258, wherein the step of differentiating comprises providing a medium to the intestinal epithelial cells which:
   b. comprises an inhibitor of Notch signaling; and
   c. does not comprise Wnt-3A; nicotamide; and SB2001190.

260. The method of paragraph 247, wherein the inhibitor of Notch signaling is DAPT.

261. The method of any of paragraphs 182-248, wherein the method further comprises co-culturing the epithelial cells and bacterial cells for at least 24 hours.

262. The method of paragraph 261, wherein the method further comprises co-culturing the epithelial cells and bacterial cells for at least 48 hours.

263. The method of any of paragraphs 261-262, wherein the co-culture step further comprises:
   a. providing medium to the intestinal epithelial cells and bacterial cells at at least 60 µL/hr;
   b. providing medium to the intestinal epithelial cells and bacterial cells at about 120 µL/hr.

264. The method of any of paragraphs 261-263, wherein the co-culture step further comprises:
   a. providing medium to the intestinal epithelial cells and bacterial cells at at least 60 µL/hr;
   b. providing medium to the intestinal epithelial cells and bacterial cells at about 120 µL/hr;
   c. causing the membrane to strain along at least one axis at about 10% strain; and/or
   d. causing the membrane to strain along at least one axis at a frequency of about 0.2 Hz.

265. The method of any of paragraphs 182-264, wherein the method further comprises contacting the intestinal epithelial cells with at least one endotoxin.

266. The method of paragraph 265, wherein the endotoxin is lipopolysaccharide (LPS).

EXAMPLES

Example 1

Described herein is the setup, maintenance and characteristics of a tissue-engineered model of the human primary intestinal mucosa that can be used, for example, for studies of basic physiology, pathophysiology of various human intestinal diseases, monitoring of drug absorption, screening and development of mucosal vaccines, analysis of host-microbiome interactions or host response to infection.

The model includes a well-differentiated epithelium derived from human biopsy or bowel resection and human microvascular intestinal endothelium co-cultured in microfluidic organ-on-a-chip culture devices in which they can be exposed to fluid flow and peristalsis-like motions, as well as immune cells, endothelium, gut microbes (e.g. pathogenic, commensal), and exogenous stimulants (e.g. LPS, cytokines) in a controlled manner. This model recapitulates many key anatomical and functional features of the intestinal wall including villi formation, differentiation into four different intestinal cell types: absorptive enterocytes, mucus-secreting goblet cells, enteroendocrine and Paneth cells and the formation of relevant barrier functions. The entire protocol takes 2-3 wk, including cell seeding, expansion and differentiation.

The intestinal epithelium is uniquely adapted to perform variety of homeostatic functions, including barrier formation and maintenance, digestion, absorption of nutrients, modulation of the microbiome and participation in host immune responses. Perturbation of these functions is implicated in gastrointestinal disorders, including infections, inflammatory bowel disease (IBD) and cancer.

Many attempts have been made to develop a culture system that mimics normal intestinal epithelial growth and differentiation and allows the dissection of complex interactions between epithelial cells and neighbouring cells as well as resident and transient intestinal microbes. Conventional intestinal organoid culture system consists of crypts isolated from mice or human intestine embedded in Matrigel and cultured in the presence of epidermal growth factor (EGF), Noggin and R-spondin 1 (collectively, ENR) as described in [1]. Although three-dimensional (3D) enteroid cultures have been used to study cell differentiation they suffer severe limitations. The most substantial one is the physical inaccessibility of their luminal surface—closed within the spheroid structure surrounded by a thick extracellular gel which makes difficult to expose the intestinal cells to nutrients, oral drugs, commensal microbes or pathogenic bacteria, selectively sample apical versus basolateral secretions as well as to determine the barrier function. Furthermore, it is not possible to expose these cells to physiological peristalsis-like motions and luminal fluid flows that are important for maintenance of gut homeostasis in vivo.

Described herein is a robust and reproducible methodology for development and maintenance of mechanically active gut-on-chip device lined with human primary intestinal epithelial cells harvested from intestinal enteroids or bowel resections in the top channel and primary microvascular intestinal endothelium in the bottom channel, that allows sustained intestinal proliferation, multilineage differentiation and intact barrier formation. The methodology described herein has been tested for epithelium derived from 5 different donors in more than 10 independent experiments.

The protocol involves 3 sequential steps:
1) Intestinal crypt isolation from, e.g., resected intestinal tissues or endoscopic biopsies and their subsequent in vitro culture in Matrigel
2) Establishment of primary intestinal epithelium and endothelium co-culture in gut-on-chip microfluidic device,
3) Organ maintenance and differentiation.

Intestinal Crypt isolation and In vitro 3D Culture: Surgically resected intestinal tissues or endoscopic biopsy samples (collected in advanced Dulbecco's modified Eagle medium/F12 supplemented with penicillin/streptomycin and 10% FBS) are obtained. Procedures for establishing and maintaining human spheroid cultures are based on protocols described in [3-4] and [5] with modifications as described herein. In brief, the resected intestinal tissues are washed with cold PBS and stripped of the underlying muscle layers and associated mucosa with surgical scissors. For endoscopic biopsy samples, at least 2 biopsy samples per patient are collected.

Intestinal fragments isolated from human small intestine, and colon are further washed with cold PBS and incubated in 2 mg/ml Collagenase I (GIBCO 17100) for 30-40 minutes at 37° C. Pieces of undigested tissue are allowed to settle down under normal gravity and removed using a 10-mL pipette. Intestinal crypts present in the supernatant are washed twice in cold DMEM/F12 medium supplemented with 20% FBS and pellet at 300 g for 5 minutes at 4° C. Extracted crypts are embedded in Matrigel (growth factor reduced, phenol red free; BD Biosciences, 356231) and seeded in 24-well plates. After 10 minutes of polymerization at 37° C., crypts are overlaid with expansion medium (EM) made of advanced Dulbecco's modified Eagle medium/F12, 100 μg/mL Primocin (Invivogen, ant-pm-2), 10 mmol/L HEPES (GIBCO 15630080), Glutamax (GLBCO 35050061), 50% vol/vol L-WRN-conditioned medium (media derived from L-cell line, created by Stappenbeck [5] that secrete Wnt3A, R-spondin, Noggin) supplemented with 1×N2 (Invitrogen 17502-048), 1×B27 (Invitrogen 17504-044) and 1 mmol/L N-acetylcysteine (Sigma A5099), 50 ng/mL murine epidermal growth Factor (Peprotech 315-09), 10 nmol/mL [Leu-15]gastrin, 10 mmol/L nicotinamide (Sigma N0636), 500 nmol/L A83-01 (Tocris 2939) and 10 mmol/L SB202190 (Sigma S7067).

The intestinal enteroids culture established in the foregoing manner can be maintained and passaged without limitations or frozen for long-term storage in liquid $N_2$.

Establishment of Primary Intestinal Epithelium and Endothelium Co-Culture in Gut-On-Chip Microfluidic Device Prior to the establishment of primary cell culture in organ-on-chip microfluidic device, the hydrophobic PDMS surface is activated by oxygen plasma treatment and aminized with (3-aminopropyl)triethoxy silane (APTMS, SIGMA 281778). This surface functionalization allows for an improved cell attachment and facilitates long-term culture of intestinal stem cells and their progeny [2]. Next ECM coating solution composed of 1% Matrigel (BD Corning, 356231) and 200 ug/ml Collagen I (BD Corning 3.36 mg/mL; 354226) is introduced in both the upper and the lower microfluidic channel and device is placed in a humidified 37° C. incubator for the minimum of 2 hours. Then human intestinal microvascular endothelial cells, e.g., purchased from ScienCell (Catalog #2900), are seeded on the bottom side of the porous stretchable PDMS membrane that separates two parallel microchannels of the organ-on-chip device. Seeding of endothelial cells on the bottom side of the PDMS membrane ensures that the majority of the pores are covered before epithelial cell addition and prevents inter-compartment cell migration through the membrane pores during the attachment and culture of the epithelial cells. Additionally, the presence of the endothelium is required for optimal epithelial cell differentiation, viability and modulation of immune response to environmental cues. Once endothelial cells are well attached, primary epithelial cell seeding is performed at the opposite side of the membrane. Briefly, human small intestinal or colon spheroids are recovered from Matrigel using cell recovery solution and dissociated into small fragments using TrypLE Express Enzyme supplemented with 10 μM Y-27632. When using fresh human bowel resections extracted crypts can be directly subjected to enzymatic treatment followed by cell seeding of top channel of gut-on-chip microfluidic device. ROCK inhibitor is present during all steps of organoid processing to avoid complete dissociation of spheroids into single cells and in order to preserve high cell viability.

Organ Maintenance and Differentiation

One day after cell seeding, the device is connected to the peristaltic pump and perfused at both channels with culture medium at a volumetric flow rate of 60 μl h$^{-1}$ in a humidified incubator maintained at 37° C. To more closely mimic the mechanical microenvironment that epithelial cells experience in the living human intestine in vivo cyclic stretching regimen can be applied (10% mean cell strain, 0.15 Hz frequency) when the monolayer reaches full confluency as in [7].

Epithelial cells are provided with the expansion medium (EM) that supports rapid proliferation and expansion of intestinal stem cells by providing all the paracrine factors important for the niche-independent growth as described in [3-6]. 10 mM Y-27632 is included in the EM medium for the first two days of on-chip growth. Endothelial channel of gut-on-chip device is perfused with EGM2-MV medium (Lonza, EGM-2MV BulletKit CC-3202 & CC-4147).

These culture conditions allow creation of well polarized intact epithelial and endothelial monolayer as assessed by dextran permeability assay and formation of intestinal villi. Primary intestinal epithelium and endothelium co-culture system can be maintained in EM and EGM-2MV medium for prolonged time (up to 3 weeks culture time tested) without any negative effect on cell viability or barrier function.

A combination of Wnt-3A, nicotamide and SB2001190 withdrawal and Notch signaling inhibition (+10 μM DAPT, SIGMA D5942) is used to allow epithelial cell differentiation as described in [5-6]. Condition medium derived from human embryonic kidney 293T cells stably expressing Rspo1 or Noggin as well as commercially available recombinant proteins can be used as a source of R-spondin or Noggin, respectively. This protocol is universal for epithelial cell cultures derived from different regions of human intestine (small and large intestine) and leads to a successful multilineage differentiation into the four different intestinal cell types: absorptive enterocytes, mucus-secreting goblet cells, enteroendocrine and Paneth cells independently of the epithelial cell source or donor to donor variability (FIGS. 1A-1H).

Described herein is a novel method for the establishment and maintenance of human primary intestinal epithelial and intestinal microvascular endothelial cells co-culture in microfluidic device. Intestinal organoids or freshly dissected bowel resection can be used as the primary epithelial tissue source for "organ-on-chip" experiment.

The methods, systems and devices described herein can be used for:

Assessing the role of mechanotransduction (flow and cyclic strain) on intestinal
epithelial and endothelial biology, drug absorption, pathophysiology etc.
Drug testing and disease modelling
Drug or food nutrients absorption studies
Assessing the effect of radiation
Studies of host-pathogen interactions
Screening and development of mucosal vaccines
Phage display-based screening for identification of peptide/protein/antibody entities that trancytose the gut or target pathologic conditions in the gut
Comparisons between healthy and disease tissues

REFERENCES

[1] Sato, T. et al. Single Lgr5 stem cells build crypt-villus structures in vitro without a mesenchymal niche. Nature 59, 262-265 (2009)
[2] Chuah Y. J., Kuddannaya S., Lee M. H. A., Zhang Y. & Kang Y., The Effects of Poly(dimethylsiloxane) Surface Silanization on Mesenchymal Stem Cell Fate. Biomater. Sci. 3, 383-390 (2015)

[3] Sato, T., R. G. Vries, et al. (2009). Single Lgr5 stem cells build crypt-villus structures in vitro without a mesenchymal niche. Nature 459: 262-265.
[4] Sato T, et al. Long-term expansion of epithelial organoids from human colon, adenoma, adenocarcinoma, and Barrett's epithelium. Gastroenterology 2011; 141:1762-72.
[5] Miyoshi H, Stappenbeck T S. In vitro expansion and genetic modification of gastrointestinal stem cells in spheroid culture. Nat Protoc 2013; 8.2471-82.
[6] VanDussen, K. L., et al. Development of an enhanced human gastrointestinal epithelial culture system to facilitate patient-based assays. Gut. (2014).
[7] H. Kim et al., Human gut-on-a-chip inhabited by microbial flora that experiences intestinal peristalsis-like motions and flow, Lab Chip, 12, pp. 2165-2174 (2012).
[8] Kim H J, Ingber D E, Gut-on-a-Chip microenvironment induces human intestinal cells to undergo villus differentiation, Integr Biol (Camb), 5, pp. 1130-40 (2013).

Example 2: Development of a Primary Human Small Intestine-On-Chip Using Patient-Derived Enteroids Organ-on-a-chip technology has been used to create microfluidic models of human intestine that offer multiple advantages over intestinal organoids (enteroids), including the ability to integrate endothelium, immune cells, and microbiome into epithelial cell cultures that experience flow and peristalsis-like deformations; however, because they currently utilize intestinal epithelial tumor cell lines with compromised mechanisms of apoptosis, cell cycle checkpoint controls and low genetic diversity, their use may be limited. Described herein is a method for fabricating a primary human small intestine-on-chip containing intestinal epithelial cells isolated from patient intestinal biopsies or surgical explants. The epithelial cells are expanded as 3D enteroids and subsequently seeded into one microchannel of an organ-on-chip device where they interface through a porous matrix-coated membrane with human intestinal microvascular endothelium cultured in a parallel microchannel under conditions of flow and cyclic deformation. This small intestine-on-chip recapitulates intestinal villus morphology with multi-lineage differentiation, and normal physiological functions of the human gut, such as digestion of nutrients, intestinal barrier function and mucus secretion. Hence, it can be used as a research tool for applications, such as drug development, metabolism, nutrition and cancer progression, where normal intestinal function is crucial for example in assessment of drug pharmacokinetics, metabolism and absorption of nutrients, host-pathogen interaction in addition to providing a novel approach to advance personalized medicine.

Introduction

The small intestine is a major site for digestion, nutrient absorption, interaction with commensal microbiome, and development of mucosal immunity, as well as a primary site for many diseases, including celiac, inflammatory bowel disease, Crohn's disease, environmental enteric dysfunction and various bacterial and viral infections. Human primary intestinal crypt cells have been isolated and cultured as three-dimensional (3D) spheroids embedded in Matrigel extracellular matrix (ECM) in the presence of Wnt3a, epidermal growth factor (EGF), Noggin and R-spondin 1 (collectively, WENR)[1, 2]. The resulting intestinal organoids, known as 'enteroids', recapitulate intestinal crypt-villus microtopography and provide exciting tools to study intestinal stem cell differentiation and morphogenesis in vitro[3-6]. However, because they are grown as closed tissue structures embedded within a 3D ECM gel, they cannot be used for long-term studies with microbiome or pathogens, and they lack the immune cells, vascular compartment, and physiologic microenvironment (fluid flow, peristalsis motions) that are key contributors to normal intestinal physiology and disease development[6].

Organs-on-chips are microfluidic culture devices the size of a computer memory stick that recreate normal tissue-tissue interfaces and mimic the complex physical and biochemical microenvironment of living human organs[7, 8]. To date, organs-on-chips for more than 10 major organs of the human body have been created, including lung[9], kidney[10, 11], liver[12-14], heart[15], brain[16] and intestine[17-21]. These devices have been shown to reproduce organ-level physiological functions, such as gas exchange in the lung[9], immune responses to cytokines or pathogens at the surface of small airway, lung or gut[9, 19, 22] and drug toxicity in kidney[11]. Moreover, this biomimetic microsystems technology has been successfully applied to develop clinically relevant human disease models of pulmonary edema2[3], chronic obstructive pulmonary disease[22] and inflammatory bowel disease[19] that can be used to identify new therapeutics and reliably predict their in vivo efficacy and toxicity.

Previous studies have utilized established human intestinal cell lines, such as Caco-2 or HT-29 cells, which were originally isolated from human tumor samples and harbour multiple culture-induced mutations. Moreover, in past gut-on-a-chip studies, the intestinal cells were either cultured alone or in the presence of a non-specialized endothelium (e.g., human umbilical vein endothelial cells). Thus, these devices likely do not fully recapitulate all normal human intestinal functions[6], and they would be inappropriate to use to study many important human conditions where genome fidelity is important (e.g., studies on intestinal cancer development or drug development).

Furthermore, in order to develop personalized treatment regiments it is necessary to establish methods that can deliver sufficient material from healthy or disease-site biopsy and to create intestine chips with patient-specific cells. Thus, described herein is the development of a primary human small intestine-on-chip that is lined exclusively by normal human intestinal epithelial cells as well as intestinal microvascular endothelium. Described herein is how the human organ-on-a-chip microfabrication strategy previously described[24] can be extended to create for the first time fully primary human small intestine chips by combining this microfluidic technology with advances in primary human intestinal stem cell isolation and culture.

To create the primary human small intestine chip, patient biopsies of normal regions of small intestine are collected and used to establish enteroid culture using previously described methods[1, 2, 25]. Enteroid fragments containing intestinal stem cells are then released by enzymatic treatment and cultured on a flexible, porous, ECM-coated membrane within one channel of a previously described, two-channel, microfluidic, organ-on-a-chip device[24]. In parallel, primary human intestinal microvascular endothelial cells from a commercial supplier are cultured on the opposite side of the same flexible membrane in a second parallel channel, a step found to be highly beneficial for efficient monolayer and intestinal villi-like structures formation by the adjacent primary epithelium. Differentiation of the villus epithelium is promoted by exposing the cells co-cultured within the chip to physiological fluid flow and peristalsis-like motions that are generated by applying cyclic suction to flexible hollow side chambers. This microengineered device recapitulates many key anatomical and functional features of its in vivo small intestine counterpart including 3D intestinal villus morphology, epithelial barrier function, multi-lineage differentiation and mucus extrusion. The resulting primary intestinal cell model provides a more relevant model for studying normal human intestinal physiology and pathophysiology, and the methods can be utilized to create patient-specific intestine chips for personalized disease modeling and drug screening. The protocols below describe how this microfluidic human small intestinal cell culture system can be established and maintained as well as it discusses several experimental techniques that can be used to analyze the cells grown inside this small intestine-on-chip.

Experimental Design

This protocol describes how to make a biomimetic microfluidic device co-culturing primary human intestinal epithelial cells and intestinal microvascular endothelial cells to create a chip-based surrogate of the human small intestine that incorporates physiological fluid flow and peristalsis-like mechanical motions. This detailed protocol includes procedures for isolating human intestinal epithelial cells from enteroids created from patient biopsies, and for seeding, growing and differentiating these human cells in the microfluidic devices. The present procedures also encompass a suite of methods to analyze formation of intestinal villus morphology, intact barrier function, multi-lineage cell differentiation and digestive activity of brush border enzymes during prolonged culture on chip.

Figures 2A, 2B, 2C:
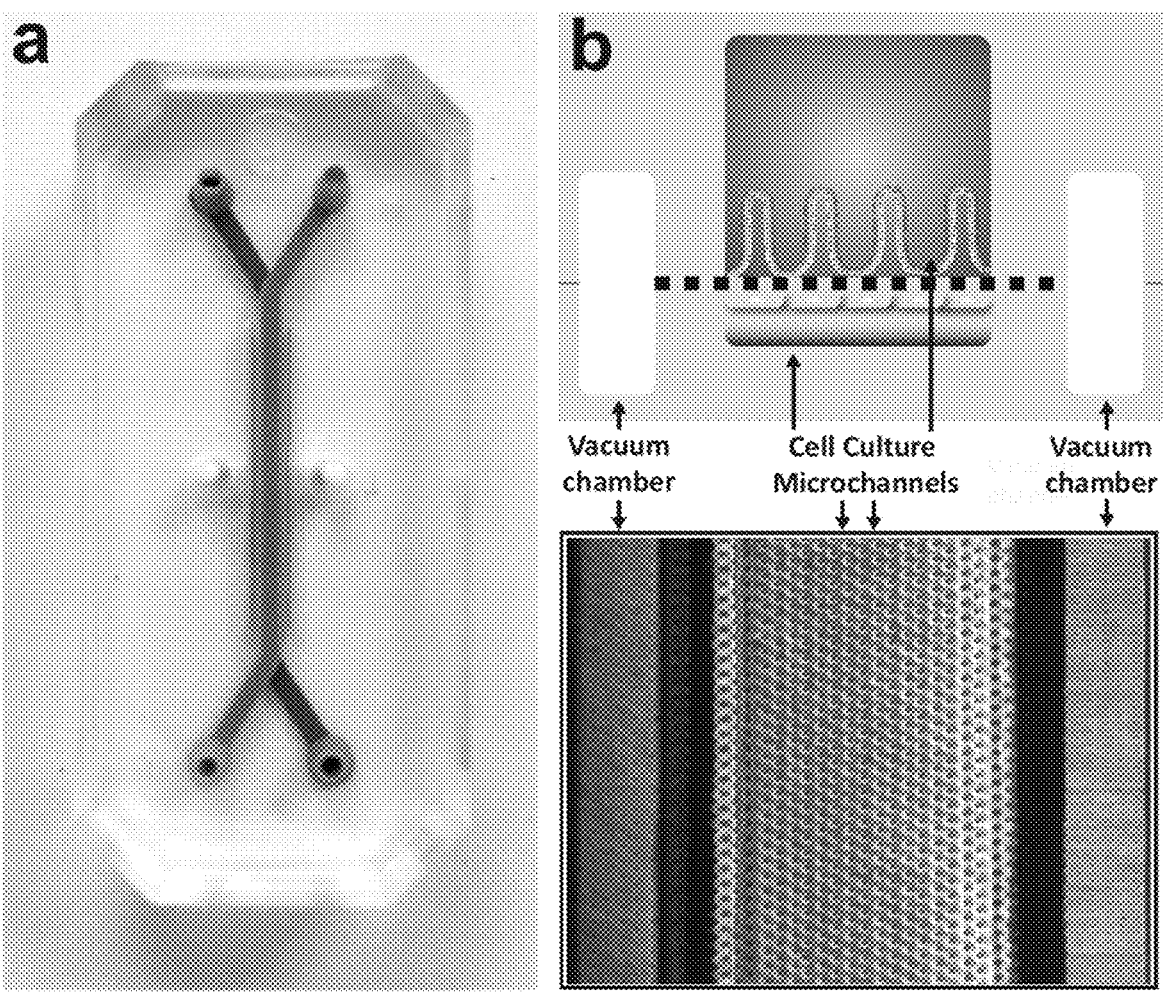
FIGS. 2A-2C depict one embodiment of the primary human small intestine-on-chip device and methods for its fabrication.

To accomplish this, poly(dimethylsiloxane) (PDMS) devices were fabricated that contain two parallel, cell culture microchannels (an upper 'epithelial' channel, 1 mm high×1 mm wide, and a lower 'vascular' channel, 0.2 mm high×1 mm wide) separated by a thin (50 μm) flexible PDMS membrane containing multiple pores (7 μm diameter, 40 μm spacing) coated with ECM (type I collagen and Matrigel), as previously described[24] (FIGS. 2A-2C). To increase the strength and stability of cell attachment to the PDMS membrane the PDMS devices were plasma treated as in past studies, but then the oxidized surfaces were exposed to the cross linker, APTMS, before the ECM was added to physically couple the proteins to the porous membrane (FIG. 2C). The epithelial and vascular channels are surrounded on either side by two hollow (1 mm high×300 μm wide) chambers (FIG. 2B) that permit application of cyclic suction to mechanically stretch and relax the sidewalls and attached flexible PDMS membrane in the central channel, thereby mimicking peristaltic motions of living human gut.

A primary cell culture model based on 3D propagation of human intestinal crypts[1, 2, 25], was used to create a bank of enteroids derived from histologically normal duodenal, jejunal, and ileal endoscopic biopsies (from Boston Children's Hospital) or surgical specimens (from Massachusetts General Hospital) which are the source of primary human intestinal epithelial cells. Briefly, intestinal crypts isolated from clinical samples were embedded in Matrigel and grown in the presence of well-defined growth factors, including Wnt3A, R-spondin and Noggin (provided as conditioned medium from the L-cell line, L-WRN CM) and EGF, as previously described 2 (FIG. 2C). After sufficient enteroid expansion (~10-20 passages over 20-40 weeks), multiple cell lines were created from the biopsy material stemming from independent patient donors. Intestinal cell fragments composed of 5 or more cells isolated from these enteroids by enzymatic dissociation were then plated in the epithelial channel of the microfluidic devices (FIG. 2C). Primarily, enteroids were from the duodenal region of the proximal small intestine because they displayed the highest culture efficiency, as previously described[26]. Primary human intestinal microvascular endothelial cells (HIMECs) were obtained from ScienCell (cat. no 2900).

To build the human small intestine-on-chip, the HIMECs were plated in the lower microchannel of the device for 1 hour under static conditions in EGM-2-MV medium before initiating fluid flow (60 μl/min; 0.02 dyne/cm2) with the same medium (FIG. 2C). As soon as 1-2 hours after the seeding HIMECs created a confluent endothelial monolayer attached to the bottom surface of the porous ECM-coated membrane, which helps to prevent inter-compartment cell migration through the membrane pores when the epithelial cells are cultured on the opposite side of the membrane. Fragments of intestinal spheroids released by enzymatic digestion using Enteroid Dissociation solution (50% (vol/vol) TrypLE in calcium/magnesium-free PBS with 10 μM Y-27632) were then seeded at high density (7×106 cells/ml, 210,000 cells/chip) in expansion medium (EM medium) on the upper side of the porous membrane (FIG. 2C). EM medium was made in a base solution of advanced Dulbecco's modified Eagle medium/F12, containing 100 μg ml-1 primocin, 10 mM HEPES, 0.2 mM GlutaMAX with 50% vol/vol L-WRN-conditioned medium, 1×B27 supplement, 1×N2 supplement, 1 mM N-acetylcysteine, 50 ng mL-1 murine epidermal growth factor, 10 nM [Leu-15] gastrin, 10 mM nicotinamide, 500 nM A83-01, 10 μM SB202190. Overnight incubation at 37° C. under static conditions allowed optimal cell attachment and recreation of the interface between human duodenal epithelium and intestinal microvascular endothelium.

Importantly, it was found that successful epithelial cell seeding and efficient monolayer formation can be achieved only if using enteroid fragments, as single intestinal cell suspensions (produced using longer exposure to the Enteroid Dissociation medium) do not expand adequately to develop a functional mucosal barrier, and whole enteroids remain in their cystic spherical form loosely adhering to the ECM-coated porous membrane under flow and fail to form a continuous monolayer (data not shown). In addition, simultaneous co-culture with primary HIMECs in the lower channel of the device greatly improved seeding efficiency, epithelial monolayer formation, and intestinal barrier formation. Specifically, it was found that following the initial plating at high density, when the epithelial and endothelial media are perfused continuously through both channels at the same rate to provide cells with nutrients and remove their metabolic waste, only cultures that contained intestinal endothelium retained a confluent epithelium in the upper channel (FIG. 3A).

Figures 3A, 3B, 3C:
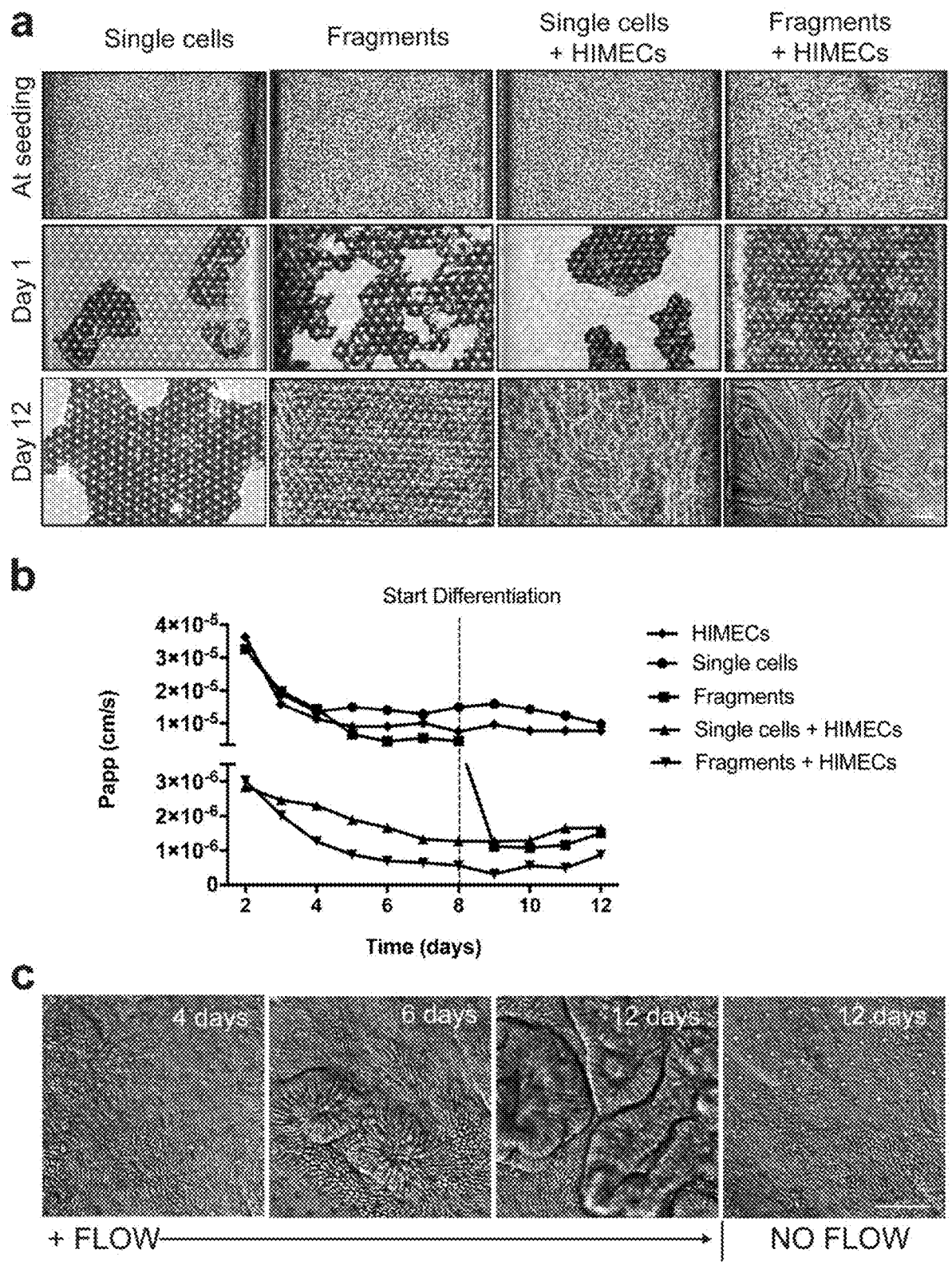
FIGS. 3A-3C depict the establishment of the primary human intestinal epithelium in an exemplary small intestine-on-chip in the presence or absence intestine-specific microvascular endothelium.

Additionally, the presence of HIMECs in the lower channel of small intestine chip is able to partially rescue the typically inefficient process of monolayer formation when enteroids are fully dissociated into single cells prior to culturing them in the microchannel, and in some cultures even formation of a villus epithelium is observed (FIG. 3B). However, the reproducibility of forming a villus intestinal epithelium was much higher using enteroid fragments versus isolated cells (~90% versus 40% success rate), and thus, the fragment method was utilized in all subsequent experiments. Once a confluent epithelial monolayer forms and optimal barrier function is obtained (typically 8 days after seeding), differentiation of the intestinal epithelium is induced by removing Wnt3A, nicotinamide and SB202190 from EM medium, and adding the Notch inhibitor DAPT to create a Differentiation Medium (DM), as previously described[1, 2, 27]. Under co-culture conditions, the switch to the DM leads to formation of intestinal villi-like structures throughout the entire length of the epithelial channel, whereas this was not observed when the endothelium was absent (FIG. 3A, left vs. right).

Application of the Protocol

This primary human small intestine-on-chip model can be adapted to a wide range of applications, including basic research studies of human intestinal development, stem cell maturation and epithelial cell function; assessment of nutrient transport, sensing, absorption, intestinal barrier function and tissue-tissue (e.g., epithelial-endothelial) interactions; evaluation of drug delivery, therapeutic efficacy or toxicity, as well as development of regenerative medicine. In addition, use of clinical biopsy specimens from individuals with specific genotypic and phenotypic characteristics can enable analysis of patient-specific disease mechanisms as well as response to therapies, and thereby help to advance personalized medicine in the future. Intestine chips also can be modified to incorporate immune cells as well as commensal or pathologic microbiota for studies on gut inflammatory disorders, host-pathogen and host-commensal interactions, as previously shown with the human gut-on-a-chip that utilized the established Caco-2 intestinal cell line[17, 19].

Applications and Advances

In some embodiments of the methods described herein, fragments from a large number of established enteroids (~60-80) are required to form a confluent intestinal epithelium on each chip. This is because enteroid fragments require high density seeding to ensure that adequate numbers of intestinal stem cells are present to support the proliferative expansion of the monolayer. Once a full monolayer is achieved, a fully differentiated epithelium with all the major differentiated intestinal epithelial cell types (absorptive enterocytes, Paneth cells, goblet cells and enteroendocrine cells) and transcriptional profile closely resembling its in vivo counterpart are generated using this method. The power of the organ-on-a-chip approach specifically lies in its ability to enable incorporation of increasing organ-level complexity by integrating increasing numbers of different cell types one-at-a-time and studying the system at varying levels of its complexity[7, 8]. Moreover, this synthetic biology approach at the organ level permits one to gain insight into mechanisms of biological regulation by manipulating potential contributing physical factors (e.g., flow, peristalsis) and cellular components one-at-a-time while simultaneously providing a window on molecular-scale biochemical and cellular responses in real-time and at multi-omics level. Application of microfluidic technology can also allow mimicking of in vivo growth factors/signaling gradients, which play important role in many biological processes, including correct intestinal differentiation and regeneration. Thus, this microfluidic human small intestine-on-chip has extraordinary experimental potential for understanding and modeling human intestinal development, homeostasis and diseases, such as intestinal enteropathy, celiac disease and cancer, as well as providing a novel approach to study intestinal interactions with pathogens and the contribution of the microbiome to health and disease using patient-specific cells.

Materials

Reagents

Tall Channel Stretchable Chip (Emulate)
(3-Aminopropyl)trimethoxysilane (APTMS, Sigma-Aldrich, cat. no. 281778)
Pure ethyl alcohol, anhydrous (100%, 200 proof; Sigma-Aldrich, cat. no. 459836)
Matrigel matrix growth factor, reduced (BD, cat. no. 354230 or 356231. Either product can be used.)
Collagen I, rat tail, 100 mg (BD, cat. no. 354226)
DMEM (Life Technologies, cat. no. 10564-011)
Dulbecco's PBS (D-PBS; pH 7.4, Ca2+- and Mg2+-free; Gibco, cat. no. 14190-144)
Human Intestinal Microvascular Endothelial Cells (HIMEC; ScienCell, cat. no. 2900)
Microvascular Endothelial Cell Growth Medium-2 BulletKit (EGM-2-MV BulletKit for culture of human intestinal microvascular endothelial cells; Lonza, cat. no. CC-3202)
Trypsin/EDTA solution (0.05% (wt/vol); Gibco, cat. no. 25300-054)
Surgically resected intestinal tissues or endoscopic biopsy samples. CAUTION Informed consent must be obtained from all subjects. Studies must conform to all relevant institutional and governmental regulations.
Collagenase 1 (Life Technologies, cat. no. 17100-017)
L-WRN (ATCC, cat. no. CRL-3276)
Cell recovery solution (BD, cat. no. 354253)
TrypLE Express with phenol red (Life Technologies, cat. no. 12605-010)
Rho-associated protein kinase (ROCK) inhibitor (Y-27632; Sigma-Aldrich, cat. no. Y0503)
DMSO (Sigma-Aldrich, cat. no. D2650)
BSA (Sigma-Aldrich, cat. no. A7030)
Advanced DMEM/F12 (Life Technologies, cat. no. 12634-010)
1-alanyl-1-glutamine (GlutaMAX; Life Technologies, cat. no. 35050-061)
HEPES, 1 M (Life Technologies, cat. no. 15630-106)
B27 supplement, 50× (Life Technologies, cat. no. 17504-044)
N2 supplement, 100× (Life Technologies, cat. no. 17502-048)
Nicotinamide (Sigma-Aldrich, cat. no. N0636)
N-acetyl-L-cysteine (Sigma-Aldrich, cat. no. A5099)
[Leu15]-gastrin I, human (Sigma-Aldrich, cat. no. G9145)
Recombinant murine epidermal growth factor (EGF; Peprotech, cat. no. 315-09)
Activin-like kinase (ALK) inhibitor (A83-01; Tocris, cat. no. 2939)
p38 Mitogen-activated kinase (MAPK) inhibitor (SB202190; Sigma-Aldrich, cat. no. S7067)
Primocin, 50 mg ml-1 (Invivogen, cat. no. ant-pm-2)
Recombinant human Noggin (Peprotech, cat. no. 120-10C)
Recombinant human R-spondin (Peprotech, cat. no. 120-38)
γ-secretase inhibitor (DAPT; Sigma-Aldrich, cat. no. D5942)
Dextran, Texas Red, 40,000 Da MW, Neutral (Thermo Fisher Scientific, cat. no. D1829)
Lucifer Yellow, 450 Da MW (MP Biomedicals, cat. no. 155267)
Paraformaldehyde (4% (wt/vol); Electron Microscopy Science, cat. no. 15710)
4',6-Diamidino-2-phenylindole dihydrochloride (DAPI; Thermo Fisher Scientific, cat. no. 62248)
Triton-X 100 0.3% (vol/vol) (Sigma, cat. no. T8787)
Primary antibodies: anti-E Cadherin antibody (mouse monoclonal, Abcam, cat. no. ab1416, 1:100), anti-ZO-1 antibody (mouse monoclonal, Life technology, cat. no.

33-9100, 1:200), anti-VE Cadherin antibody (rabbit polyclonal, Abcam, cat. no. ab33168, 1:400), anti-Mucin 5AC antibody (mouse monoclonal, Thermo Fisher Scientific, cat. no. 45M1, 1:100), anti-lysozyme antibody (polyclonal, Dako, cat. no. A0099, 1:1000), anti-Chr-A (C-20) antibody (goat polyclonal IgG, Santa Cruz Biotechnology, cat. no. sc-1488, 1:100), anti-villin antibody (monoclonal mouse, Abcam, cat. no. ab3304, 1:100), anti-NHE3 antibody (rabbit polyclonal, Novus Biologicals, cat. no. NBP1-82574, 1:100), anti-alpha 1 Sodium Potassium ATPase antibody (mouse monoclonal, Abcam, cat. no. ab7671, 1:100)

Alexa Fluor™ secondary antibodies (Thermo Fisher Scientific)

Phalloidin, Alexa Fluor 647 (Thermo Fisher Scientific, cat. no. a22287)

Sucrose (Sigma-Aldrich, cat. no S1888)

D-Mannitol (Sigma-Aldrich, cat. no M4125)

Amplex™ Red Glucose assay kit (Molecular Probes, cat. no A22189)

RIPA buffer (Thermo Fisher Scientific, cat. no 89900)

Pierce BCA Protein Assay Kit (Thermo Fisher Scientific, cat. no 23225)

RNeasy™ Mini Kit (Qiagen, cat. no 74106)

RNase-Free DNase Set (Qiagen, cat. no 79254)

SuperScript™ VILO cDNA Synthesis Kit (Invitrogen, cat. no 11754050)

TaqMan™ Fast Advanced Master Mix (Applied Biosystems, cat. no 4444963)

TaqMan™ gene expression assays (Thermo Fisher Scientific): Hs00357579_g1 for intestinal-type alkaline phosphatase (ALPI), Hs00356112_m1 for sucrase isomaltose (SI), Hs00894025_m1 for mucin 2 (MUC2), Hs00873651_g1 for mucin 5AC (MUC5AC), Hs00900375_m1 for chromogranin A (CHGA), Hs00300531_m1 for synaptophysin (SYP), Hs00426232_m1 for lysozyme (LYZ), Hs00969422_m1 for leucine-rich-repeat-containing G-protein-coupled receptor 5 (LGR5), Hs00409825_g1 for Bmi1 (BMI1), Hs02758991_g1 for glyceraldehyde-3-phosphate dehydrogenase (GAPDH).

Human Mucin 2/MUC2 ELISA Kit (Sandwich ELISA) (LSBio, cat. no. LS-12102)

Equipment

Standard cell-culture equipment

T75 flasks (BD Falcon, cat. no. 137787)

Tissue culture plates; 24 well, flat bottom (Corning, cat. no. 3524)

Oxygen plasma etcher (SPI Supplies and Plasma Etch PE-100, Plasma Prep II)

Blunt needles (18 gauge; VWR, cat. no. KT868280)

Silicone tubing (Saint-Gobain Tygon sanitary tubing, inner diameter=1/32 inches; Fisher Scientific, cat. no ABW00001)

2-Stop PharMed™ BPT Tubing, 0.25 mm, 12/pack (Cole-Parmer, cat. no. EW-95723-12)

Peristaltic pumps (Ismatec IP16, cat. no ISM 943)

Programmable vacuum actuator with an electronic vacuum regulator (ITV009, SMC Corp.) controlled by an Arduino microcontroller to stretch a membrane in small intestine-on-chip.

Microplate reader (Synergy Neo, BioTek)

Inverted laser-scanning confocal microscope (Leica SP5× MP DMI-6000)

QuantStudio™ 7 Flex Real-Time PCR System (Thermo Fisher Scientific)

Reagent Setup

2% APTMS. Mix APTMS and pure anhydrous ethyl alcohol to obtain 2% (vol/vol) solution. CAUTION Wear safety glasses, gloves, face protection and a respirator if necessary when you are working with this material. Adequate ventilation is highly recommended in order to avoid breathing the vapors IMPORTANT This reagent must be made fresh for each use.

ECM solutions. Mix type I collagen (200 μg ml-1 final concentration) and Matrigel™ (1% final concentration) in pre-chilled serum-free DMEM. IMPORTANT Prepare these ECM solutions immediately before use, and keep collagen and Matrigel-containing solution at 4° C. or on ice to prevent unwanted premature polymerization of matrix proteins.

EGM-2-MV—Human microvascular endothelial cell culture medium. Add growth supplements contained in each SingleQuots™ vial to the basal medium included in the EGM-2-MV medium BulletKit, as instructed by the vendor. IMPORTANT Store the medium protected from light at 4° C. and use within 1 month.

Wnt3A, R-spondin and Noggin Conditioned Medium. Use L-WRN (ATCC® CRL3276) cells and vendor protocols to prepare conditioned medium.

Enteroid Dissociation Solution. Mix TrypLE™ (Life Technologies) in Ca2+/Mg2+-free PBS to obtain 50% (vol/vol) solution and supplement with 10 μM of Y-27632 (Sigma-Aldrich) supplier).

Growth factor stock solutions. Reconstitute growth factors below in 0.1% BSA solution in PBS or DMSO according to the vendor's recommendation to generate the following concentrations: nicotinamide 1M, N-acetyl-L-cysteine (NAC) 500 mM, gastrin I 100 μM, EGF 500 μg ml-1, Noggin 100 μg ml-1, R-spondin 1 mg ml-1, Y-2763210 mM, A83-01 500 μM, SB202190 30 mM and DAPT 10 mM. Aliquots can be stored at −20° C. for 1 month Intestinal epithelial cell culture media. Make expansion (EM) medium and differentiation (DM) medium according to the following table. The prepared media is best when freshly made, but it can be stored at 4° C. for up to 1 week.

| Component | Volume (final concentration) | |
|---|---|---|
| | Expansion Medium (EM) | Differentiation Medium (DM) |
| Advanced DMEM/F12 | 45 ml | 95 ml |
| Glutamax | 1 ml | 1 ml |
| HEPES | 1 ml | 1 ml |
| Primocin | 200 μl (100 μg ml − 1) | 200 μl |
| B27 supplement | 1 ml | 1 ml |
| N2 supplement | 500 μl | 500 μl |
| NAC | 200 μl (1mM) | 200 μl (1 mM) |
| L-WRN-conditioned medium | 50 ml | — |
| Gastrin I | 10 μl (10 nM) | 10 μl (10 nM) |
| EGF | 10 μl (50 ng ml − 1) | 10 μl (50 ng ml − 1) |
| A83-01 | 100 μl (500 nM) | 100 μl (500 nM) |
| Nicotinamide | 1 ml (10 mM) | — |
| SB202190 | 33.2 μl (10 uM) | — |
| R-spondin | — | 100 μl (1 μg ml − 1) |
| Noggin | — | 100 μl (100 ng ml − 1) |
| DAPT | — | 100 μl (10 μM) |
| Total | 100 ml | 100 ml |

PROCEDURE. All steps in the procedure are summarized in FIG. 2C

Fabrication and assembly of PDMS small intestine chip device TIMING ~3.5 d Follow the procedures described in Huh et al.[24] for the microfabrication of the gut-on-a-chip using the dimensions described above.

PAUSE POINT The PDMS microdevice can be stored indefinitely at room temperature.

Chemical activation of PDMS membrane in the small intestine-on-chip TIMING 1 d Treat the PDMS microfluidic device with oxygen plasma for 1.5 min.

Add 50 μl of 2% APTMS (see Reagent Setup) into the upper and lower channels of microfluidic device seal the inlet and outlet ports of both microchannels with 200 μl filter pipette tips to prevent APTMS solution from leaking out of the device and incubate for 30 min at RT.

IMPORTANT STEP Ensure that the entire microchannels are filled with the APTMS solution without any trapped air bubbles to achieve uniform surface treatment.

Flush the channels twice with 100% anhydrous ethyl alcohol to remove APTMS solution and once with 70% ethyl alcohol to sterilize the microchannels.

IMPORTANT STEP Avoid unwanted contact of the APTMS solution with the external surface of PDMS device that leads to its damage and loss of transparency.

Place the sterile device in a Petri dish and transfer to an 80° C. oven overnight to remove residual ethanol and achieve covalent surface functionalization.

ECM Coating of the PDMS membrane on-chip TIMING 2.5 h

Transfer the device to a biosafety cabinet and introduce 50 μl of the ECM coating solution (see Reagent Setup) into both the upper and lower central microfluidic channels, then seal the inlet and outlet ports of both microchannels with 200 μl filter pipette tips to prevent coating solution from leaking out of the device.

IMPORTANT STEP Ensure that the entire microchannel is filled with the ECM solution without any trapped air bubbles.

Trouble Shooting

Place the microdevice in a humidified 37° C. incubator for over 2 h and proceed to the Seeding of Human Intestinal Microvascular Endothelial Cells or store the microdevice at 4° C.

PAUSE POINT The coated microdevice can be stored at 4° C. for up to one week.

Seeding of Human Intestinal Microvascular Endothelial Cells (HIMECs) TIMING 1.5 h Flush the channels with serum-free DMEM or DPBS to remove residual coating solution Remove the EGM-2-MV culture medium from a T75 flask containing 80-90% confluent Human Intestinal Microvascular Endothelial Cells (HIMECs). Wash the cells with Ca2+-free, Mg2+-free PBS twice.

Add 2 ml of prewarmed trypsin/EDTA solution (0.05%) to the cell culture flask, and incubate the mixture in a humidified incubator (37° C., 5% CO2) for 2-3 min or until the cells are released from the growth surface. Count and pellet 250,000 cells by centrifugation at 220 g for 5 min.

Thoroughly resuspend the HIMEC cell pellet in 30 μl of Microvascular Endothelial Cell Growth Medium-2 (EGM-2-MV) (see Reagent Setup).

Introduce the concentrated HIMEC cell suspension into the endothelial compartment (lower central microfluidic channel) and seal the inlet and outlet ports of both upper and lower microfluidic channels with 200 μl filter pipette tips.

IMPORTANT STEP Inject the cell suspension solution very slowly to prevent introduction of air bubbles.

Troubleshooting

Inspect the microchannels under a microscope to ensure homogenous cell distribution within the channel and immediately invert the microdevice to allow endothelial cell attachment to the bottom side of PDMS membrane.

IMPORTANT STEP Invert the device shortly after the seeding to prevent cell deposition on the under-surface of the lower cell culture channel Troubleshooting Incubate the device at 37° C. for 1 h.

Inspect the microchannels under a microscope to ensure cell adhesion to the membrane.

IMPORTANT STEP Make sure that the majority of the pores on the PDMS membrane are covered by the attached endothelial cells to prevent inter-compartment cell migration through the membrane pores during subsequent epithelial cell seeding and co-culture.

Troubleshooting

Wash the bottom channel with 100 μl of EGM-2-MV to remove unattached cells.

Crypt isolation and maintenance of human small intestinal enteroids TIMING ~7-14 d Follow the procedures described in Fujii et al.[28] for the isolation and culture of human intestinal crypts with minor modifications: (1) to release crypt cells incubate with 2 mg/ml Collagenase I for 30-40 minutes at 37° C. instead of 2.5 mM EDTA and (2) use conditioned medium from L-WRN Cells as a source of Wnt3A, R-spondin and Noggin (see Reagent Setup).

Grow enteroids in the presence of Expansion Medium (EM) (see Reagent Setup) for 7-14 days.

Use enteroids before passage 30 because higher passage numbers result in reduced cell attachment to the ECM-coated membrane.

Harvesting primary human intestinal cells from 3D enteroids TIMING ~1.5 h Aspirate the medium from 2 wells containing approximately 50-100 enteroids each and add 500 μl of Cell Recovery solution to each well.

Scrape the Matrigel™ off of the bottom of the wells with a 1,000-μl pipette and collect the enteroids, together with the Matrigel™, into a 15-ml low-binding centrifuge tube. Place the tube on ice for 30-40 min and vortex intermittently.

Centrifuge the tube at 4° C. at 300 g for 5 min, 4° C.

Aspirate the supernatant and suspend the pellet with Enteroid Dissociation Solution (see Reagent Setup). Use sufficient volume of Dissociation Solution to completely submerge the enteroid pellet. As an example, 2 mL total of solution is appropriate for 24 wells of enteroids.

IMPORTANT STEP Make sure that all the Matrigel™ is efficiently removed. The presence of residual gel covering enteroids may prevent efficient digestion and cell attachment to ECM in the microfluidic device.

Troubleshooting

Pipette pellet in Dissociation Solution briefly with a 1,000-μl pipette to resuspend.

Place the tube in a 37° C. water bath for 2 min.

Add complete EM medium (supplemented with 10 μM of Y-27632) up to 10 ml, and centrifuge it at 4° C. at 300 g for 5 min, RT (1st washing).

Aspirate the supernatant and repeat foregoing step (2nd washing).

Suspend the pellet with EM medium (supplemented with 10 μM of Y-27632). Typically, a pellet generated from two wells of enteroids (approximately 210,000 cells)

can be suspended in 30 µl of EM medium and used for the seeding of one small intestine-on-chip.

Pipette the pellet with media briefly with a 200-µl pipette and inspect the size of enteroid fragments under a microscope to ensure sufficient level of enteroid dissociation.

IMPORTANT STEP Make sure all enteroids are thoroughly fragmented. Inadequate dissociation can result in reformation of cystic enteroid structures in the microfluidic device instead of monolayer formation. Avoid excessive dissociation into the single cells it results in diminished cell survival and recovery.

Troubleshooting

Seeding of primary intestinal epithelial cells TIMING 3.5 h to 1 d

Flush the upper channel gently with medium to remove any residual coating solution. Slowly inject the epithelial cell suspension into the outlet port of the upper channel (Inspect the microchannels under a microscope to ensure homogenous cell distribution within the channel and keep the microdevice upright to allow cell attachment to the top side of PDMS membrane).

Inspect the microchannel under a microscope to ensure even cell distribution across the upper cell culture channel.

IMPORTANT STEP Evaluate homogenous cells distribution throughout entire cell culture channel.

Troubleshooting

Incubate the device for at least 3 hours (up to overnight) at 37° C. to allow for optimal cell attachment.

Once epithelial cell attachment is accomplished, wash upper channel thoroughly with EM to remove unattached cells.

Microfluidic culture of the small intestine-on-chip TIMING 12-21 d

Connect the device to the peristaltic pump and perfuse the upper and lower channels with EM and EGM-2-MV medium, respectively, at a volumetric flow rate of 60 µl $h^{-1}$ in a humidified incubator maintained at 37° C.

Allow the cells to grow to confluence over the course of 3-4 d. Apply cyclic strain of 10% at a frequency of 0.2 Hz to the cell populations via the side chambers by using a vacuum pump controlled by the a programmable actuator consisting of an electronic vacuum regulator (ITV009, SMC Corp.) and Arduino microcontroller to mimic physiological peristaltic motions in the human gut.

Continue microfluidic cell culture in this manner until the barrier function reaches optimal impermeability (see "Assessment of intestinal barrier function" below for measurement details) and villi-like structures will form—usually up to 8 days and is accompanied by the formation of undulating intestinal villi-like structures that can be visualized using phase contrast or differential interference contrast microscopy.

IMPORTANT STEP At day 7, replace the culture medium in the lower channel with a 0.5% FBS EGM-2-MV medium.

Replace the apical EM with DM to trigger differentiation on day 8. Allow the cells to reach fully differentiated state by culturing them in the presence of this medium for additional 3-4 days.

Functional analysis of the small intestine-on-chip TIMING 5 h-2.5 d

When the microfluidic cell culture is fully established, assess the intestinal permeability (see "Assessment of intestinal barrier function" below for measurement details), epithelial and endothelial tissue composition and morphology via immunofluorescence staining and confocal imaging (see "Immunofluoresence staining of intestinal epithelial cells on chip" below for measurement details), measure enzymatic activity of brush border disaccharide (see "Measurement of sucrose activity" below for measurement details), expression of different intestinal cell-types specific transcripts by qRT-PCR (see "Evaluation of lineage differentiation by qRT-PCR" below for measurement details) and assess mucus secretion using Muc2 ELISA.

Assessment of intestinal barrier function TIMING 1 d

Dilute Lucifer Yellow (450 Da) and Dextran (400,000 Da) to final concentration of 100 µg ml-1 in EM or DM media depending on the phase of epithelial growth at which the barrier function measurement is performed.

Connect the device to the peristaltic pump and perfuse the upper and lower channels with epithelial medium containing fluorescent tracers and endothelial culture medium respectively, at a volumetric flow rate of 60 µl h-1 in a humidified incubator maintained at 37° C.

Collect the apical and basal effluents overnight.

Measure the fluorescence intensity of effluents using a microplate reader and calculate the apparent permeability using the following formula:

$$P\_app = J/(A \cdot \Delta C)$$

With Papp=Apparent permeability, J=Molecular flux, A=Total area of diffusion, and ΔC=Average gradient (~1 because of the low flow rate)[22].

Optimal Papp for small intestine-on-chip is ~1×10$^6$ for 450 Da Lucifer Yellow and ~1-2×10$^7$ for 40 kDa Dextran (~1% and ~0.1-0.2% of tracer leakage into the basal channel)

Immunofluorescence staining of intestinal epithelial cells on-chip TIMING 2.5 d Flow PBS through the top and bottom channels.

Introduce 4% paraformaldehyde into the channels, and incubate the device without flow for 15 min at room temperature.

Flow the channels gently with additional PBS to remove the paraformaldehyde and introduce BSA blocking solution (5% (wt/vol) to the channels. If permeabilization for optimal antibody staining efficiency is needed, add 0.1% (vol/vol) Triton-X100 to blocking solution. Incubate the device in static at room temperature for 1 hour.

Dilute primary antibody in BSA solution (2% (wt/vol) at the optimal ratio (see Reagents), and introduce it into the upper channel. Incubate at 4° C. overnight. To measure negative background signal, use appropriate isotype controls at identical concentrations and staining conditions as the target primary antibody.

Remove antibody solution by flushing the channels with D-PBS three times.

Dilute fluorescently labeled secondary antibody 1:100 (Alexa Fluor secondary antibody, Thermo Fisher Scientific) in BSA solution and introduce it into the channels. Incubate it in the dark at 4° C. overnight.

For staining nuclei, incubate the cells with DAPI antibody at room temperature for 5 min. For F-actin staining, incubate the cells with fluorescently labeled phalloidin at room temperature for 30 min.

Remove antibody solution by flushing the channels with D-PBS three times. The device is now ready for imaging using fluorescence confocal microscopy.

Measurement of sucrose activity TIMING 5 h

Prepare sucrose and mannitol reaction buffers: 30 mM sucrose or mannitol in PBS with Ca2+- and Mg2+, pH 6.5. Adjust the NaCl concentration in PBS to 120 mM to adjust for osmolarity in the presence of 30 mM sucrose. Sterilize by autoclaving or by filter sterilization.

Perfuse cells in the upper and lower channels with PBS with Ca2+ and Mg2+pH 6.5 at a volumetric flow rate of 60 μl h-1 in a humidified incubator maintained at 37° C. for 1 h to remove any residual glucose from the standard media.

Wash the upper and lower channels twice with PBS with Ca2+ and Mg2+pH 6.5 and introduce sucrose reaction buffer (or mannitol reaction buffer in control devices) in the upper microfluidic channel and PBS with Ca2+ and Mg2+pH 7.0 into the lower channel. Collect samples from the apical and basal cell culture compartments at different time intervals (every hour for the total time of 3 h) and collect in a 96-well plate with black, flat bottom.

Measure the concentration of glucose in collected samples using Amplex™ Red Glucose assay kit following the vendor's instructions.

At the end of the experiment, remove endothelial cells from the device by using TrypLE™ solution and lyse the epithelium using RIPA buffer to determine the total protein content using Pierce BCA Protein Assay following the vendor's instructions. Determine glucose concentration from a standard curve and calculate sucrase isomaltose activity as units per milligram of protein. 1 unit (1 U) is defined as the activity that hydrolyzes 1 μmol substrate/min at 37° C.

Evaluation of lineage differentiation by qRT-PCR TIMING 1.5 d

Extract total RNA from undifferentiated and differentiated epithelial cells in situ on-chip using RNeasy™ Mini Kit following the vendor's instructions. Remove any residual contaminating genomic DNA by on-column incubation with DNase I for 15 minutes at room temperature.

Reverse transcribe into cDNA using SuperScript™ VILO cDNA Synthesis Kit.

Carry out Real time PCR using a QuantStudio™ 7 Flex Real-Time PCR System using TaqMan™ Fast Advanced Master Mix and Taqman gene expression assays.

Quantify the results using 2-ΔΔCt method.

Assessment of Mucin 2 secretion into the luminal effluent TIMING 1 d

Collect the apical effluents overnight.

Carry out ELISA using Human Mucin 2/MUC2 ELISA Kit (Sandwich ELISA) following the vendor's protocol. Use 1 to 5 sample dilution.

Read the optical density at 450 nm wavelength using a microplate reader.

Determine Muc2 concentration from a standard curve generated using a four parameter logistic (4-PL) curve fit.

Results

This procedure outlines a step-by-step procedure for creating a human small intestine-on-chip composed of biopsy-derived, primary small intestinal epithelium interfaced with an intestinal microvascular endothelium exposed to physiologically-relevant mechanical and biochemical cues in a polarized microenvironment (FIG. 2C). Use of these dynamic culture conditions, in combination with a shift from an expansion to a differentiation medium on day 8, results in the appearance of undulating, 3D, intestinal villus-like structures within the epithelium within 12 days of culture, whereas culture of these same cells in the absence of flow for 12 days does not despite continued application of 10% cyclic strain (FIG. 2C), confirming results of previous gut-on-a-chip studies using the Caco-2 cell line[18].

Figures 4A, 4B, 4C, 4D:
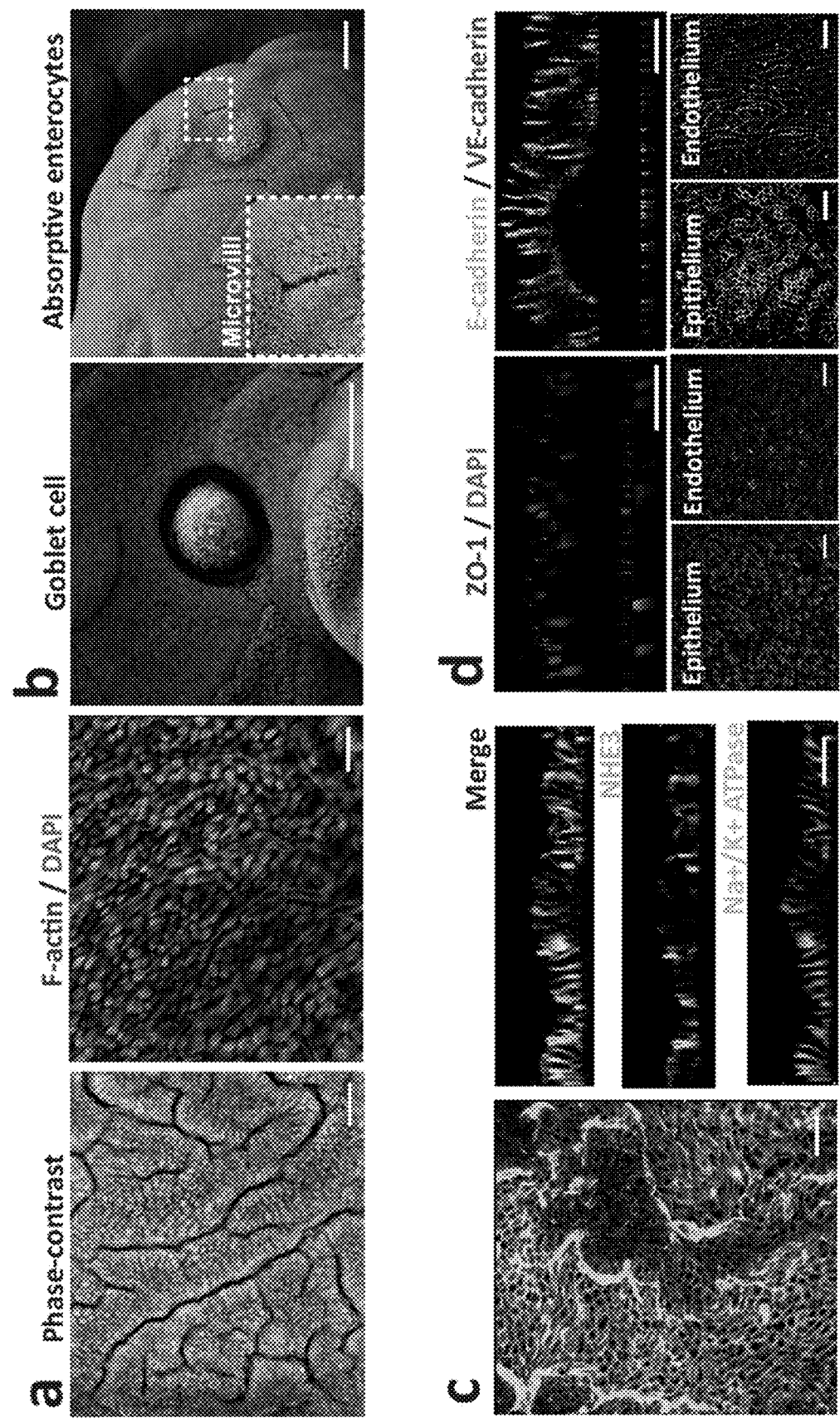
FIGS. 4A-4D depict morphological analysis of the primary human small intestine-on-chip performed at the day 4 of differentiation (8 days in EM medium, followed by 4 days in DM)

Phase contrast and confocal fluorescence microscopy confirms the presence of a continuous, polarized, epithelial cell monolayer with an apical brush border membrane labeled with F-actin (magenta) and basal nuclei (blue) aligned along the boundary of each villus-like extension into the lumen of the epithelial microchannel of the device (FIG. 4A). Scanning electron microscopic (SEM) analysis of the apical surface of the epithelial cells lining the villus-like luminal extensions reveals the presence of mucus producing goblet cells and well-polarized absorptive enterocytes with densely-packed apical microvilli (FIG. 4B). The villus epithelium lining the small intestine-on-chip also expresses the major apical and basolateral ion transporters, NHE3 and Na+/K+-ATPase, respectively (FIG. 4C). NHE3 is responsible for electroneutral Na+ absorption in the small intestine[29] and localizes to the brush border membrane of the microfluidic epithelial cell culture, as it does in living intestine. On the other hand, Na+/K+-ATPase, the major ion transporter responsible for regulating the intracellular Na+ gradient necessary for luminal absorption of nutrients[30], is exclusively localized to the basolateral membrane of the small intestine-on-chip, again recapitulating their native location in human intestine (FIG. 4C).

Figures 5A, 5B, 5C, 5D, 5E:
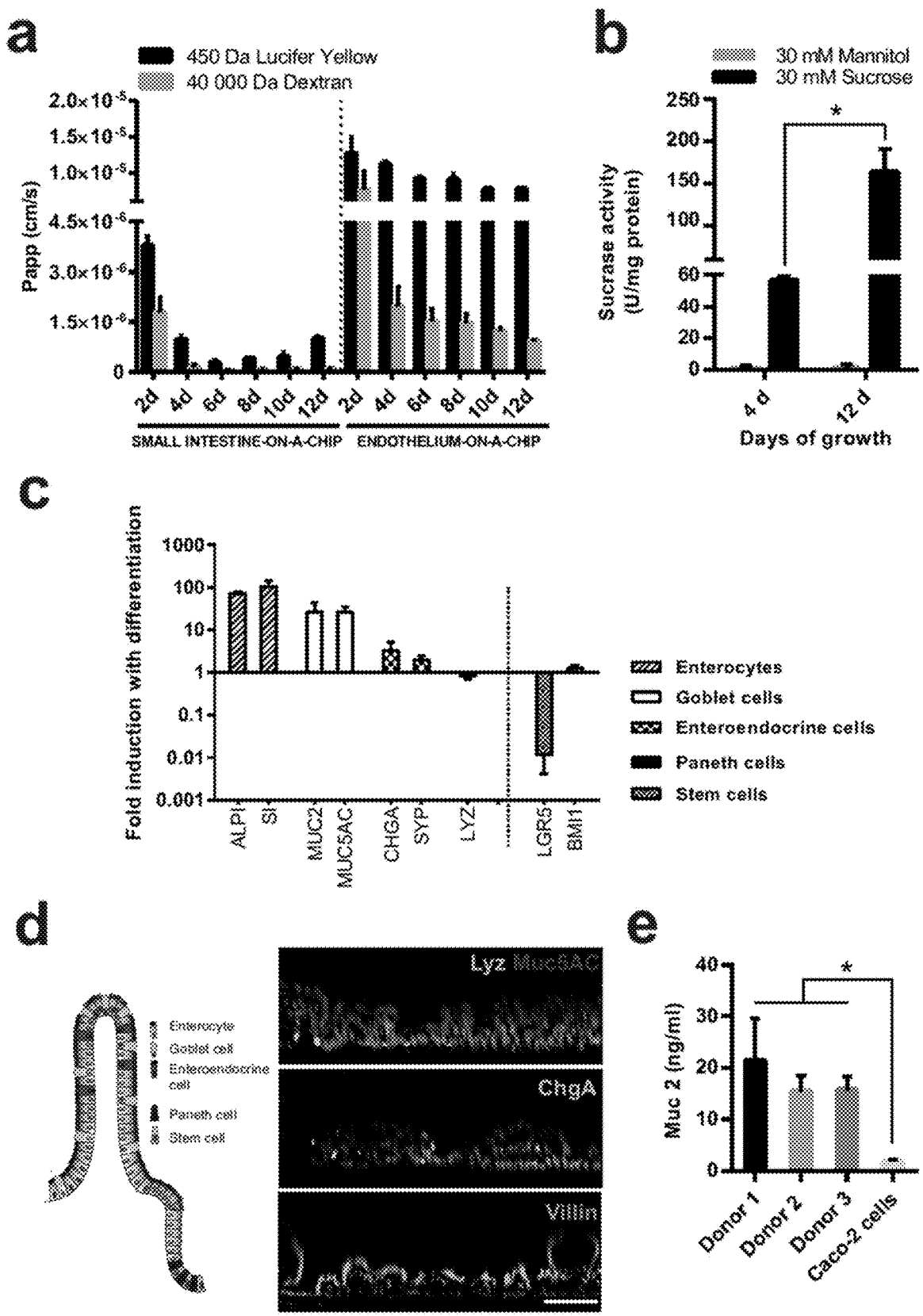
FIGS. 5A-5E demonstrate that an exemplary primary human small intestine-on-chip exhibits relevant barrier function, digestive capacity and multi-lineage differentiation.

Correct cell polarity is maintained by the presence of intact tight and adherens junctions identified through immunofluorescent staining of zonula occludens-1 (ZO-1) and E-cadherin in the epithelium, and ZO-1 and VE-cadherin in microvascular endothelium, respectively (FIG. 4D). These junctional complexes are responsible for the selective permeability of the intestinal epithelium and microvascular endothelium, and formation of these barriers is confirmed by restriction of the paracellular passage of small (450 Da lucifer yellow) and large (40 kDa dextran) fluorescent tracers from the apical to basal compartment. As expected the small intestine chips lined by both intestinal epithelium and endothelium exhibit a much greater barrier to the transfer of both sized dyes than chips lined by endothelium alone, and the growth and maturation of these microfluidic cultures is associated with parallel increases in barrier function from 2 to 12 days of culture (FIG. 5A). Interestingly, the optimal level of apparent permeability in the small intestine chip is reached by 4 days when using a 40 KDa fluorescent dextran as a probe, and by 6 days when the much smaller (450 Da) Lucifer yellow dye is utilized. This barrier is at least 10 times more restrictive than the barrier generated by the endothelium alone (FIG. 5A), highlighting the importance of a tissue-tissue interface for the functional separation of the gut lumen and the vascular compartment. Thus, these studies demonstrate that this human small intestine chip can provide a useful tool for assessing effects on normal intestinal barrier function in vitro.

Additionally, the small intestine-on-chip exhibits digestive capacity, as determined by measuring the activity of the brush border enzyme, sucrase isomaltose that breaks down sucrose to release glucose. When the in situ release of glucose into the apical channel was measured after infusing sucrose through the epithelial microchannel[31], we found that the concentrations of released glucose increased 3 fold from day 4 to 12 when the villus epithelium is fully mature, whereas no change was observed when control experiments were carried out by replacing sucrose with mannitol (FIG. 5B). These data demonstrate that the primary small intestine chip also can provide a new in vitro tool to study intestinal digestion mechanisms, in normal epithelium obtained from individual patient donors.

Importantly, the differentiation of the intestinal monolayer formed from enteroid fragments closely mimics in vivo intestine development. It was confirmed that Lgr5-expression, a marker for adult intestinal stem cells, was enriched in the epithelial monolayer when cultured in expansion media and that markers for absorptive enterocytes and secretory cell lineages (including Paneth cells, goblet cells and enteroendocrine cells) were increased, while Lgr5-expression reduced upon removal of Wnt3A and inhibition of Notch signaling (FIG. 5C). Additionally the small intestine chip recapitulated the native spatial organization of the epithelial cells along the crypt-villus axis with lysozyme-positive Paneth cells localizing at the base of the villus-like luminal invagination and differentiated intestinal cell types (goblet, enteroendocrine cells and absorptive enterocytes) being positioned in the upper villus regions, as visualized by immunofluorescence staining of cell-type specific markers (Lyz, Muc5AC, ChrgA and Villin, respectively) (FIG. 5D). As previously observed in primary human enteroid cultures[26], small intestine-chips established from duodenal biopsies exhibited the characteristics more typical of gastric epithelium, where a more prominent Muc5AC staining can be observed the apical surface of differentiated epithelium. Moreover the presence of gel-forming mucin 2 secreted into the apical effluents of chips (obtained from enteroids fragments derived from 3 different patients) was detected. The total Muc 2 concentration was 10-fold higher than that measured in a previously described gut-on-a-chip[17-19] that is lined by the established Caco-2 intestinal cell line (FIG. 5E). Thus, the Muc2 antigen may be masked by other contents in the protein-rich granules of these differentiated Goblet cells or washed out with the luminal contents.

The primary human small intestine chip may therefore provide a novel tool for studying intestinal stem cell fate switching and multi-lineage development in vitro, which is not possible using gut chips lined by established, tumor-derived cell lines. To date, small intestine chips with similar results using enteroid fragments obtained from ten pediatric patients have been successfully created. These microfluidic co-cultures have been maintained in small intestine chips for up to 3 weeks with no loss of phenotype and there is no reason that these cultures could not be maintained for much longer periods of time, if culture conditions are appropriately maintained.

REFERENCES

1. Sato, T. et al. Long-term expansion of epithelial organoids from human colon, adenoma, adenocarcinoma, and Barrett's epithelium. Gastroenterology 141, 1762-1772 (2011).
2. VanDussen, K. L. et al. Development of an enhanced human gastrointestinal epithelial culture system to facilitate patient-based assays. Gut 64, 911-920 (2015).
3. Sasai, Y., Eiraku, M. & Suga, H. In vitro organogenesis in three dimensions: self-organising stem cells. Development 139, 4111-4121 (2012).
4. Sato, T. & Clevers, H. Growing self-organizing mini-guts from a single intestinal stem cell: mechanism and applications. Science 340, 1190-1194 (2013).
5. Wells, J. M. & Spence, J. R. How to make an intestine. Development 141, 752-760 (2014).
6. Fatehullah, A., Tan, S. H. & Barker, N. Organoids as an in vitro model of human development and disease. Nat Cell Biol 18, 246-254 (2016).
7. Bhatia, S. N. & Ingber, D. E. Microfluidic organs-on-chips. Nat Biotechnol 32, 760-772 (2014).
8. Ingber, D. E. Reverse Engineering Human Pathophysiology with Organs-on-Chips. Cell 164, 1105-1109 (2016).
9. Huh, D. et al. Reconstituting organ-level lung functions on a chip. Science 328, 1662-1668 (2010).
10. Baudoin, R., Griscom, L., Monge, M., Legallais, C. & Leclerc, E. Development of a renal microchip for in vitro distal tubule models. Biotechnol Prog 23, 1245-1253 (2007).
11. Jang, K. J. et al. Human kidney proximal tubule-on-a-chip for drug transport and nephrotoxicity assessment. Integr Biol (Camb) 5, 1119-1129 (2013).
12. Leclerc, E., Sakai, Y. & Fujii, T. Microfluidic PDMS (polydimethylsiloxane) bioreactor for large-scale culture of hepatocytes. Biotechnol Prog 20, 750-755 (2004).
13. Powers, M. J. et al. A microfabricated array bioreactor for perfused 3D liver culture. Biotechnol Bioeng 78, 257-269 (2002).
14. Tilles, A. W., Baskaran, H., Roy, P., Yarmush, M. L. & Toner, M. Effects of oxygenation and flow on the viability and function of rat hepatocytes cocultured in a microchannel flat-plate bioreactor. Biotechnol Bioeng 73, 379-389 (2001).
15. Grosberg, A., Alford, P. W., McCain, M. L. & Parker, K. K. Ensembles of engineered cardiac tissues for physiological and pharmacological study: heart on a chip. Lab Chip 11, 4165-4173 (2011).
16. Park, J. et al. Three-dimensional brain-on-a-chip with an interstitial level of flow and its application as an in vitro model of Alzheimer's disease. Lab Chip 15, 141-150 (2015).
17. Kim, H. J., Huh, D., Hamilton, G. & Ingber, D. E. Human gut-on-a-chip inhabited by microbial flora that experiences intestinal peristalsis-like motions and flow. Lab Chip 12, 2165-2174 (2012).
18. Kim, H. J. & Ingber, D. E. Gut-on-a-Chip microenvironment induces human intestinal cells to undergo villus differentiation. Integr Biol (Camb) 5, 1130-1140 (2013).
19. Kim, H. J., Li, H., Collins, J. J. & Ingber, D. E. Contributions of microbiome and mechanical deformation to intestinal bacterial overgrowth and inflammation in a human gut-on-a-chip. Proc Natl Acad Sci USA 113, E7-15 (2016).
20. Imura, Y., Asano, Y., Sato, K. & Yoshimura, E. A microfluidic system to evaluate intestinal absorption. Anal Sci 25, 1403-1407 (2009).
21. Kimura, H., Yamamoto, T., Sakai, H., Sakai, Y. & Fujii, T. An integrated microfluidic system for long-term perfusion culture and on-line monitoring of intestinal tissue models. Lab Chip 8, 741-746 (2008).
22. Benam, K. H. et al. Small airway-on-a-chip enables analysis of human lung inflammation and drug responses in vitro. Nat Methods 13, 151-157 (2016).
23. Huh, D. et al. A human disease model of drug toxicity-induced pulmonary edema in a lung-on-a-chip microdevice. Sci Transl Med 4, 159ra147 (2012).

24. Huh, D. et al. Microfabrication of human organs-on-chips. Nat Protoc 8, 2135-2157 (2013).
25. Sato, T. et al. Single Lgr5 stem cells build crypt-villus structures in vitro without a mesenchymal niche. Nature 459, 262-265 (2009).
26. Zietek, T., Rath, E., Haller, D. & Daniel, H. Intestinal organoids for assessing nutrient transport, sensing and incretin secretion. Sci Rep 5, 16831 (2015).
27. Yin, X. et al. Niche-independent high-purity cultures of Lgr5+ intestinal stem cells and their progeny. Nat Methods 11, 106-112 (2014).
28. Fujii, M., Matano, M., Nanki, K. & Sato, T. Efficient genetic engineering of human intestinal organoids using electroporation. Nat Protoc 10, 1474-1485 (2015).
29. Foulke-Abel, J. et al. Human Enteroids as a Model of Upper Small Intestinal Ion Transport Physiology and Pathophysiology. Gastroenterology 150, 638-649 e638 (2016).
30. Charney, A. N. & Donowitz, M. Functional significance of intestinal Na+-K+-ATPase: in vivo ouabain inhibition. Am J Physiol 234, E629-636 (1978).
31. Ferruzza, S., Rossi, C., Scarino, M. L. & Sambuy, Y. A protocol for in situ enzyme assays to assess the differentiation of human intestinal Caco-2 cells. Toxicol In Vitro 26, 1247-1251 (2012).

TABLE 1

Troubleshooting Table

| Step | Problem | Possible reason | Solution |
|---|---|---|---|
| ECM Coating of the PDMS membrane on-chip | Trapped air bubbles | Rapid injection of ECM solution into hydrophobic PDMS channels | Insert 200 µl pipette tips filled with ECM solution into inlets of upper and lower microchannels and empty pipette tips into the corresponding outlets. Push ECM solution through cell culture microchannels until the trapped air bubbles are removed. |
| Seeding of Human Intestinal Microvascular Endothelial Cells (HIMECs) | Air bubbles in the cell culture channels after cell seeding | Trapped air in the pipette tip used for cell seeding or inadvertent injection of air after the total volume of cell suspension solution is dispensed | Flush the channels with fresh culture medium to remove the bubbles, and re-seed endothelial cells |
| | Uneven cell distribution within the microchannel | Insufficient removal of ECM solution, cell aggregation, overly rapid injection of cell suspension | Flush the channels twice with fresh culture medium to remove the cells and residual ECM solution. Before seeding, pipette the cell solution up and down to evenly suspend the cells, re-seed endothelial cells, make sure to inject the cell suspension slowly to allow homogenous cell distribution |
| | Subconfluent cellular monolayers | Inadequate initial cell seeding density or cell loss due to delayed flipping of PDMS device and cell attachment to the bottom side of lower microchannel | Increase the number of cells used for the generation of cell seeding suspension, re-seed endothelial cells, make sure to invert the device immediately after cell injection |
| Harvesting primary human intestinal cells from 3D enteroids | Presence of residual Matrigel covering the pellet | Inefficient Matrigel digestion process | Resuspend the pellet in fresh Cell recovery solution, incubate on ice for additional 5-10 min, repeat Steps 23-24 |
| Seeding of primary intestinal epithelial cells | Presence of intact enteroids in cell seeding suspension | Inefficient digestion of enteroids | Dissociate enteroids mechanically by pipetting them briefly with a bent 200-ul pipette tip. |
| | Uneven distribution of enteroids fragments | Cell aggregation, too fast injection of cell suspension | Flush the channels twice with fresh medium to remove cells and residual ECM before seeding. Pipette cell solution up and down to evenly suspend the cells, re-seed epithelial cells, make sure to inject the cell suspension slowly to allow homogenous cell distribution |

Example 3

Figure 6:
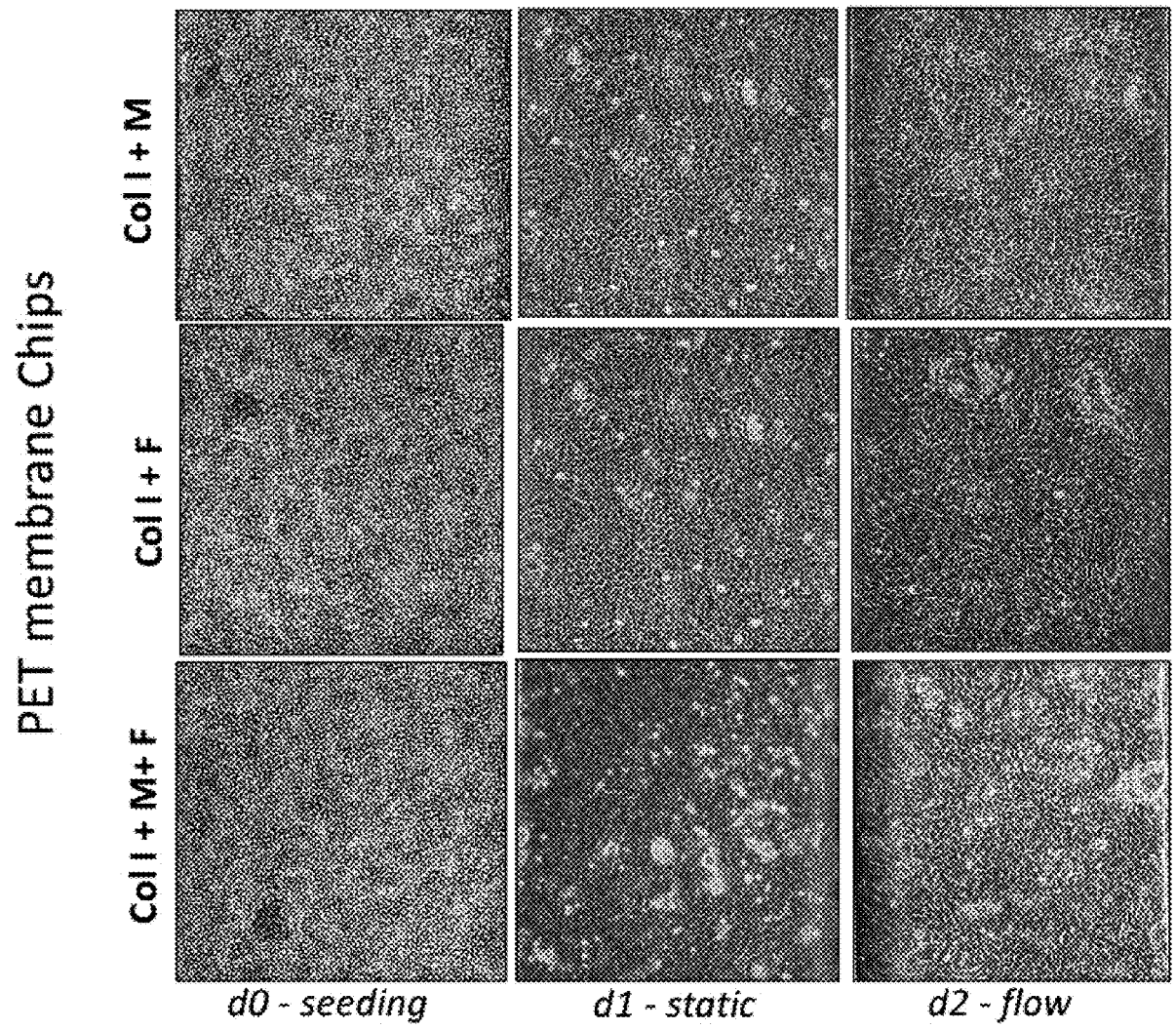
FIG. 6 depicts images of cells grown on PET membrane chips.

Described herein is a comparison of primary intestinal cell attachment and growth on:
1) membranes made of PET or PDMS
2) membranes coated with 3 different coating compositions:
   Collagen I+Matrigel (C+M)
   Collagen I+Fibronectin (C+F)
   Collagen I+Matrigel+Fibronectin Good cell spreading and fast monolayer formation was observed on PET membrane (FIG. 6). Flow was initiated after overnight incubation to allow good cell attachment. Cells attached well to all types of coating mixtures tested.

Figure 7:
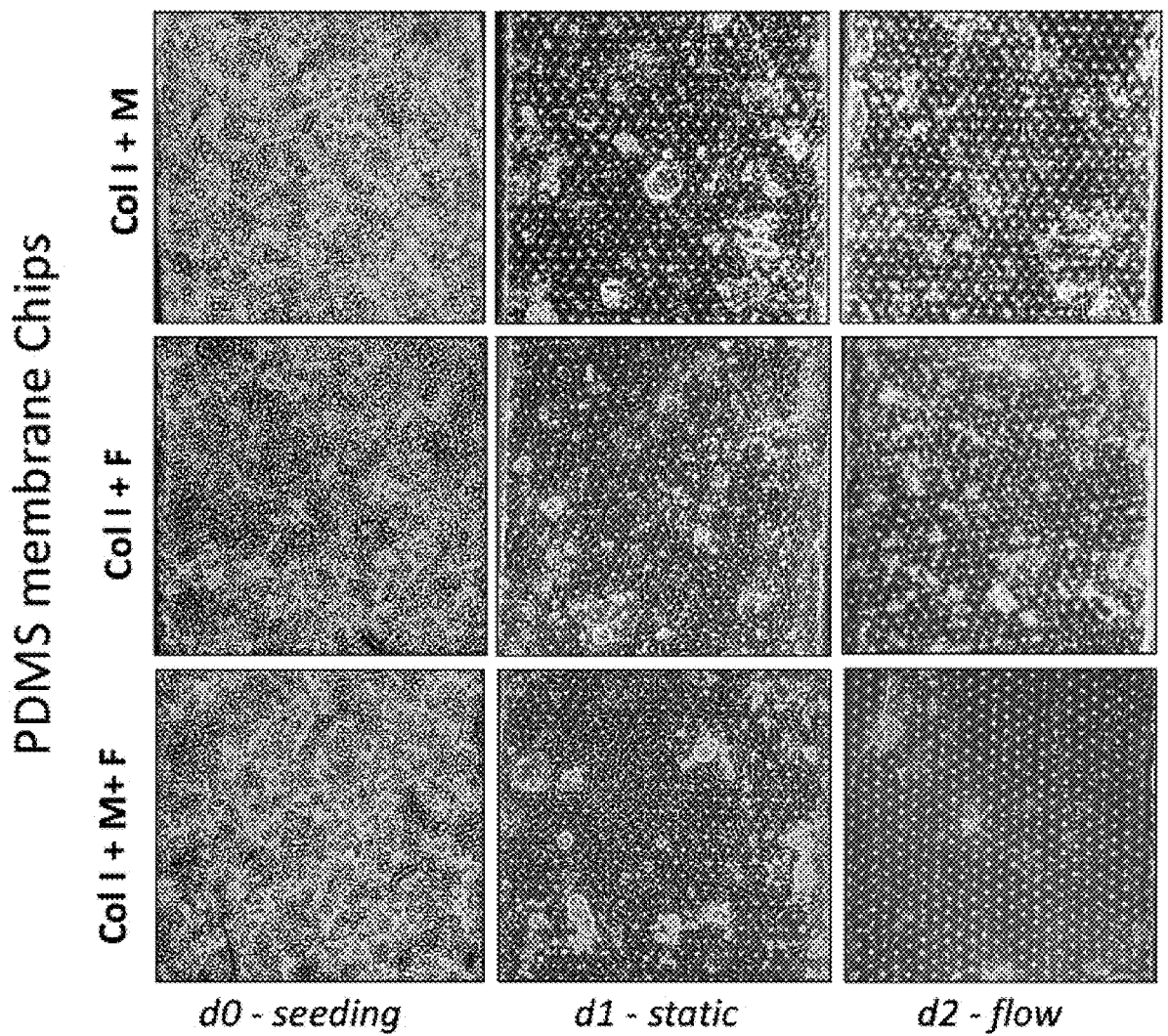
FIG. 7 depicts images of cells grown on PDMS membrane chips.

Good cell attachment and monolayer formation was observed on PDMS membrane (FIG. 7). Flow was initiated after overnight incubation to allow good cell attachment. Cells attached well to all types of coating mixtures tested.

Figure 8:
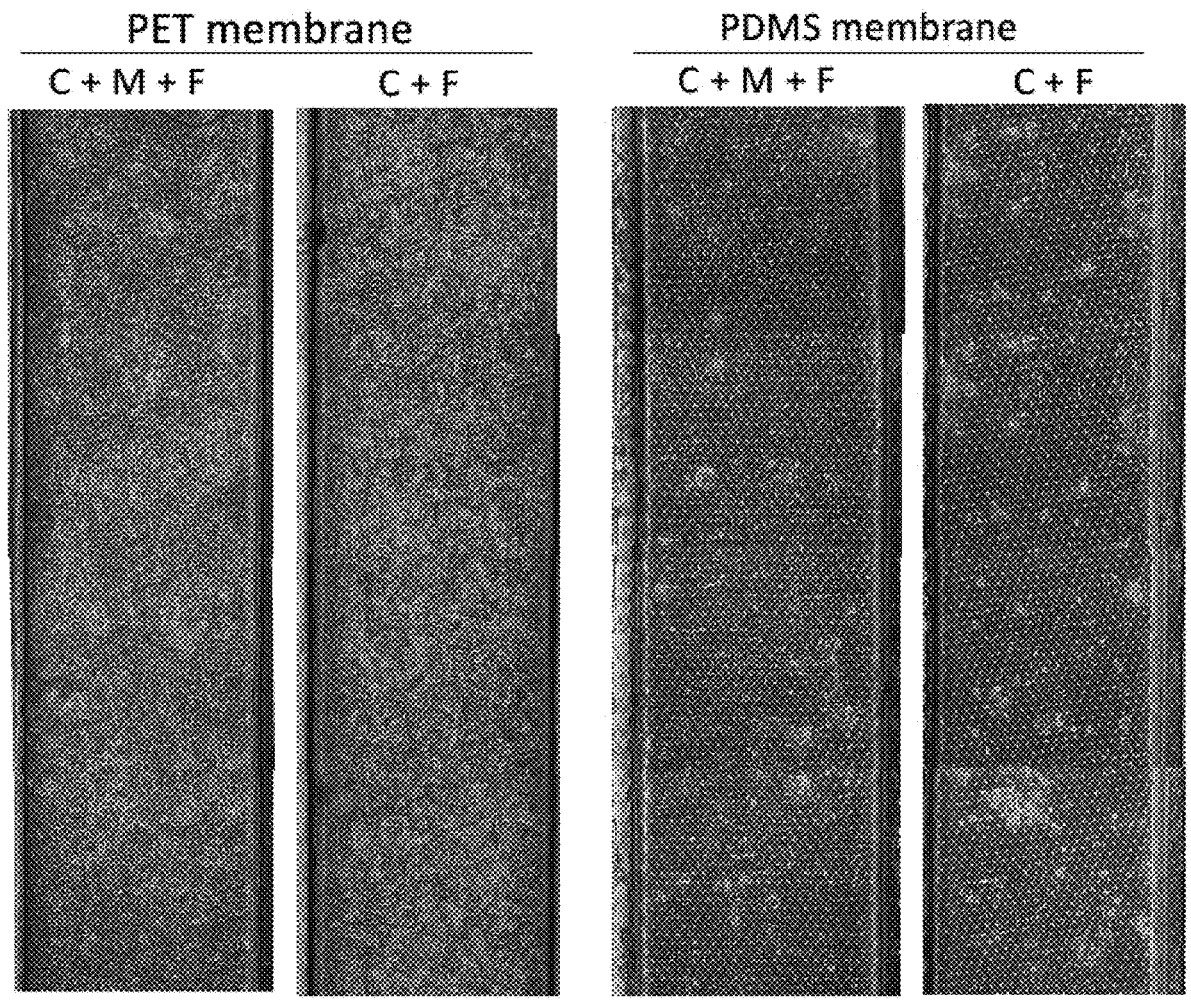
FIGS. 8 and 9 depict images of cells after at least 4 days of microfluidic culture.

Formation of intact monolayer was achieved by day 4 of microfluidic culture (FIG. 8). Confluent monolayer formation was achieved by day 4 of microfluidic culture in all conditions tested:
on PET and PDMS membrane
on coating composed of:
   Collagen I+Matrigel+Fibronectin
   Collagen I+Fibronectin
   Collagen+Matrigel (data not shown)

Figure 9:
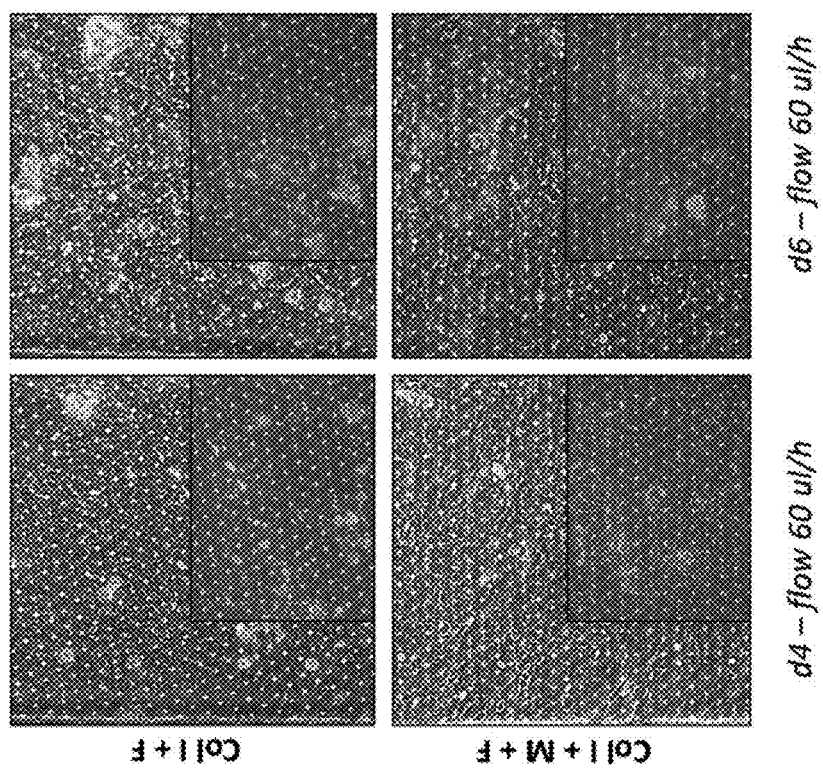
Figure 9:
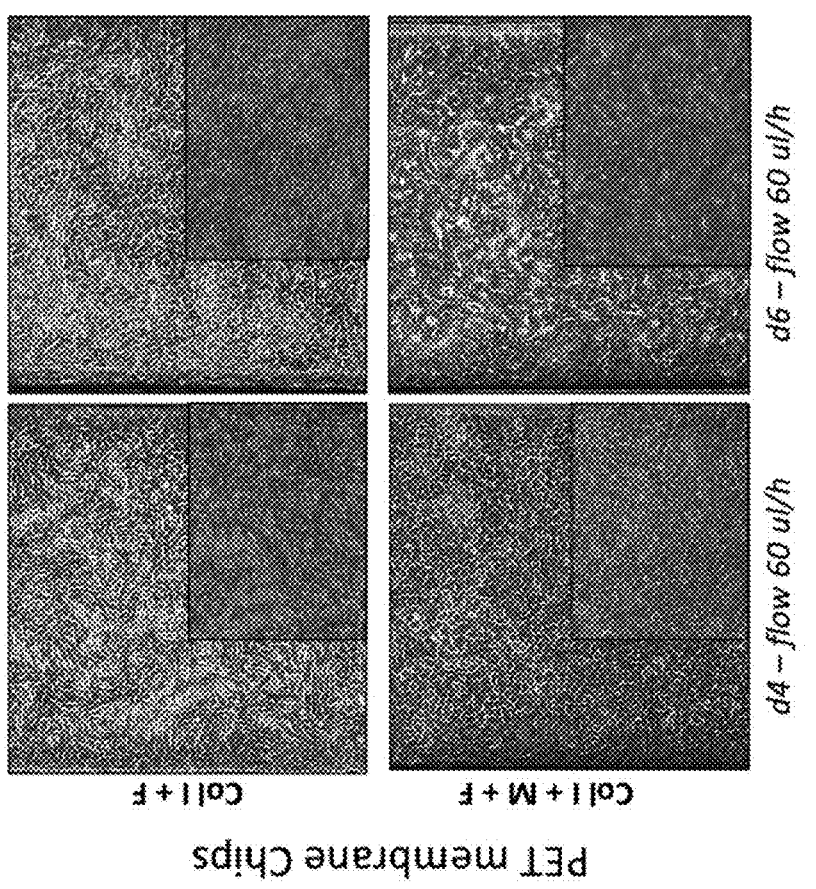
Figure 10A:
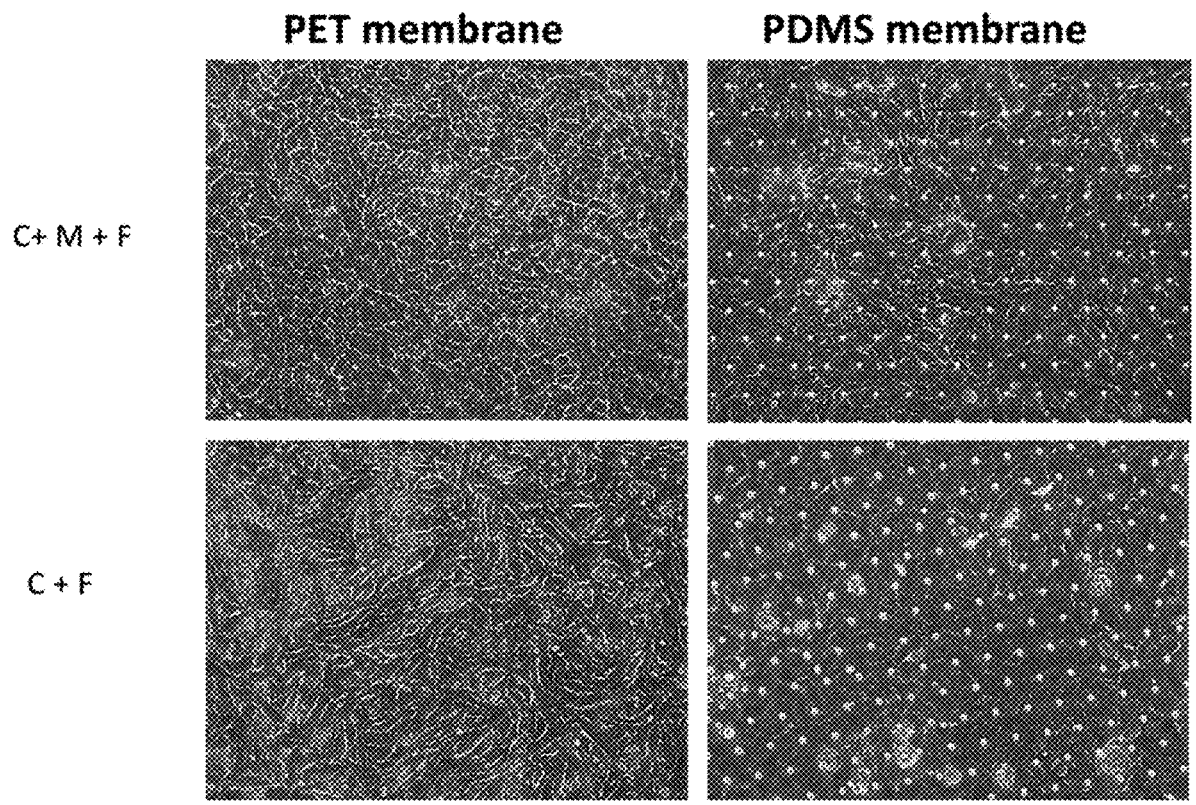
FIGS. 10A-10C depict images of cells after 4 days (FIG. 10A), 5 days (FIG. 10B), or 6 days (FIG. 10C) of growth, demonstrating changes in morphology.
Figure 10B:
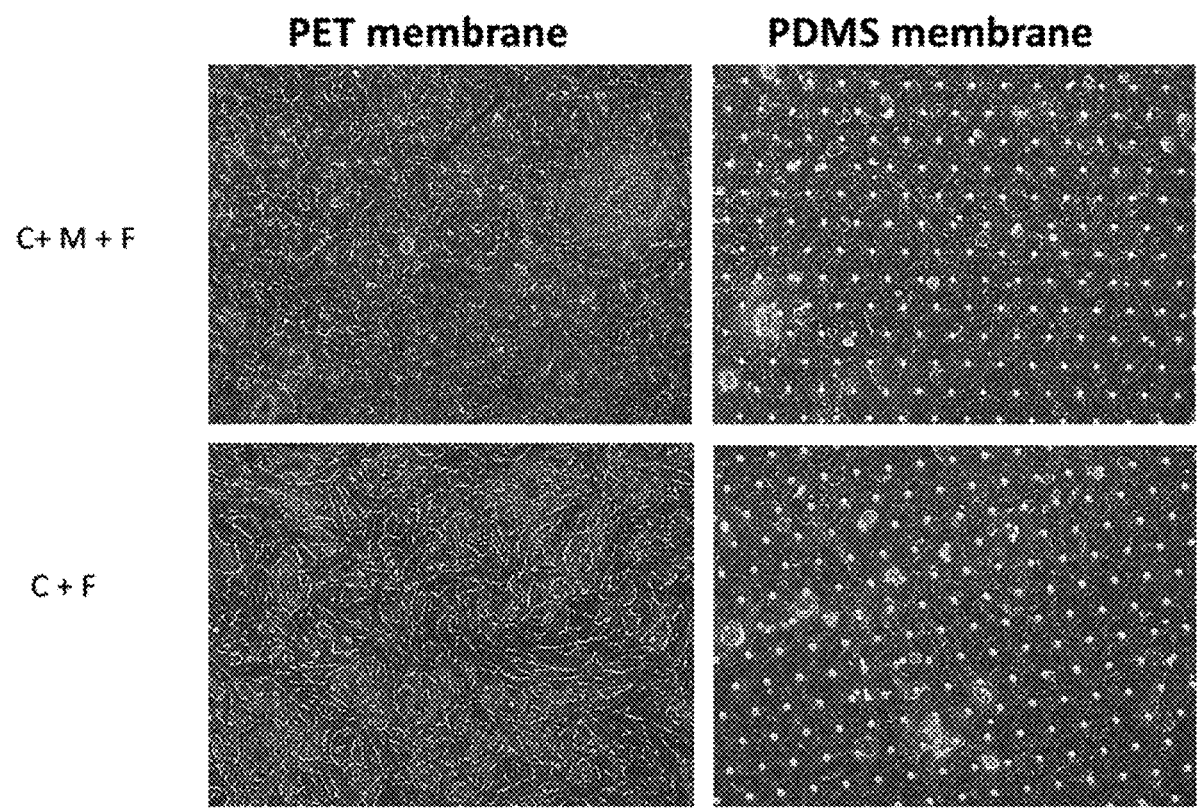
Figure 10C:
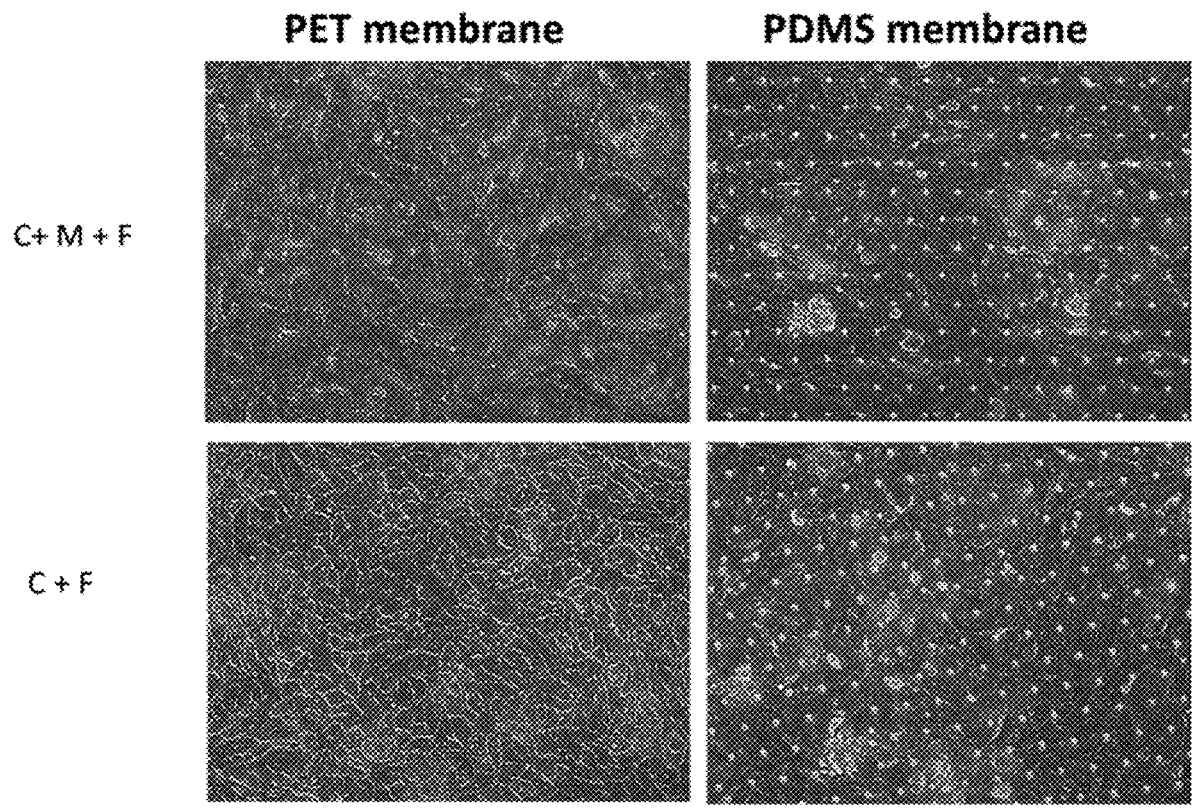

Cells remain well attached on PET as well PDMS membrane chips subjected to flow (FIG. 9). Morphological changes of cell shape could be observed in chips subjected to flow (FIG. 10).

Figure 11:
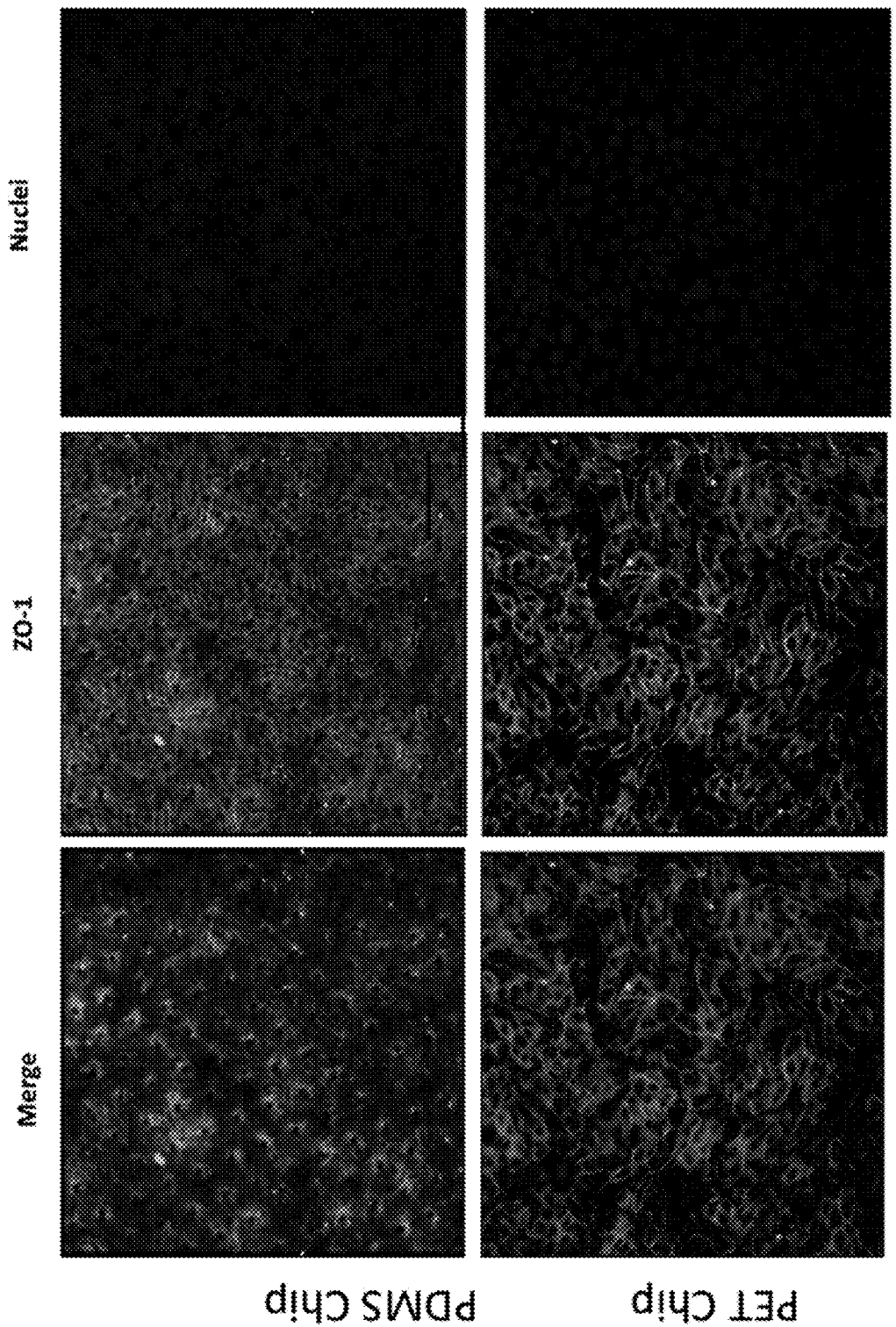
FIG. 11 depicts images of cells grown on PET or PDMS chips, demonstrating the varying cell densities.
Figure 12:
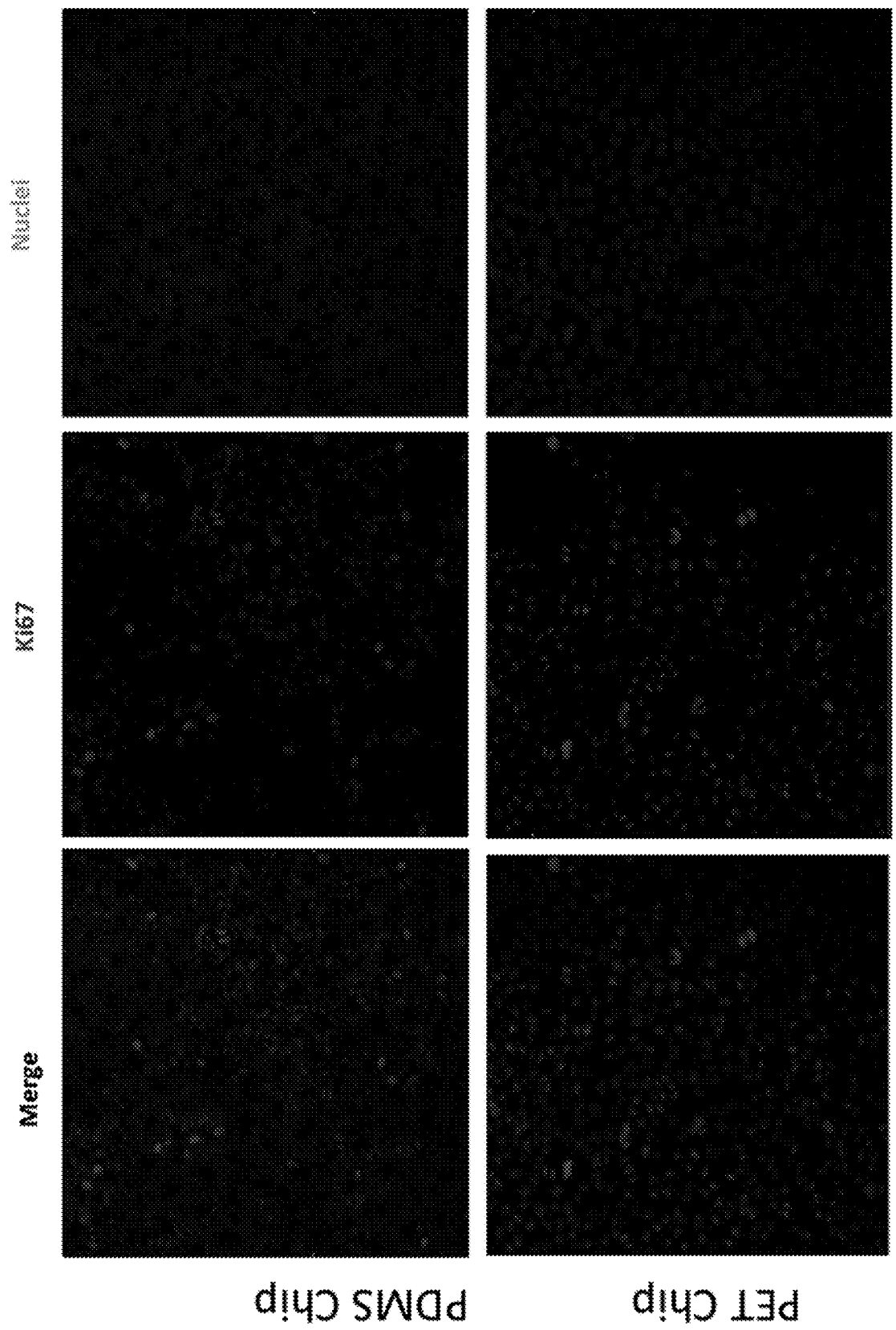
FIG. 12 depicts images of cells grown on under the depicted conditions.
Figure 13:
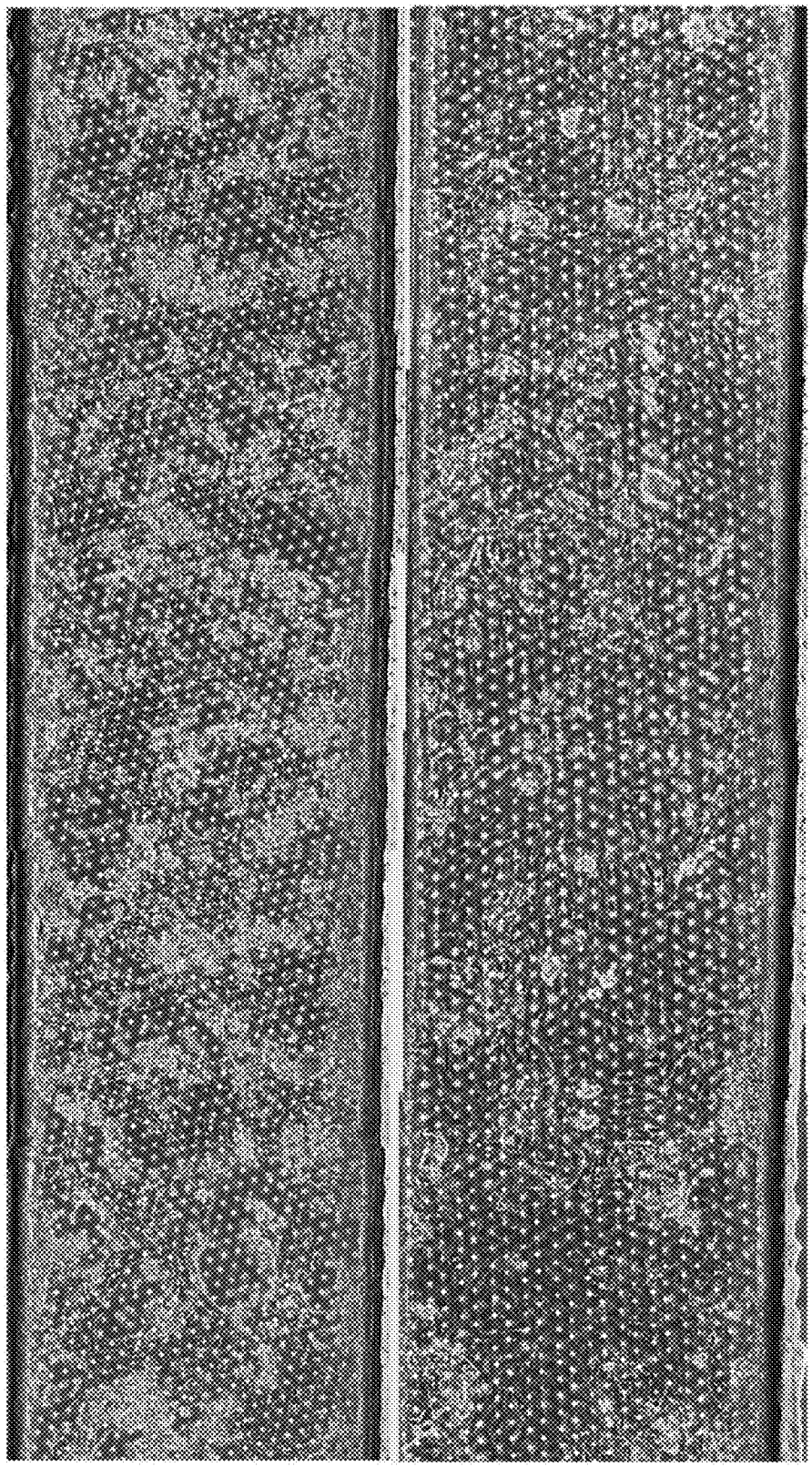
FIG. 13 depicts images of cells grown with and without HUVECs. Representative images depict devices seeded with enteroid fragments in the presence (+HUVEC) or absence (−HUVEC) of endothelial cells acquired 24 h post-seeding.

Chips of differing materials supported different cell densities (FIG. 11). The high cell proliferation rate on PDMS & PET membrane chips is depicted in FIG. 12, along with a demonstration that epithelial cells displayed improved attachment in the presence of HUVECs (FIG. 13). In the absence of HUVECs, higher number of round cells were observed, indicating that the cells didn't attach and spread well on the membrane. Additionally, empty spaces remained, indicating cells detached from the membrane after the wash. In the presence of HUVECs, cells spread well and attached to the membrane, almost fully covering the channel 1 day after epithelial cell seeding.

Figure 14:
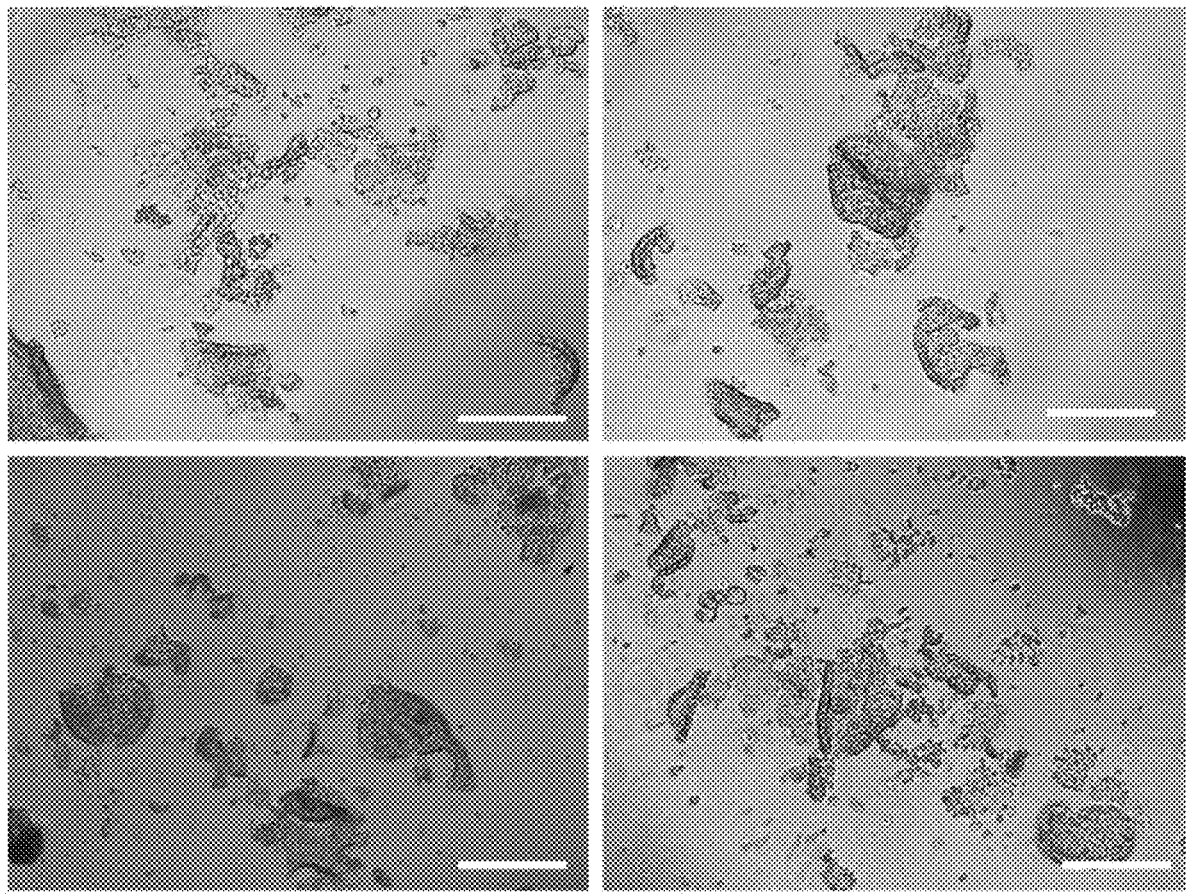
FIG. 14 depicts representative images of optimal size of entroid fragments generating by enzymatic digestion. Representative images taken from 4 independent experiments.

Fragments generated by enzymatic digestion of intestinal enteroids were examined (FIG. 14). The number of cells in each fragment was around 10-30 cells while fragment size was about 40-100 μm.

Figure 15:
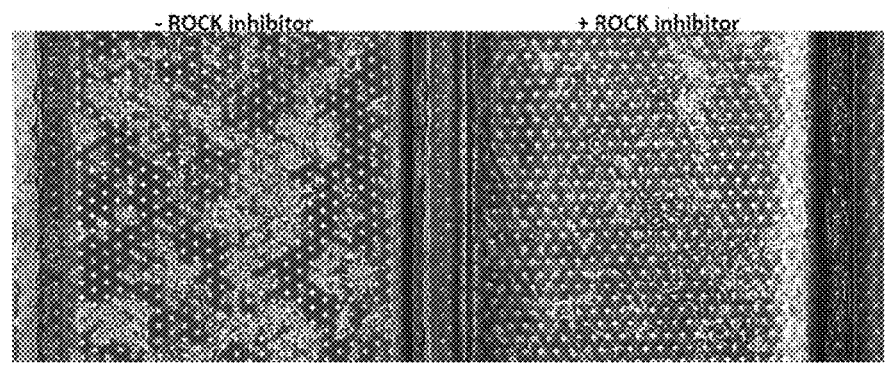
FIG. 15 depicts images of cell culture demonstrating enhanced epithelial cell survival and attachment in the presence of ROCK inhibitor during intestinal fragment isolation and seeding. Representative images showing device seeded with enteroid fragments generated in the absence (−ROCK inhibitor) or presence (+ROCK inhibitor) were acquired 24 h post seeding. Equal cell seeding density and time was used for both of the conditions tested.

Improved epithelial cells recovery and on-chip seeding was observed in the presence of ROCK inhibitor (FIG. 15).

Figure 16:
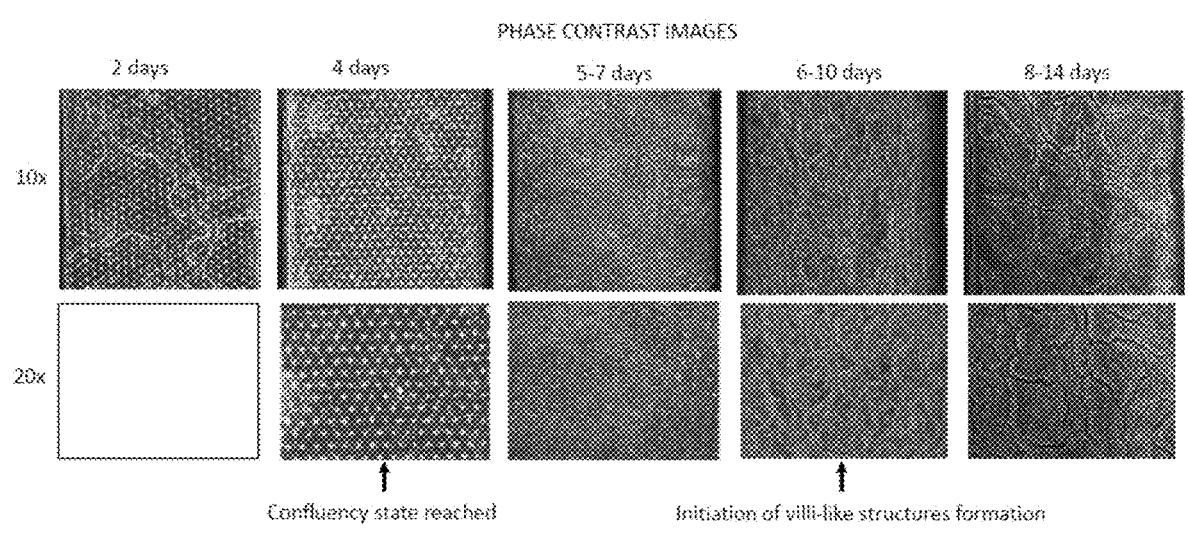
FIG. 16 depicts phase contrast images of cell cultures, providing a timeline of epithelial monolayer and villi-like structure formation over the time of on-chip growth.

A timeline of epithelial monolayer and villi-like structure formation over the time of on-chip growth is provided in FIG. 16.

Example 4

Described herein is a method for fabricating a primary human Small Intestine-on-a-Chip (Small Intestine Chip) containing intestinal epithelial cells isolated from patient intestinal biopsies or surgical explants. The primary epithelial cells are expanded as 3D enteroids and subsequently seeded into one microchannel of an organ-on-a-chip microfluidic device where they interface through a porous matrix-coated membrane with human intestinal microvascular endothelium cultured in a parallel microchannel under conditions of flow and cyclic deformation. This Small Intestine Chip recapitulates intestinal villus tissue morphology with multi-lineage differentiation similar to that of small intestinal organoids, however, transcriptomic analysis indicates that the Small Intestine Chip more closely mimics the proliferation and host defense response to infection functions of human duodenum than enteroids. Moreover, because fluids flowing through the lumen of the Small Intestine Chip can be collected continuously, they also can be used to study and quantify nutrient digestion, mucus secretion and barrier function, as well as drug absorption and pharmacokinetics, in the presence or absence of bacterial pathogens over a period of one and/or multiple days, and discriminate between infection by pathogenic versus non-pathogenic bacteria. Hence, the Small Intestine Chip is useful as a research tool for many applications where normal intestinal function is crucial, including drug development, metabolism, nutrition and cancer progression, in addition to providing a novel approach to advanced personalized medicine.

The small intestine is the major site for digestion, drug and nutrient absorption, interaction with commensal microbiome, and development of mucosal immunity, as well as a primary site for many diseases, such as bacterial, viral and parasitic infections, irritable bowel syndrome and inflammatory bowel disease. While the lack of human-relevant responses may render animal models unsuitable to study causal factors and treatment strategies for human intestinal infections and disorders[1], three-dimensional (3D) human tissue surrogates, such as intestinal organoids (enteroids) have emerged as promising alternatives. These spheroidal ex vivo tissue cultures are believed to originate from Lgr5+ intestinal stem cells[2] and are grown embedded within Matrigel, which is a complex mixture of extracellular matrix (ECM) proteins, and in the presence of Wnt3a, epidermal growth factor (EGF), Noggin and R-spondin 1 (collectively, WENR) that support their indefinite propagation[3,4]. Enteroids faithfully recapitulate the cellular diversity of the intestinal epithelium and are ideally suited for in situ visualization and continuous monitoring of epithelial development and differentiation[4-8]. However, the presence of an enclosed lumen is non-physiological, as secreted material from goblet, enteroendocrine and Paneth cells, as well as shed apoptotic cells, accumulate within this central space instead of being removed, as it occurs in vivo, due to peristalsis and luminal flow. In addition, the inaccessibility of apical cell surface renders the use of enteroids experimentally challenging for transport studies or exposure to living microbiome or pathogens for more than approximately one day in culture. Finally, enteroid cultures lack a tissue-tissue interface, mechanical forces (fluid flow and peristalsis-like motions), immune cells, and a vascular compartment, which are all key contributors to normal intestinal physiology and disease development. Thus, there still remains a compelling need for more complex and physiologically relevant intestinal organ culture systems.

One alternative approach involves the use of 2-channel Organs-on-Chips (Organ Chips), which are microfluidic cell culture devices that contains two parallel hollow culture chambers lined by living human cells and separated by a porous ECM-coated membrane, which recapitulate normal tissue-tissue interfaces and mimic the complex physical and biochemical microenvironment of living human organs[9-23]. This technology has been previously applied to develop human Gut Chips that emulate many features of human intestinal structure and function, however, these studies utilized established human intestinal cell lines, such as Caco-2 or HT-29 cellst[19-21,24], which were originally isolated from tumor samples, and thus, likely harbor multiple gene mutations. In these studies, the intestinal cells also were either cultured alone or in the presence of a non-specialized endothelium (e.g., human umbilical vein endothelial cells)[21]. So these human Gut Chips may not fully recapitulate normal human intestinal functions, and they would be inappropriate to use to study many important human conditions where genome fidelity is important (e.g., intestinal cancer, drug development, etc.). Other investigators have engineered in vitro intestine models using fetal intestinal tissue explants, but these progressively deteriorate after 24 h of culture[25,26]. Thus, in the present study, a primary human Small Intestine Chip (Small Intestine Chip) was developed using an approach that combines two of the most advanced tissue engineering technologies: intestinal organoids[3,4,27] and Organs-on-Chips[9,10].

The Small Intestine Chip contains normal human intestinal epithelial cells derived from enteroids established from endoscopic biopsies or tissue resections of living human intestine, and intestinal tissue-specific microvascular endothelial cells. This microengineered environment recapitulates many key anatomical and functional features of its in vivo small intestine counterpart including 3D intestinal tissue architecture, multi-lineage differentiation, epithelial barrier function, enzymatic activity of brush border enzyme and mucus production. Importantly, the transcriptome of the primary Small Intestine Chip more closely resembles that of adult human duodenum in vivo than that of the enteroids that were used to plate the chips, especially with regard to expression of genes relating to cell proliferation and host defense response to infection. Indeed, it is also demonstrated herein that the Intestine Chip is able to emulate in vitro important hallmarks of human enteric infection, including vascular release of inflammatory cytokines and loss of intestinal barrier function, and to discriminate between infection with pathogenic versus non-pathogenic bacteria. Thus, the Small Intestine Chip provides a more human-relevant microenvironment for studying human intestinal physiology and diseases than intestinal organoids, particularly in the context of studies on infection.

Results

Figures 17A, 17B:
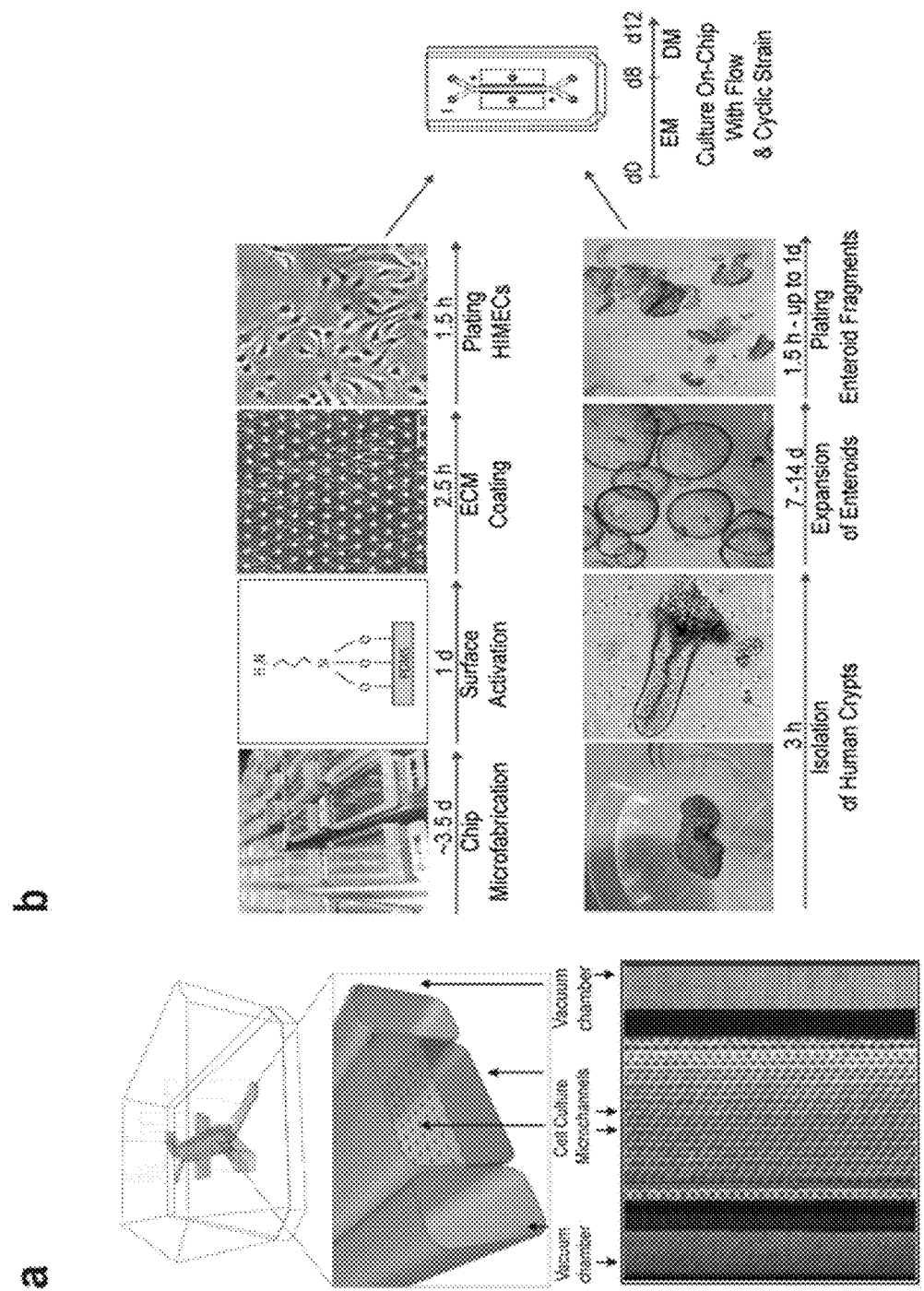
FIGS. 17A-17B demonstrate methods for fabrication of the primary human Small Intestine Chip.

Primary human Small Intestine Chip developed using patient-derived enteroids. An Organ Chip-based surrogate of the human small intestine was developed that incorporates patient-derived epithelium, intestinal endothelial cells, physiological fluid flow and peristalsis-like mechanical motions that would allow longer term monitoring of host cell-pathogen interactions than is possible with conventional intestinal organoid culture. To accomplish this, enteroid cultures were first established using intestinal crypts containing intestinal stem cells derived from histologically normal regions of human intestinal endoscopic biopsies or surgical specimens, then enteroid fragments were released through enzymatic treatment after 5 to 25 passages in culture, and finally these fragments were seeded on the upper surface of the ECM-coated porous membrane of a microfluidic Organ Chip (FIGS. 17A-17B). The polydimethylsiloxane (PDMS) chip devices we used contain two parallel, cell culture microchannels: an upper 'epithelial' channel (1 mm high×1 mm wide) and a lower 'vascular' channel (0.2 mm high×1 mm wide) separated by a thin (50 µm) flexible PDMS membrane containing multiple pores (7 µm diameter, 40 µm spacing) coated with ECM (type I collagen and Matrigel) (FIG. 17A). Each microchannel has a dedicated inlet and outlet for the inoculation of human cells, molecules or microbes as well as for the precise control of physicochemical parameters through the perfusion of laminar flow of appropriate culture medium. Dedicated outlets provide means to collect effluents from the individual chambers for downstream characterization. The upper epithelial channel and lower vascular channel are surrounded on either side by two hollow (1 mm high×300 µm wide) chambers that permit application of cyclic suction to mechanically stretch and relax the sidewalls, as well as the attached flexible PDMS membrane and adherent tissues in the central channel, thereby emulating peristaltic motions of a living human small intestine.

To obtain primary human intestinal epithelial cells, a cell culture model based on 3D propagation of human intestinal crypts containing functional stem cells to create a bank of enteroids derived from normal duodenal endoscopic biopsies or surgical specimens[3,4,28]. Duodenal enteroids cultured for 3-5 days after passaging in expansion medium (EM) were than dissociated into fragments and plated in the epithelial channel of the microfluidic devices. Enteroids from the duodenal region of the proximal small intestine were used in this study because they displayed higher culture efficiency that ones formed from ileum or jejunum, as previously described[28]. On the opposite side of the same flexible membrane and within the second adjacent channel, primary human intestinal microvascular endothelial cells (HIMECs) were cultured.

Figures 18A, 18B, 18C, 18D:
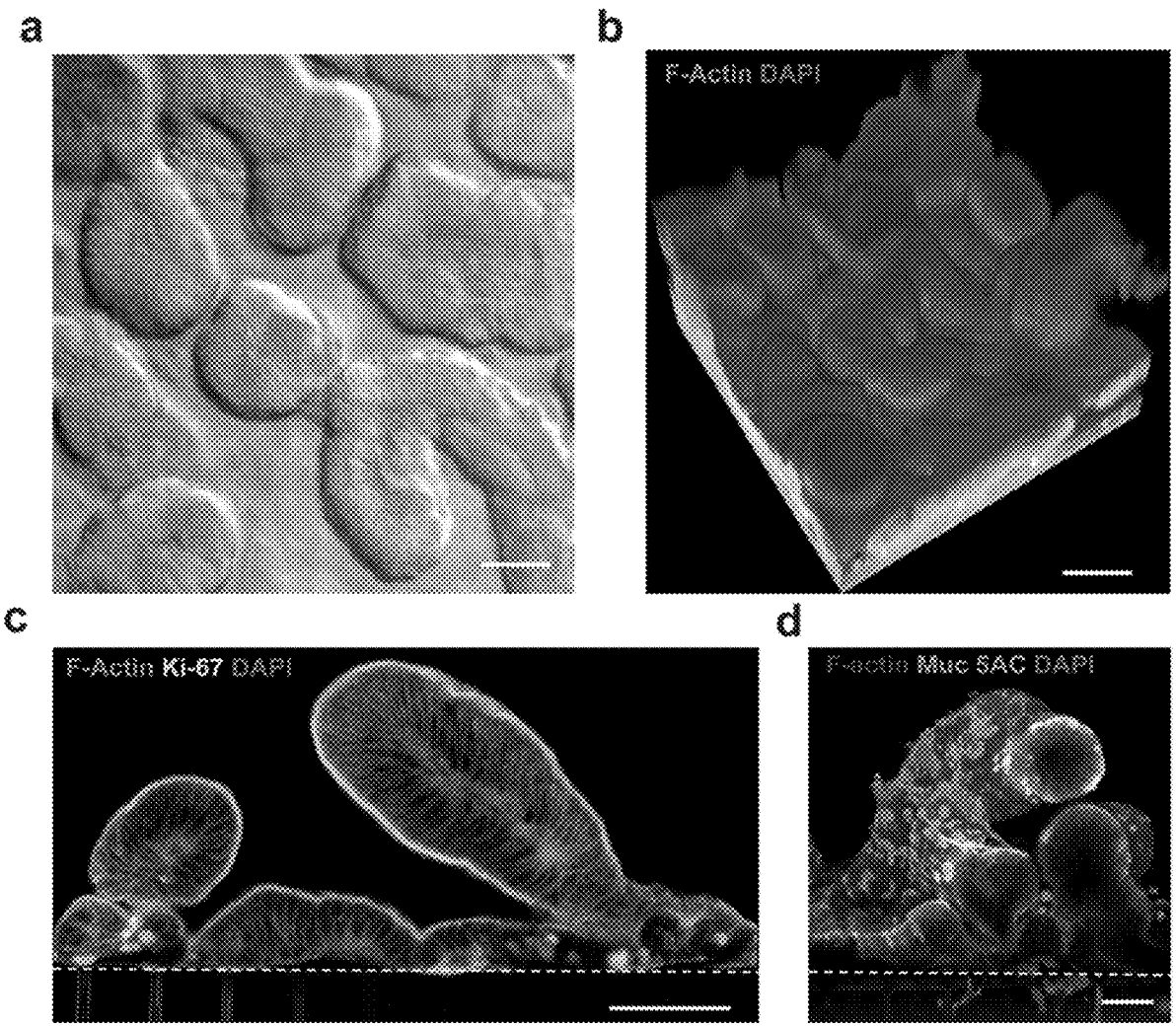
FIGS. 18A-18D demonstrate morphological analysis of the human Small Intestine Chip lined by primary duodenal enteroid-derived epithelial cells.

Exploratory studies were initiated by culturing the enteroid fragment-derived intestinal epithelial cells alone in the upper channel without endothelium while perfusing both channels with epithelial expansion medium (EM). Formation of a well-developed intestinal epithelium with characteristic villus morphology was observed at 12 days of culture, as detected by differential interference contrast (DIC) microscopy (FIG. 18A) and 3D confocal microscopy (FIG. 18B). Immunofluorescence staining of the engineered intestinal villi for Ki67 and mucin 5AC (MUC5AC) confirmed that the proliferative Ki67-positive cells were limited to regions at the base of the villi (FIG. 18C) whereas mucin producing cells were present primarily along their apical regions (FIG. 18D), much as is observed in living intestinal villi. Computerized image analysis of these cross-sectional immunofluorescence views revealed that the maximum villus height was approximately 250 µm in these studies.

In the course of these studies, it was found that more effective epithelial cell seeding and efficient monolayer formation can be achieved if enteroid fragments are used, as single cell suspensions (produced using longer enzymatic dissociation times) do not expand adequately to develop a functional intestinal epithelial barrier (FIG. 3A), and whole enteroids remain in their cystic spherical form and fail to form a continuous monolayer (data not shown). In some studies, it was found that cultures that contained HIMECs were more effective at retaining a confluent epithelium in the upper channel when enteroid fragments were plated (FIG. 3A). The presence of HIMECs also did not compromise barrier function and possibly enhanced it to a slight degree; with or without HIMEC, $P_{app}$ was sustained at $1\text{-}2\times10^{-6}$ cm $s^{-1}$ for up to 12 days of culture (FIG. 3B). The presence of HIMECs in the lower channel also appeared increase the efficiency of monolayer formation when enteroids were fully dissociated into single cells prior to culturing them in the microchannel, and formation of putative villi-like structures was observed in some of these cultures (FIG. 3A). However, the reproducibility of seeding protocol was much higher using enteroid fragments versus isolated cells (~90% versus 40% success rate), and thus, we used the fragment method in all subsequent experiments.

Once confluent epithelial and endothelial monolayers were formed in the presence of physiological fluid flow (60 µl/h), the Intestine Chip was exposed to peristalsis-like motions (10%/% strain, 0.2 Hz) generated by applying cyclic suction to the flexible hollow side chambers. Use of these dynamic co-culture conditions, in combination with a shift from use of the EM to a differentiation medium (DM) in the upper channel on day 8, led to formation of well-defined intestinal folds throughout the entire length of the epithelial channel (FIG. 3A). Interestingly, culture of these same cells in the absence of flow did not result in changes of epithelial tissue architecture despite continued application of 10% cyclic strain (FIG. 3C), which is consistent with previous studies using Caco-2 intestinal cells in a Gut Chip[19]. Importantly, phase contrast and confocal fluorescence microscopic analysis of this dynamic tissue-tissue interface confirmed the presence of a continuous, polarized, epithelial cell monolayer with an apical F-actin-containing brush border and basal nuclei aligned along the boundary of each villus-like extension into the lumen of the epithelial microchannel of the chip (FIG. 4A). Scanning electron microscopic (SEM) analysis of the apical surface of the epithelial cells lining these villus-like luminal extensions revealed the presence of cells with morphology similar to that previously described in SEMs for mucus-producing Goblet cells[29,30] and well-polarized absorptive enterocytes with densely-packed apical microvilli[31] (FIG. 4B). The primary Small Intestine Chip also recapitulated the polarized epithelial cell distribution of the major apical and basolateral ion transporters, NHE3 and $Na^+/K^+$-ATPase, respectively (FIG. 4C). NHE3, which is responsible for electroneutral $Na^+$ absorption in the small intestine[26], localizes to the apical brush border membrane of the microfluidic epithelial cell culture, as it does in living intestine. On the other hand, $Na^+/K^+$-ATPase, the major ion transporter responsible for regulating the intracellular $Na^+$ gradient necessary for absorption of nutrients[32], was exclusively localized to the basolateral membrane of the epithelial cells on-chip, again recapitulating their native location in human intestine (FIG. 4C). Maintenance of correct cell polarity in the epithelium was evidenced by the presence of intact tight and adherens junctions identified through immunofluorescent staining of zonula occludens-1 (ZO-1) and E-cadherin, and by the distribution of ZO-1 and VE-cadherin in the microvascular endothelium (FIG. 4D). Taken together, these data confirm that primary human intestinal epithelial cells derived from enteroids can be grown in co-culture with human organ-specific (intestinal) capillary endothelial cells to form a polarized and dynamic intestinal microenvironment using Organ Chip technology.

Figures 19A, 19B:
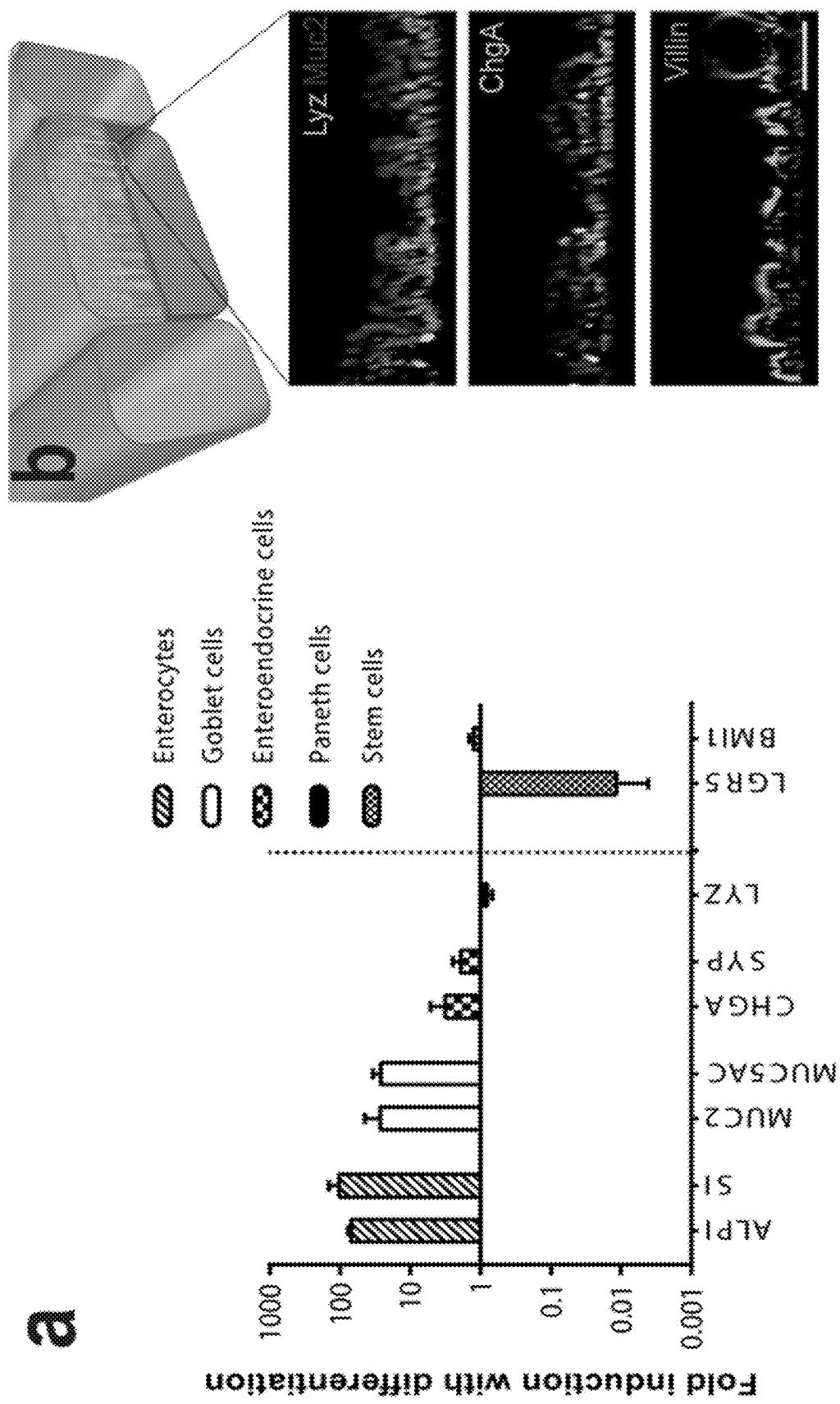
FIGS. 19A-19B demonstrate that the primary human Small Intestine Chip exhibits multi-lineage differentiation.

It was next explored whether the primary Small Intestine Chip faithfully recapitulates normal intestinal differentiation in vitro, in which adult intestinal stem cells give the rise to multiple intestinal epithelial cell types, including absorptive enterocytes, enteroendocrine cells, Goblet cell and Paneth cells. Removal of Wnt3A and inhibition of Notch signaling, driven by switching the medium in which the epithelial cells are cultured from EM to DM, induced the formation of multiple differentiated intestinal cell lineages. This was demonstrated by detection of increased expression by qRT-PCR of mRNAs encoding alkaline phosphatase and sucrase isomaltose that are specific for absorptive enterocytes; mucin 2 (MUC2) and MUC5AC that are produced by Goblet cells; and chromogranin A and synaptophysin (SYP) that are expressed by enteroendocrine cells (FIG. 19A). Similar results were obtained using primary intestinal epithelial cells isolated from three different donors, and this increase in intestinal cell differentiation also was accompanied by down regulation of expression of the adult intestinal stem cell marker, leucine-rich-repeat-containing G-protein-coupled receptor 5 (LGR5)[33], whereas there was no detectable change in the marker of quiescent stem cells, polycomb complex protein BMI1, which is known to be insensitive to Wnt withdrawal[34] (FIG. 19A). While changes in the Paneth cell marker, lysozyme, were not detected by qRT-PCR because these are low incidence cells, we were able to detect positive lysozyme-expressing cells in the putative crypt regions at the base of the villi, as well as chromogranin A-containing cells higher up on the villi and enterocytes with positive villin-stained apical brush borders by immunofluorescence microscopy (FIG. 19B).

Figure 20:
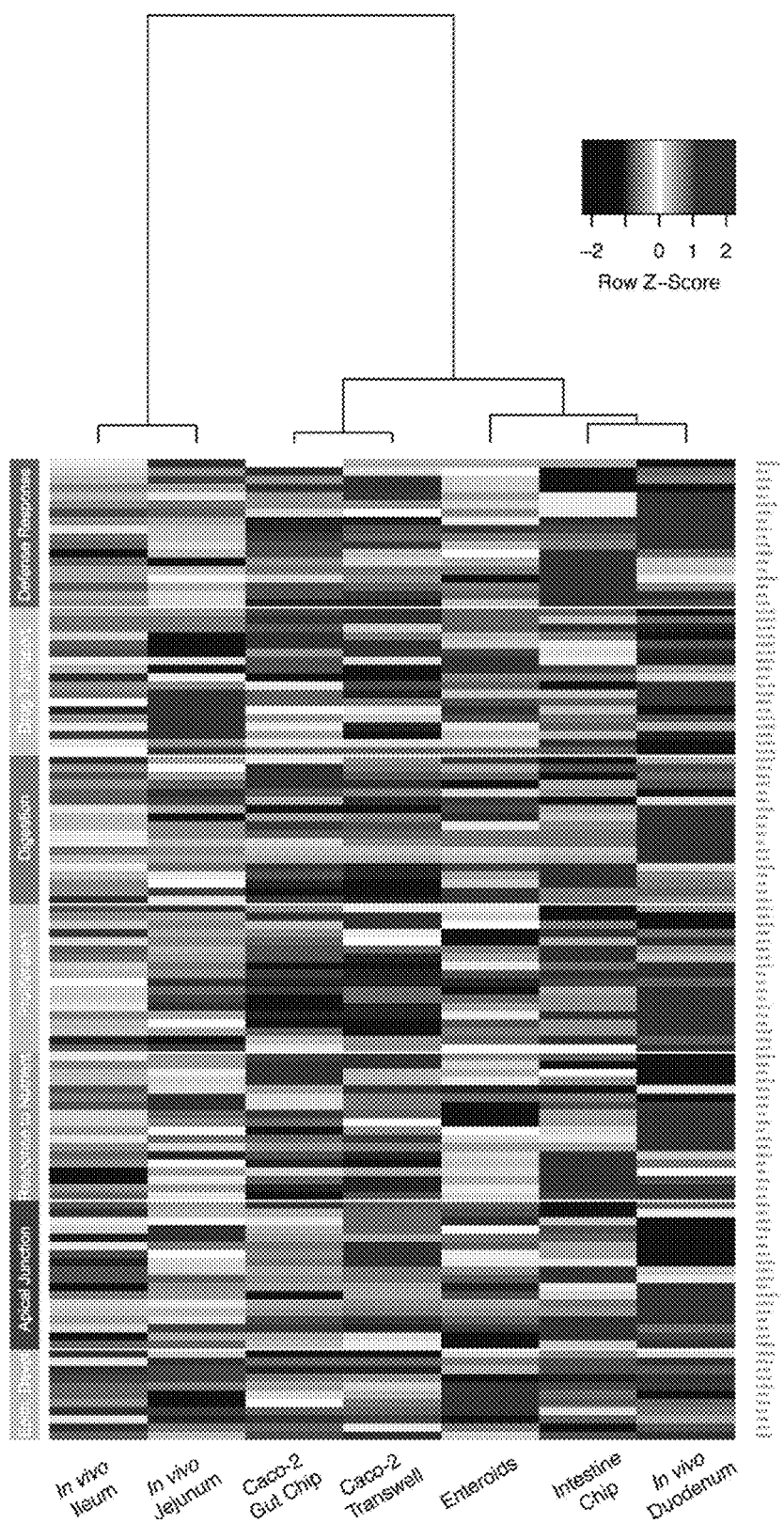
FIG. 20 demonstrates that the Small Intestine Chip resembles human native duodenum. A curated heatmap was generated for genes selected through template matching method as being some of the most highly differentially expressed in the mechanically active Small Intestine Chip (with fluid flow at 60 µL/h and cyclic stretching at 10%, 0.2 Hz; Intestine Chip) and In vivo Duodenum in comparison to In vivo Jejunum and Ileum, 3D enteroids and Caco-2 based systems, including Caco-2 BBE intestinal epithelial cells cultured in the static Transwell or Gut-on-a-Chip (Caco-2 Gut Chip). 3D enteroids and Intestine Chip were established from duodenal tissue biopsies derived from 3 healthy donors and differentiated (in the presence of DM medium) for 4 days before assessment. Gene expression data for normal human small intestine (duodenum, jejunum, and ileum), Caco-2 Gut Chip, and Caco-2 Transwell were obtained from the National Center for Biotechnology Information (NCBI) Gene Expression Omnibus (GEO) database. Selected genes showed to belong to the specific GO terms, including Defense Response (GO:0006952), Drug Transport (GO:0015893), Digestive System Process (GO:0022600), Regulation of Epithelial Cell Proliferation (GO:0050678), Response to Nutrients (GO:0007584), and Apical Junction Complex (GO:0043296).

Transcriptomic analysis of Small Intestine Chip versus enteroids. To further characterize the degree of intestinal differentiation induced on-chip, transcriptome-wide analysis of the Intestine-Chip was carried out after 12 days of culture in the presence of flow and peristalsis-like motions, and the results compared with gene profiles obtained from in vivo analysis of human ileum, jejunum and duodenum. These results were also compared to those previously obtained with the human Gut Chip or Transwell cultures lined with Caco-2 intestinal epithelial cells. Importantly, for the first time, a head-on-head comparison of the Organ Chip approach versus the commonly used Organoid culture approach by comparing these results to the transcriptome of enteroids isolated from human duodenum biopsies from three different patients, which were the same ones used to seed the Intestine Chips in this study cultured in the same differentiation medium. The comparison was focused on genes associated with crucial intestinal functions including digestive function, response to nutrients, drug transport, regulation of intestinal cell proliferation, apical cell junctions, and host defense as defined by Gene Ontology (GO) (FIG. 20). As expected, it was found that the primary cell-based Small Intestine Chip and enteroid better matched the in vivo duodenum transcriptome than the culture models that utilized the Caco-2 cell line, both when we compared these GO gene sets (FIG. 20) and when the entire transcriptome was analyzed (data not shown). This finding is consistent with past work that showed the human Caco-2 Gut Chip more closely mimics the human ileum than duodenum[21]. Importantly, identification of differentially expressed genes by template matching revealed functional areas, including those related to host defense response to infection, cell proliferation, response to nutrients, and apical junctions, where the Small Intestine Chip was much more similar in phenotype to the living human duodenum than the enteroids from which they were derived (FIG. 20). Taken together, these results indicate that the Small Intestine Chip better recapitulates the morphology, multicellular composition, and gene expression patterns of the intestinal segment from which it was derived than any of the other in vitro intestinal culture systems assessed in this study, including 3D intestinal organoids.

Figures 21A, 21B, 21C, 21D, 21E, 21F, 21G:
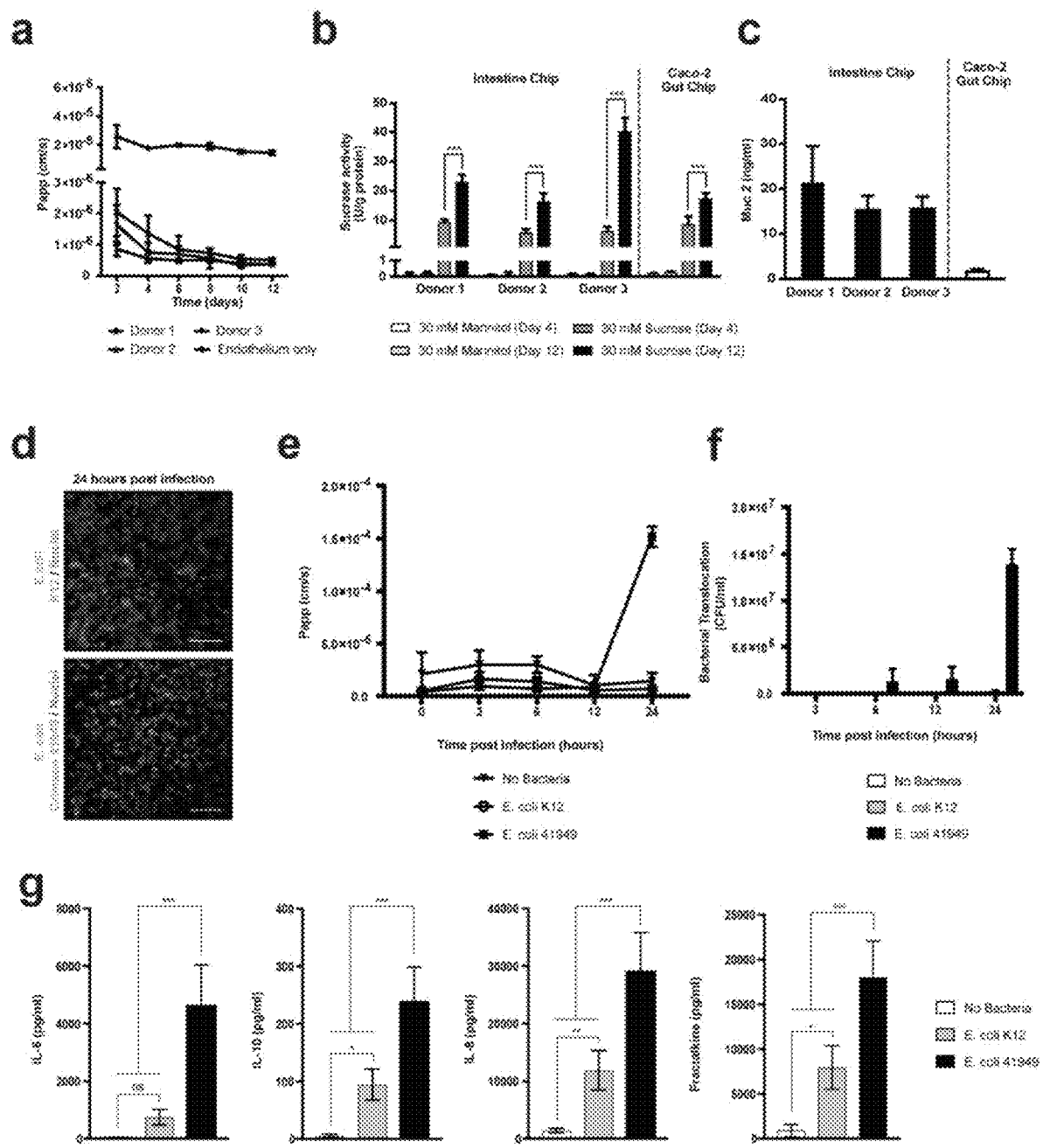
FIGS. 21A-21G demonstrate modeling normal intestinal physiology and pathophysiology in the Small Intestine Chip.

Recapitulation of normal intestinal functions To further explore the ability of the primary Small Intestine Chip to emulate normal intestinal functions in a robust manner, the selective permeability of intestinal barrier, the digestive capacity of enterocyte brush border enzymes, and secretion of mucins from goblet cells were analyzed. Importantly, Intestine Chips generated with duodenal biopsies from three different donors similarly developed strong intestinal barrier function over a period of 12 days (FIG. 21A) that was similar to that observed previously (FIG. 21B). These Small Intestine Chips from the three different donors also were assessed for their digestive capacity by measuring the activity of the brush border enzyme, sucrase isomaltose, which breaks down sucrose to glucose. Enzyme activity was quantified based on measuring glucose levels in the apical effluents of Intestine Chips that were infused through the epithelial microchannel either with sucrose, or with the non-metabolizable disaccharide mannitol being used as a control[31]. These studies revealed similar rates of only sucrose hydrolysis in all three differentiated primary Intestine Chips, with glucose production levels that increased over the 12 days of culture and were comparable to those measured in the previously described Caco2 cell-lined Gut Chip (FIG. 21B). In contrast, the activity of sucrase isomaltose was not detectable in the undifferentiated enteroids (cultured in expansion medium) that were used to seed these Small Intestine Chips (data not shown). These data confirm the presence of functional absorptive enterocytes in the Small Intestine Chip and indicate that this Organ Chip model of human intestine is useful for studies of both normal digestion and malabsorption, as well as for analyzing differences in intestinal digestive function between different patients.

Another important function of intestinal epithelium is the secretion of mucus, which protects the gut lining from chemical or physical injury as well as enteric pathogens. When the presence of MUC2 was evaluated in the apical effluents of the Intestine Chips from the 3 donors, it was found that its presence was deleted in all of the chips at a 10 times higher concentration than that measured in the human Gut Chip lined with Caco-2 intestinal cells[19-21] (FIG. 21C). Thus, the primary Small Intestine Chip exhibits enhanced functionality relative to the human Caco-2 Gut Chip as well as primary human enteroids.

Discrimination between infection by pathogenic versus non-pathogenic bacteria. Given that the transcriptomic analysis indicated that the primary Small Intestine Chip more closely mimics the living human intestine's response to infection than other existing in vitro human intestine models (FIG. 20), it was set out to model enteric bacterial infection on-chip. Two different strains of *E. coli*—one non-pathogenic (*E. coli* K12) and the other, a clinical isolate obtained from a patient with sepsis (*E. coli* 41949)—were introduced into the apical epithelial channel of the Intestine Chip. Both strains of *E. coli* colonized the biopsy-derived intestinal epithelium, however, chips inoculated with the pathogenic *E. coli* 41949 resulted in higher numbers of bacteria found in close association with the epithelial lining after 24 hours post infections in comparison to the inoculation performed with the non-pathogenic *E. coli* K12 (FIG. 21D). It was found that the pathogenic *E. coli* 41949 induced disruption of the epithelial barrier within the first day of co-culture as measured by an increase in intestinal permeability (FIG. 21E) as well as translocation of these pathogenic bacteria into the vascular channel (FIG. 21F) whereas *E. coli* K12 had no detectable effects at the same time points. Both strains of *E. coli* also induced time-dependent increases in secretion of multiple pro-inflammatory cytokines and chemokines, including various interleukins (IL-1α, IL-1β, IL-6, IL-8, IFN-γ, GM-CSF) and Fractalkine (CX3CL1), as well as the regulatory cytokine IL-10, into the vascular channel of the chip when compared to uninfected controls, which were detected as early as 3 hours after infection (data not shown). Importantly, the pathogenic *E. coli* 41949 induced significantly higher levels of secretion of IL-6, IL-8, 11-10 and Fractalkine at 6 hours post infection compared to uninfected Small Intestine Chips or chips infected with non-pathogenic *E. coli* K12 (FIG. 21G and data not shown). These cytokines and chemokines act as potent activators and chemoattractants for neutrophils, monocytes, T lymphocytes, and NK cells, and they have been proven to be useful as biomarkers of disease severity and outcome in sepsis patients[35,36]. Thus, the Small Intestine Chip is able to model intestinal pathophysiology, including the mucosal immune response to bacterial enteric infection in a controlled manner, with high temporal resolution, and with a sensitivity for pathogenic versus non-pathogenic microbes.

Discussion

Described herein is the development of a bioengineered in vitro model of the duodenum portion of the human small intestine by combining microfluidic Organ Chip technology with organoid-based methods for culture of primary epithelial stem cells from duodenal biopsies. The Small Intestine Chip recapitulates important structural features and functions of the native duodenum, including its villus architecture, barrier function, digestive capacity and an ability to model enteric infections. This Organ Chip technology differs substantially from past in vitro microfluidic models of human intestine, including a microfluidic human Gut Chip previously described[20,21,37], as it incorporates the use of primary intestinal epithelium isolated from patient-derived enteroids as well as gut-specific microvascular endothelial cells.

The vascularized Organ Chip design utilized enables application of physiologically relevant mechanical cues, including luminal fluid flow within both the epithelial and vascular channels that is critical for villi formation, as well as peristalsis-like cyclic deformations, in addition to providing precise independent control over the chemical composition of culture medium in each channel. The ability to collect effluents of the two separate channels independently also enables dynamic sampling and analysis of biochemical compounds that are produced or secreted by the intestinal epithelial cells or endothelial cells, such as inflammatory cytokines or metabolic products, which is not possible with conventional enteroid cultures. The apical surface of intestinal epithelial cells can also be exposed to pathogens, or potentially co-culture them with commensal microbes for extended periods of time (weeks) to model the natural microbiome as done in the past studies with the human Gut Chip[19], which again is difficult to do with organoids. Although not pursued in the present study, the presence of the endothelium-lined microchannel (which is absent in enteroid cultures) also can enable analysis of nutrient or oral drug absorption and bioavailability, as well as characterization of physiologically relevant pharmacokinetic parameters because they are significantly influenced by the passage of drug compounds back and forth across the endothelium-parenchymal tissue-tissue interface. In addition, the presence of the endothelium permits analysis of the contributions of circulating immune cells that may be recruited under physiological flow conditions within microfluidic Organ Chips, as demonstrated in previous studies[11,21,38]. But most importantly, the head-to-head transcriptomic comparison of the Small Intestine Chip with the intestinal enteroids used to supply the cells for the chips revealed that the Intestine Chip more closely mimics many key functions of the living duodenum than the enteroids, including host defense response to infection and cell proliferation. Thus, these findings indicate that while organoids may be an outstanding tool to study and probe intestinal stem cell differentiation and histogenesis, they have multiple limitations compared to the Organ Chip technology when it comes to studying organ-level functions and pathophysiology, particularly in relation to mechanobiology, immunology, infectious disease and drug development.

This primary human Small Intestine Chip can be adapted for a wide range of applications, including basic research studies on the development of human intestinal villi, stem cell maturation and intestinal epithelial cell differentiation; assessment of nutrient transport, sensing, absorption, intestinal barrier function and tissue-tissue (e.g., epithelial-endothelial) interactions; evaluation of drug delivery, therapeutic efficacy or toxicity; characterization of host-pathogen responses at the mucosal interface; and regenerative medicine studies. In addition, the ability to integrate intestinal stem cells from individual patient donors demonstrated in this study opens the possibility of creating Small Intestine Chips lined by cells from individuals with specific genotypic and disease-related phenotypic characteristics. These chips can be used to investigate patient-specific disease mechanisms as well as response to therapies, and thereby help to advance personalized medicine in the future.

The methods described herein can further comprise contacting one or both channels with intestinal fibroblasts, immune cells (e.g., macrophages, intraepithelial lymphocytes and dendritic cells) and cells of the enteric nervous system.

The power of the Organ Chip technology approach specifically lies in its ability to mimic organ-level complexity by progressively integrating different cell types one-at-a-time and studying the system at varying levels of system complexity. Moreover, this organ-level synthetic biology approach permits one to gain insight into mechanisms of biological regulation by manipulating potential contributing physical factors (e.g., flow, peristalsis) and cellular components separately while simultaneously providing a window on molecular-scale biochemical, genetic and cellular responses in real-time. The microengineered nature of this technology also allows users to reconstitute and control molecular gradients (e.g., Wnt, growth factors, etc.), which are thought to play a key role in intestinal development and regeneration. Thus, the primary human Small Intestine Chip described herein has extraordinary experimental potential for understanding and modeling development, homeostasis and diseases of the human intestine, including intestinal enteropathies, inflammatory bowel disease, celiac disease and cancer. It also provides a new approach to study intestinal interactions with pathogens and the contribution of the microbiome to health and disease using patient-specific cells.

Methods

In vitro culture of human small intestinal enteroids containing epithelial stem cells. Tissue biopsies were collected at Boston Children's Hospital in accordance with institutional review board (LRB) approval. Tissue was digested in 2 mg/ml collagenase I for 40 min at 37° C. followed by mechanical dissociation. Isolated crypts were then resuspended in growth factor reduced matrigel (BD) and incubated for 10 min at 37° C. to allow extracellular matrix polymerization. Enteroids were grown in expansion medium (EM) that consisted of Advanced DMEM F12 supplemented with L-WRN conditioned medium (50% vol/vol, ATCC, cat. no. CRL-3276)[2], glutamax, HEPES, 50 ng ml$^{-1}$ murine epidermal growth factor, N2 supplement, B27 supplement, 10 nM human [Leu15]-gastrin I, 1 mM n-acetyl cysteine, 10 mM nicotinamide, 10 μM SB202190, 500 nM A83-01, as previously described[4,6]. Differentiation medium (DM) was prepared as previously described[4]. Briefly, Wnt3a, nicotinamide and SB202190 were removed and 10 μM of the γ-secretase inhibitor DAPT was added the culture medium. Enteroids were passaged every 7 days by incubating in Cell Recovery Solution for 40 min at 4° C., followed by mechanical dissociation. Enteroids were seeded on chips between passage number 5 and 25 and karyotyping was performed to confirm the absence of chromosomal anomalies.

The Small Intestine Chip culture system. Small Intestine chips were fabricated from PDMS and assembled as described previously[19-21], or they were obtained from Emulate Inc. (Boston, MA). Chips were activated by oxygen plasma treatment for 1.5 min followed by incubation with APTMS (2% vol/vol in ethyl alcohol) for 30 min at RT. After several washes with ethyl alcohol, the microfluidic devices were incubated at 80° C. overnight. A coating of type I collagen (200 μg ml$^{-1}$) and Matrigel (1% in PBS) was applied and chips were incubated in a humidified 37° C. incubator for 2 h before excessive coating was gently removed with PBS washes. Epithelial enteroids cells were isolated from Matrigel and the cells dissociated with TrypLE supplemented with 10 μM of Y-27632. Epithelial cells were then resuspended in EM (approximately 210,000 cells per chip) and incubated overnight at 37° C. EM was perfused at 60 μl h$^{-1}$ through top and bottom channels until day 12.

To culture primary vascular endothelial cells in the vicinity of intestinal epithelium, similar to what occurs in vivo, 250,000 Human Intestinal Microvascular Endothelial Cells (HIMEC; ScienCell) were seeded on the lower side of the ECM-coated porous membrane in the basal compartment in EGM2-MV medium (Lonza); chips were inverted and incubated 1 h at 37° C. to promote HLMEC cell adhesion to the membrane. For these chips, EM and EGM2-MV were perfused through top and bottom channels, respectively, at the same flow rate described above. To mimic mechanical deformations of intestinal cells caused by physiological peristaltic motions, cyclic membrane deformations (10% strain; 0.2 Hz) were applied after formation of confluent monolayers (3-4 days) using a vacuum pump controlled by a programmable actuator consisting of an electronic vacuum regulator (ITV009, SMC Corp.) and an Arduino microcontroller.

Small Intestine Chip co-culture with enteric bacteria. All bacterial strains were reviewed, and research was approved by Harvard's Committee on Microbiological Safety (COMS). Nonpathogenic E. coli K12 strain and a sepsis-associated E. coli (41949) obtained from a human clinical isolate (Brigham and Women's Hospital Crimson Bioreposi-tory, USA), were cultured in RPMI media supplemented with 10 mM glucose. E. coli (41949)-GFP was generated using the vector pAW81 (Chloramphenical resistant version of pGEN-GFP). Briefly a double stranded DNA fragment, gblock (Integrated DNA Technologies), containing the chloramphenicol acetyl transferase gene and its promoter (the 81 nucleotides on its 5' end) from pACYC184 book-ended with 40 nucleotides homologous to pGEN-GFP, was cloned into the Aat1 restriction site of pGEN-GFP vector using standard Gibson Assembly techniques. Bacteria were grown to a 0.5 McFarland (McF) standard (Becton Dickinson, USA), pelleted and resuspended in differentiation medium at 10$^7$ cfu/ml for injection. Small Intestine chips were grown 7 days in EM followed by 1 day in antibiotic-free DM medium. Bacteria were injected into the lumen of the epithelial channel of the Small Intestine Chip and incubated for 1 h under static conditions to allow bacteria adhesion to the epithelium; medium fluid flow (120 μl h$^{-1}$) and cyclic mechanical deformations (10% strain; 0.2 Hz) were then applied throughout the remaining duration of the experiment. Media effluents were sampled from the vascular compartment of the infected Intestine Chips at 3, 6, 12, and 24 h post inoculation to quantify bacterial translocation. Bacteria were diluted in antibiotic-free DM medium and plated on soy agar plates with sheep blood with an Eddy Jet 2 automated spiral plater (UL Instruments). Plates were incubated overnight at 37° C. and cfu were quantified using a Flash & Go automatic colony counter (UL Instruments).

Intestinal functional assessment and cytokine measurements. Lucifer Yellow (450 Da) was added to the epithelial channel of the Small Intestine Chip to assess intestinal barrier permeability in the presence or absence of enteric bacteria. Cascade Blue hydrazide, Trilithium Salt (550 Da) was used instead of Lucifer Yellow when the experiments required the use GFP-labeled E. coli. The concentration of dye that diffused through the membrane into endothelial channel was measured in the effluent, and apparent paracellular permeability ($P_{app}$) was calculated using the following formula:

$$P_{app} = \frac{V_{rec} \cdot dC_{rec}}{A\, dt\, C_{den;i=0}}$$

where $V_{rec}$ is volume receiver (endothelial compartment), $C_{rec}$ concentration receiver, A the seeded area and $C_{don}$ concentration donor (epithelial compartment). Cytokines released in the medium were quantified using U-PLEX Biomarker Assays for human Fractalkine, GM-CSF, IFN-γ, IL-1α, IL-1β, IL-6, IL-8, and IL-10 (Mesoscale Discovery).

To measure sucrase activity, upper and lower chamber of the Small Intestine chip device were perfused PBS with $Ca^{2+}$ and $Mg^{2+}$ for 1 h to remove any residual glucose from the standard media. 30 mM sucrose reaction buffer or 30 mM mannitol reaction buffer were prepared in in PBS with $Ca^{2+}$ and $Mg^{2+}$. NaCl concentration in PBS was adjusted to 120 mM to adjust for osmolarity in the presence of 30 mM sucrose. The sucrose or mannitol reaction buffer was then introduced in the upper microfluidic channel and PBS with $Ca^{2+}$ and $Mg^{2+}$ into the lower channel. Glucose content in apical and basal compartment was measured using Amplex Red Glucose assay kit following the vendor's instructions (Thermo Fisher). Epithelial cells were then lysed using RIPA buffer to determine the total protein content using Pierce BCA Protein Assay following the vendor's instructions (Thermo Fisher). Glucose concentration was determined from a standard curve and sucrase activity expressed as units per gram of protein. 1 unit (1 U) is defined as the activity that hydrolyzes 1 μmol substrate/min at 37° C.

For the assessment of MUC2 in the luminal effluent, apical effluent was collected over night. MUC2 content was measured using a Human Mucin 2/MUC2 ELISA Kit (LS-Bio) following the vendor's protocol. The samples were diluted 1 to 5. Optical density was measured at 450 nm wavelength using a microplate reader. The results were quantified by creating a standard curve using a four parameter logistic (4-PL) curve-fit.

Morphological analysis. Small Intestine Chips were fixed with 4% paraformaldehyde for 15 min at room temperature followed by permeabilization in a blocking solution containing 5% (wt/vol) BSA, 0.1% (vol/vol) Triton-X100 for 1 h at room temperature. Chips were then incubated at 4° C. overnight with primary antibodies directed against E-cadherin (mouse monoclonal, Abcam, 1:100), ZO-1 (mouse monoclonal, Life technology, 1:200), VE-cadherin (rabbit polyclonal, Abcam, 1:400), mucin 5AC (mouse monoclonal, Thermo Fisher Scientific, 1:100), lysozyme (polyclonal, Dako, 1:1000), chromogranin A (goat polyclonal IgG, Santa Cruz Biotechnology), villin (monoclonal mouse, Abcam, 1:100), NHE3 (rabbit polyclonal, Novus Biologicals), alpha 1 Sodium/Potassium ATPase (mouse monoclonal, Abcam) and Ki67 (rabbit polyclonal, Abcam). Appropriate Alexa Fluor secondary antibodies were flowed into the two channels of the chip and incubated in the dark at 4° C. overnight. Images were acquired with an inverted laser-scanning confocal microscope (Leica SP5×MP DMI-6000).

Samples for scanning electron microscopy (SEM) were fixed in 2.5% glutaraldehyde, followed by 1% osmium tetroxide in 0.1 M sodium cacodylate buffer treatment, and progressive dehydration in a graded series of ethanols. The samples were subsequently dried by critical point drying with a liquid $CO_2$ dryer (AutoSamdri-815, Tousimis Research Corp.). The samples were coated with a thin (10 nm) layer of Pt/Pd using a sputter coater (Leica Baltec MED-020, Leica, Wetzlar, Germany)[40] prior to imaging using a scanning electron microscope (Zeiss Supra 55 VP SEM, Carl Zeiss SMT Inc) at a voltage of 2~3 kV.

Villus morphology was evaluated using differential interface contrast (DIC) microscopy (Zeiss Axio Observer Z1 2, AXIO2). 3D confocal immunofluorescence micrographic reconstruction of the human villus intestinal epithelium was obtained using immunofluorescence microscopy with a laser scanning confocal microscopes (Leica SP5×MP DMI-6000 and Zeiss TIRF/LSM 710). After sectioning the chips using a sharp surgical blade, images of the cross sections were acquired with a confocal immunofluorescence microscope and high-resolution images were obtained applying deconvolution (Huygens) followed by a 2D projection processing.

RNA isolation, reverse transcription and qRT-PCR. RNA was extracted using RNeasy Mini Kit followed by cDNA synthesis with SuperScript VILO™ cDNA Synthesis Kit (Thermo Fisher Scientific) following vendor's protocol. RT-PCR was performed using TaqMan Fast Advanced Master Mix™ (Applied Biosystems), TaqMan gene expression assays (Thermo Fisher Scientific; Hs00357579_g1 for intestinal-type alkaline phosphatase (ALPI), Hs00356112_m1 for sucrase isomaltose (SI), Hs00873651_g1 for mucin 5AC (MUC5AC), Hs00894025_m1 for mucin 2 (MUC2), Hs00900375_m1 for chromogranin A (CHGA), Hs00300531_m1 for synaptophysin (SYP), Hs00426232_m1 for lysozyme (LYZ), Hs00969422_m1 for leucine-rich-repeat-containing G-protein-coupled receptor 5 (LGR5), Hs00409825_g1 for Bmi1 (BMI1), Hs02758991_g1 for glyceraldehyde-3-phosphate dehydrogenase (GAPDH)), and run on a QuantStudio 7™ Flex Real-Time PCR System (Thermo Fisher Scientific). Results were normalized relative to GAPDH expression.

Gene microarray studies and differential expression analysis. Total RNA samples (100 ng) were processed using the GeneChip WT PLUS™ Reagent Kit and hybridized to Affymetrix Human Clariom D arrays following the manufacturer's protocol. Current and past batches of Small Intestine Chip, Caco-2 Gut Chip and Caco-2 Transwell samples, as well as samples of human intestinal tissues from GEO, were pre-processed with SCAN (SCAN.UPC package)[39,40] to generate expression values. These expression values were then quantile-normalized together. Differential analysis was performed with limma package for each pair of comparison[41].

To visualize differences and similarity between conditions, gene expression values for each experimental condition (in vivo ileum, jejunum, and duodenum; Caco-2 Gut Chip, Caco-2 Transwell, 3D Enteroids and Small Intestine Chip) were averaged for each condition to produce averaged gene expression for these 7 conditions. Template matching method was used to extract genes that are differentially expressed between these conditions[42,43]. Relevant GO terms covered by these genes were selected and gene lists for the selected GO terms were collected from the Gene Ontology Consortium (available on the World Wide Web at geneontology.org/). For each GO term, no more than 18 genes with the most variance were selected, and a curated heatmap for these selected genes grouped by GO terms was generated by clustering the conditions according to the averaged gene expression values using Canberra distance and complete linkage.

Gene expression data for primary human small intestine (duodenum, jejunum, and ileum), Caco-2 Gut Chip, and Caco-2 Transwell were obtained from the National Center for Biotechnology Information (NCBI) Gene Expression Omnibus (GEO) database[44] (accession no. GSE65790[21]). Global gene expression profiles were visually represented using self-organizing maps generated using the Gene Expression Dynamics Inspector (GEDI) program[45].

Statistical analysis. A 2-way ANOVA was used to compare sucrose activity or cytokines profiles. Error bars Indicate standard error of the mean. P values<0.05 are indicated as significant.

REFERENCES

1. Shanks, N., Greek, R. & Greek, J. Are animal models predictive for humans? *Philos. Ethics. Humanit. Med* 4, 2 (2009).
2. Sato, T. et al. Single Lgr5 stem cells build crypt-villus structures in vitro without a mesenchymal niche. *Nature* 459, 262-5 (2009).
3. Sato, T. et al. Long-term expansion of epithelial organoids from human colon, adenoma, adenocarcinoma, and Barrett's epithelium. *Gastroenterology* 141, 1762-72 (2011).
4. Vandussen, K. L. et al. Development of an enhanced human gastrointestinal epithelial culture system to facilitate patient-based assays. (2014). doi:10.1136/gutjnl-2013-306651
5. Sasai, Y., Eiraku, M. & Suga, H. In vitro organogenesis in three dimensions: self-organising stem cells. *Development* 139,4111-21 (2012).
6. Sato, T. & Clevers, H. Growing self-organizing mini-guts from a single intestinal stem cell: mechanism and applications. *Science* 340, 1190-4 (2013).
7. Wells, J. M. & Spence, J. R. How to make an intestine. *Development* 141, 752-60 (2014).
8. Fatehullah, A., Tan, S. H. & Barker, N. Organoids as an in vitro model of human development and disease. *Nat. Cell Biol.* 18, 246-54 (2016).
9. Bhatia, S. N. & Ingber, D. E. Microfluidic organs-on-chips. *Nat. Biotechnol.* 32, 760-72 (2014).
10. Ingber, D. E. Reverse Engineering Human Pathophysiology with Organs-on-Chips. *Cell* 164, 1105-9 (2016).
11. Huh, D. et al. Reconstituting organ-level lung functions on a chip. *Science* 328, 1662-8 (2010).
12. Baudoin, R., Griscom, L., Monge, M., Legallais, C. & Leclerc, E. Development of a renal microchip for in vitro distal tubule models. *Biotechnol. Prog.* 23, 1245-53
13. Jang, K.-J. et al. Human kidney proximal tubule-on-a-chip for drug transport and nephrotoxicity assessment. *Integr. Biol.* (Camb). 5, 1119-29 (2013).
14. Leclerc, E., Sakai, Y. & Fujii, T. Microfluidic PDMS (polydimethylsiloxane) bioreactor for large-scale culture of hepatocytes. *Biotechnol. Prog.* 20, 750-5
15. Powers, M. J. et al. A microfabricated array bioreactor for perfused 3D liver culture. *Biotechnol. Bioeng.* 78, 257-69 (2002).
16. Tilles, A. W., Baskaran, H., Roy, P., Yarmush, M. L. & Toner, M. Effects of oxygenation and flow on the viability and function of rat hepatocytes cocultured in a microchannel flat-plate bioreactor. *Biotechnol. Bioeng.* 73, 379-89 (2001).
17. Grosberg, A., Alford, P. W., McCain, M. L. & Parker, K. K. Ensembles of engineered cardiac tissues for physiological and pharmacological study: heart on a chip. *Lab Chip* 11, 4165-73 (2011).
18. Park, J. et al. Three-dimensional brain-on-a-chip with an interstitial level of flow and its application as an in vitro model of Alzheimer's disease. *Lab Chip* 15, 141-50 (2015).
19. Kim, H. J., Huh, D., Hamilton, G. & Ingber, D. E. Human gut-on-a-chip inhabited by microbial flora that experiences intestinal peristalsis-like motions and flow. *Lab Chip* 12, 2165-74 (2012).
20. Kim, H. J. & Ingber, D. E. Gut-on-a-Chip microenvironment induces human intestinal cells to undergo villus differentiation. *Integr. Biol.* (Camb). 5, 1130-40 (2013).
21. Kim, H. J., Li, H., Collins, J. J. & Ingber, D. E. Contributions of microbiome and mechanical deformation to intestinal bacterial overgrowth and inflammation in a human gut-on-a-chip. *Proc. Natl. Acad. Sci. U.S.A* 113, E7-15 (2016).
22. Imura, Y., Asano, Y., Sato, K. & Yoshimura, E. A microfluidic system to evaluate intestinal absorption. *Anal. Sci.* 25, 1403-7 (2009).
23. Kimura, H., Yamamoto, T., Sakai, H., Sakai, Y. & Fujii, T. An integrated microfluidic system for long-term perfusion culture and on-line monitoring of intestinal tissue models. *Lab Chip* 8, 741-6 (2008).
24. Shah, P. et al. A microfluidics-based in vitro model of the gastrointestinal human-microbe interface. *Nat. Commun.* 7, 11535 (2016).
25. Yissachar, N. et al. An Intestinal Organ Culture System Uncovers a Role for the Nervous System in Microbe-Immune Crosstalk. *Cell* 168, 1135-1148.e12 (2017).
26. Tsilingiri, K., Sonzogni, A., Caprioli, F. & Rescigno, M. A novel method for the culture and polarized stimulation of human intestinal mucosa explants. *J. Vis. Exp.* e4368 (2013). doi:10.3791/4368
27. Sato, T. et al. Single Lgr5 stem cells build crypt—villus structures in vitro without a mesenchymal niche. *Nature* 459, 262-265 (2009).
28. Zietek, T., Rath, E., Haller, D. & Daniel, H. Intestinal organoids for assessing nutrient transport, sensing and incretin secretion. *Sci. Rep.* 5, 16831 (2015).
29. Elnasharty M. A., Abou-Ghanema I. I., Sayed-Ahmed A., and A. A. E. Mucosal-Submucosal Changes in Rabbit Duodenum during Development. in *International Journal of Biological, Biomolecular, Agricultural, Food and Biotechnological Engineering* 7, 500-508 (2013).
30. Hassan, S. A. & Moussa, E. A. Light and scanning electron microscopy of the small intestine of goat (Capra hircus). *J. Cell Anim. Biol. Full* 9, 1-8 (2015).
31. Skrzypek, T. et al. Light and scanning electron microscopy evaluation of the postnatal small intestinal mucosa development in pigs. *J. Physiol. Pharmacol.* 56 Suppl 3, 71-87 (2005).
32. Charney, A. N. & Donowitz, M. Functional significance of intestinal Na+-K+-ATPase: in vivo ouabain inhibition. *Am. J. Physiol.* 234, E629-36 (1978).
33. Barker, N. et al. Identification of stem cells in small intestine and colon by marker gene Lgr5. 449, (2007).
34. Yan, K. S. et al. The intestinal stem cell markers Bmi1 and Lgr5 identify two functionally distinct populations. *Proc. Natl. Acad. Sci. U.S.A* 109, 466-71 (2012).

35. Kraft, R. et al. Predictive Value of IL-8 for Sepsis and Severe Infections After Burn Injury: A Clinical Study. *Shock* 43, 222-7 (2015).
36. Hoogendijk, A. J. et al. Plasma fractalkine is a sustained marker of disease severity and outcome in sepsis patients. *Crit. Care* 19, 412 (2015).
37. Kim, H. J. Human gut-on-a-chip inhabited by microbial flora that experiences intestinal peristalsis-like motions and flow. Lab Chip Lab on a Chip. (2015). doi:10.1039/c21c40074j
38. Huh, D. et al. A human disease model of drug toxicity-induced pulmonary edema in a lung-on-a-chip microdevice. *Sci. Transl. Med.* 4, 159ra147 (2012).
39. Piccolo, S. R., Withers, M. R., Francis, O. E., Bild, A. H. & Johnson, W. E. Multiplatform single-sample estimates of transcriptional activation. *Proc. Natl. Acad. Sci. U.S.A* 110, 17778-83 (2013).
40. Piccolo, S. R. et al. A single-sample microarray normalization method to facilitate personalized-medicine workflows. *Genomics* 100, 337-44 (2012).
41. Ritchie, M. E. et al. limma powers differential expression analyses for RNA-sequencing and microarray studies. *Nucleic Acids Res.* 43, e47 (2015).
42. Pavlidis, P. & Noble, W. S. Analysis of strain and regional variation in gene expression in mouse brain. *Genome Biol.* 2, RESEARCH0042 (2001).
43. Lance, G. N. & Williams, W. T. Mixed-data classificatory programs. 1. Agglomerative Systems. *Aust. Comput. J.* (1967).
44. Edgar, R., Domrachev, M. & Lash, A. E. Gene Expression Omnibus: NCBI gene expression and hybridization array data repository. *Nucleic Acids Res.* 30, 207-10 (2002).
45. Eichler, G. S., Huang, S. & Ingber, D. E. Gene Expression Dynamics Inspector (GEDI). for integrative analysis of expression profiles. *Bioinformatics* 19, 2321-2 (2003).

Example 5

Any of the embodiments of any of the aspects described herein can also be performed in the absence of endothelial cells, although such embodiments require longer time for the epithelial monolayer to form. Alternatively, the endothelial cells can be replaced with fibroblasts or a mix of fibroblasts and other cell types (e.g., immune cells). Alternatively, fibroblasts and/or a mix of fibroblasts and other cell types (e.g., immune cells) and/or immune cells can be added to the endothelial cells, e.g., by perfusing the cells through the channel comprising endothelial cells. In some embodiments, immune cells, circulating cancer cells, and/or blood or blood cells can be perfused through the vascular channel of the system.

Endothelial cell growth in any of the aspects and embodiments described herein can be maintained with EGM2-MV media or Expansion Media or Differentiation media, or a modification of EGM2 media by addition of one or more of: Wnt3A, Rspo1, Noggin, EGF, gastrin, TGF-beta receptor inhibitor, p38 MAPK inhibitor, Jag, GSK inhibitor, or a modification of Expansion Media by the addition of EGM-2 MV SingleQuot Kit Suppl. & Growth Factors.

Epithelial cells can, in the alternative to an enteroid, be provided by means of an iPSC-derived intestinal organoid. Intestinal organoids (from primary or iPS cells) can be derived from human or different animals, including mice, primates, etc. Epithelial cells can also be provided as iPSC-derived endothelial cells.

Example 6

Figure 22A:
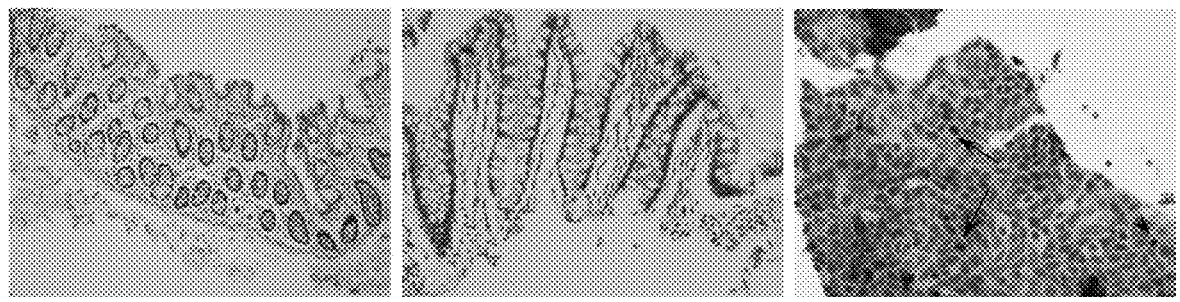
FIGS. 22A-22B demonstrate establishment of a primary human colonoid cultures from human colon resections.
Figure 22B:
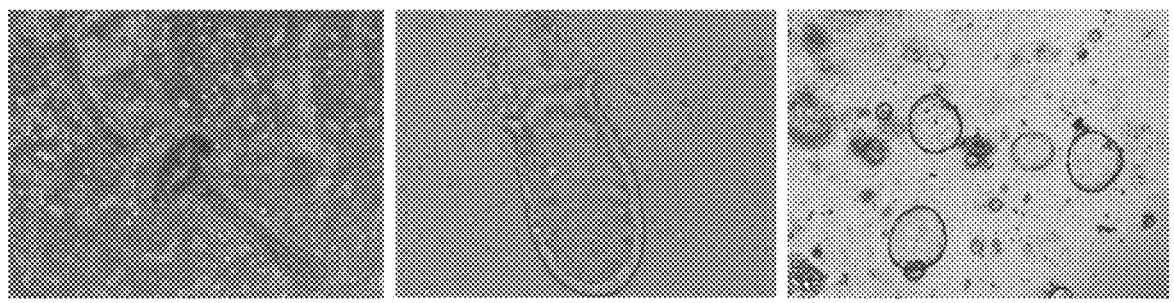
Figure 23A:
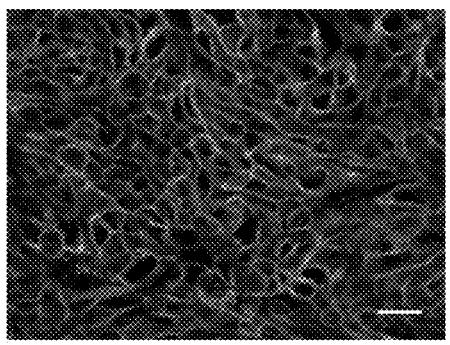
FIGS. 23A-23F demonstrate the development of a primary human colon-on-a-chip model from human colon resections.
Figure 23A:
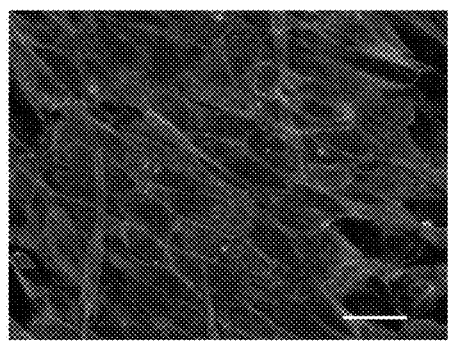
Figure 23B:
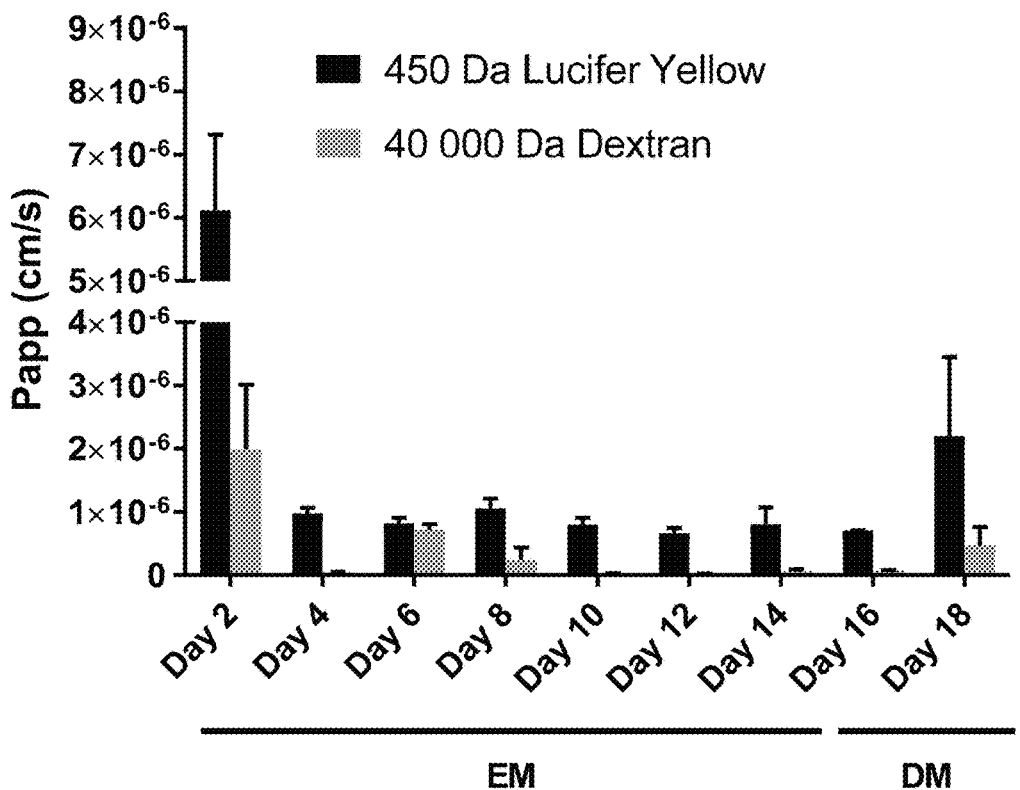
Figure 23C:
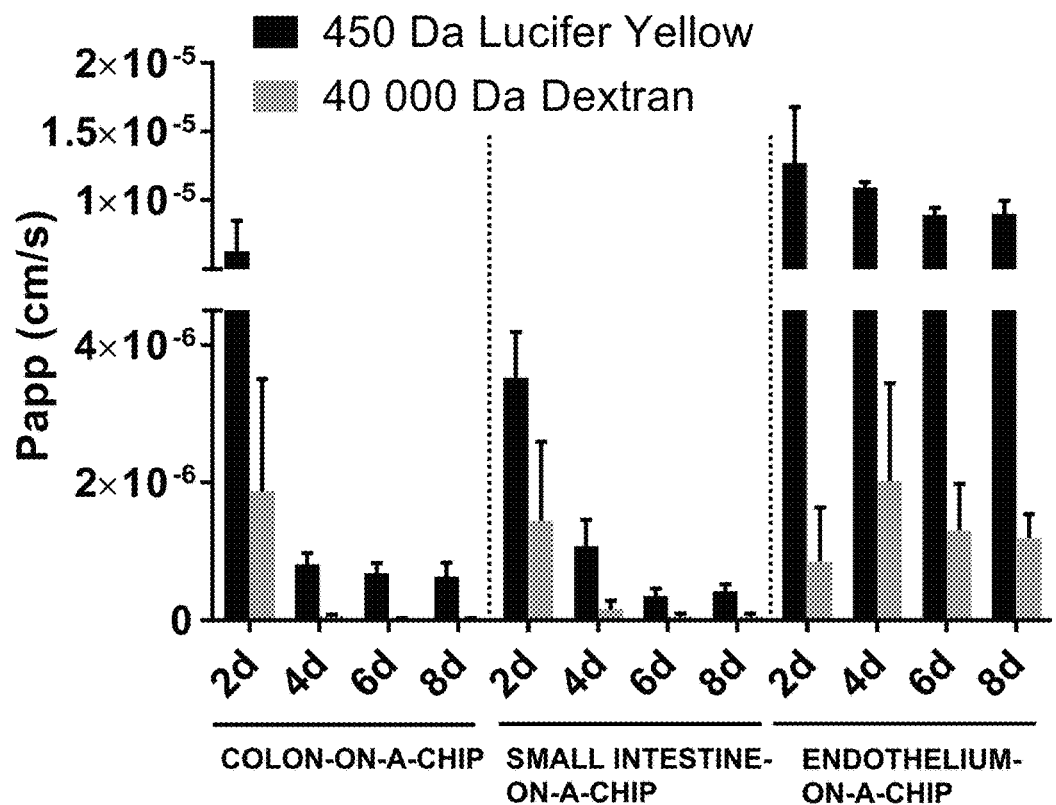
Figure 23D:
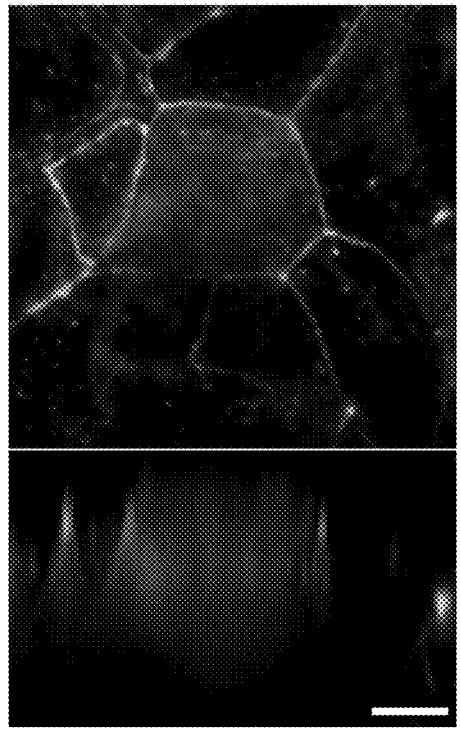
Figure 23E:
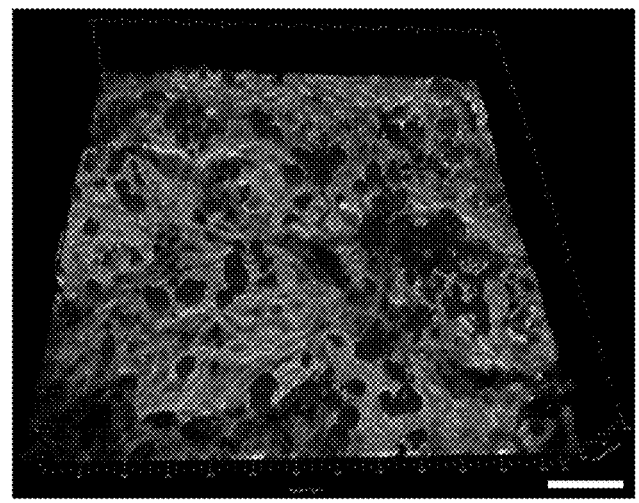
Figure 23F:
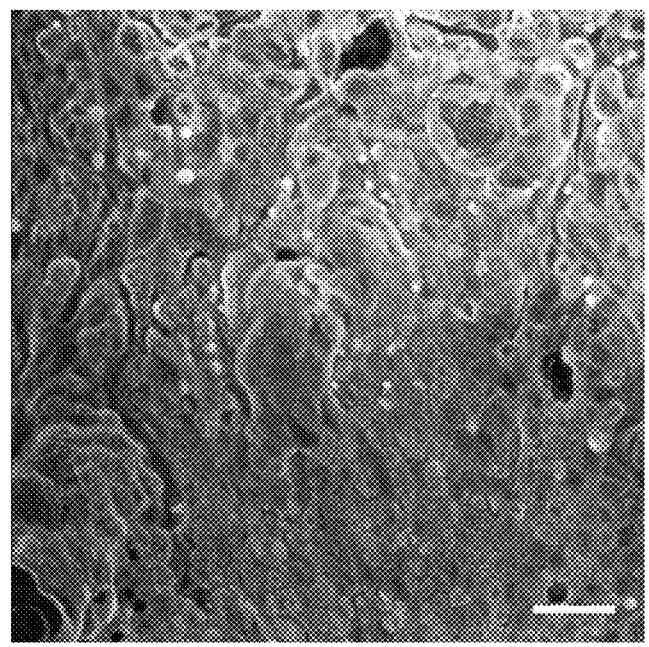
Figure 24A:
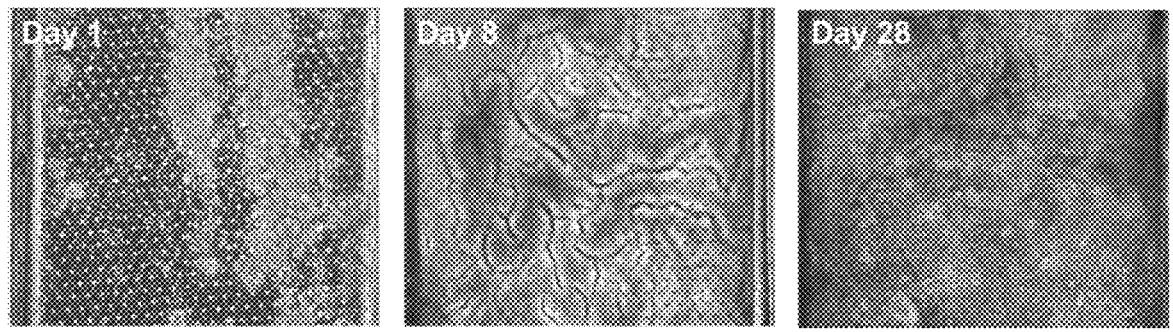
FIGS. 24A-24E demonstrate the development of a primary human colon-on-a-chip model without endothelium from human colon resections.
Figure 24B:
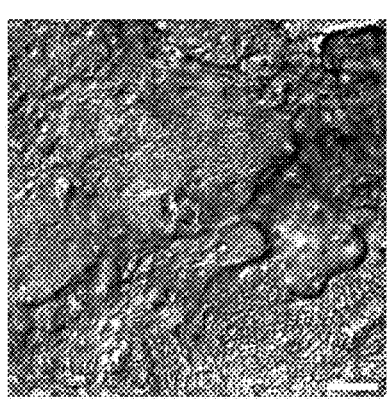
Figure 24C:
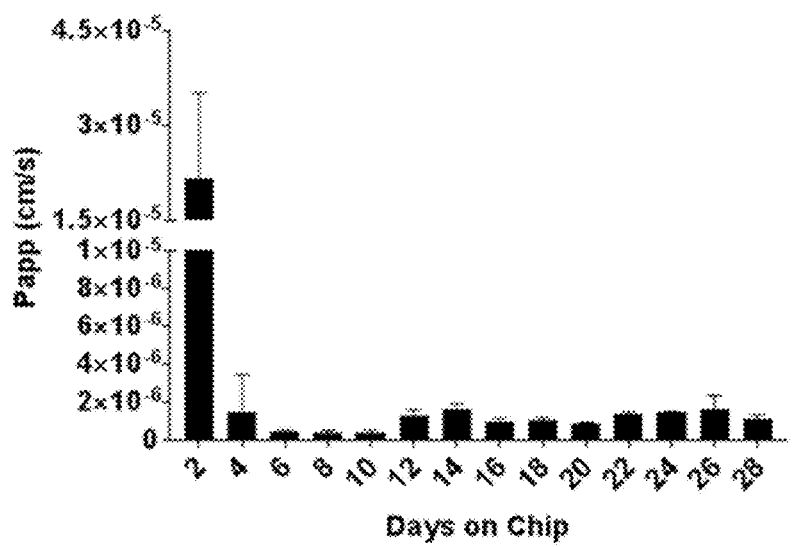
Figure 24D:
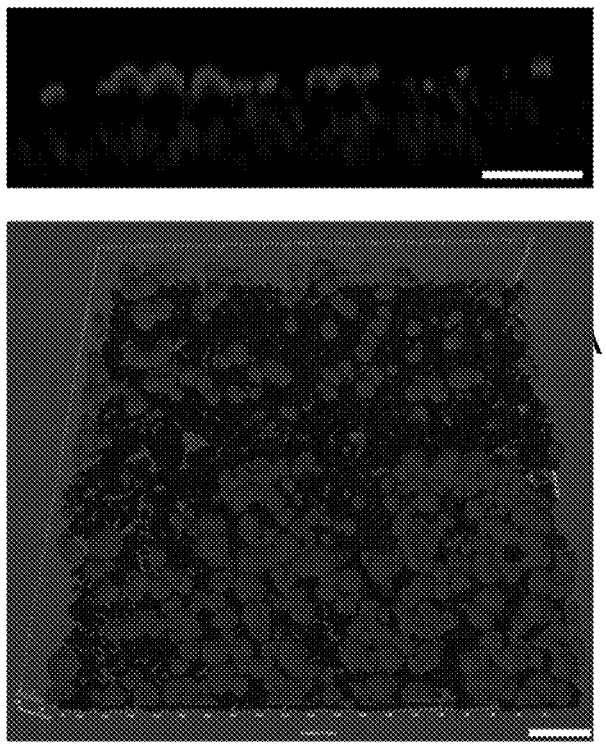
Figure 24E:
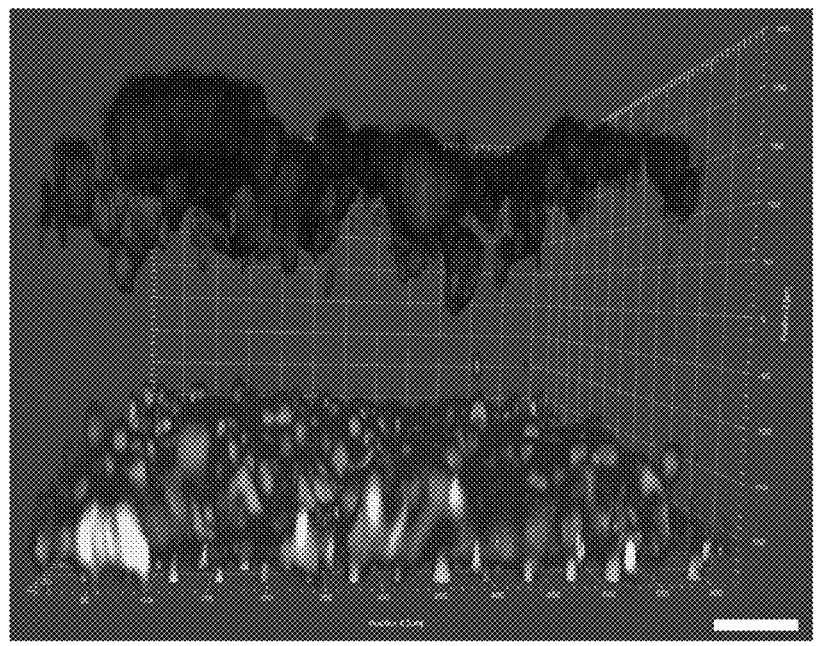

Colonoids were prepared by growing colonic crypts in matrigel after isolation from human resection samples (FIGS. 22A-22B).

Figure 25:
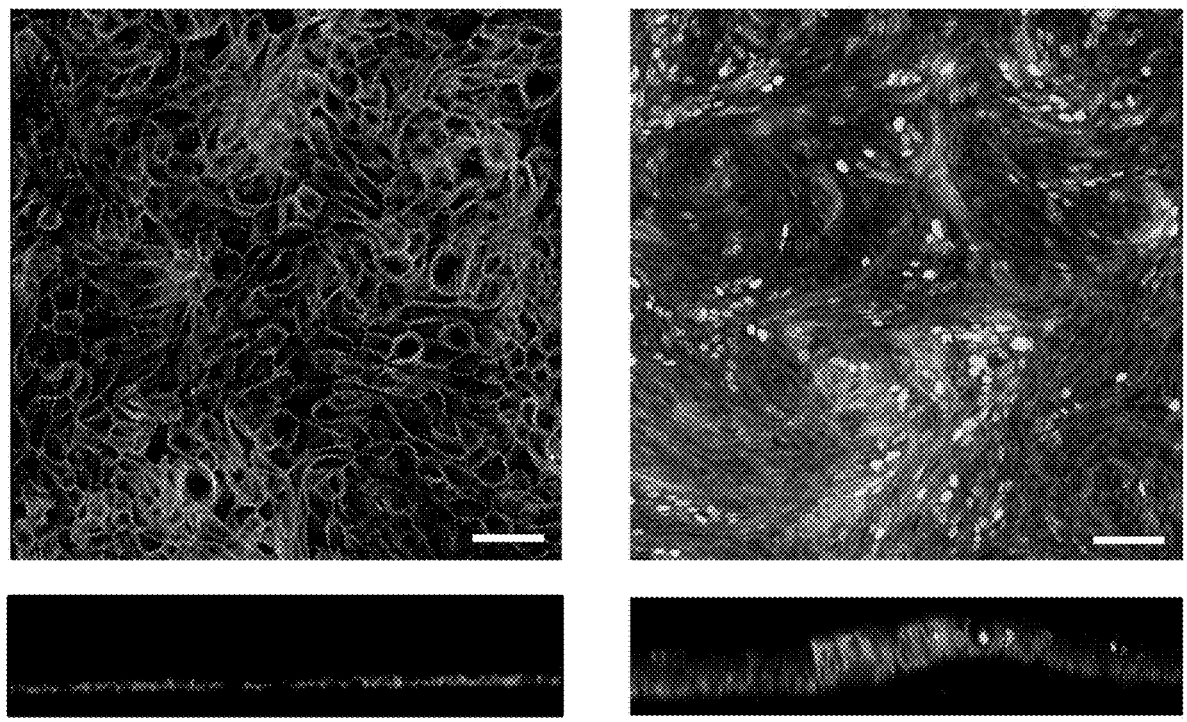
FIG. 25 demonstrates that expansion media on basal side promotes proliferation of colonic epithelial cells on transwell. Immunofluorescence microscopic top views (top) or cross sections (bottom) of the human primary colon epithelium cultured transwell for 13 days. EdU was added to the cell culture media for 20 h before fixation. EdU positive cells indicate proliferating cells, F-Actin and hoechststained nuclei are also depicted. Cells were cultured with expansion media apical and EGM2-MV in the basal compartment (left) or expansion media in both compartments (right). Expansion media on the basal side promotes proliferation. (control: EGM2-MV media on apical side and expansion media in basal compartment also promotes proliferation, data no shown) (bar, 50 μm).

Enteroid fragments were seeded in the apical channel without endothelial cells and expansion media was added in both channels. Cultures were maintained with expansion media on the apical and basal side under 60 ul/h flow conditions for 12 days. Experiments were conducted using transwell and organ on chip devices with colonoids using expansion media apical and basal, or expansion media basal only and apical Hank's balanced salt solution (HBSS) or phosphate-buffered saline with magnesium and calcium (PBS). With those conditions increased proliferation (EdU incorporation) of primary intestinal epithelial cells were observed, as compared to expansion media on the apical side only (FIGS. 24A-24E; FIG. 25).

Characterization of cells grown with EGM2-MV on the endothelial side and expansion media on the epithelial side of the device is depicted in FIGS. 23A-23F.

In embodiments relating to intestinal epithelial cells, expansion media on the basal side leads to increased villi formation compared to culture conditions with expansion media on only the apical side.

Example 7

Intestine chips (epithelial+endothelial cells) were co cultured with pathogenic and non-pathogenic bacteria. Flow rate was 120 µl h-1 during bacteria co-culture and cyclic mechanical deformations (10% strain, 0.2 Hz).

Additionally, during bacterial co-culture, culture media was routed from reservoirs to a pump to the chip, instead of moving from reservoirs, to the chip, to the pump. This setup reduces potential reservoirs contamination and reduces distance between chip and collection reservoirs.

Inflammatory response of the endothelial cells to bacteria was measured, e.g., the level of cytokines. Also measured was the amount of barrier disruption caused by bacteria and the amount of bacterial translocation.

Example 8

Colonoid fragments were seeded in the apical channel without endothelial cells and expansion media was added in both channels. Cultures were maintained with expansion media on the apical and basal side under 60 ul/h flow conditions for 7 days. Chips were detached from flow and the basal channel was seeded with HIMEC in EGM2-MV medium and flipped for 2 h. Chips were flipped back and re-attached to flow 60 ul/h, expansion media in the apical channel and expansion media with EGM2-MV bulletkit in the basal channel. Endothelial cells were maintained for 2 days after seeding and displayed functional cytokine release in response to bacterial stimuli.

What is claimed herein is:
1. A method of providing an in vitro intestinal model system, the method comprising:
 a) providing
  i) intestinal endothelial cells,
  ii) an intestinal enteroid or colonoid comprising primary intestinal epithelial cells,
  iii) a microfluidic culture device, the device comprising a porous membrane having a first surface and a second surface, said membrane in fluidic communi- cation with a microchannel, said microchannel in fluidic communication with a source of fluid;

b) disrupting said intestinal enteroid or colonoid comprising primary intestinal epithelial cells into enteroid or colonoid fragments;

c) seeding said first surface of said porous membrane with said enteroid or colonoid fragments so as to create seeded primary intestinal epithelial cells;

d) seeding said second surface of said porous membrane with said intestinal endothelial cells;

e) expanding said seeded primary intestinal epithelial cells in a first media comprising Wnt-3A so as to create a monolayer of the intestinal epithelial cells;

f) replacing said first media comprising Wnt-3A and culturing said intestinal epithelial cells with a second media lacking Wnt-3A; and g) culturing said intestinal endothelial cells in a third media comprising Wnt-3A.

2. The method of claim 1, wherein said first media further comprises Noggin.

3. The method of claim 1, wherein said first media further comprises a ROCK inhibitor.

4. The method of claim 1, wherein said first media further comprises R-spondin.

* * * * *